(12) United States Patent
Mori et al.

(10) Patent No.: US 7,795,390 B2
(45) Date of Patent: Sep. 14, 2010

(54) BIOLOGICAL SUBSTANCE NESFATIN AND ITS RELATED SUBSTANCES AND USES THEREOF

(75) Inventors: Masatomo Mori, Maebashi (JP); Hiroyuki Shimizu, Maebashi (JP); Hiroshi Eguchi, Hino (JP); Masanori Yamamoto, Hino (JP)

(73) Assignees: Teijin Pharma Limited, Tokyo (JP); National University Corporation Gunma University, Gunma (JP)

( * ) Notice: Subject to any disclaimer, the term of this patent is extended or adjusted under 35 U.S.C. 154(b) by 328 days.

(21) Appl. No.: 11/474,282

(22) Filed: Jun. 26, 2006

(65) Prior Publication Data

US 2008/0115231 A1    May 15, 2008

Related U.S. Application Data

(60) Provisional application No. 60/703,864, filed on Aug. 1, 2005, provisional application No. 60/780,514, filed on Mar. 9, 2006.

(30) Foreign Application Priority Data

Jun. 24, 2005    (JP) ............................. 2005-184441

(51) Int. Cl.
C12N 9/00    (2006.01)
C12N 1/20    (2006.01)
C12N 15/00   (2006.01)
C07K 14/00   (2006.01)
C07H 21/02   (2006.01)

(52) U.S. Cl. .................... 530/350; 435/183; 435/252.3; 435/320.1; 536/23.1

(58) Field of Classification Search ........................ None
See application file for complete search history.

(56) References Cited

U.S. PATENT DOCUMENTS

| | | | |
|---|---|---|---|
| 4,873,191 | A | 10/1989 | Wagner et al. |
| 6,753,314 | B1 * | 6/2004 | Giot et al. ..................... 514/12 |
| 2002/0161210 | A1 | 10/2002 | Lazar | 
| 2004/0235019 | A1 | 11/2004 | Chapman et al. |

FOREIGN PATENT DOCUMENTS

| | | |
|---|---|---|
| WO | 00/63435 A2 | 10/2000 |
| WO | 00/64919 A1 | 11/2000 |
| WO | 01/96359 A1 | 12/2001 |
| WO | 01/96865 A1 | 12/2001 |
| WO | 01/96866 A1 | 12/2001 |

OTHER PUBLICATIONS

Cowley et al. Cell Metab. Dec. 2006;4(6):421-2.*
Chica et al. (Curr Opin Biotechnol. Aug. 2005;16(4):378-84.*
Sen et al. Appl Biochem Biotechnol. Dec. 2007;143(3):212-23.*
Accession P80303, published Feb. 1, 1994.*
Alignment of SEQ ID No. 13 to SEQ ID No. 1229 of Giot et al. US Patent 6,753,314.*
Subhi Abu-Abid et al: "Obesity and Cancer", Journal of Medicine, vol. 33, Nos. 1-4, 2002, pp. 73-86.
Satheesh Nair et al: "Is Obesity an Independent Risk Factor for Hepatocellular Carcinoma in Cirrhosis?", Hepatology, vol. 36, No. 1, 2002, pp. 150-155.
N. J. Talley et al: "Functional gastroduodenal disorders", Gut 1999, vol. 45(Suppl II): II37-II42.
Steven B. Heymsfield et al: "Recombinant Leptin for Weight Loss in Obese and Lean Adults", Journal of American Medical Association, Oct. 27, 1999, vol. 282, No. 16, pp. 1568-1575.
Robert V. Considine: "Human Leptin: An Adipocyte Hormone with Weight-Regulatory and Endocrine Functions", Seminars in Vascular Medicine, vol. 5, No. 1, 2005, pp. 15-24.
Shitsu Barnikol-Watanabe et al: "Human Protein NEFA, a Novel DNA Binding /EF-Hand /Leucine Zipper Protein, Molecular Cloning and Sequence Analysis of the cDNA, Isolation and Characterization of the Protein", Biol. Chem. Hoppe-Seyler, vol. 375, pp. 497-512, Aug. 1994.
Anton Karabinos et al: "The Divergent Domains of the NEFA and Nucleobindin Proteins are Derived from an EF-Hand Ancestor", Mol. Biol. Evol. 13(7):990-998, 1996.
Katja A. Kroll et al: "Heterologous Overexpression of Human NEFA and Studies on the Two EF-Hand Calcium-Binding Sites", Biochemical and Biophysical Research Communications, vol. 260, No. 1-8, 1999.
Naoko Taniguchi et al: "The Postmitotic Growth Suppressor Necdin Interacts with a Calcium-binding Protein (NEFA) in Neuronal Cytoplasm", The Journal of Biological Chemistry, vol. 275, No. 41, Issue of Oct. 13, pp. 31674-31681, 2000.
Margaret M. Deangelis et al: "Assembly of a high-resolution map of the Acadian Usher syndrome region and localization of the nuclear EF-hand acidic gene", Biochimica et Biophysica Acta 1407 (1998), 84-91.
A Line et al: "Serological identification and expression analysis of gastric cancer-associated genes", British Journal of Cancer (2002) 86, 1824-1830.

(Continued)

*Primary Examiner*—Christian L Fronda
(74) *Attorney, Agent, or Firm*—Sughrue Mion, PLLC

(57) ABSTRACT

The present invention relates to a novel method of obtaining a factor involved in appetite control and/or body weight control, as well as genes obtained by said method, polypeptides encoded by said genes, or novel polypeptides obtained from the information on polypeptides encoded by said genes as a means for treating, controlling or diagnosing diseases associated with eating disorders and/or body weight control. Also the present invention relates to substances that inhibit the effects of said genes or said polypeptides as a means for treating, controlling or diagnosing diseases associated with appetite control and/or body weight control. By using thiazolidine diones having a PPAR γ agonist activity, genes and polypeptides involved in appetite regulation and/or body weight reduction can be obtained. NESFATIN or the like obtained by said method can be used as a means for treating, controlling or diagnosing diseases associated with eating disorders and/or body weight control.

7 Claims, 40 Drawing Sheets

OTHER PUBLICATIONS

Teturou Satoh et al: "Activation of peroxisome proliferator-activated receptor-γ stimulates the growth arrest and DNA-damage inducible 153 gene in non-small cell lung carcinoma cells", Oncogene (2002) 21, 2171-2180.

N.G. Seidah et al: "cDNA Sequence of Two Distinct Pituitary Proteins Homologous to Kex2 and Furin Gene Products: Tissue-Specific mRNAs Encoding Candidates for Pro-Hormone Processing Proteinases", DNA and Cell Biology, vol. 9, No. 6, 1990, pp. 415-424.

W. John Wilbur: "On the PAM Matrix Model of Protein Evolution", Mol. Biol. Evol. 2(5): 434-447, 1985.

Steven Henikoff et al: "Amino acid substitution matrices from protein blocks", Proc. Natl. Acad. Sci. USA, vol. 89, pp. 10915-10919, Nov. 1992, Biochemistry.

Neil A. Taylor: "Curbing activation: proprotein convertases in homeostasis and pathology", The FASEB Journal, vol. 17, Jul. 2003, pp. 1215-1227.

Suresh Subramani et al: "Expression of the Mouse Dihydrofolate Reductase Complementary Deoxyribonucleic Acid in Simian Virus 40 Vectors", Molecular and Cellular Biology, Sep. 1981, vol. 1, No. 9, pp. 854-864.

Hitoshi Niwa et al: "Efficient selection for high-expression transfectants with a novel eukaryotic vector", Gene, 108 (1991), pp. 193-200.

C. Milstein et al: "Hybrid hybridomas and their use in immunohistochemistry", Nature, vol. 305, Oct. 6, 1983, pp. 537-540.

Jens Kurreck: "Antisense technologies Improvement through novel chemical modifications", Eur. J. Biochem., vol. 270, pp. 1628-1644, 2003.

Ollivier Milhavet et al: "RNA Interference in Biology and Medicine", Pharmacological Reviews, vol. 55, No. 4, 2003, pp. 629-648.

Marialuisa Lavitrano et al: "Sperm Cells as Vectors for Introducing Foreign DNA into Eggs: Genetic Transformation of Mice", Cell, vol. 57, pp. 717-723, Jun. 2, 1989.

Keiichi Itakura et al: "Expression in *Escherichia coli* of a Chemically Synthesized Gene for the Hormone Somatostatin", Science, vol. 198, pp. 1056-1063, Dec. 1977.

Tsutomu Arakawa et al: "Structure of Unfolded and Refolded Recombinant Derived [Ala$^{125}$]Interleukin 2", Biochemistry, vol. 25, No. 25, 1986, pp. 8274-8277.

Keith E. Langley et al: "Recombinant-DNA-derived bovine growth hormone from *Escherichia coli* 1. Demonstration that the hormone is expressed in reduced form, and isolation of the hormone in oxidized, native form", Eur. J. Biochem. 163, pp. 313-321, 1987.

Jose G. Teodoro et al: "Phosphorylation at the Carboxy Terminus of the 55-Kilodalton Adenovirus Type 5 E1B Protein Regulates Transforming Activity", Journal of Virology, Feb. 1994, vol. 68, No. 2, pp. 776-786.

Thomas P. Hopp et al: "A Short Polypeptide Marker Sequence Useful for Recombinant Protein Identification and Purification", Bio/Technology, vol. 6, Oct. 1988, pp. 1204-1210.

Chul-Seung Park et al: "Design, synthesis, and functional expression of a gene for charybdotoxin, a peptide blocker of K$^+$channels", Proc. Natl. Acad. Sci. USA, vol. 88, pp. 2046-2050, Mar. 1991.

Hiroyuki Shimizu et al: "The brain-adipose axis: A review of involvement of molecules", Nutritional Neuroscience, Feb. 2005; 8(1): 7-20.

Michael S. Phillips et al: "Leptin receptor missense mutation in the *fatty* Zucker rat", Nature Genetics, vol. 13, May 1996, pp. 18-19.

Julie D. Thompson: "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.

Toshihiro Imaki et al: "Chlordiazepoxide attenuates stress-included accumulation of corticotropin-releasing factor mRNA in the paraventricular nucleus", Brain Research, 623 91993), pp. 223-228.

Bradford B. Lowell: "PPARγ: An Essential Regulator of Adipogenesis and Modulator of Fat Cell Function", Cell, vol. 99, Oct. 29, 1999, pp. 239-242, Minireview.

EP Communication, dated Jul. 6, 2009, issued in corresponding EP Application No. 06780673.7, 8 pages.

UniProt Accession No. P81117; Source: http://srs.ebi.ac.uk/srsbin/cgi-bin/wgetz?-e+[UNIPROT-acc:P81117]+-vn+2, Published Jul. 15, 1998.

UniProt Accession No. Q9JI85, Source: http://srs.ebi.ac.uk/srsbin/cgi-bin/wgetz?-e+[UNIPROT-acc:Q9JI85]+-vn+2, Published Nov. 2, 2001.

Nonogaki et al., "Serotonin systems upregulate the expression of hypothalamic NUCB2 via 5-HT2C receptors and induce anorexia via a leptin-independent pathway in mice," Biochemical and Biophysical Research Communications, vol. 372, No. 1, Jul. 18, 2008, pp. 186-190, XP022705365.

Chinese Office Action issued Feb. 12, 2010, in CN 200680022622.8, English Translation.

GenBank Accession No. AAM73810, published Sep. 15, 2003, Retrieved Jan. 29, 2010.

Singapore Office Action dated Apr. 14, 2010, in Singapore Patent Application No. 200719157-0.

* cited by examiner

Fig.9A

```
                    Signal peptide
                    ◄─────────────┐
NEFA_human  MRWRTILLQYCFLLITCLLTALEAVPIDIDKTKVQNIHPVESAKIEPPDTGLYYDEYLKQ  60
NEFA_mouse  MRWRIIQVQYCFLLVPCTLTALEAVPIDVDKTKVHNTEPVENARIEPPDTGLYYDEYLKQ  60
NEFA_rat    MRWRTIQARYCFLLVPCVLTALEAVPIDVDKTKVHNVEPVESARIEPPDTGLYYDEYLKQ  60
            ****  *  :****:.* **********:*****:  .***.*:**************

▼
NEFA_human  VIDVLETDKHFREKLQKADIEEIKSGRLSKELDLVSHHVRTKLDEL̲K̲R̲QEVGRLRMLIKA  120
NEFA_mouse  VIEVLETDPHFREKLQKADIEEIRSGRLSQELDLVSHKVRTRLDEL̲K̲R̲QEVGRLRMLIKA  120
NEFA_rat    VIEVLETDPHFREKLQKADIEEIRSGRLSQELDLVSHKVRTRLDEL̲K̲R̲QEVGRLRMLIKA  120
            **:***** ************** *****:******:***:****  ************

NEFA_human  KLDSLQDIGMDHQALLKQFDHLNHLNPDKFESTDLDMLIKAATSDLEHYDKTRHEEFKKY  180
NEFA_mouse  KLDALQDTGMNHHLLLKQFEHLNHQNPNTFESRDLDMLIKAATADLEQYDRTRHEEFKKY  180
NEFA_rat    KLDALQDTGMNHHLLLKQFEHLNHQNPDTFESKDLDMLIKAATADLEQYDRTRHEEFKKY  180
            ***:***  **:*:* *****:*** **: ***:********:***:**:*********

▼              ▼
NEFA_human  EMMKEHE̲R̲R̲EYLKTLNEE̲K̲R̲KEEESKFEEMKKKHENHPKVNHPGSKDQLKEVWEETDGLD  240
NEFA_mouse  EMMKEHE̲R̲R̲EYLKTLSEE̲K̲R̲KEEESKFEEM̲K̲R̲KHEDHPKVNHPGSKDQLKEVWEETDGLD  240
NEFA_rat    EMMKEHE̲R̲R̲EYLKTLSEE̲K̲R̲KEEEAKFAEM̲K̲R̲KHEDHPKVNHPGSKDQLKEVWEETDGLD  240
            ***************.*********:** ***  **:***********************

NEFA_human  PNDFDPKTFFKLHDVNSDGFLDEQELEALFTKELEKVYDPKNEEDDMVEMEEERLRMREH  300
NEFA_mouse  PNDFDPKTFFKLHDVNNDGFLDEQELEALFTRELEKVYNPQNAEDDMIEMEEERLRMREH  300
NEFA_rat    PNDFDPKTFFKLHDVNNDGFLDEQELEALFTKELDKVYNPQNAEDDMIEMEEERLRMREH  300
            ****************.**************:**:***:*:*.***:************

NEFA_human  VMNEVDTNKDRLVTLEEFLKATEKKEFLEPDSWETLDQQQFFTEEELKEYENIIALQENE  360
NEFA_mouse  VMSEIDNNKDRLVTLEEFLRATEKKEFLEPDSWETLDQQQLFTEDELKEYESIIAIQENE  360
NEFA_rat    VMNEIDNNKDRLVTLEEFLRATEKKEFLEPDSWETLDQQQLFTEEELKEYESIIAIQESE  360
            **.* *:*:**********:*******************:***:******.*** **. *

NEFA_human  LKKKADELQKQKEELQRQHDQLEAQKLEYHQVIQQMEQKKLQQGIPPSGPAGELKFEPHI  420
NEFA_mouse  LK̲K̲R̲AEELQKQKEDLQRQHDHLEAQKQEYHQAVQHLEQKKLQQGIAPSGPAGELKFEPHT  420
NEFA_rat    LKKKADELQKQKEELQRQHDHLEAQKQEYQQAVQQLEQKKFQQGIAPSGPAGELKFEPHT  420
            **:::*:*******:*****:****** **:*.:*:****:****.************

▼:Expected prohormone cleaving site
```

Fig.9A

Fig.11
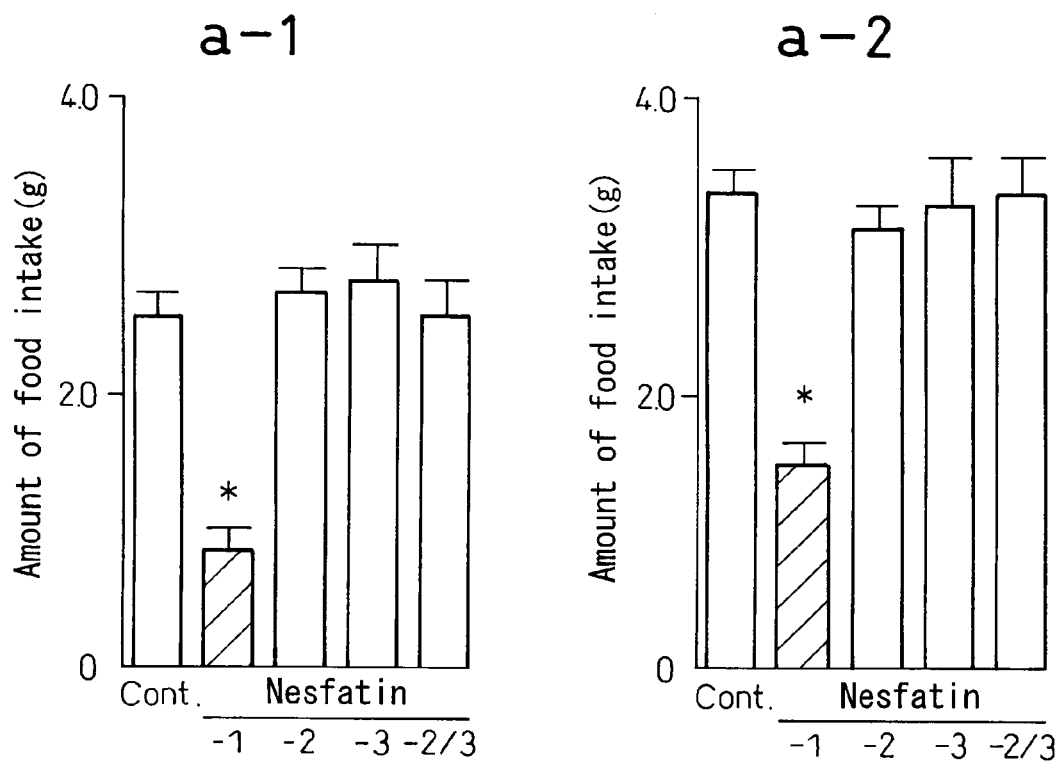
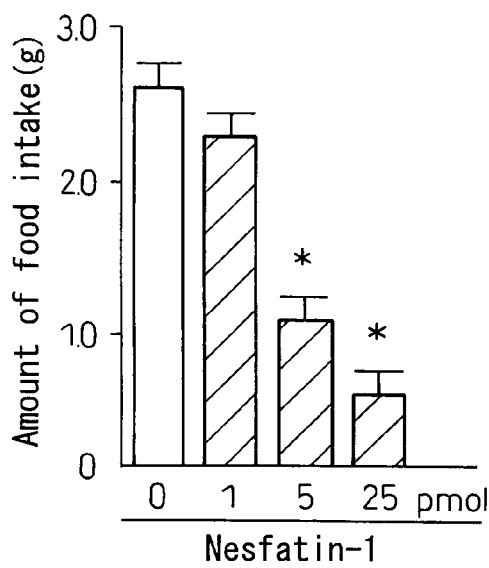

Fig.12
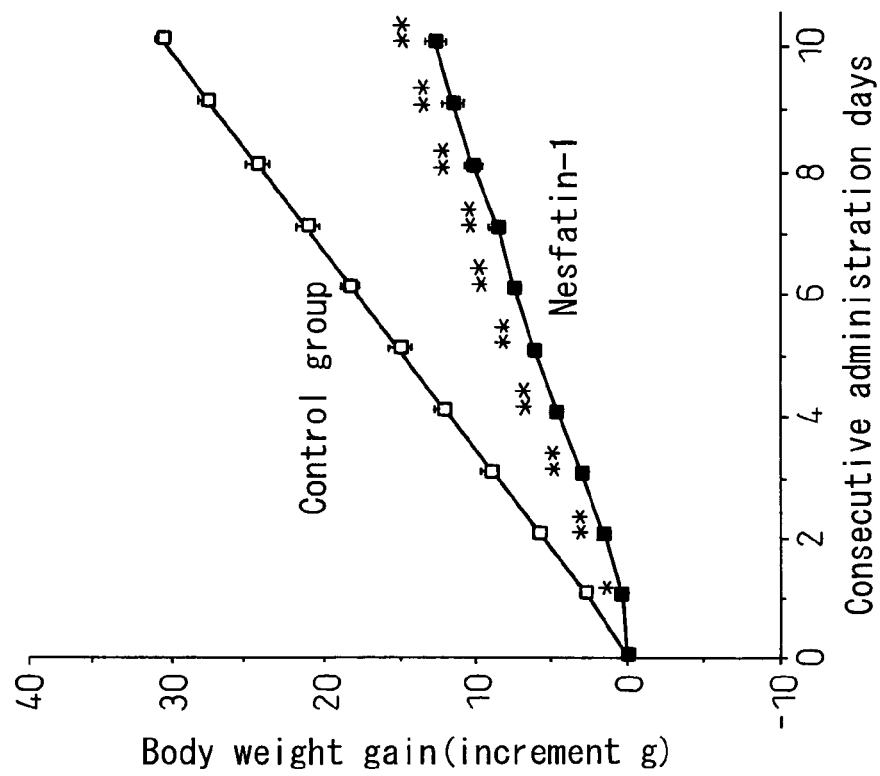
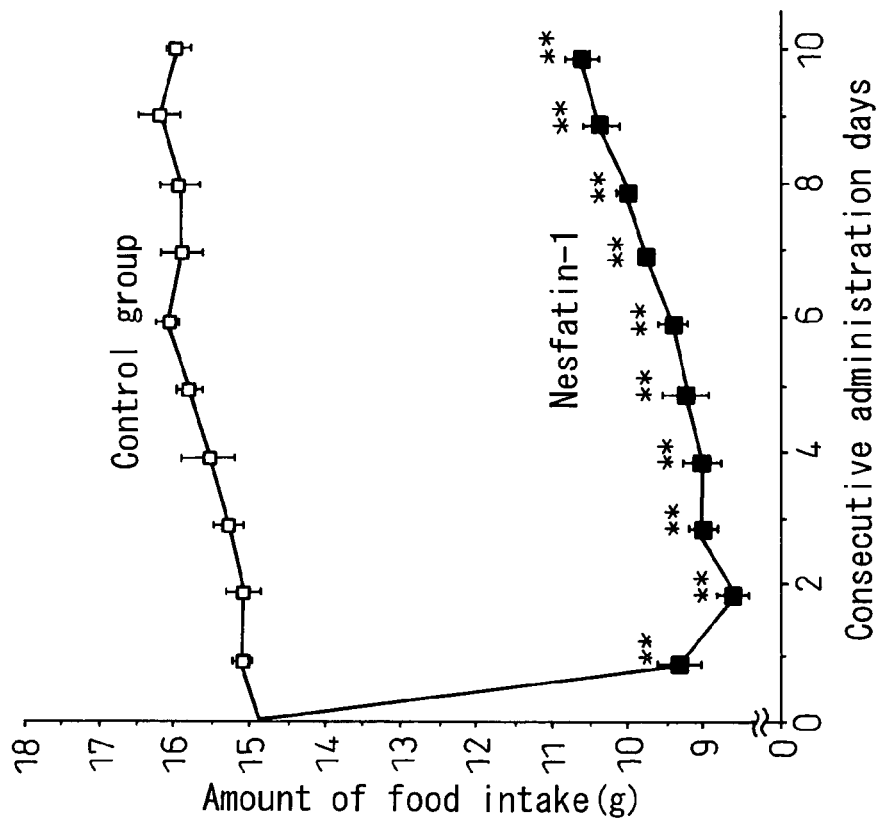

Fig.13B
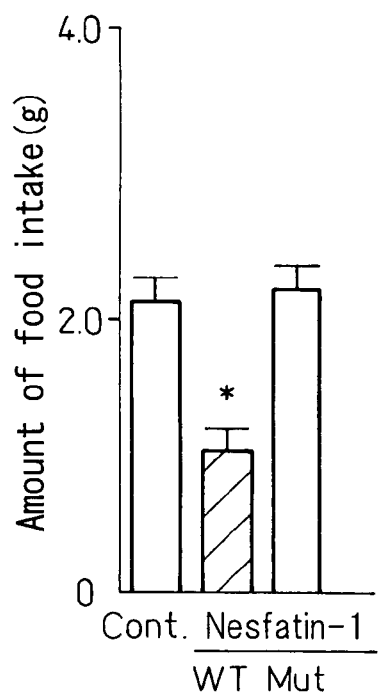
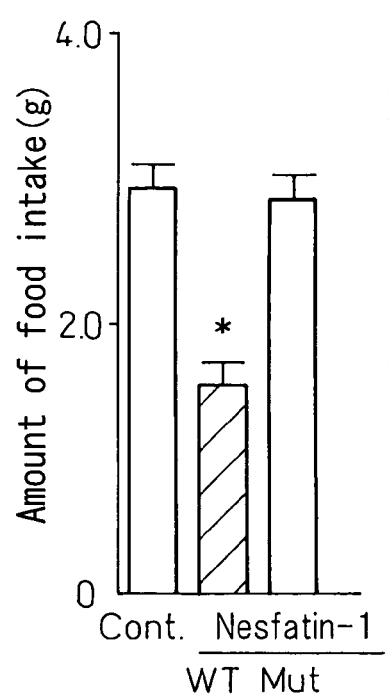
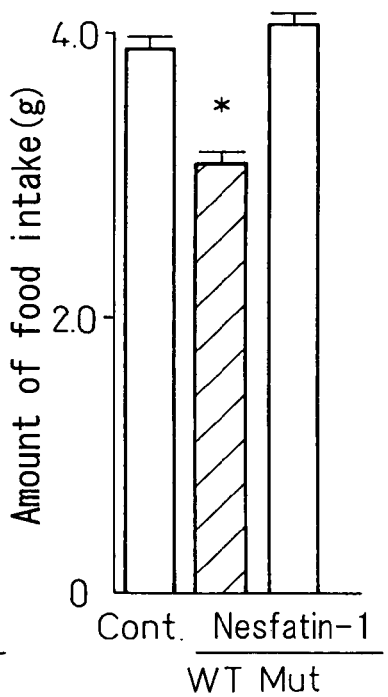

Fig.18B

```
NESFATIN-1_human    VPIDIDKTKVQNIHPVESAKIEPPDTGLYYDEYLKQVIDVLETDKHFREKLQKADIEEIK  60
NESFATIN-1_rat      VPIDVDKTKVHNVDPVESARIEPPDTGLYYDEYLKQVIEVLETDPHFREKLQKADIEEIR  60
NESFATIN-1_mouse    VPIDVDKTKVHNTEPVENARIEPPDTGLYYDEYLKQVIEVLETDPHFREKLQKADIEEIR  60
                    ****:****.  . ***.:.*************:*:****  ************:
                    |—————————|  |—|   |—————————————————————————————————————|
                    1  NESFATIN-1N23  23 24  NESFATIN-1M30           53 54

NESFATIN-1_human    SGRLSKELDLVSHHVRTKLDEL  82
NESFATIN-1_rat      SGRLSQELDLVSHKVRTRLDEL  82
NESFATIN-1_mouse    SGRLSQELDLVSHKVRTRLDEL  82
                    ****::*****:****:*****
                    |————————————————————|
                    NESFATIN-1C29         82
```

Fig.19A-2

Measured value (ng/ml)

| Sample | | Dilition |
|---|---|---|
| Cerebrospinal fluid (FCS M1) | 232 | 1.0 |
| | 233 | 2.0 | n=2

Fig. 21B

```
                 |—Signal peptide—|—————————— NESFATIN-1 ——————————
Human_NESFATIN   MRWR-TILLQYCFLLITCLLTALEAVPIDIDKTKVQNIHPVESAKIEPPDTGLYYDEYLK  59
Rat_NESFATIN     MRWR-TIQARYCFLLVPCVLTALEAVPIDVDKTKVHNVEPVESARIEPPDTGLYYDEYLK  59
Mouse_NESFATIN   MRWR-IIQVQYCFLLVPCMLTALEAVPIDVDKTKVHNTEPVENARIEPPDTGLYYDEYLK  59
Human_NUCB1      MPPSGPRGTLLLLSLLLLLLLRAVLAVPLERGAPNKE-----ETPATESPDTGLYYHRYLQ  55
Rat_NUCB1        MPTSVPRGAPFLLLPPLLMLSAVLAVPVDRAAPHQE-----DNQATETPDTGLYYHRYLQ  55
Mouse_NUCB1      MPTSVPRGAPFLLLPPLLMLSAVLAVPVDRAAPPQE-----DSQATETPDTGLYYHRYLQ  55
                   *         *    :* *: ***::        ::   *.*******..**:

= NESFATIN-1M30 =|
                 ——————————————————————————————————————————————————|
Human_NESFATIN   QVIDVLETDKHFREKLQKADIEEIKSGRLSKELDLVSHHVRTKLDELKRQEVGRLRMLIK  119
Rat_NESFATIN     QVIEVLETDPHFREKLQKADIEEIRSGRLSQELDLVSHKVRTRLDELKRQEVGRLRMLIK  119
Mouse_NESFATIN   QVIEVLETDPHFREKLQKADIEEIRSGRLSQELDLVSHKVRTRLDELKRQEVGRLRMLIK  119
Human_NUCB1      EVIDVLETDGHFREKLQAANAEDIKSGKLSRELDFVSHHVRTKLDELKRQEVSRLRMLLK  115
Rat_NUCB1        EVINVLETDGHFREKLQAANAEDIKSGKLSQELDFVSHNVRTKLDELKRQEVSRLRMLLK  115
Mouse_NUCB1      EVINVLETDGHFREKLQAANAEDIKSGKLSQELDFVSHNVRTKLDELKRQEVSRLRMLLK  115
                 :**:***** ******* *: *:*:**:**:***:***:*********.*****:*

Human_NESFATIN   AKLDSLQD--IGMDHQALLKQFDHLNHLNPDKFESTDLDMLIKAATSDLEHYDKTRHEEF  177
Rat_NESFATIN     AKLDALQD--TGMNHHLLLKQFEHLNHQNPDTFESKDLDMLIKAATADLEQYDRTRHEEF  177
Mouse_NESFATIN   AKLDALQD--TGMNHHLLLKQFEHLNHQNPNTFESRDLDMLIKAATADLEQYDRTRHEEF  177
Human_NUCB1      AKMDAEQDPNVQVDHLNLLKQFEHLDPQNQHTFEARDLELLIQTATRDLAQYDAAHHEEF  175
Rat_NUCB1        AKMDAKQEPNLQVDHMNLLKQFEHLDPQNQHTFEARDLELLIQTATRDLAQYDAAHHEEF  175
Mouse_NUCB1      AKMDAKQEPNLQVDHMNLLKQFEHLDPQNQHTFEARDLELLIQTATRDLAQYDAAHHEEF  175
                 **:*: *:    ::* *****:**:  .. **: **::**:**  :** ::**

Human_NESFATIN   KKYEMMKEHERREYLKTLNEEKRKEEESKFEEMKKKHENHPKVNHPGSKDQLKEVWEETD  237
Rat_NESFATIN     KKYEMMKEHERREYLKTLSEEKRKEEEAKFAEMKRKHEDHPKVNHPGSKDQLKEVWEETD  237
Mouse_NESFATIN   KKYEMMKEHERREYLKTLSEEKRKEEESKFEEMKRKHEDHPKVNHPGSKDQLKEVWEETD  237
Human_NUCB1      KRYEMLKEHERRRYLESLGEEQRKEAERKLEEQQRRHREHPKVNVPGSQAQLKEVWEELD  235
Rat_NUCB1        KRYEMLKEHERRRYLESLGEEQRKEAERKLQEQQRRHREHPKVNVPGSQAQLKEVWEELD  235
Mouse_NUCB1      KRYEMLKEHERRRYLESLGEEQRKEAERKLQEQQRRHREHPKVNVPGSQAQLKEVWEELD  235
                 *:***:******.**:.**.**:**:  *: * :::*.:***** ***:.********  *
```

Fig. 21C

```
Human_NESFATIN  GLDPNDFDPKTFFKLHDVNSDGFLDEQELEALFTKELEKVYDPKNEEDDMVEMEEERLRM 297
Rat_NESFATIN    GLDPNDFDPKTFFKLHDVNNDGFLDEQELEALFTKELDKVYNPQNAEDDMIEMEEERLRM 297
Mouse_NESFATIN  GLDPNDFDPKTFFKLHDVNNDGFLDEQELEALFTRELEKVYNPQNAEDDMIEMEEERLRM 297
Human_NUCB1     GLDPNRFNPKTFFILHDINSDGVLDEQELEALFTKELEKVYDPKNEEDDMREMEEERLRM 295
Rat_NUCB1       GLDPNRFNPKTFFILHDINSDGVLDEQELEALFTKELEKVYDPKNEEDDMREMEEERLRM 295
Mouse_NUCB1     GLDPNRFNPKTFFILHDINSDGVLDEQELEALFTKELEKVYDPKNEEDDMREMEEERLRM 295
                ***** *:***** ***:*.**.************:**:***:*:* **** *********

Human_NESFATIN  REHVMNEVDTNKDRLVTLEEFLKATEKKEFLEP-DSWETLDQQQFFTEEELKEYENIIAL 356
Rat_NESFATIN    REHVMNEIDNNKDRLVTLEEFLRATEKKEFLEP-DSWETLDQQQLFTEEELKEYESIIAI 356
Mouse_NESFATIN  REHVMSEIDNNKDRLVTLEEFLRATEKKEFLEP-DSWETLDQQQLFTEDELKEYESIIAI 356
Human_NUCB1     REQLMKNVDTNQDRLVTLEEFLASTQRKEFGDTGEGWETVEMHPAYTEEELRRFEEELAA 355
Rat_NUCB1       REHVMKNVDTNQDRLVTLEEFLASTQRKEFGETAEGWKTVEMYPAYTEEELKRFEEELAA 355
Mouse_NUCB1     REHVMKNVDTNQDRLVTLEEFLASTQRKEFGDTGEGWKTVEMSPAYTEEELKRFEEELAA 355
                **::*.::*.*:********** :*:***  :.  :.*:*::     :**:**.:*. :*

Human_NESFATIN  QENELKKKADELQKQKEELQRQHDQLEAQKLEYHQVIQQMEQKKLQG--------IPPSGP 409
Rat_NESFATIN    QESELKKKADELQKQKEELQRQHDHLEAQKQEYQQAVQQLEQKKFQQG-------IAPSGP 410
Mouse_NESFATIN  QENELKKRAEELQKQKEDLQRQHDHLEAQKQEYHQAVQHLEQKKLQQG-------IAPSGP 410
Human_NUCB1     REAELNAKAQRLSQETEALGRSQGRLEAKKRELLLAVLHMEQRKQQQQQQGHKAPAAHP 415
Rat_NUCB1       REAELNARAQRLSQETEALGRSQDRLEAQKRELQQAVLQMEQRKQQQQEQS---APPSQP 412
Mouse_NUCB1     REAELNARAQRLSQETEALGRSQDRLEAQKRELQ----QMEQRKQQLQEQS---APPSKP 408
                :* **: :*:.*.:.:* * *: *:***:*  : ::**:*  * : ::**:* *  ..:*

Human_NESFATIN  AGELKFEPHI---------------------------------------- 419
Rat_NESFATIN    AGELKFEPHT---------------------------------------- 420
Mouse_NESFATIN  AGELKFEPHT---------------------------------------- 420
Human_NUCB1     EGQLKFHPDTDDVPVPAPAGDQKEVDTSEKKLLERLPEVEVP--QHL 460
Rat_NUCB1       DGQLQFRADTGDAPVPAPAGDQKDVPASEKKVPEQPPVLPQLDSQHL 459
Mouse_NUCB1     DGQLQFRADTDDAPVPAPAGDQKDVPASEKKVPEQPPELPQLDSQHL 455
                *:*:*...
```

Fig.22
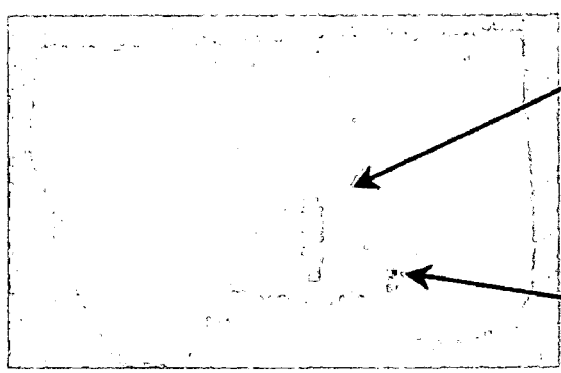
A — Paraventricular nucleus (PVN); Supraoptic nucleus (SON)
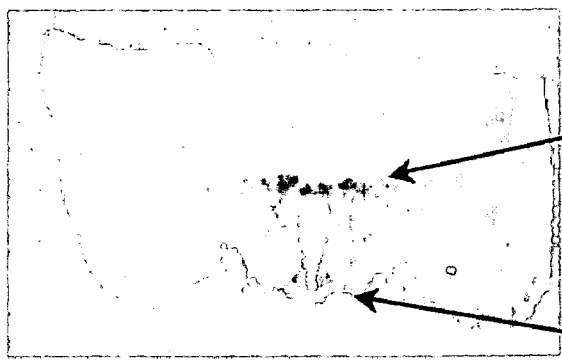
B — Zona incerta (Zi); Arcuate nucleus (Arc)
C — Lateral Hypothalamic area (LHA)

BIOLOGICAL SUBSTANCE NESFATIN AND ITS RELATED SUBSTANCES AND USES THEREOF

CROSS REFERENCE TO RELATED APPLICATION

This application claims the benefit of U.S. Provisional Application No. 60/703,864 filed Aug. 1, 2005 and U.S. Provisional Application No. 60/780,514 filed Mar. 9, 2006 the entire disclosures of which are incorporated herein by reference.

FIELD OF THE INVENTION

The present invention relates to a novel method of obtaining a factor that is involved in food intake control and/or body weight control. The present invention also relates to a polypeptide obtained by said method, said polypeptide being involved in food intake control and/or body weight control, a nucleic acid molecule encoding said polypeptide, as well as a means for treating, preventing and diagnosing diseases associated with the suppression of food intake and/or the suppression of body weight gain using them. The present invention also relates to a means for treating, preventing and diagnosing diseases associated with enhanced appetite and/or enhanced body weight gain using a substance that inhibits the effect of said polypeptide or said gene. Furthermore, the present invention relates to an animal model of diseases associated with food intake control and/or body weight control obtained by said polypeptide, said gene, and a substance that inhibits activities thereof, and a method of screening compounds that controls the effect or expression of said polypeptide using the model. The present invention also relates to a compound that is selected by said screening method, and a diagnostic means and therapeutic agents for diseases using said compound.

BACKGROUND OF THE INVENTION

Obesity is a condition in which body weight, especially white adipose tissue, occurs in excess, and is generally classified as having a body mass index (BMI) of $\geq 25$ kg/m$^2$ and as having a body fat percentage of 25% or greater for male adults and 30% or greater for female adults. Due to habits of eating high-fat diets and a lack of exercises in modern society, the percentage of people classified as obese is on the rise. According to the result of the national nutrition survey by the Ministry of Health, Labor and Welfare in 2000, the number of men who are diagnosed as obese have certainly increased during the last 10 and 20 years and about 30% of men from 40-69 years old are diagnosed as obese, and for women as well, about 30% of those 60-69 years old are diagnosed as obese.

In the past, obesity was viewed as an aesthetic problem, but today, rather than obesity per se, health impairments accompanied (or potentially accompanied) by obesity pose major clinical challenges, providing a medical grounds for the prevention and treatment of obesity. Under such circumstances, the Japan Society for the Study of Obesity (JASSO) has defined obesity as "a pathological condition that is accompanied or suspected of being accompanied by health impairments resulting from or associated with obesity and that requires medical reduction in body weight", and proposes to deal with it as a disease entity. The health impairments as used herein include type 2 diabetes and impaired glucose tolerance as well as hypertension, hyperlipidemia, hyperuricemia, fatty liver, cardiac and cerebral vascular diseases, sleep apnea syndrome, orthopedic diseases such as osteoarthritis, menstrual disorders and the like (The Japanese Journal of Clinical Medicine (Nippon Rinsho), Supplement "Adiposis", issued by Nippon Rinshosha Co., Ltd. on Jul. 28, 2003). As diseases resulting from obesity, malignant tumors are mentioned, and specifically, obesity has been reported to be a risk factor for the onset of breast cancer, uterine cancer, colon cancer, kidney cancer, esophageal cancer, pancreatic cancer, liver cancer, and gallbladder cancer (The Japanese Journal of Clinical Medicine (Nippon Rinsho), Supplement "Adiposis", issued by Nippon Rinshosha Co., Ltd. on Jul. 28, 2003; Non-patent document 1, Abu-Abid et al., Journal of Medicine (USA), Jan. 1, 2002, Vol. 33, Nos. 1-4, pp. 73-86; and Nair et al., Hepatology (USA), Jul. 1, 2002, Vol. 36, No. 1, pp. 150-155).

In recent years, furthermore, there has been proposed a multiple risk syndrome that increases the risk of arteriosclerotic diseases (myocardial infarction, cerebral infarction etc.) called "metabolic syndrome", which is attracting attention since cerebral vascular diseases and cardiovascular diseases account for 30% of all deaths in Japan. Therefore, the Japan Society for the Study of Obesity, the Japan Atherosclerosis Society, the Japan Diabetes Society, the Japanese Society of Hypertension, the Japanese Circulation Society, the Japanese Society of Nephrology, the Japanese Society on Thrombosis and Hemostasis, the Japanese Society of Internal Medicine collaborated to draw up its diagnostic criteria and announced the criteria at the press conference of the Meeting of the Japanese Society of Internal Medicine on Apr. 8, 2005. According to the criteria, with visceral fat (fat accumulation in internal organs) set at the center of the criteria, men with a waist circumference of 85 cm or greater and women with a waist circumference of 90 cm or greater who have two or more risks of serum lipid abnormality (either one or both of a triglyceride value of 150 mg/dL or more and a HDL cholesterol value of 40 mg/dL or less), high blood pressure value (either one or both of a systolic pressure of 130 mmHg or more and a diastolic pressure of 85 mmHg) and high blood glucose (a fasting blood glucose level of 110 mg/dL or more) are diagnosed as having the metabolic syndrome (Journal of the Japanese Society of Internal Medicine, A research committee on the diagnostic criteria for metabolic syndrome, April, 2005 issue, Vol. 94, pp. 188-203). When this criteria was used, it is reported, among 290 male adults who were undergoing health screening, 61 people (21%) were diagnosed as obese, whereas 27 people (9%) were diagnosed as having the metabolic syndrome, and 9 people (3%) were not included in obesity but were diagnosed as having the metabolic syndrome (Igaku no Ayumi, Kazuo Takahashi and Yasushi Saito, 2005, Vol. 213, No. 6, pp. 549-554).

Since the possible cause of obesity is essentially the persistent excess of energy (calorie) taken in over energy (calorie) consumed, it is recommended that obese people or people with obesity undergo the diet therapy and/or the exercise therapy in order to lower body weight, especially body fat percentage. However, since the continuance of these therapies poses considerable stress on an enhanced appetite, adaptation to changes in life styles, and exercise tolerance, various difficulties must be overcome to continue the therapies. It is likely that when the calorie intake was decreased in the diet therapy, the so-called rebound phenomenon, i.e., that the intestinal absorption of nutrients increases and energy metabolism lowers, may occur, and therefore the continuance of the diet therapy may be abandoned. Though medical treatments of obesity include central anorectic drugs, agents promoting thermal metabolism, absorption-inhibiting agents, steatogenesis-inhibiting agents, etc., the only agent that can be used under the health insurance system in Japan at present is mazindol which is classified as a central anorexigenic drug. However, mazindol is a stimulant-like compound, and has side effects of excitation, irritation, cardiovascular load, dysuria etc., and the period of use has been limited to within 3 months, and thus it is not considered a drug that can be easily used (Novartis Pharma KK, "Sanorex 0.5 mg tablet", package insert).

Excessive reduction in body weight (so-called "emaciation") or food intake (so-called "anorexia") concerning obesity is problematic since it can cause infection due to a reduced defense reaction (immunity), hematopoietic disorders, amenorrhea or irregular menstruation, infertility, mental disorders, peripheral nerve paralysis, hypotension, osteoporosis etc. Generally, when BMI is <18.5 Kg/m$^2$, or men with a body fat percentage of 10% or less and women with a body fat percentage of 15% or less are classified as emaciated. According to the result of a national nutrition survey by the Ministry of Health, Labor and Welfare in 2000, the percentage of women with BMI of <18.5 Kg/m$^2$ in the 20-39 year-old bracket has risen steadily in the past 10 and 20 years, and in the 20-29 year-old bracket about 24% are classified as "emaciated". This is possibly caused by intentional reduction in food intake by young women due to excessive concern over weight. However, in anorexia nervosa (food refusal), one of the central food intake disorders prevalent among this age group, appetite per se extremely decreases and hence the nutritional condition aggravates, sometimes leading to death due to general prostration. Also, as appetite-lowering diseases that include concepts formerly called gastroptosis, gastroatonia, or neurogenic gastritis, there is a disease termed functional dyspepsia, which is said to exhibit symptoms of early satiety after meals and reduced appetite etc. (Talley et al., Gut 1999, 45, Suppl. 2:1137-42). Furthermore, as causes of anorexia, there can be mentioned cancer, inflammatory diseases, reduced function of the pituitary, the thyroid, or the adrenal etc., post-surgery, excessive stress and the like, and persistent anorexia for a long time under these conditions may cause body weakening.

Under these circumstances, in recent years, vigorous research has been under taken on biological factors that control food intake and also on the relationships of factors such as leptin, adiponectin and ghrelin on the control of food intake. At present, however, no conclusions have been made on factors that play a leading role in food intake control and/or body weight control, and no factors such as those described above have yet been used in therapies. Thus, there is a strong need for identifying factors that play a leading role in the control of food intake and/or the control of body weight and for applying them into the treatment of obesity and adipogenesis. However, few factors have been reported to be involved in food intake control and/or body weight control and for the PPARγ agonist widely used as a therapeutic agent for diabetes mellitus, no direct involvement in food intake control and/or body weight control has been reported.

On the other hand, nuclear EF-hand acidic (NEFA) is also called nucleobindin II (NUCB 2), and a polypeptide encoded by the NEFA gene has a calcium-binding domain (EF domain) and a DNA-binding domain (Biol Chem Hoppe Seyler 1994, Aug; 375(8):497-512). NEFA has a high homology with nucleobindin and is considered to be a member of the DNA-binding factor called the EF-hand superfamily having a reactivity with calcium (Karabinos et al., Mol Biol Evol 1996 September; 13(7):990-8). Though NEFA is being investigated regarding its calcium-binding ability, its binding with necdin, a cellular growth control factor, etc. (Kroll et al., Biochem. Biophys. Res. Commun. 1999, 24, pp. 1-8 and Tanimura et al., J. Biol. Chem. 2000, October 13:275(41): 31674-81), there are no reports on its detailed functions. NEFA has been studied regarding the possibility of being a causative gene of Usher's syndrome, an opthalmological disease, and gastric cancer (Doucet et al., Biochim. Biophys. Acta. 1998 July 1; 1407(1):84-91 and Line et al., Br. J. Cancer 2002, June 5:86(11):1824-30). Furthermore, though the possibility of the NEFA polypeptide being extracellularly secreted has been demonstrated because it has a signal sequence at the amino terminal end (Non-patent document 5), there are no reports on the physiological or pharmacological role as a result of extracellular secretion thereof. Also, there are no reports that suggest a relationship between NEFA and food intake control and/or body weight control.

OBJECTS AND SUMMARY OF THE INVENTION

Problems to be solved by the present invention are to provide a novel method of obtaining a factor that is involved in food intake control and/or body weight control, and to provide a gene obtained by said method, a polypeptide encoded by said gene and a novel polypeptide obtained using information on the polypeptide encoded by said gene as a means for treating, controlling and diagnosing food intake disorders and/or diseases associated with the control of body weight. It is also to provide a substance that inhibits the effect of said gene or polypeptide as a means for treating, controlling and diagnosing diseases associated with food intake control and/or body weight control. Furthermore, it is to provide an animal model of diseases associated with the control of food intake and/or the control of body weight obtained by said gene or polypeptide, or a substance that inhibits them. It is also to provide a method of screening compounds that control the effect or expression of said polypeptide using the model, compounds selected by said screening method, and a diagnostic means and therapeutic agents using said compounds.

After intensive and extensive study to find a novel method of obtaining a factor involved in food intake control and/or body weight control, the present inventors have found that, by using thiazolidine diones having a PPARγ agonist activity, genes and polypeptides involved in the suppression of food intake and/or the reduction in body weight can be obtained. Furthermore, it was found that the factor obtained by said method was NEFA whose function has not reported, and thus said polypeptide factor was designated as nesfatin. After investigating on nesfatin, the present inventors have found that the partial sequence for which no functional domains were indicated in the previous reports has an activity on the suppression of food intake and/or the reduction in body weight, and therefore have disclosed novel polypeptides nesfatin-1, nesfatin-1M30, nesfatin-1M16, nesfatin-1M14 and nesfatin-1M10. In Nucleobindin I (NUCB1) having a high homology in the amino acid sequence and the base sequence of the gene with NEFA/nesfatin and belonging to the same family as the NEFA/nesfatin, it was also found, NUCB1-M30 which is a site corresponding to the nesfatin-1M30 of NUCB1 exhibits a similar activity.

Furthermore, it was found that an antibody that binds to nesfatin, nesfatin-1 or nesfatin-1M30 has an activity of enhancing food intake and increasing body weight, and it was confirmed that the inhibition of activity of nesfatin, nesfatin-1 or nesfatin-1M30 is effective for enhancing food intake and increasing body weight.

Thus, the present invention provides the following:
(1) A method of obtaining a factor related to food intake control and/or body weight control, said method comprising the steps of:

acting a thiazolidine dione compound having a PPARγ agonist activity to a mammalian cell, and identifying a gene of which expression is induced by said compound;

(2) The method according to (1) wherein said thiazolidine dione compound is troglitazone;

(3) The method according to (1) or (2) wherein said mammalian cell is a non-small cell lung cancer cell line, an adipose cell or a cerebral nerve-derived cell;

(4) The method according to (1), (2) or (3) wherein food intake control and/or body weight control is the suppression of food intake and/or the suppression of body weight gain;

(5) A polypeptide comprising an amino acid sequence set forth in any of SEQ ID NOs: 65-73 or SEQ ID NOs: 107-115;

(6) A polypeptide comprising an amino acid sequence set forth in any of SEQ ID NOs: 39-41 or SEQ ID NOs: 101-103;

(7) A polypeptide comprising an amino acid sequence set forth in SEQ ID NOs: 13-15;

(8) A polypeptide comprising an amino acid sequence set forth in SEQ ID NOs: 3, 6 and 9, said polypeptide having an activity of suppressing food intake and/or suppressing body weight gain;

(9) A polypeptide having an activity of suppressing food intake and/or suppressing body weight gain, said polypeptide comprising an amino acid sequence having a homology of at least 60% with any of the amino acid sequence set forth in SEQ ID NOs: 13-15, 39-41, 65-73, 101-103 and 107-115; or an amino acid sequence in which some of the amino acids have been deleted, inserted or substituted in an amino acid sequence set forth in any of SEQ ID NOs: 13-15, 39-41, 65-73, 101-103 or 107-115;

(10) A polypeptide having an activity of suppressing food intake and/or suppressing body weight gain, said polypeptide comprising an amino acid sequence having a homology of at least 60% with any of the amino acid sequence set forth in SEQ ID NOs: 3, 6 and 9; or an amino acid sequence in which some of the amino acids have been deleted, inserted or substituted in an amino acid sequence set forth in SEQ ID NO: 3, 6 or 9; or an amino acid sequence in which some of the amino acids have been deleted, inserted or substituted in any of the amino acid sequence set forth in SEQ ID NOs: 3, 6 and 9, said polypeptide comprising at least one recognition site for a cleaving enzyme contained in a living body in an amino acid sequence corresponding to amino acid numbers 82-162 in SEQ ID NO: 3, 6 or 9;

(11) The polypeptide according to any of (5) to (10) wherein at least one amino acid has been added to the N terminal or the C terminal;

(12) The polypeptide according to any of (5) to (10) wherein at least one amino acid residue has been modified by a compound or a peptide;

(13) The polypeptide according to any of (5) to (12) wherein said activity of suppressing body weight gain is an activity of suppressing body fat gain;

(14) A nucleic acid molecule encoding a polypeptide set forth in any of (5) to (13);

(15) A nucleic acid molecule comprising a base sequence set forth in any of SEQ ID NOs: 74-82 and 116-124;

(16) A nucleic acid molecule comprising a base sequence set forth in any of SEQ ID NOs: 44-46 and 104-106;

(17) A nucleic acid molecule comprising a base sequence set forth in SEQ ID NOs: 18-20;

(18) A nucleic acid molecule that comprises a base sequence set forth in SEQ ID NO: 10, 11 or 12 and that encodes a polypeptide having an activity of suppressing food intake and/or suppressing body weight gain;

(19) A nucleic acid molecule that hybridizes to a base sequence set forth in SEQ ID NOs: 10-12, 18-20, 44-46, 74-82, 104-106, or 116-124, or a partial sequence thereof under a stringent condition, and that encodes a polypeptide having an activity of suppressing food intake and/or suppressing body weight gain;

(20) The nucleic acid molecule according to any of (14) to (19) wherein said activity of suppressing body weight gain is an activity of suppressing body fat gain;

(21) A vector comprising the nucleic acid molecule according to any of (14) to (20);

(22) The vector according to (21) to which a nucleic acid molecule is operably linked under the control of a regulatory nucleic acid molecule that controls the expression of said nucleic acid molecule;

(23) A transformant comprising the nucleic acid molecule according to any of (14) to (20);

(24) The transformant according to (23) that expresses the transcription product of said nucleic acid molecule;

(25) The transformant according to (23) or (24) that expresses the polypeptide encoded by said nucleic acid molecule;

(26) The transformant according to (23), (24) or (25) wherein the transformant is a microorganism;

(27) The transformant according to (26) wherein said microorganism is *Escherichia coli*;

(28) The transformant according to (23), (24) or (25) wherein the transformant is a mammalian cell;

(29) The transformant according to (23), (24) or (25) wherein the transformant is a plant cell;

(30) A pharmaceutical composition for suppressing food intake and/or suppressing body weight gain, said composition comprising, as an active ingredient, the polypeptide according to any of (5) to (13) or a peptide that contains some of the amino acid sequence of said polypeptide, the vector according to (21) or (22), or the transformant according to any of (23) to (29);

(31) The pharmaceutical composition according to (30) wherein said activity of suppressing body weight gain is an activity of suppressing body fat gain;

(32) The pharmaceutical composition according to (30) or (31) for patients with a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors;

(33) The pharmaceutical composition according to (30) or (31) wherein the malignant tumor is any of breast cancer, uterine cancer, colon cancer, kidney cancer, esophageal cancer, pancreatic cancer, liver cancer and gallbladder cancer;

(34) The pharmaceutical composition according to any of (30) to (33) comprising a pharmaceutically acceptable additive;

(35) An antibody that binds to any polypeptide according to (5) to (13);

(36) The antibody according to (35) that binds to a peptide comprising an amino acid sequence set forth in SEQ ID NO: 24, 32;

(37) A substance that suppresses the activity or production of the polypeptide according to any of (5) to (13);

(38) The substance according to (37) that suppresses the activity of said polypeptide by binding to said polypeptide;

(39) The substance according to (37) wherein said substance that suppresses the activity of said polypeptides is the antibody according to (35) or (36);

(40) A substance that suppresses the expression of a gene encoding the polypeptide according to (5) to (13);

(41) The gene expression-suppressing substance according to (40) wherein said gene expression-suppressing substance is an antisense oligonucleotide molecule;

(42) The gene expression-suppressing substance according to (41) wherein the antisense oligonucleotide molecule comprises a base sequence set forth in SEQ ID NO: 31;

(43) The gene expression-suppressing substance according to (40) wherein said gene expression-suppressing substance is a RNAi molecule;

(44) A vector for producing an antisense oligonucleotide molecule or a RNAi molecule, said vector comprising a nucleic acid molecule comprising a base sequence that is complementary to the nucleic acid sequence of the antisense oligonucleotide molecule according to (41) or (42) or of the RNAi molecule according to (43);

(45) A pharmaceutical composition for enhancing appetite or enhancing body weight gain, said composition comprising the substance according to any of (37) to (43) or the vector according to (44);

(46) The pharmaceutical composition according to (45) containing a pharmaceutically acceptable additive;

(47) A transgenic non-human organism comprising the nucleic acid molecule according to any of (14) to (20) or the vector according to any of (21) to (22);

(48) The transgenic non-human organism according to (47) wherein the nucleic acid molecule according to any of (14) to (20) is expressed;

(49) The transgenic non-human organism according to (47) or (48) wherein the transformant according to any of (23) to (28) has been introduced;

(50) The transgenic non-human organism according to (47), (48) or (49) wherein said transgenic non-human organism is a transgenic non-human animal that exhibits the state of suppressed food intake or the state of suppressed body weight gain;

(51) The transgenic non-human organism according to (47), (48) or (49) wherein said transgenic non-human organism is a transgenic plant;

(52) A transgenic non-human animal that has introduced therein the antibody according to (35) or (36), the suppressing substance according to any of (37) to (39), the gene expression-suppressing substance according to any of (40) to (43) or the vector according to (44), and that exhibits the state of enhanced food intake or the state of enhanced body weight gain;

(53) A knock-out non-human animal wherein the entire region or part thereof of a gene comprising a nucleotide sequence set forth in any of SEQ ID NOs: 10-12, 18-20, 44-46, 74-82, 104-106 and 116-124 has been deleted;

(54) The knock-out non-human animal according to (53) that exhibits enhanced appetite or enhanced body weight gain;

(55) The non-human animal according to (52), (53) or (54) that can be used as an animal model for a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors;

(56) A method of producing the peptide according to any of (5) to (13) by a cell-free protein synthetic method or a chemical synthetic method;

(57) The method of producing the peptide according to any of (5) to (13) using the transformant according to any of (23) to (29), the transgenic non-human organism according to any of (47) to (51), or the non-human animal according to any of (52) to (55);

(58) The production method according to (56) or (57) comprising a purification process by desorption of said peptide from the antibody according to (35) or (36);

(59) The production method according to (56) or (57) comprising a process wherein said peptide is expressed as a GST-fused protein and then is purified using a glutathione-bound carrier;

(60) The production method according to (56) or (57) comprising a process wherein said peptide is expressed as a His tag-fused protein and then is purified using a metal ion chelate carrier;

(61) The production method according to (56) or (57) comprising a process wherein said peptide is expressed as a FLAG tag-fused protein and then is purified using an anti-FLAG tag antibody-bound carrier;

(62) An assay method of predicting or diagnosing the state of enhanced food intake or enhanced body weight gain comprising the step of detecting the amount contained of a nucleic acid molecule comprising a nucleotide sequence set forth in any of SEQ ID NOs: 10-12, 18-20, 44-46, 74-82, 104-106 and 116-124, or of a polypeptide comprising an amino acid sequence set forth in any of SEQ ID NOs: 3, 6, 9, 13-15, 39-41, 65-73, 101-103 and 107-115 in a biological sample from a mammal;

(63) The assay method according to (62) comprising a step of comparing the amount contained of said nucleic acid molecule or said polypeptide in a biological sample from a mammal with that in a biological sample from a normal individual;

(64) The assay method according to (62) or (63) comprising a step of judging the state of decreased amount contained of said nucleic acid molecule or said polypeptide in a biological sample from a mammal as a state of enhanced food intake or enhanced body weight gain;

(65) The assay method according to any of (62) to (64) comprising the step of judging the state of decreased amount contained of said nucleic acid molecule or said polypeptide in a biological sample from a mammal as a state or a risk of developing a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors;

(66) The assay method according to (62) or (63) comprising the step of judging the state of increased amount contained of said nucleic acid molecule or said polypeptide in a biological sample from a mammal as the state of suppressed food intake or suppressed body weight gain;

(67) The assay method according to any of (62) to (66) wherein the amount contained of said polypeptide is detected using the antibody according to (35) or (36);

(68) The assay method according to any of (62) to (66) wherein the amount contained of said nucleic acid molecule is detected using at least one of a PCR primer, a probe or a DNA chip for detecting a nucleic acid molecule comprising a nucleotide sequence set forth in any of SEQ ID NOs: 10-12, 18-20, 44-46, 74-82, 104-106 and 116-124;

(69) An assay kit for use in the assay method according to any of (62) to (68), said kit comprising at least one of a PCR primer, a probe or a DNA chip for detecting a nucleic acid molecule comprising a nucleotide sequence set forth in any of SEQ ID NOs: 10-12, 18-20, 44-46, 74-82, 104-106 and 116-124; or an antibody recognizing a polypeptide comprising an amino acid sequence set forth in SEQ ID NOs: 3, 6, 9, 13-15, 39-41, 65-73, 101-103 or 107-115, a standard peptide, or a modified peptide for the binding competitive reaction;

(70) A method of screening a therapeutic or preventive agent having an effect of suppressing food intake and/or suppressing body weight gain, said method comprising the steps of:

contacting a test substance with a mammalian cell, and detecting the increased expression of a gene in said cell comprising a nucleotide sequence set forth in any of SEQ ID NOs: 10-12, 18-20, 44-46, 74-82, 104-106 and 116-124, or the increased amount of a polypeptide intracellularly contained in said cell or extracellularly secreted comprising an amino acid sequence set forth in any of in SEQ ID NOs: 3, 6, 9, 13-15, 39-41, 65-73, 101-103 and 107-115;

(71) The screening method according to (70) wherein the mammalian cell is one in which a regulatory nucleic acid molecule that controls the expression of a gene comprising a nucleotide sequence set forth in any of SEQ ID NOs: 10-12, 18-20, 44-46, 74-82, 104-106 and 116-124 and the nucleic acid molecule of a reporter gene have been introduced, and the induced expression of a gene comprising a nucleotide sequence set forth in any of SEQ ID NOs: 10-12, 18-20, 44-46, 74-82, 104-106 and 116-124 is detected by the induced expression of the reporter gene;

(72) A method of screening a therapeutic or preventive agent having an effect of suppressing food intake and/or suppressing body weight gain, said method comprising the steps of:

administering a test substance to a mammal, and detecting the enhanced expression of a gene comprising a nucleotide sequence set forth in any of SEQ ID NOs: 10-12, 18-20, 44-46, 74-82, 104-106 and 116-124 or the enhanced production of a polypeptide comprising an amino acid sequence set forth in any of SEQ ID NOs: 3, 6, 9, 13-15, 39-41, 65-73, 101-103 and 107-115 in a biological sample from said test animal;

(73) A method of screening a therapeutic or preventive agent having an effect of suppressing food intake and/or suppressing body weight gain, said method comprising the steps of:

administering a test substance to the transgenic non-human organism according to any of (47) to (50) or the non-human animal according to any of (52) to (55), and detecting the suppression of food intake or the suppression of body weight gain in said transgenic non-human organism or said non-human animal;

(74) The screening method according to any of (70) to (73) wherein the therapeutic or preventive agent having an effect of suppressing food intake and/or suppressing body weight gain is a therapeutic or preventive agent for a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors;

(75) The therapeutic or preventive agent having an effect of suppressing food intake and/or suppressing body weight gain, said agent being obtained by the method according to any of (70) to (74);

(76) The therapeutic or preventive agent according to (75) wherein the therapeutic or preventive agent having an effect of suppressing food intake and/or suppressing body weight gain is a therapeutic or preventive agent for a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors;

(77) A method of screening a therapeutic or preventive agent having an effect of enhancing food intake and/or enhancing body weight gain, said method comprising the steps of:

contacting a test substance with a mammalian cell, and detecting the decreased expression of a gene comprising a nucleotide sequence set forth in any of SEQ ID NOs: 10-12, 18-20, 44-46, 74-82, 104-106 and 116-124 in said cell, or the decreased amount of a polypeptide comprising an amino acid sequence set forth in any of SEQ ID NOs: 3, 6, 9, 13-15, 39-41, 65-73, 101-103 and 107-115 intracellularly contained in said cell or extracellularly secreted;

(78) The screening method according to (77) wherein the mammalian cell is one in which a regulatory nucleic acid molecule that controls the expression of a gene comprising a nucleotide sequence set forth in any of SEQ ID NOs: 10-12, 18-20, 44-46, 74-82, 104-106 and 116-124 and the nucleic acid molecule of a reporter gene have been introduced, and the suppressed expression of a gene comprising a nucleotide sequence set forth in any of SEQ ID NOs: 10-12, 18-20, 44-46, 74-82, 104-106 and 116-124 is detected by the suppressed expression of the reporter gene;

(79) A method of screening a therapeutic or preventive agent having an effect of enhancing food intake and/or enhancing body weight gain, said method comprising the steps of:

administering a test substance to a mammal, and detecting the suppressed expression of a gene comprising a nucleotide sequence set forth in any of SEQ ID NOs: 10-12, 18-20, 44-46, 74-82, 104-106 and 116-124 or the suppressed production of a polypeptide comprising an amino acid sequence set forth in any of SEQ ID NOs: 3, 6, 9, 13-15, 39-41, 65-73, 101-103 and 107-115 in a biological sample from said test animal;

(80) A method of screening a therapeutic or preventive agent having an effect of enhancing food intake and/or enhancing body weight gain, said method comprising the steps of:

administering a test substance to the transgenic non-human organism according to any of (47) to (50) or the non-human animal according to any of (52) to (55), and detecting the enhancement of food intake or the enhancement of body weight gain in said transgenic non-human organism or said non-human animal; and

(81) The therapeutic or preventive agent having an effect of enhancing food intake and/or enhancing body weight gain, said agent being obtained by the method according to any of (77) to (80).

Figure 2:
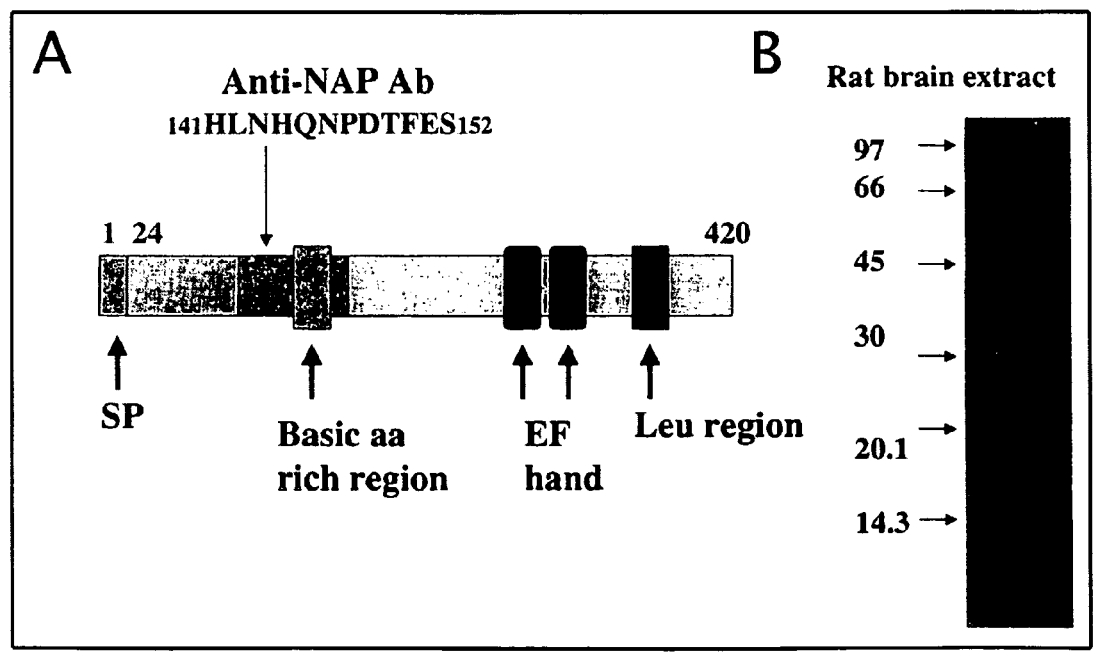

A of FIG. 2 is a drawing that shows a schematic diagram of the domain structure of a polypeptide encoded by the NEFA gene and a figure of the sequence of the NAP peptide used for preparing anti-nesfatin antibody. B of FIG. 2 is an image of Western blotting using a polyclonal antibody prepared with the NAP peptide, showing that a polypeptide encoded by the NEFA gene is present in the extract of the rat brain.

Figure 3:
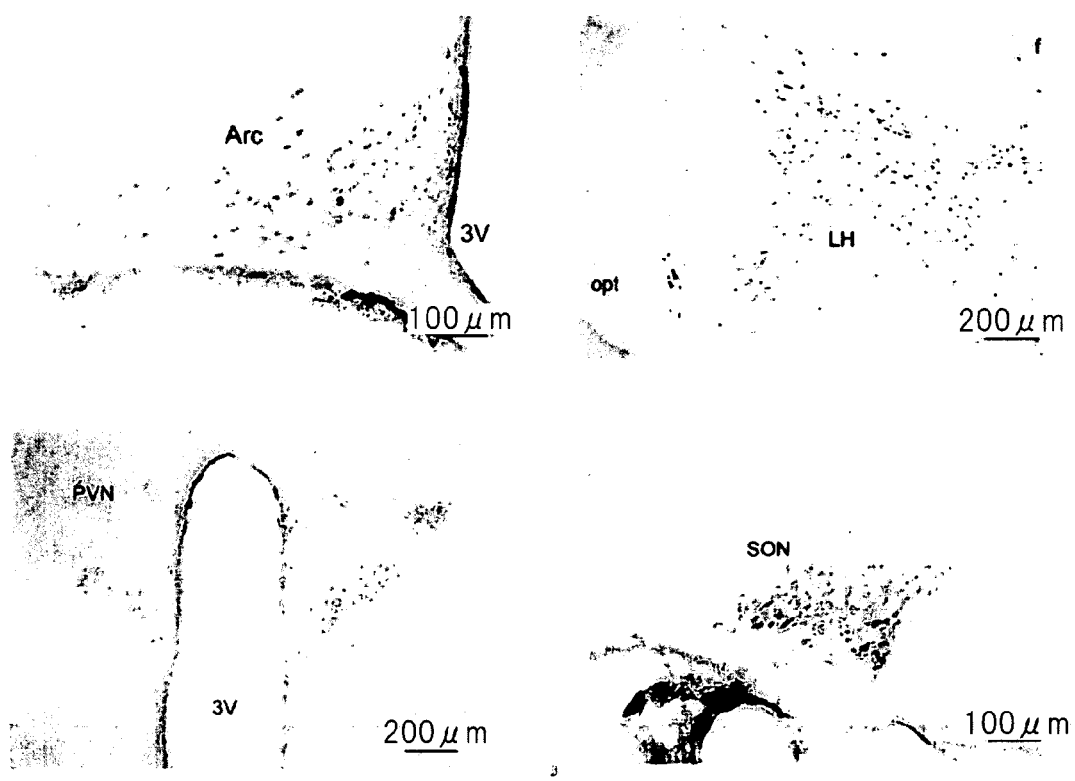

FIG. 3 is an image of immunohistochemical staining using a polyclonal antibody against the NAP peptide, showing that the NEFA gene is expressed in sites associated with food intake control such as the arcuate nucleus (Arc), paraventricular nucleus (PVN), the supraoptic nucleus (SON) and the lateral hypothalamic area (LH) of the hypothalamus of the rat brain.

Figure 4:
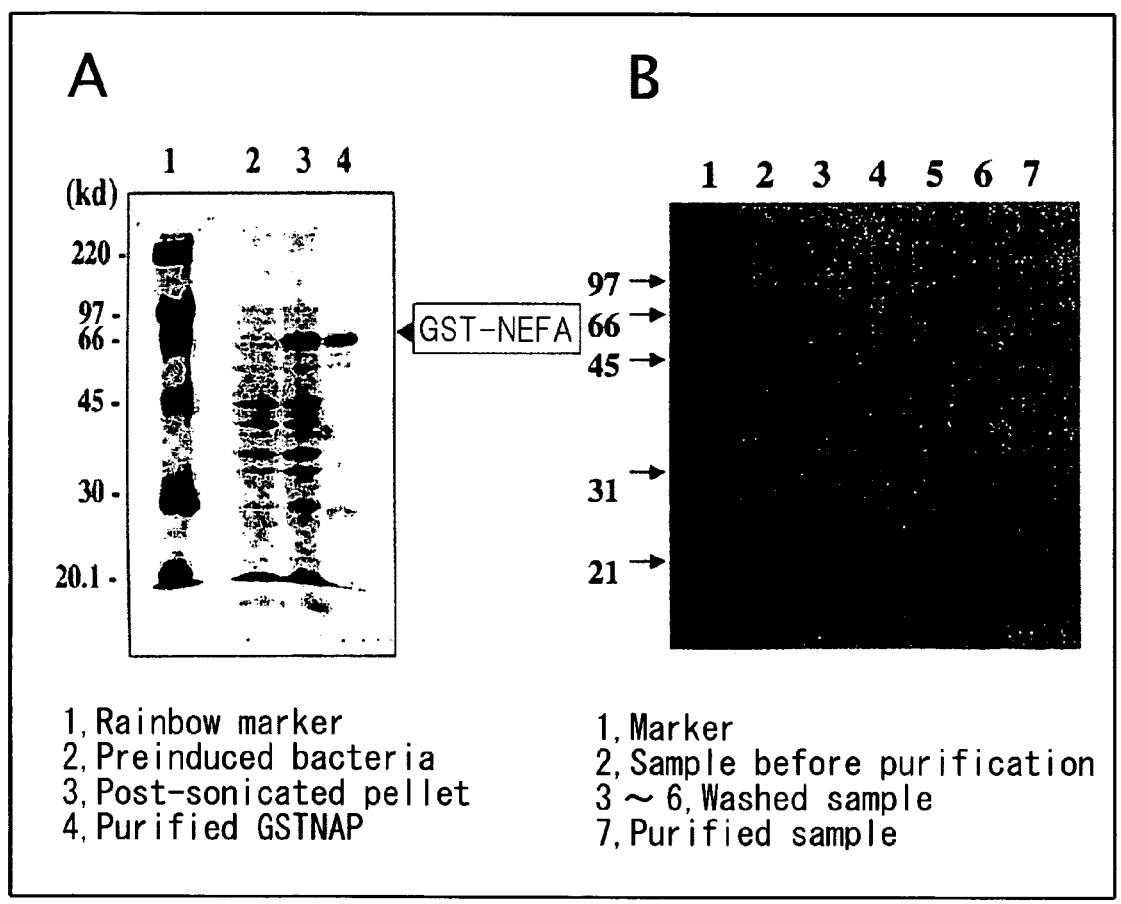

A of FIG. 4 is an image of Western blotting using a polyclonal antibody against the NAP peptide showing the expression and the purification of GST-NEFA which is a bound form of GST and mouse matured nesfatin. In A of FIG. 4, lanes 1-4 represent the rainbow marker, the preinduced bacteria, the post-sonicated pellet and the purified GSTNAP, respectively. Also, B of FIG. 4 is an image of Western blotting using anti-nesfatin antibody showing the process of GST-NEFA being cleaved with thrombin and purified. In B of FIG. 4, lane 1 represents the marker, lane 2 represents the sample before purification, lanes 3-6 represent washed samples, and lane 7 the purified sample.

Figure 5:
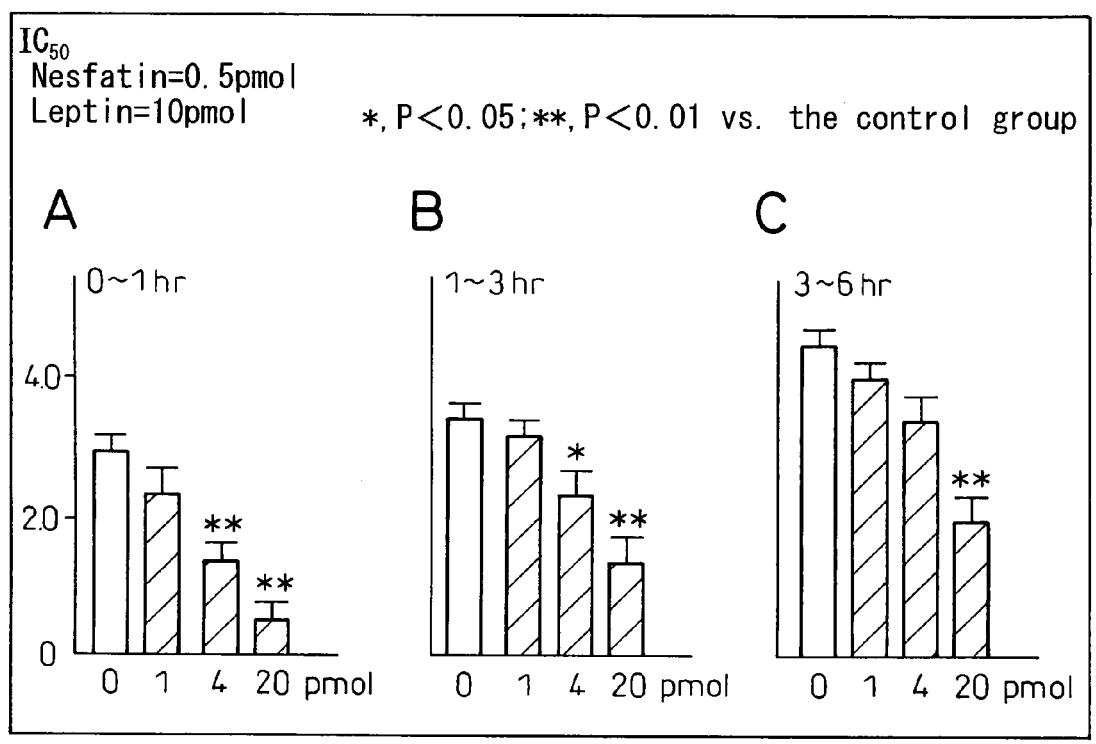

FIG. 5 is a graph showing that the food intake behavior by rats is suppressed by the administration of recombinant nesfatin into the third ventricle of the rat brain. In FIG. 5, * and ** represent a significant difference P<0.05 and P<0.01, respectively, relative to the control group.

Figure 6:
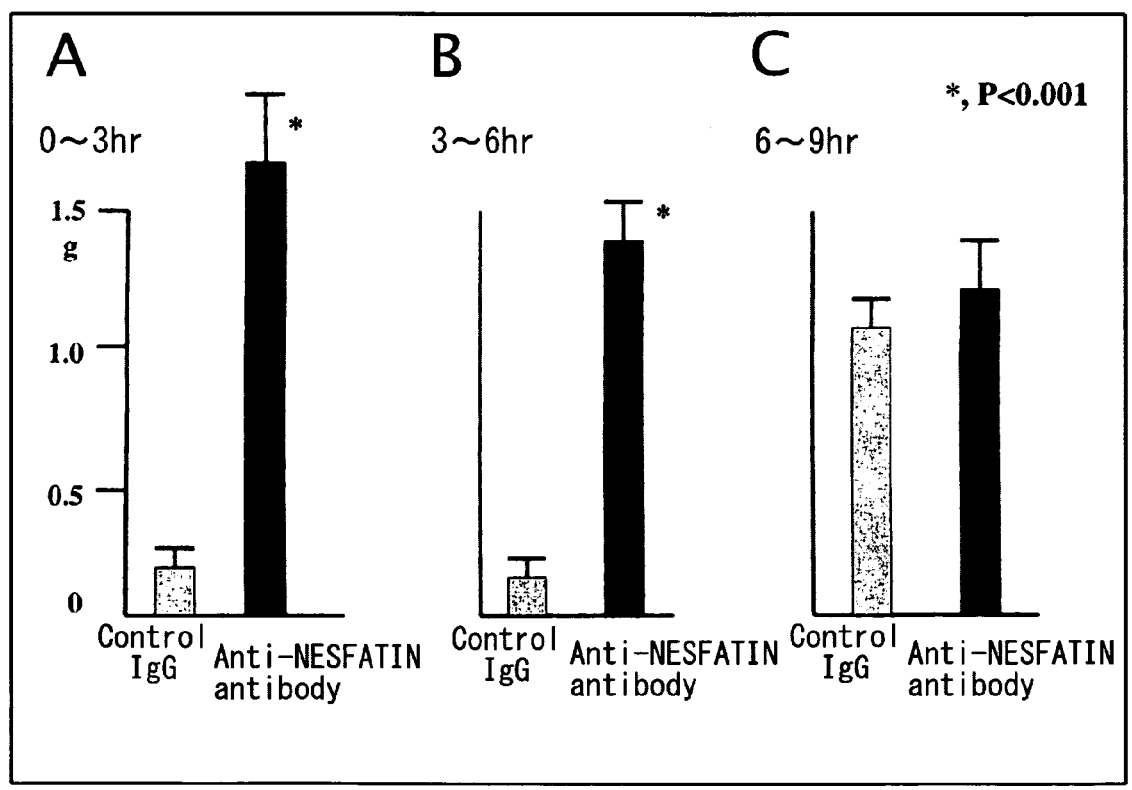

FIG. 6 is a graph showing that the food intake behavior by rats is enhanced by the administration of anti-nesfatin antibody into the third ventricle of the rat brain. In FIG. 6, * represents a significant difference P<0.001 relative to the control IgG.

Figure 7:
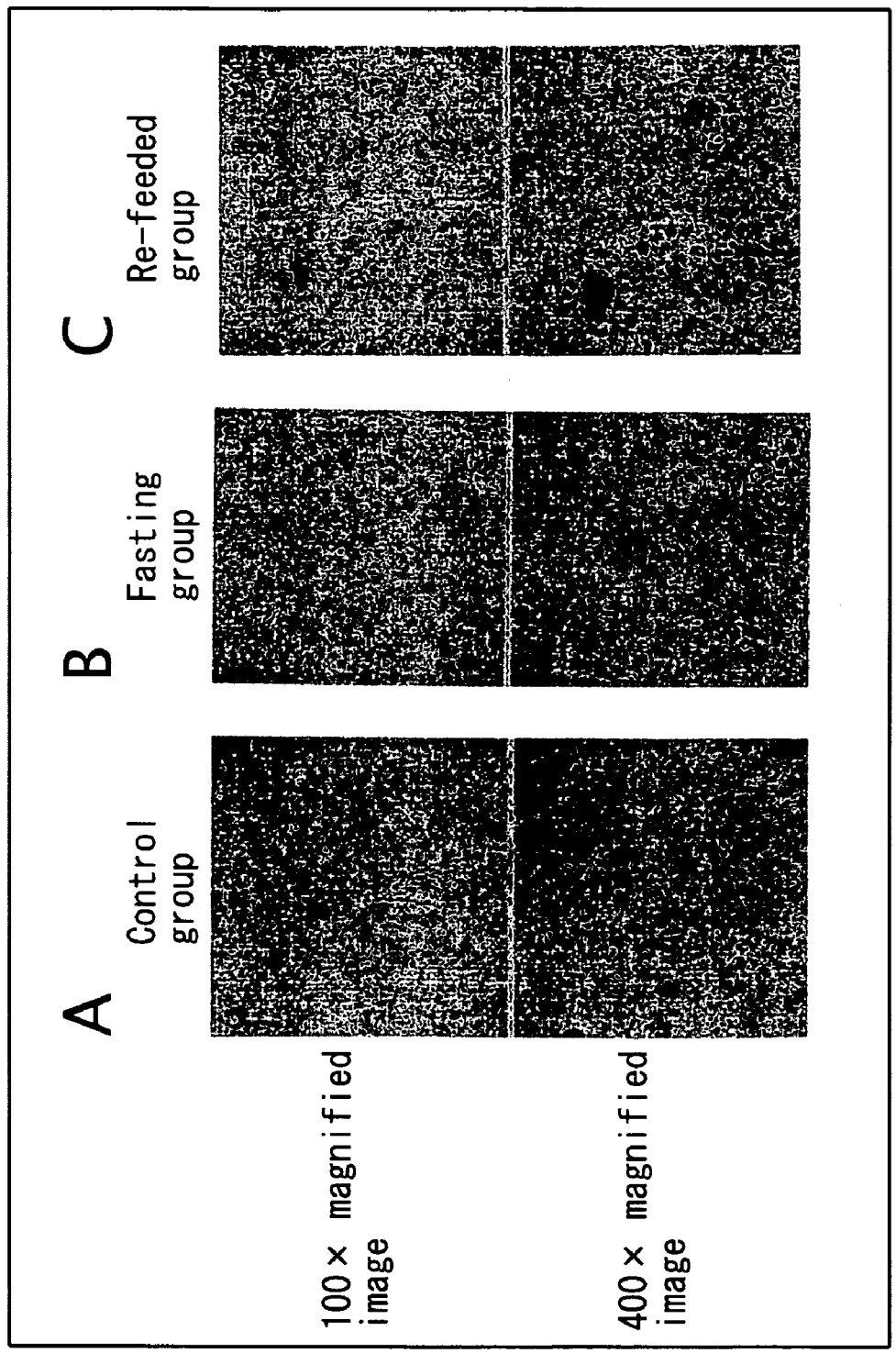

FIG. 7 shows an image of in situ hybridization in the brain tissue, showing that fasting can lower the expression of the nesfatin gene in the rat hypothalamus and re-feeding can restore the expression. In FIG. 7, A represents the control group, B represents the fasting group and C represents the re-feeding group, and the upper figures represent 100-magnified images and the bottom figures represent 400-magnified images.

Figure 8:
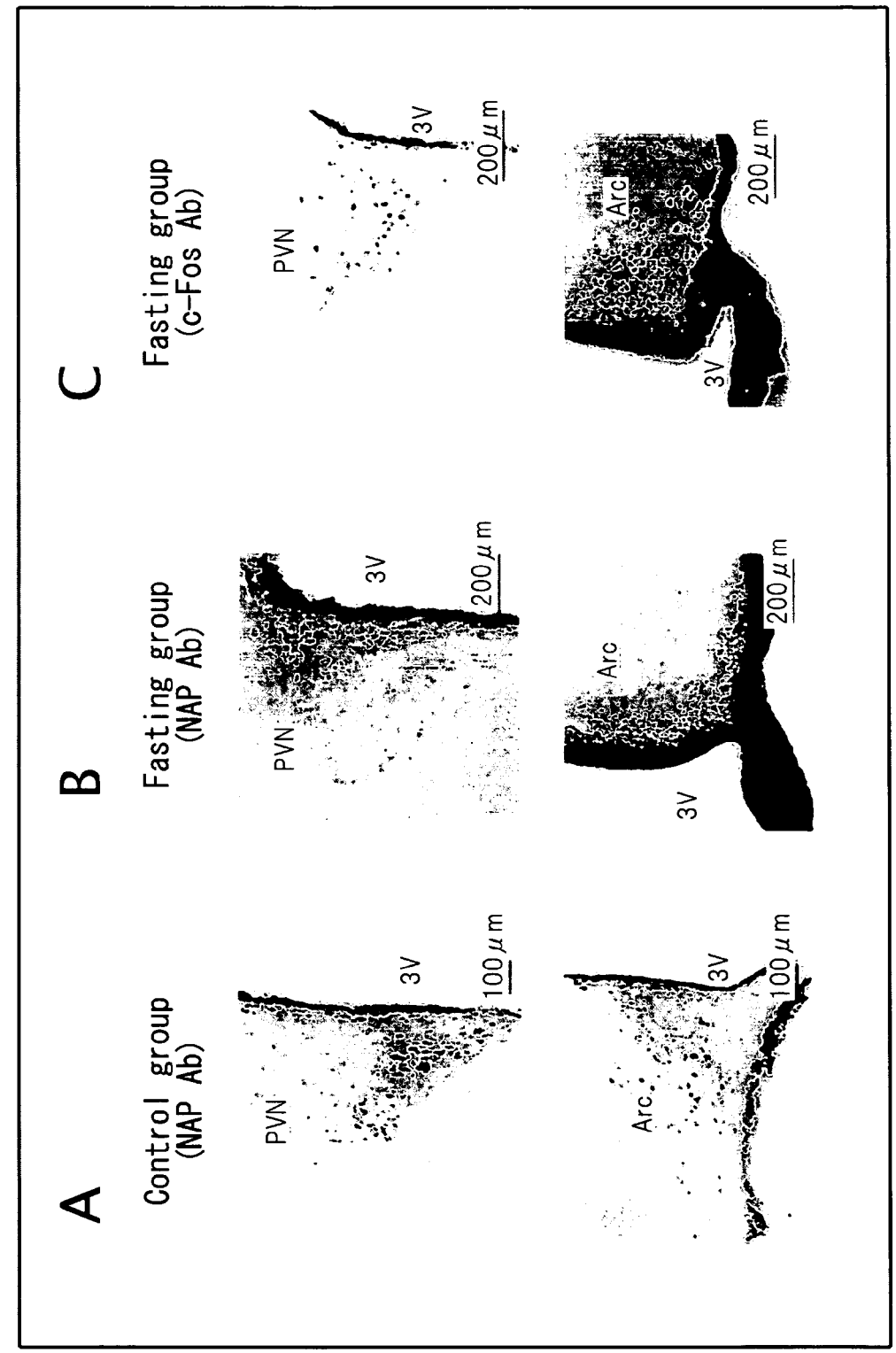

FIG. 8 shows an image of immunohistochemical stain using anti-nesfatin antibody, showing that fasting can lower the expression of nesfatin in the rat hypothalamus. In FIG. 8, A represents the control group and B represents the fasting group. It is also an image of immunohistochemical stain (C) using anti-C-Fos antibody, showing that the reduced expression of nesfatin during fasting is due to enhanced appetite. In FIG. 8 the upper figures represent paraventricular nucleus (PVN) and the bottom figures represent arcuate nucleus (Arc).

FIG. 9A is a drawing that shows the amino acid sequences of human and rat nesfatin and the estimated cleavage site for prohormone convertase. ▼ represents the estimated cleavage site for prohormone convertase.

Figure 9B:
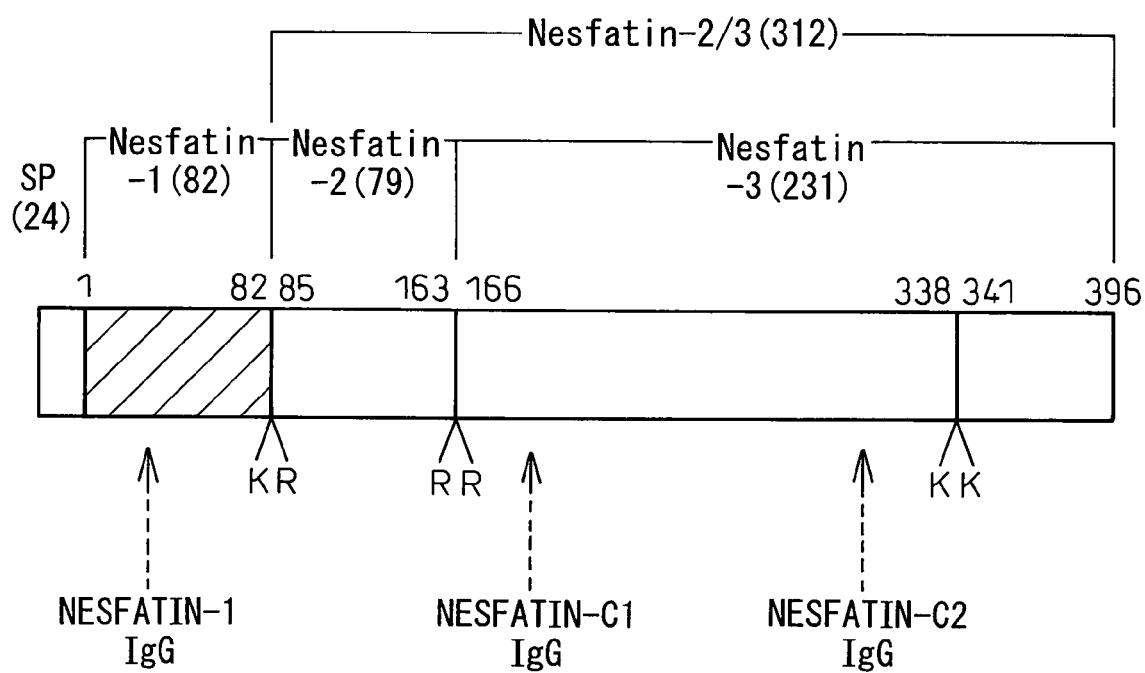

FIG. 9B is a schematic diagram showing the position of peptides in nesfatin for preparing antibody against nesfatin-1, nesfatin-2, nesfatin-3, nesfatin-2/3, as well as nesfatin-1, nesfatin-2/3 and nesfatin-3 thought to be formed by prohormone convertase.

Figure 9C:
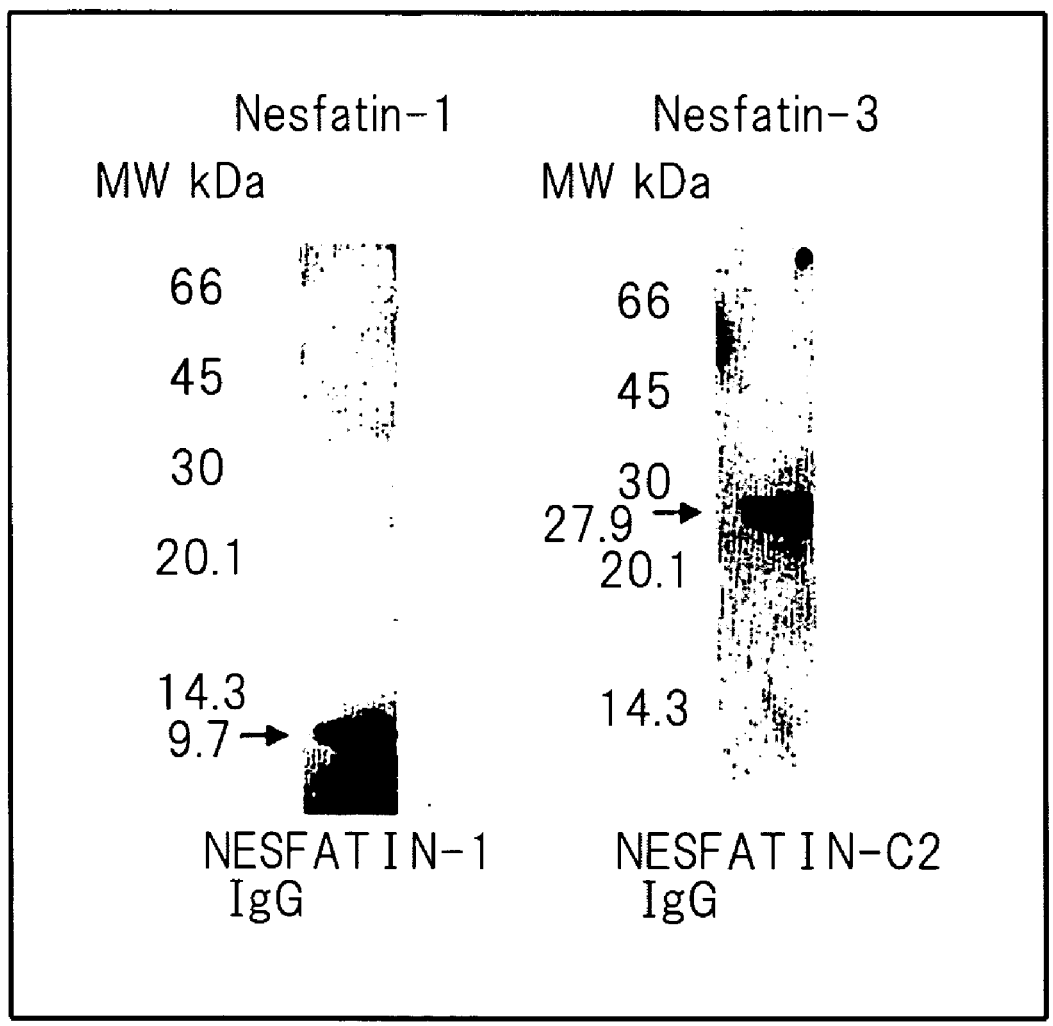

FIG. 9C is a drawing of Western blotting showing that the antibody per se against nesfatin-1 and nesfatin-3 bind to the antigen of interest. In FIG. 9C, the drawing on the left shows the result of an experiment in which the nesfatin-1 peptide was migrated and subjected to Western blotting with nesfatin-1 IgG, and the drawing on the right shows the result of an experiment in which the nesfatin-3 peptide was migrated and subjected to Western blotting with nesfatin C2 IgG.

Figure 10:
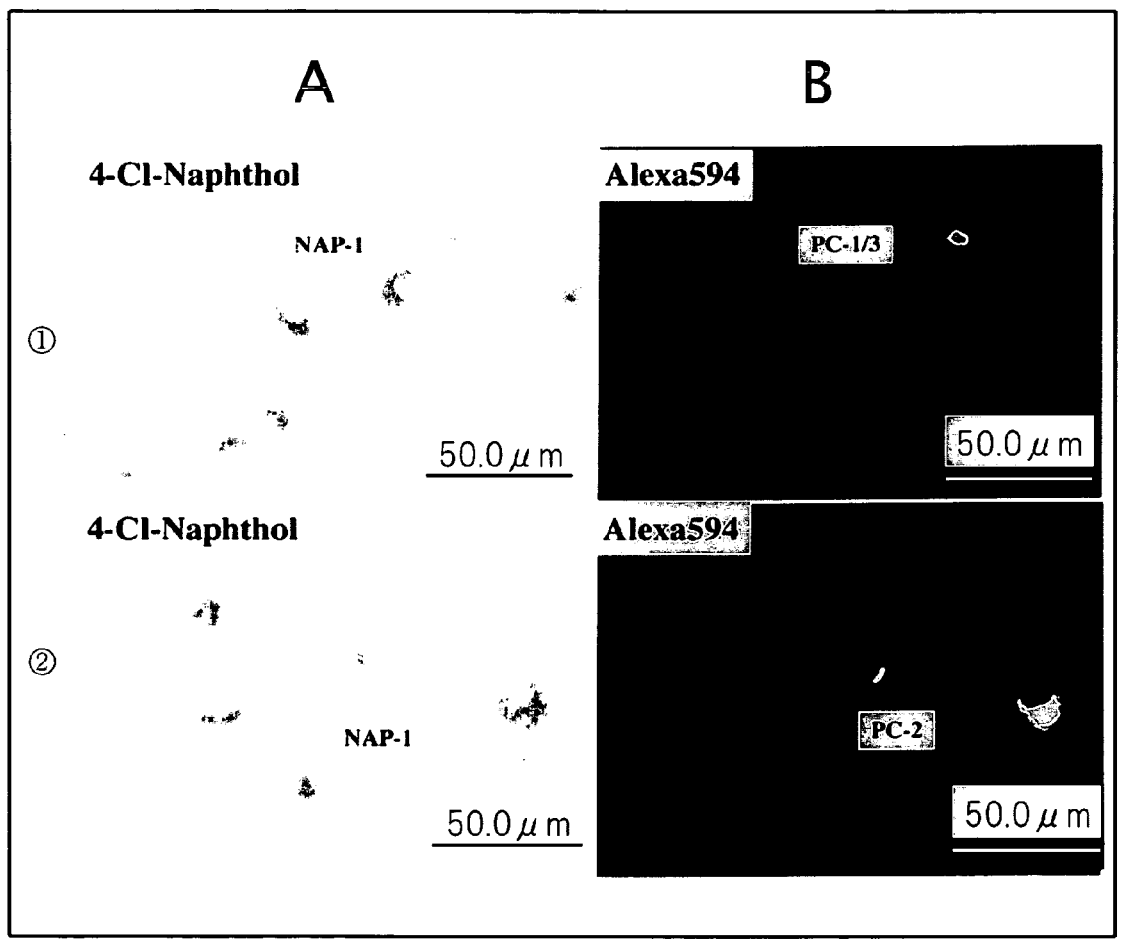

FIG. 10 is an image of double immunohistochemical stain using anti-nesfatin-1 antibody and anti-PC-1/3 antibody or anti-PC-2 antibody showing the presence of a cell that is simultaneously expressing nesfatin-1 and prohormone convertase (PC-1/3 or PC-2) in the rat brain. The upper panel and the lower panel of A of FIG. 10 represent the stained images with nesfatin-1 IgG in the immunohistochemical image of the rat hypothalamus tissue, and the upper panel in B of FIG. 10 represents a fluorescent image with PC-1/3 and the lower panel in B of FIG. 10 represents a fluorescent image with PC-2.

FIG. 11 is a graph showing that the administration of nesfatin-1 into the third ventricle of a rat suppresses the food intake behavior of the rat, but the administration of nesfatin-2 or nesfatin-3 does not cause any changes in food intake behavior.

FIG. 12 is a graph showing that the continuous administration of nesfatin-1 into the third ventricle of a rat results in persistent suppression in food intake behavior (A) and persistent suppression in body weight gain (B).

Figure 13A:
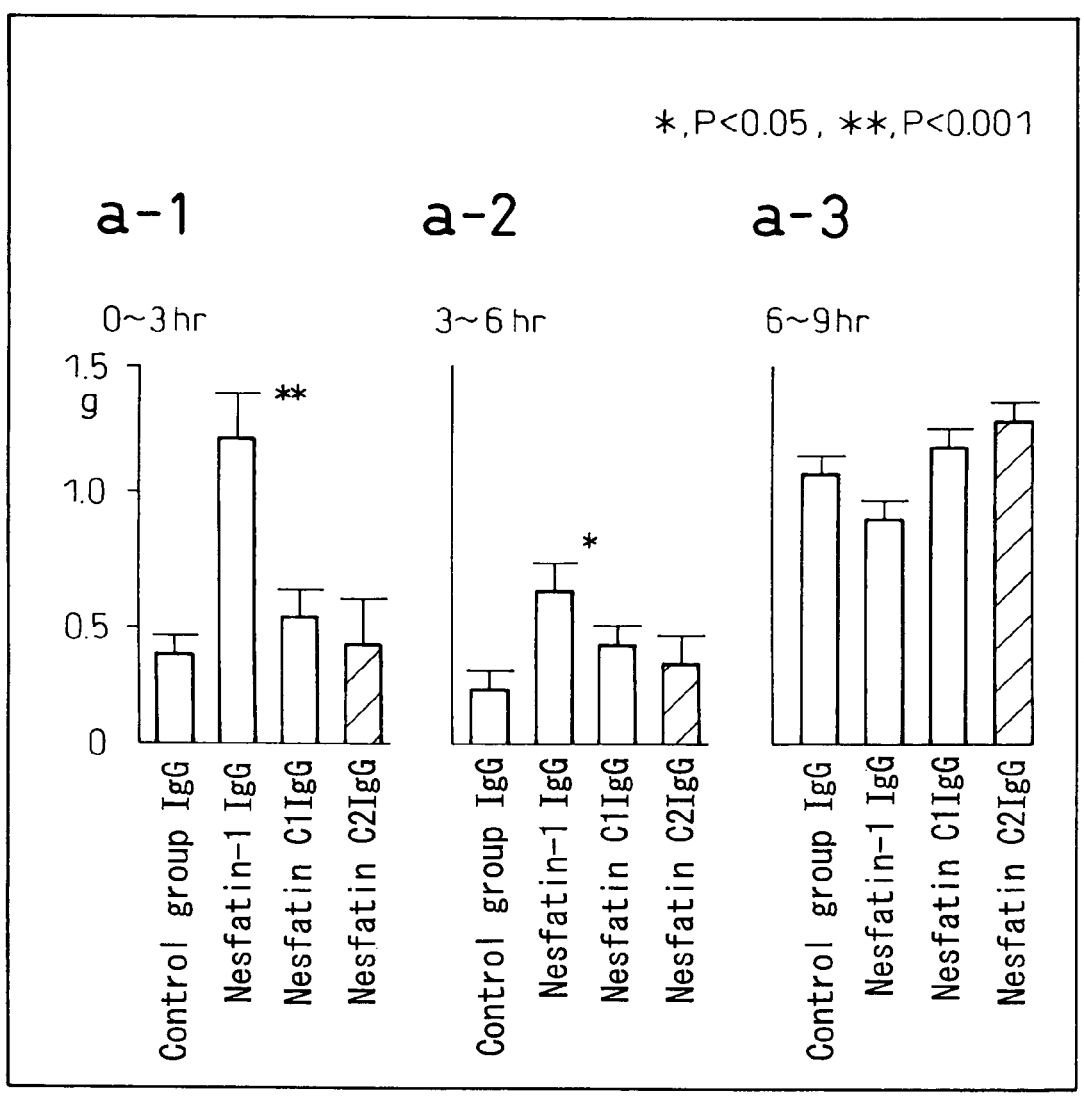

FIG. 13A is a graph showing that the administration of an antibody against nesfatin-1 into the ventricle of a rat enhances appetite. In FIG. 13A, * and ** represent a significant difference P<0.05 and P<0.001, respectively, relative to the control IgG-administration group.

FIG. 13B is a graph showing that the administration of a mutant in which nesfatin-1 cannot be excised from nesfatin into the ventricle of a rat does not cause enhanced appetite relative to nesfatin.

Figure 14:
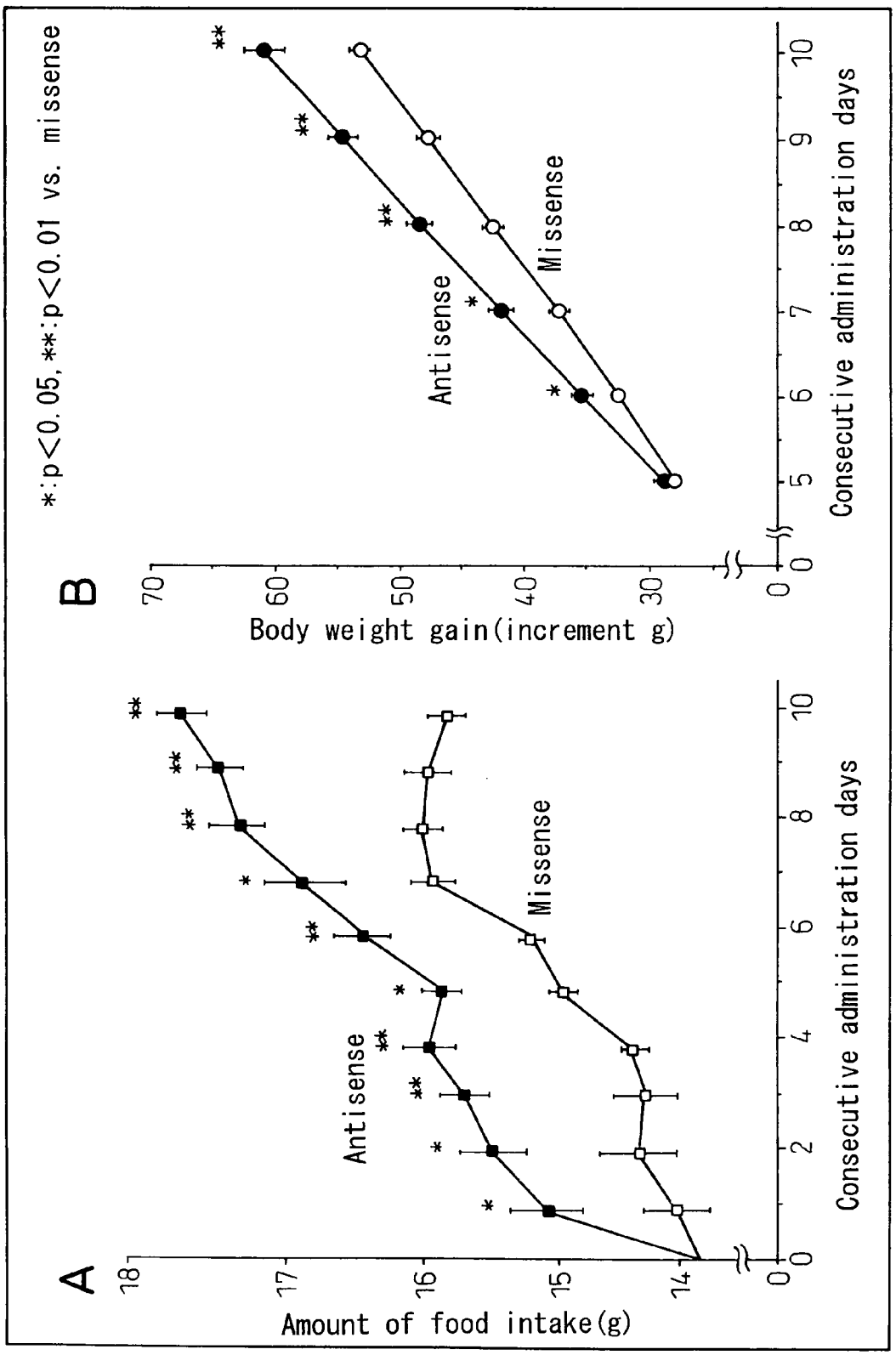

FIG. 14 is a graph showing that the continuous administration of antisense RNA against nesfatin into the ventricle of a rat results in suppression in food intake behavior (A) and suppression in body weight gain (B). In FIG. 14, * and ** represent a significant difference P<0.05 and P<0.01, respectively, relative to the missense.

Figure 15:
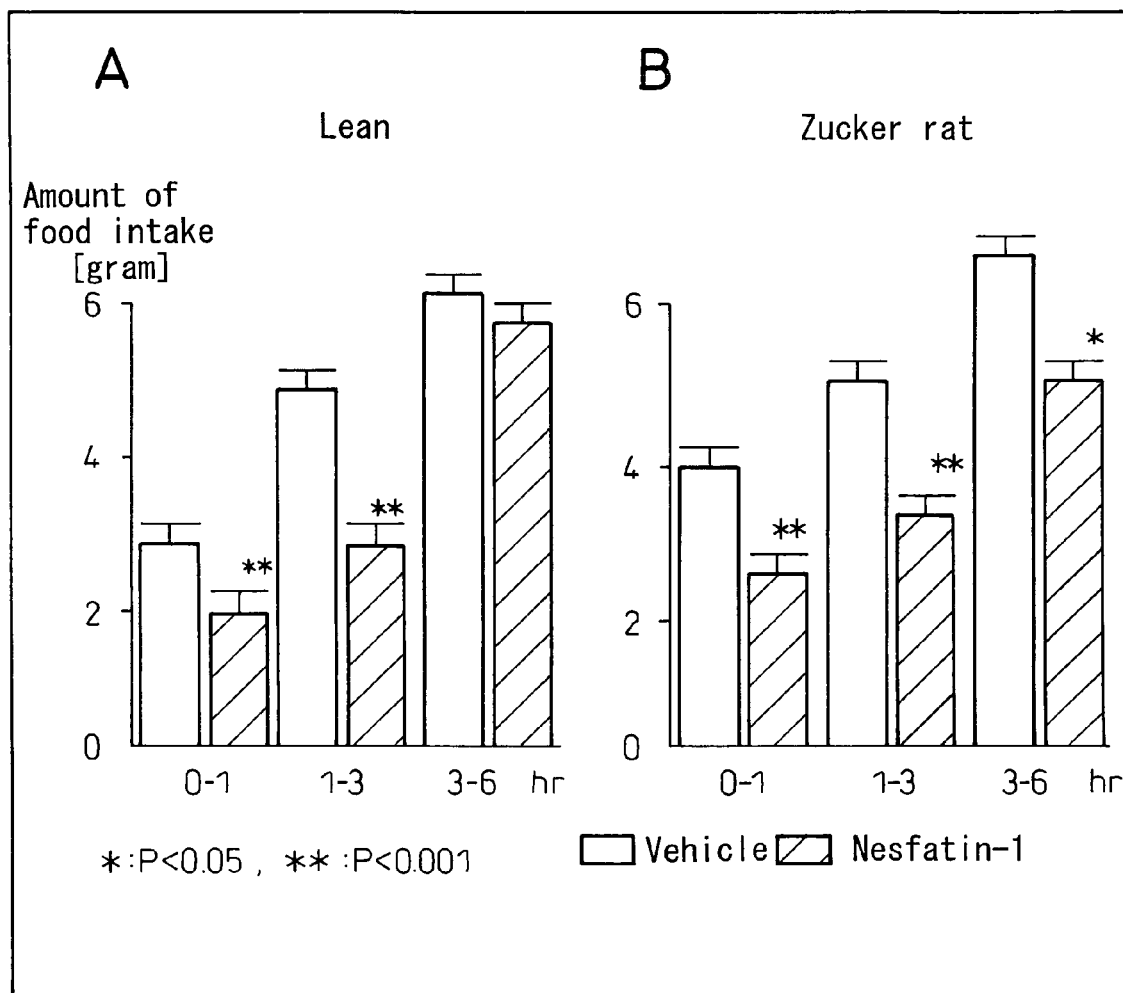

FIG. 15 is a graph showing the result of measuring the amount of food intake after the administration of nesfatin-1 into the ventricle of a Lean rat and a Zucker rat which is an animal model of leptin-resistant obesity. In the Zucker rat, as in the Lean rat (normal animal), the suppression of food intake is noted by the intraventricular administration of nesfatin-1. In FIG. 15, * and ** represent a significant difference P<0.05 and P<0.001, respectively, relative to the physiological saline-administration group. White boxes and hatched boxes represent the physiological saline-administration group and the nesfatin-1 administration group, respectively.

Figure 16:
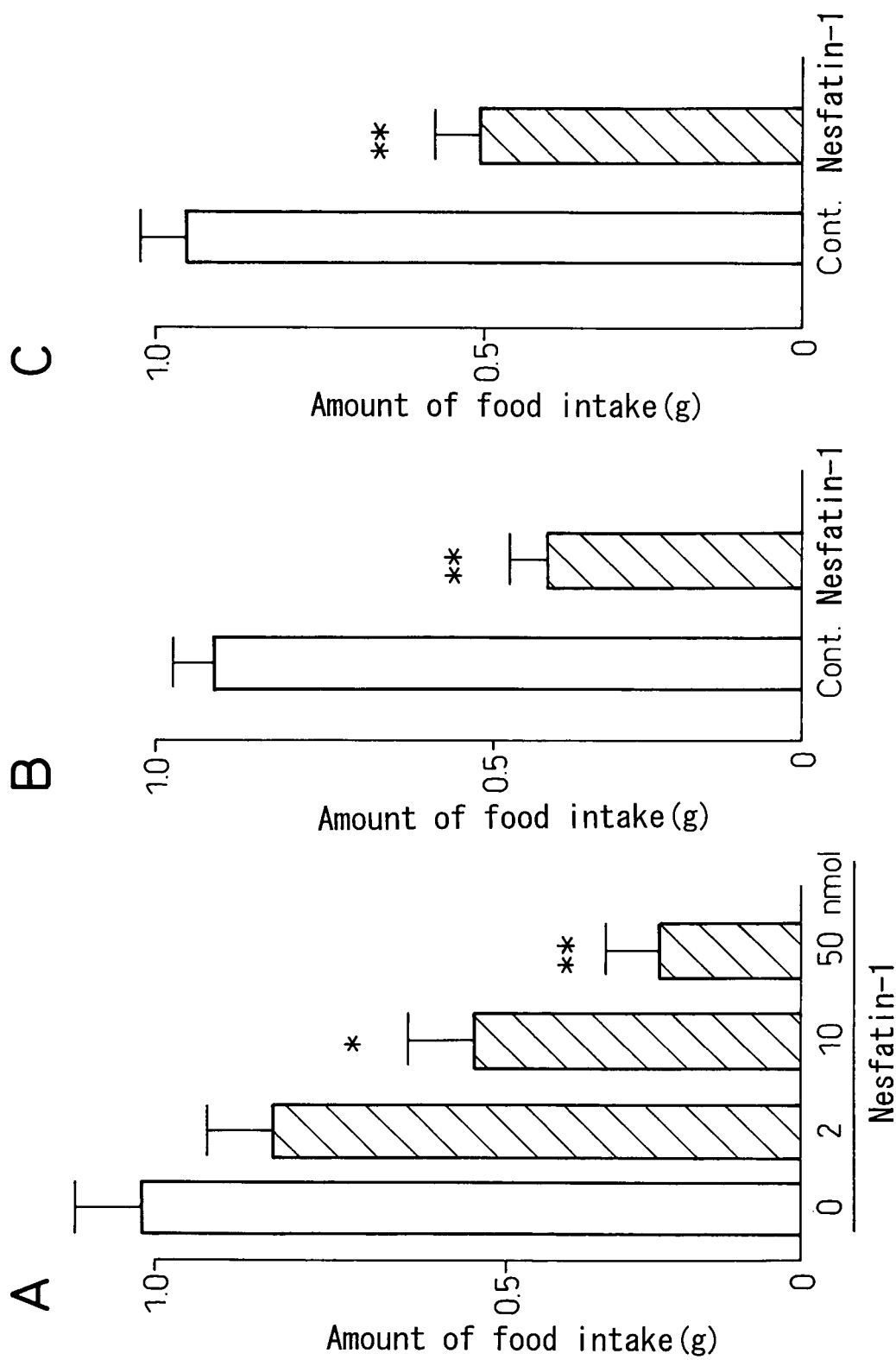

FIG. 16 is a graph showing the effect of intraperitoneal nesfatin-1 administration into a mouse on the amount of food intake. It shows that the activity by nesfatin-1 of suppressing food intake can be seen in the intraperitoneal administration into the mouse as well (A). It also shows the result when nesfatin-1 was intraperitoneally administered into an Agouti-yellow mouse which is a mouse model of obesity and the control mouse. It shows that the intraperitoneal administration of nesfatin-1 yields a similar effect in the control mouse (B) and the Agouti-yellow mouse (C) as well.

Figure 17:
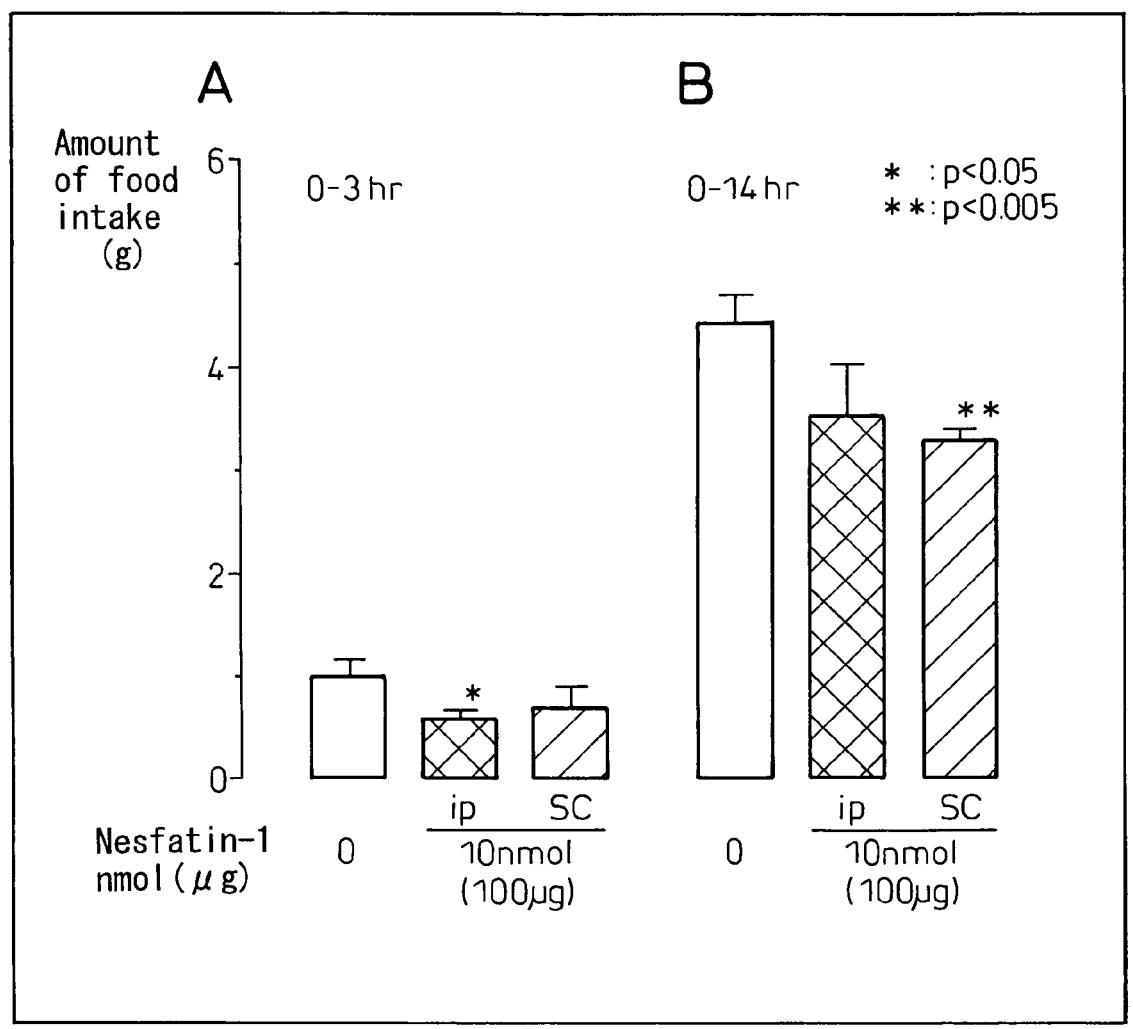

FIG. 17 is a graph showing the effect of subcutaneous nesfatin-1 administration into a mouse on the amount of food intake. Though nesfatin-1 exhibited an effect of suppressing food intake both by the intraperitoneal administration (ip) and the subcutaneous administration (sc), the development of the effect tended to lag in the subcutaneous administration. In FIG. 17, * and ** represent a significant difference P<0.05 and P<0.005, respectively, relative to the physiological saline-administration group.

Figure 18A:
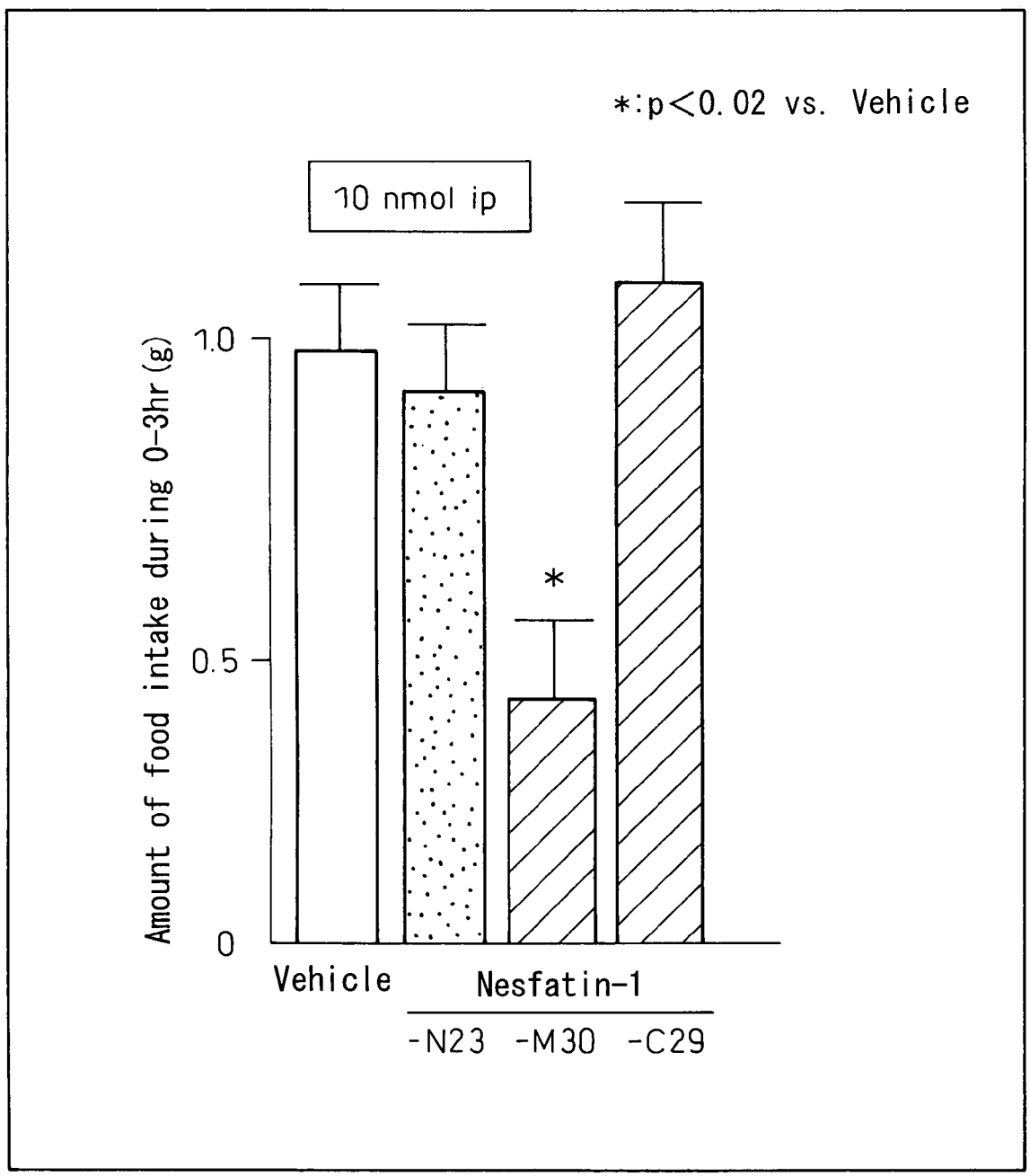

FIG. 18A is a graph showing the effect on the amount of food intake by the intraperitoneal administration of nesfatin-1N23, nesfatin-1M30, and nesfatin-1C29 into a mouse. Among the partial peptides of nesfatin-1, nesfatin-1M30 was only shown to exhibit the effect of suppressing food intake. In FIG. 18A, * represents a significant difference P<0.02 relative to the physiological saline-administration group.

FIG. 18B is a drawing that shows the result of amino acid alignment of human, mouse and rat nesfatin-1 and the sites of nesfatin-1N23, nesfatin-1M30 and nesfatin-1C29. It was shown that amino acid sequences are highly conserved between species in the site of nesfatin-1M30.

Figure 1:
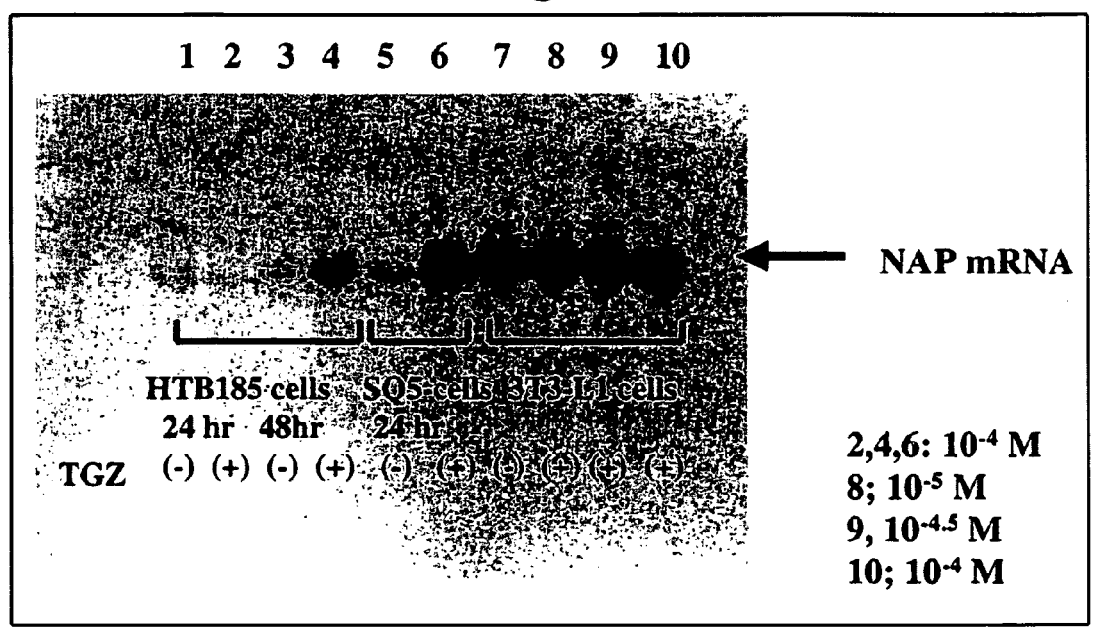
FIG. 1 is an image of Northern blotting using a NEFA probe, which shows that the expression of the NEFA gene is induced by troglitazone, and that the NEFA gene is constantly expressed in 3T3-L1 cells that were differentiated to precursor adipose cells, in human cerebrospinal blastocytoma cell line HBT185 cells and SQ-5 cells.
Figures 1, 19A:
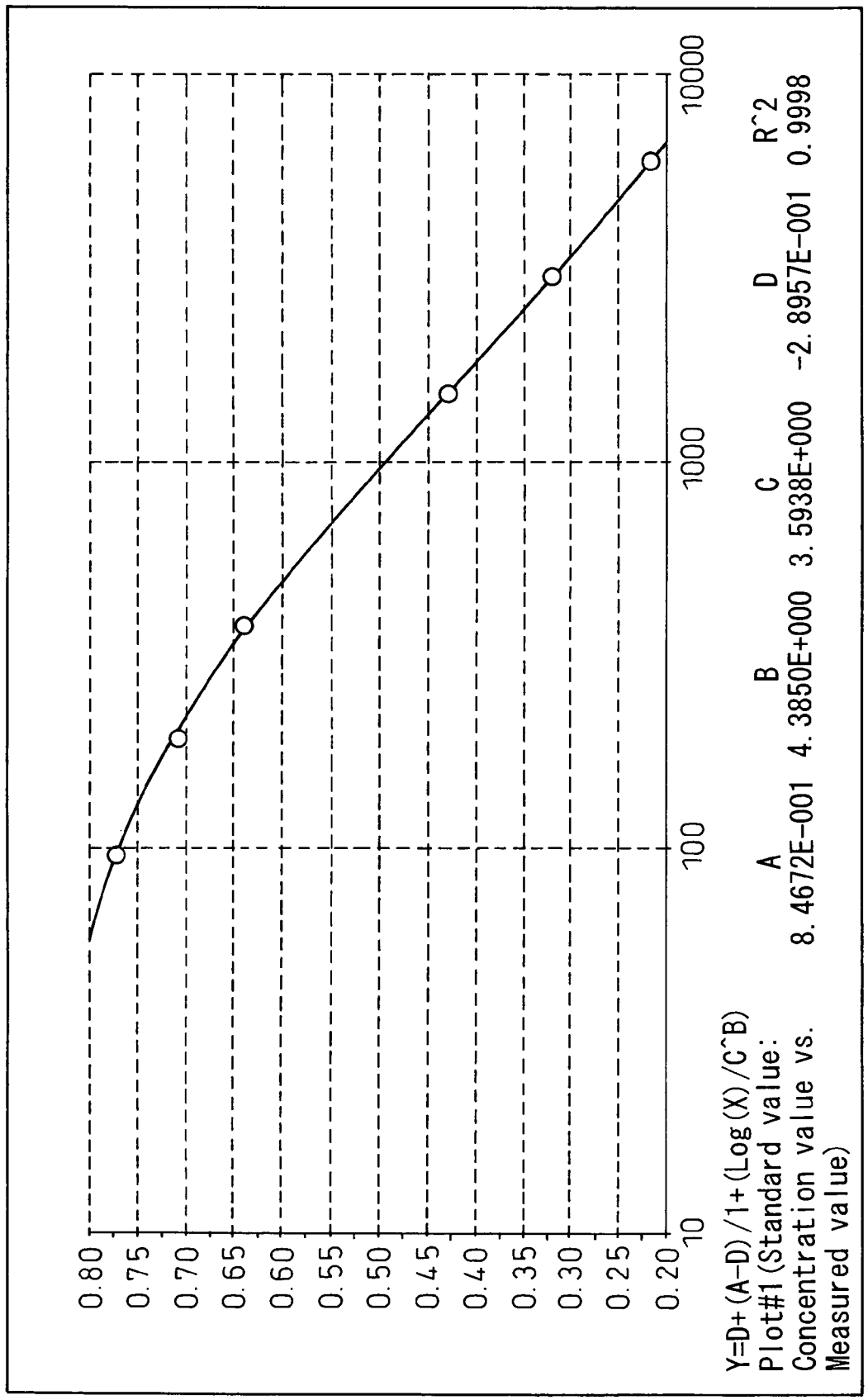

FIG. 19A-1 is a graph (A-1) showing a standard curve in a competitive EIA system that determines the concentration of nesfatin or nesfatin-1 in a sample, and is a table (A-2) showing the result of measurement in the cerebrospinal fluid. The equation of the standard curve: $Y=D+(A-D)/1+(Log(X)/C\char`\^B)$. Plot #1 (standard value: concentration value vs measured value). A=8.4672E-001; B=4.3850E+000; C=3.5938E+000; D=−2.8957E-001; R^2=0.9998.

FIG. 19A-2 is a graph (A-1) showing a standard curve in a competitive EIA system that determines the concentration of nesfatin or nesfatin-1 in a sample and is a table (A-2) showing the result of measurement in the cerebrospinal fluid.

Figure 19B:
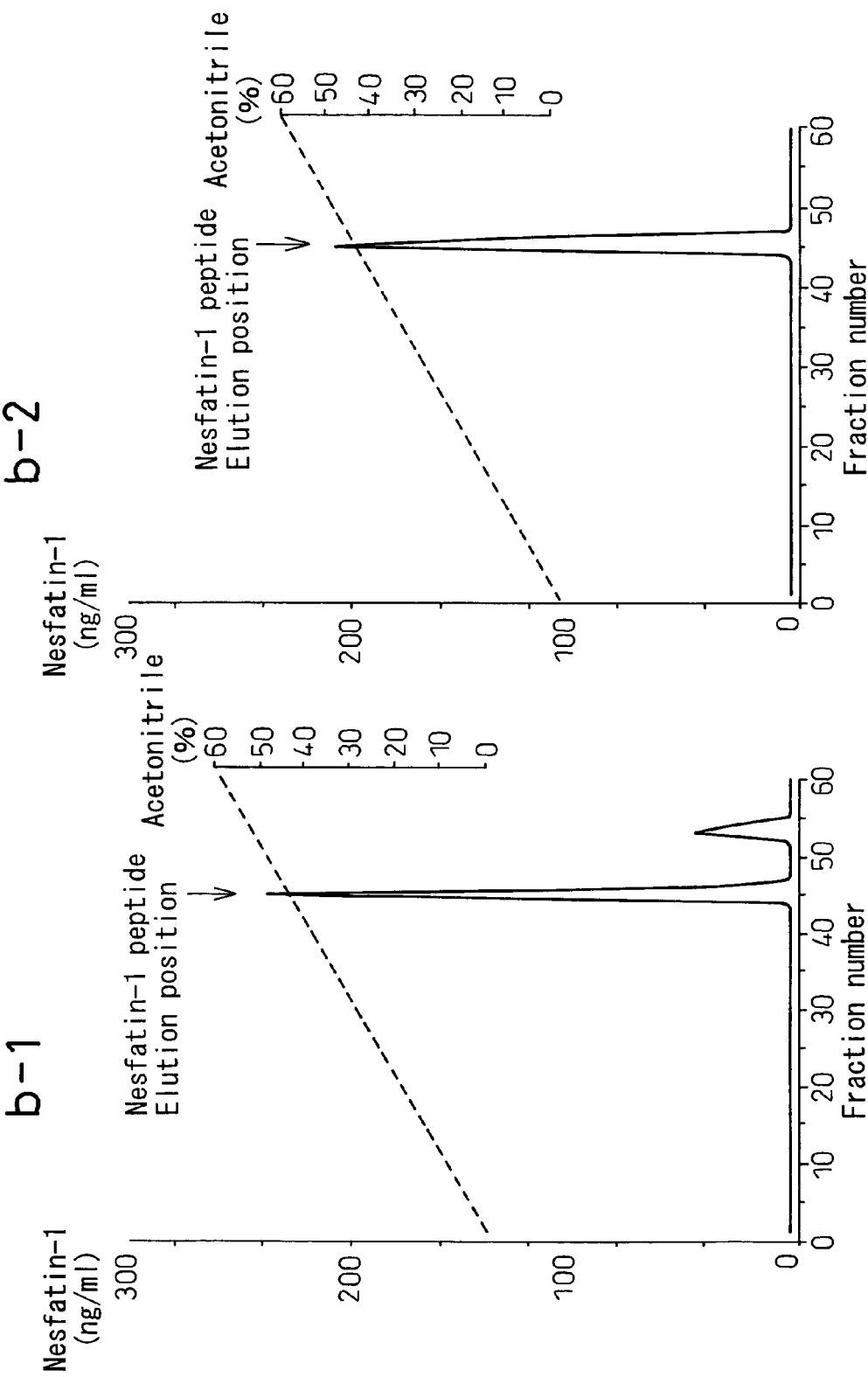

FIG. 19B is a graph (b-1 and b-2) showing the assay result in which peptide samples extracted from the hypothalamus tissue and the cerebrospinal fluid were fractionated by HPLC and nesfatin-1 in the fractions were determined by a competitive EIA system.

Figure 20:
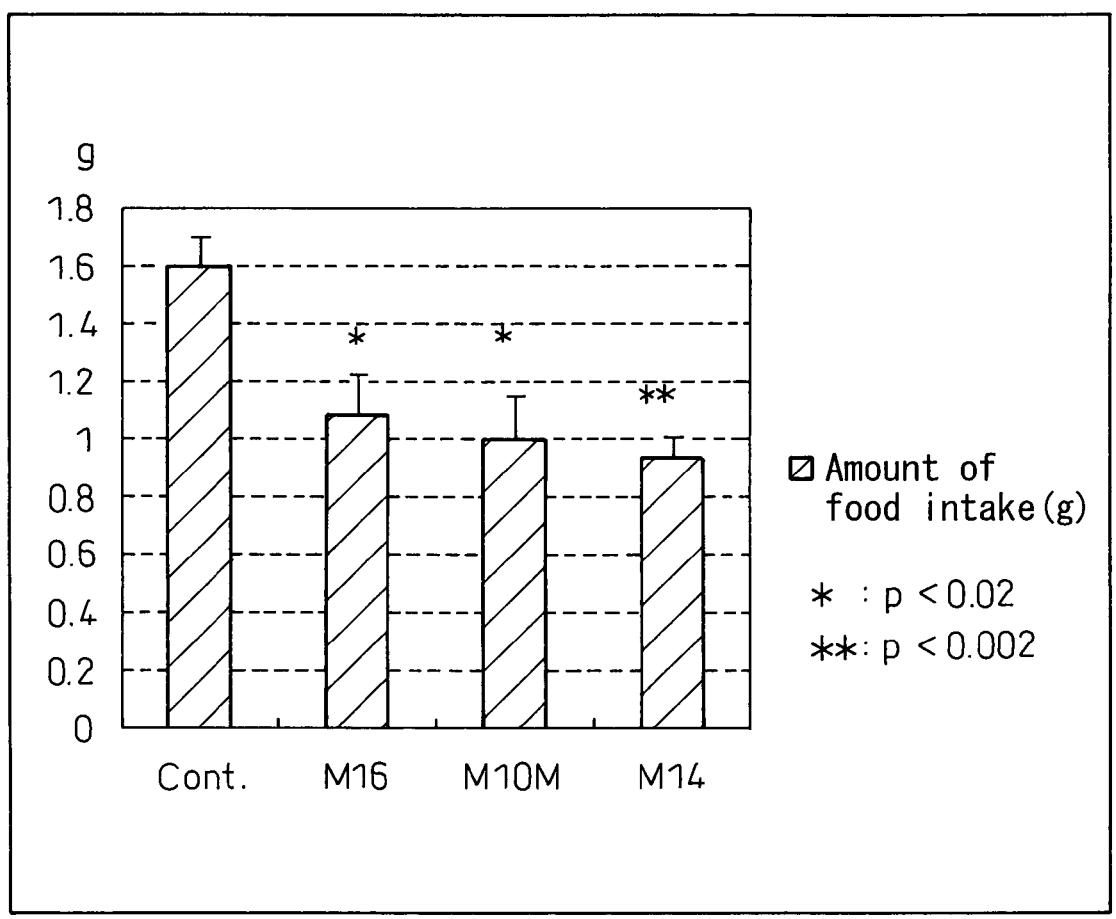

FIG. 20 is a graph showing the effect on the amount of food intake by the intraperitoneal administration of partial peptides of nesfatin-1M30 into a mouse. In all cases of nesfatin-1M16M (M16M), nesfatin-1M10M (M10M) or nesfatin-M14 (M14) administered, the effect of suppressing food intake was noted. In FIG. 20, * and ** represent a significant difference $P<0.02$ and $P<0.002$, respectively, relative to the physiological saline-administration group.

Figure 21A:
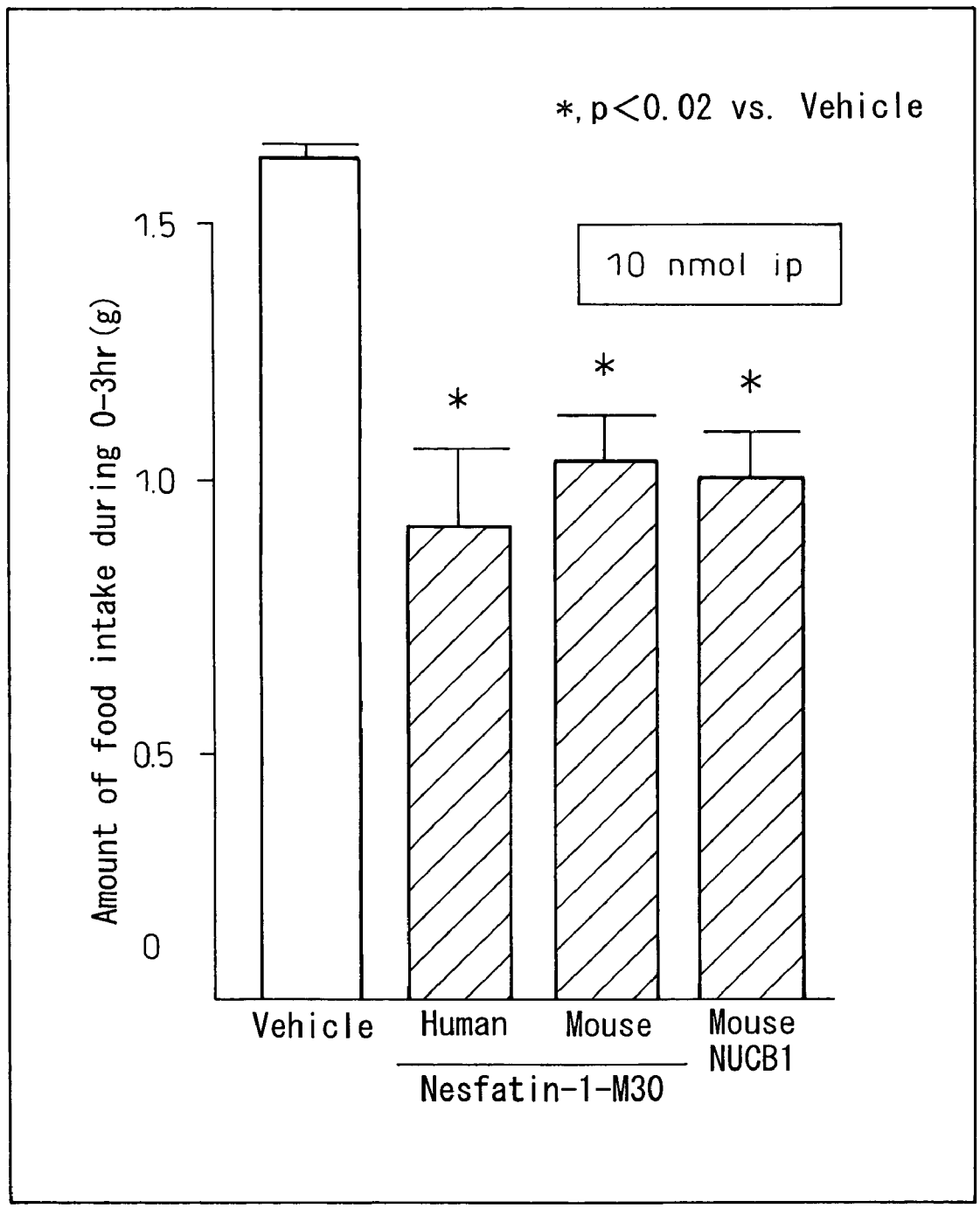

FIG. 21A is a graph showing the effect on the amount of food intake by the intraperitoneal administration of human nesfatin-1M30 and mouse NUCB1-M30 into a mouse. It shows that the effect of suppressing food intake can be noted for human nesfatin-1M30 (human/nesfatin-1M30) and mouse NUCB1-M30 (mouse NUCB1) as well as mouse nesfatin-1M30 (mouse/nesfatin-1M30). In FIG. 20, * represents a significant difference $P<0.02$ relative to the physiological saline-administration group.

FIG. 21B is a drawing that shows the result of amino acid alignment of human, rat and mouse nesfatin and human, rat and mouse NUCB1 and the site corresponding to nesfatin-1 and the site corresponding to nesfatin-1M30. It is shown that amino acid sequences are highly conserved at a site corresponding to nesfatin and nesfatin-1 of NUCB2, specifically nesfatin-1M30.

FIG. 21C is a drawing that shows the result of amino acid alignment of human, rat and mouse nesfatin and human, rat and mouse NUCB1 and the site corresponding to nesfatin-1 and the site corresponding to nesfatin-1M30, and represents the continuation of FIG. 21B.

FIG. 22 shows an image of in situ hybridization using a NEFA probe in various tissues. A of FIG. 22 represents a tissue section containing paraventricular nucleus (PVN) and supraoptic nucleus (SON), B of FIG. 22 represents a tissue section containing zona incerta (Zi) and arcuate nucleus (Arc), and C of FIG. 22 represents a tissue section containing lateral hypothalamic area (LHA) of the hypothalamus.

Figure 23:
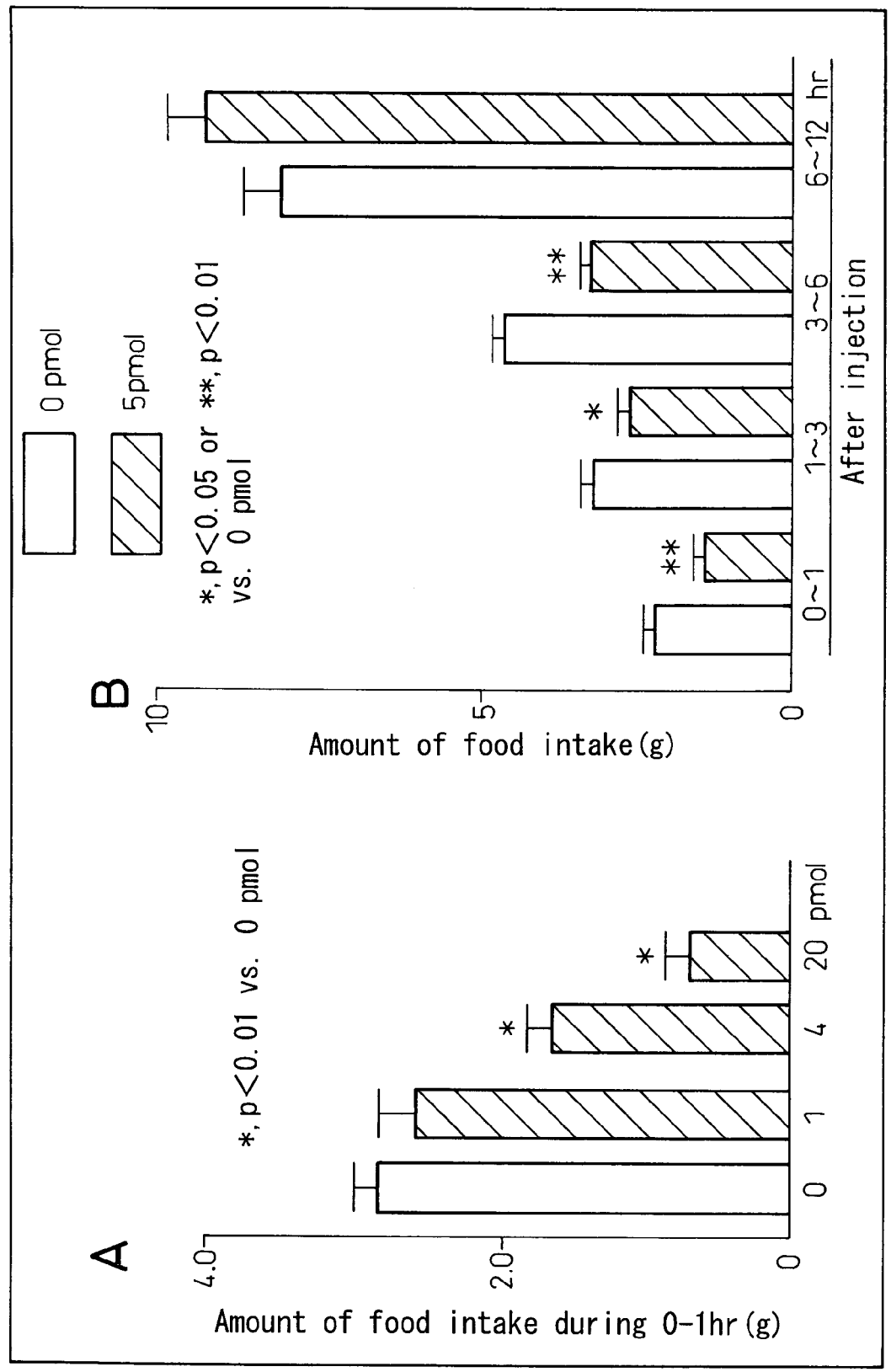

A of FIG. 23 is a graph showing that the administration of recombinant nesfatin into the third ventricle of the rat brain can suppress the amount of food intake by the rat. B of FIG. 23 is a drawing that shows the amount of food intake during 0-1 hour, 1-3 hours, 3-6 hours and 6-12 hours for the nesfatin administration group (hatched box) that received 5 pmol of nesfatin into the third ventricle of the rat brain and the control group (0 pmol of nesfatin, white box). In A of FIG. 23, * represents a significant difference $P<0.01$ relative to 0 pmol, and in B of FIG. 23, * represents a significant difference $P<0.05$ and ** represents a significant difference $P<0.01$.

Figure 24:
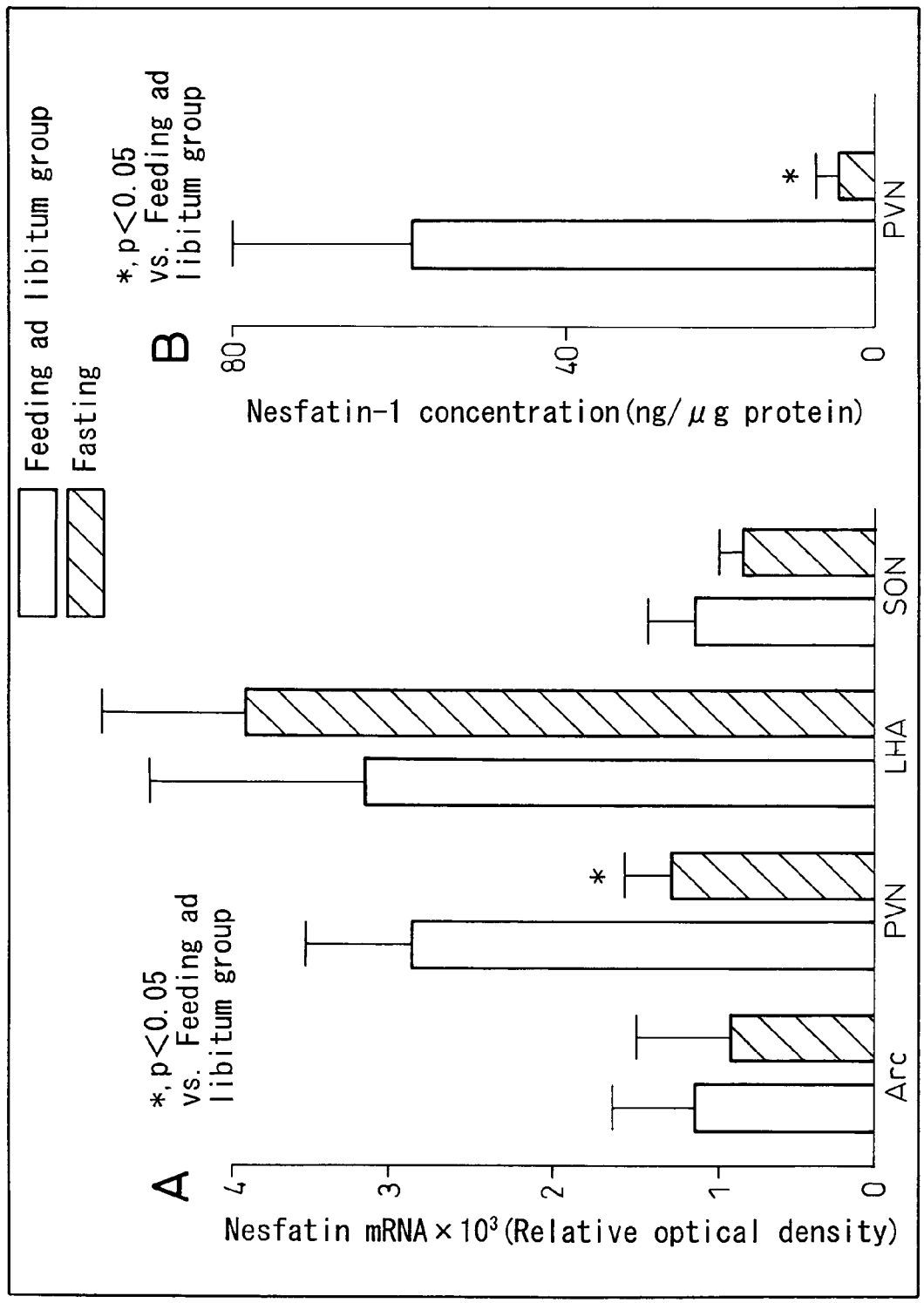

A of FIG. 24 shows the result of image analysis by in situ hybridization of the nesfatin mRNA expression at various sites of arcuate nucleus (Arc), paraventricular nucleus (PVN), lateral hypothalamic area (LHA) and supraoptic nucleus (SON) in the hypothalamus region of the rat brain in the feeding ad libitum group (control group) and those in the fasting group. B of FIG. 24 shows the result of image analysis by a competitive EIA method of the expression of nesfatin-1 peptides at paraventricular nucleus (PVN) among the hypothalamic area of the rats in the feeding ad libitum group (control group: white box) and those in the fasting group (hatched box).

Figure 25:
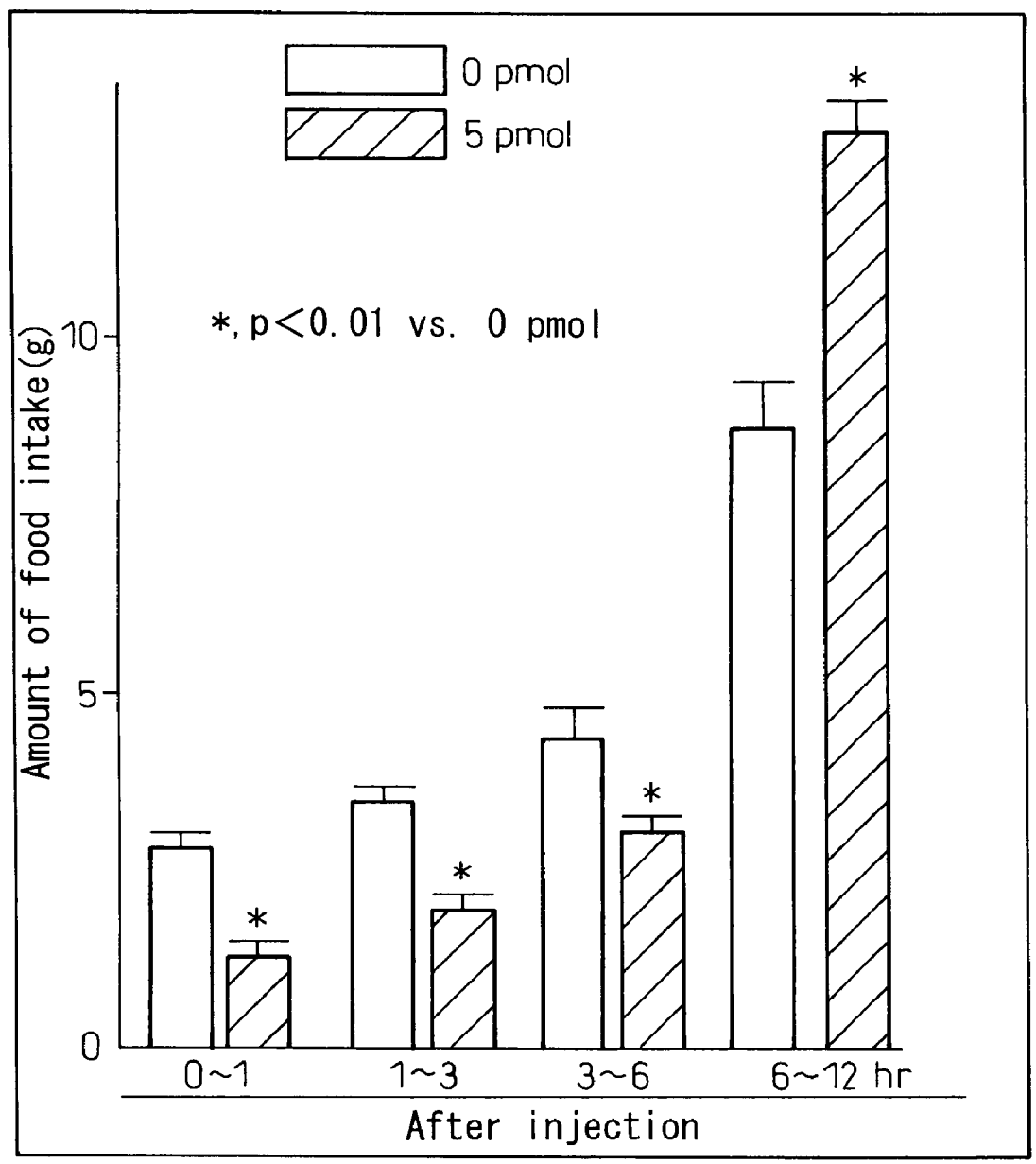

FIG. 25 is a drawing that shows the amount of food intake during 0-1 hour, 1-3 hours, 3-6 hours and 6-12 hours for the nesfatin administration group (hatched box) that received 5 pmol of nesfatin into the third ventricle of the rat brain and the control group (0 pmol of nesfatin, white box). * represents a significant difference $P<0.01$ relative to 0 pmol.

Figure 26:
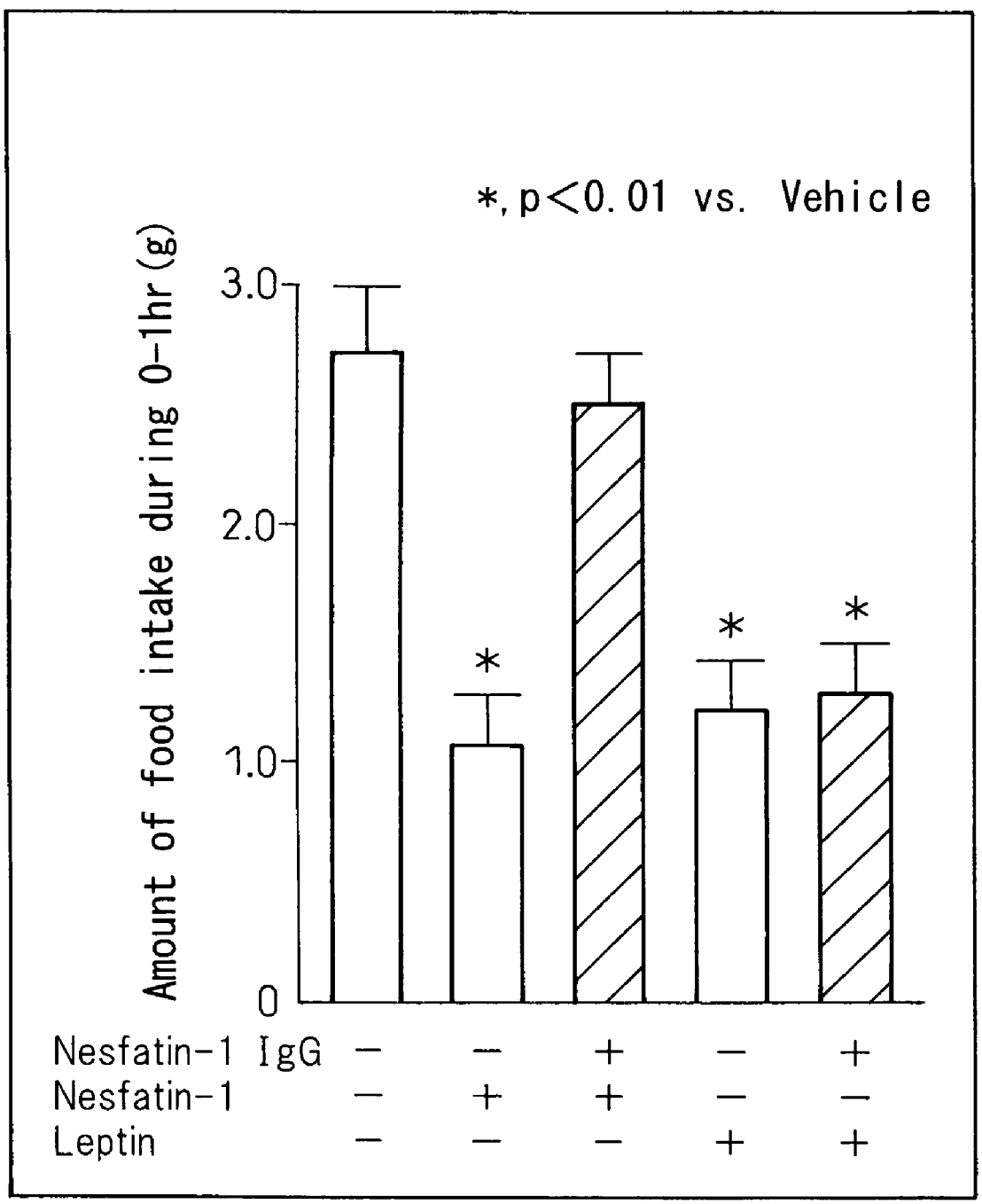

FIG. 26 is a graph showing the amount of food intake for 1 hour after administration for the control group that received physiological saline alone (nesfatin-1 IgG/nesfatin-1/leptin: −/−/−), the group that received nesfatin-1 alone (nesfatin-1 IgG/nesfatin-1/leptin: −/+/−), the group that received nesfatin-1 and anti-nesfatin-1 antibody (nesfatin-1 IgG/nesfatin-1/leptin: +/+/−), the group that received leptin alone (nesfatin-1 IgG/nesfatin-1/leptin: −/−/+), and the group that received leptin and anti-nesfatin-1 antibody (nesfatin-1 IgG/nesfatin-1/leptin: +/−/+). * represents a significant difference $P<0.01$ relative to the control group.

Figure 27:
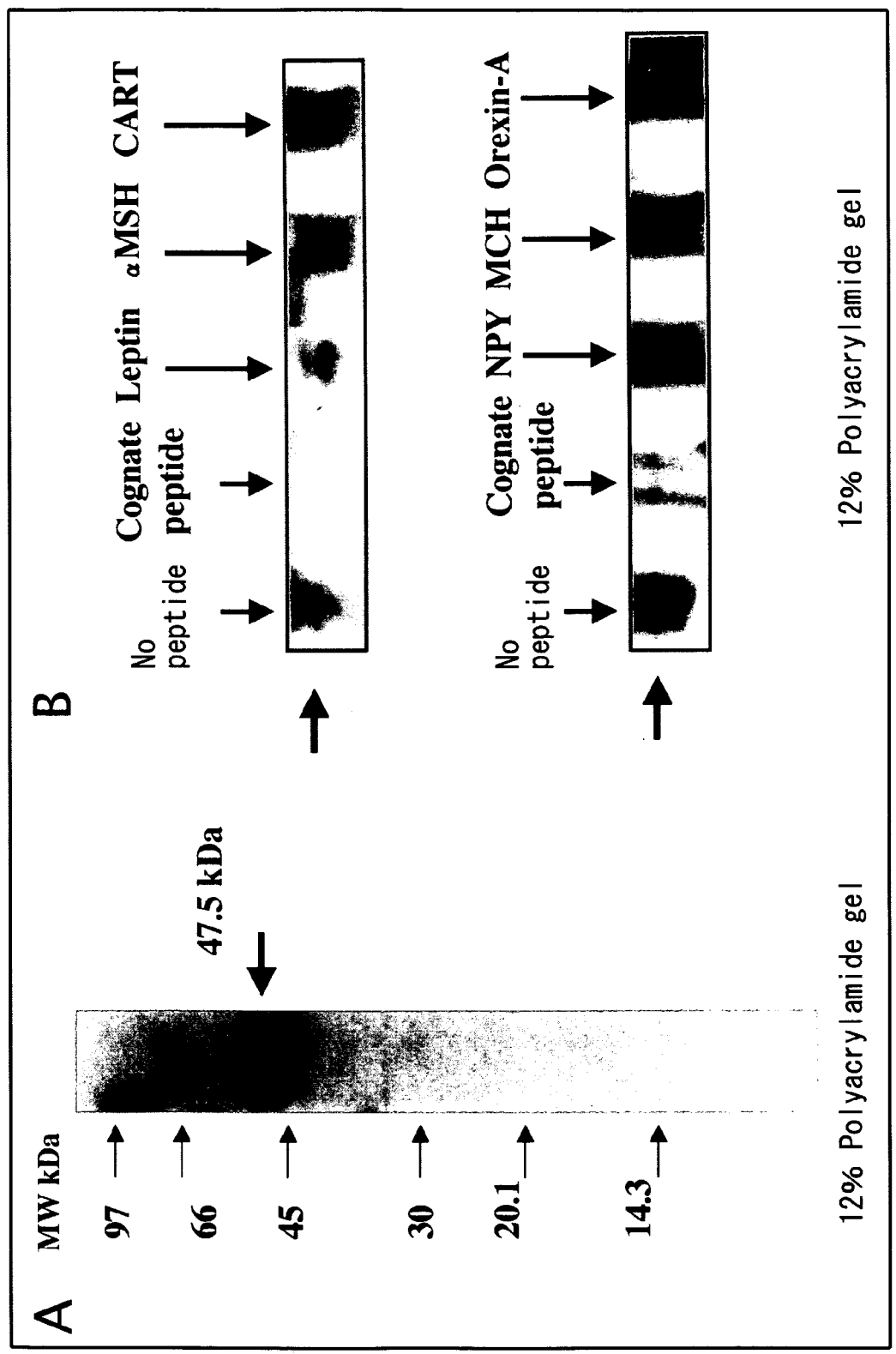

A of FIG. 27 shows an image of Western blotting carried out with anti-nesfatin-1 antibody using protein extracts from the rat brain. B of FIG. 27 shows an image of Western blotting at about 47.5 kd carried out after anti-nesfatin-1 antibody and various peptides were previously reacted. In the top of B of FIG. 27, the types of peptides reacted to anti-nesfatin-1 antibody were no peptides, NAP1-Ab peptide (cognate peptide), leptin, αMSH and CART from the left, and in the bottom of B of FIG. 27, no peptides, NAP1-Ab peptide (cognate peptide) NPY, MCH and Orexin-A from the left.

Figure 28:
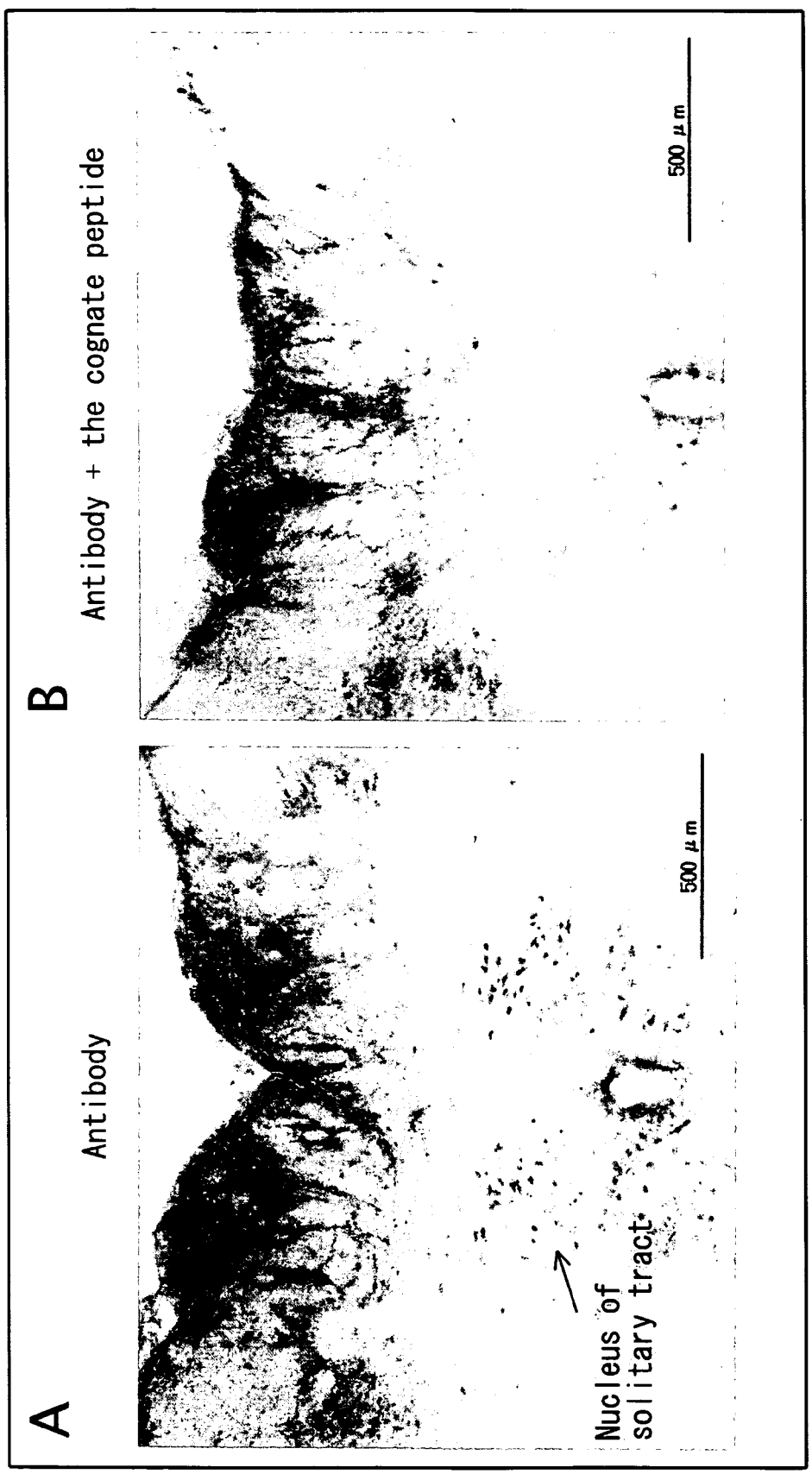

A of FIG. 28 shows an image of immunohistochemical stain using a NAP peptide antibody in the brain tissue containing the medulla oblongata. B of FIG. 28 shows an image of immunohistochemical stain carried out after an antibody against the NAP peptide and the NAP peptide (cognate peptide) were previously reacted.

Figure 29:
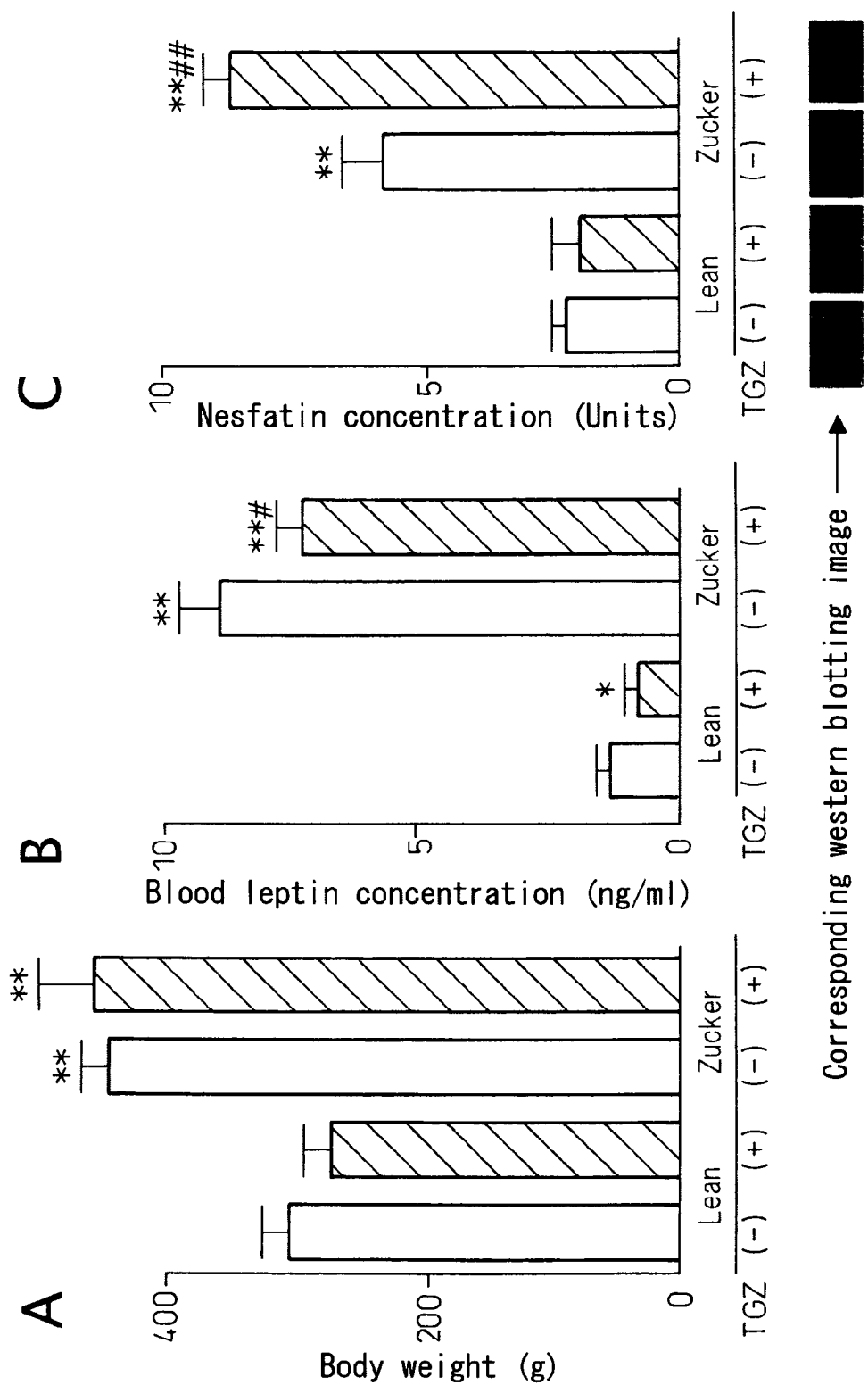

A of FIG. 29 is a graph showing the body weight of the group (TGZ: +) in which the troglitazone-containing food was given to the normal rats (Lean) and the Zucker fa/fa rats (Zucker), and the group (TGZ: −) in which the troglitazone-free food was given thereto. B of FIG. 29 is a graph showing the concentration of leptin in the blood of the group (TGZ: +) in which the troglitazone-containing food was given to the normal rats (Lean) and the Zucker fa/fa rats and the group (TGZ: −) in which the troglitazone-free food was given thereto. C of FIG. 29 is a graph showing the concentration of nesfatin in the brain of the group (TGZ: +) in which the troglitazone-containing food was given to the normal rats (Lean) and the Zucker fa/fa rats and the group (TGZ: −) in which the troglitazone-free food was given thereto. In FIG. 29, * and ** represent a significant difference $P<0.05$ and $P<0.01$, respectively, relative to the group (TGZ: −) in which the troglitazone-free food was given to the normal rats (Lean), and in FIG. 29 # and ## represent a significant difference P<0.05 and P<0.01, respectively, relative to the group (TGZ: −) in which the troglitazone-free food was given to the Zucker fa/fa rats.

Figure 30:
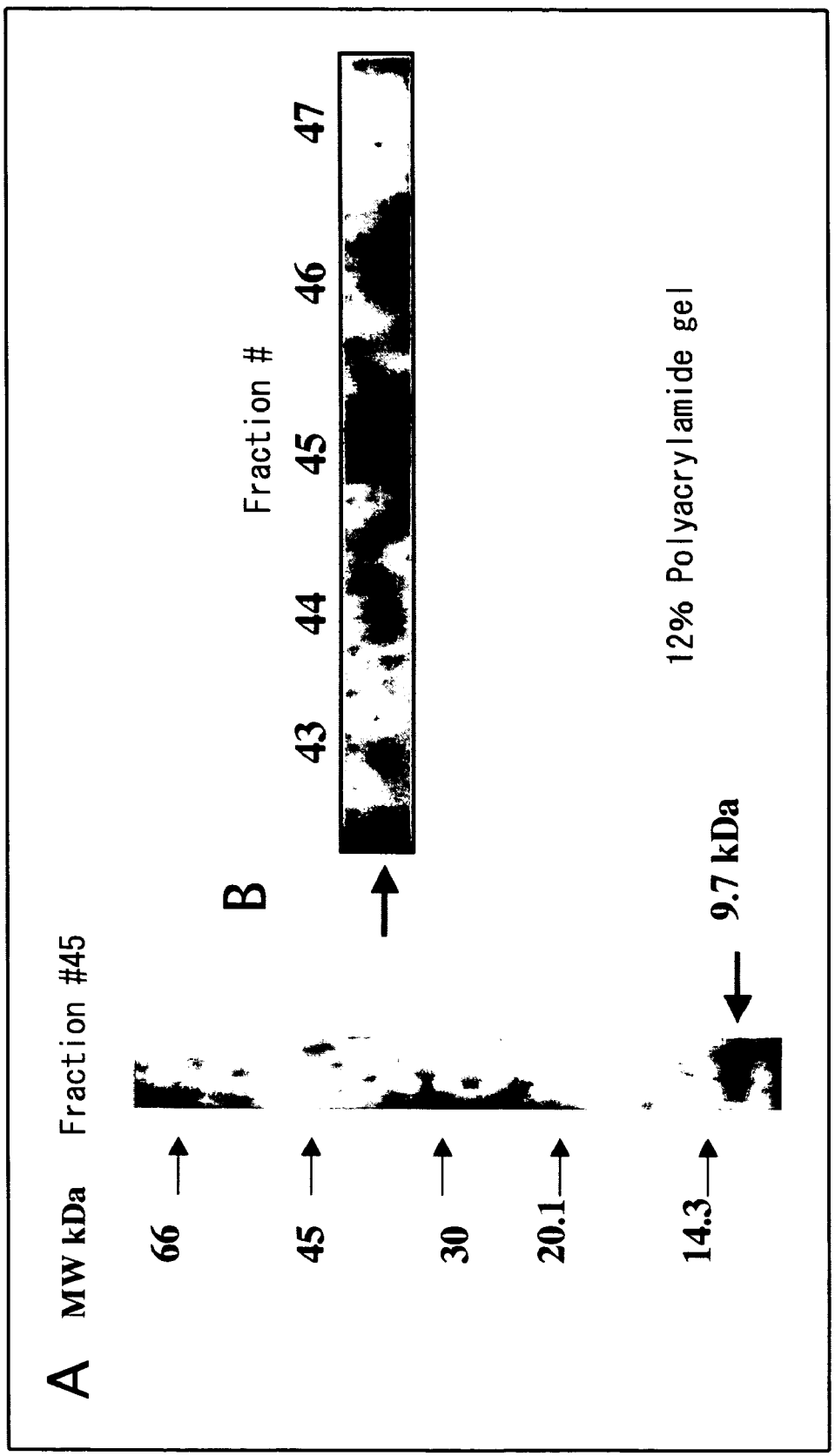

A of FIG. 30 shows an image of Western blotting of the fraction No. 45 obtained by fractionating a peptide extract from the rat hypothalamus by HPLC. B of FIG. 30 shows an image of the part at a molecular weight of about 9.7 kd in the Western blotting image of the fraction Nos. 43-47 obtained by fractionating a peptide extract from the rat hypothalamus by HPLC.

Figure 31:
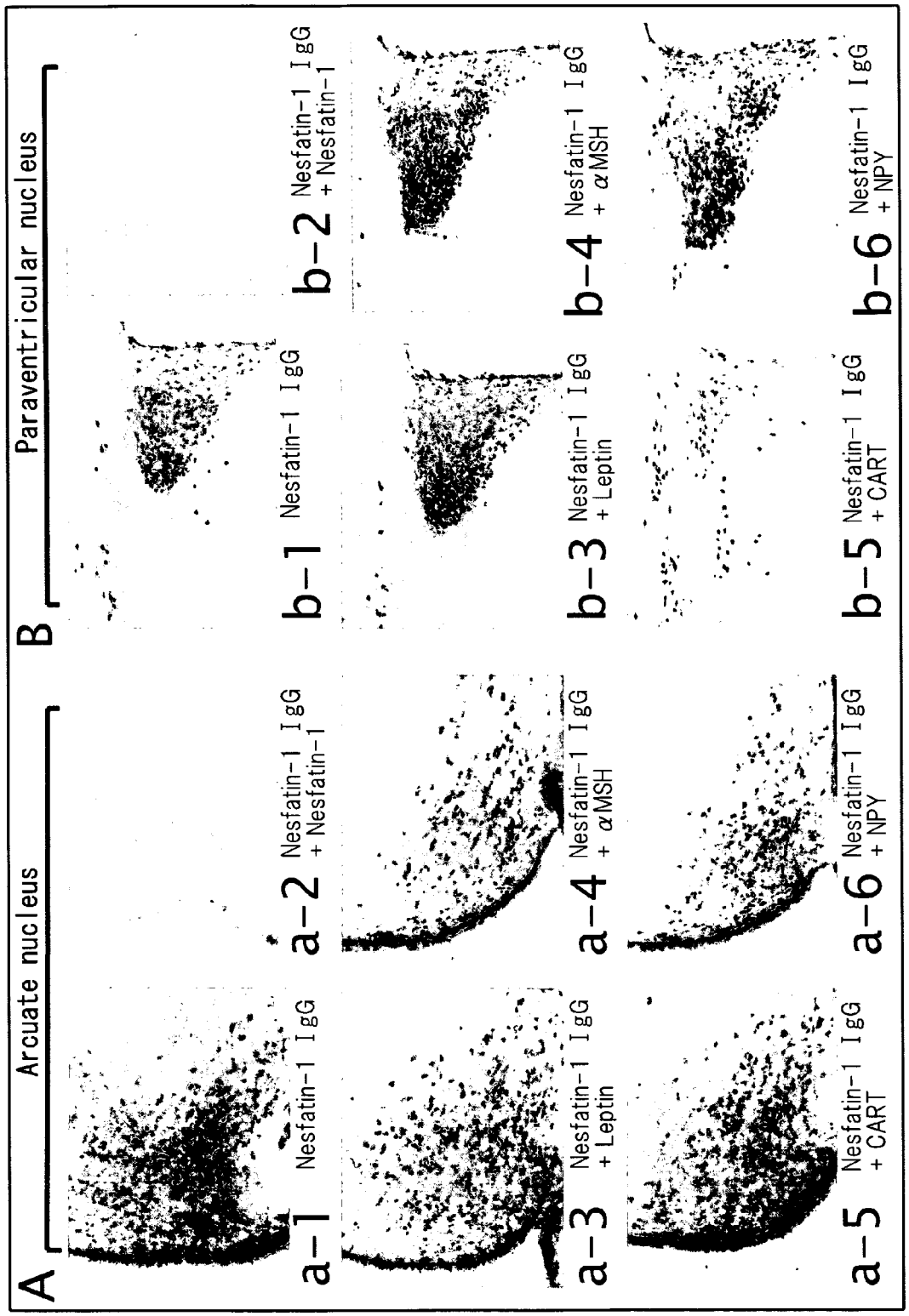

A of FIG. 31 shows the result of immunohistochemical stain using an anti-nesfatin-1 antibody in the rat brain tissue containing the arcuate nucleus, and the result of immunohistochemical stain carried out after the anti-nesfatin-1 antibody and various peptides were previously reacted. In A of FIG. 31, a-1 represents an image of immunological stain with anti-nesfatin-1 antibody, a-2 to a-6 represent an image of immunological stain when the anti-nesfatin-1 antibody was previously reacted with the nesfatin-1 peptide (a-2), leptin (a-3), αMSH (a-4), CART (a-5) and NPY (a-6), respectively.

B of FIG. 31 shows the result of immunohistochemical stain using an anti-nesfatin-1 antibody in the rat brain tissue containing the paraventricular nucleus, and the result of immunohistochemical stain carried out after the anti-nesfatin-1 antibody and various peptides were previously reacted. In B, b-1 represents an image of immunological stain with the anti-nesfatin-1 antibody, b-2 to b-6 represent an image of immunological stain when the anti-nesfatin-1 antibody was previously reacted with nesfatin-1 peptide (b-2), leptin (b-3), αMSH (b-4), CART (b-5) and NPY (b-6), respectively.

Figure 32:
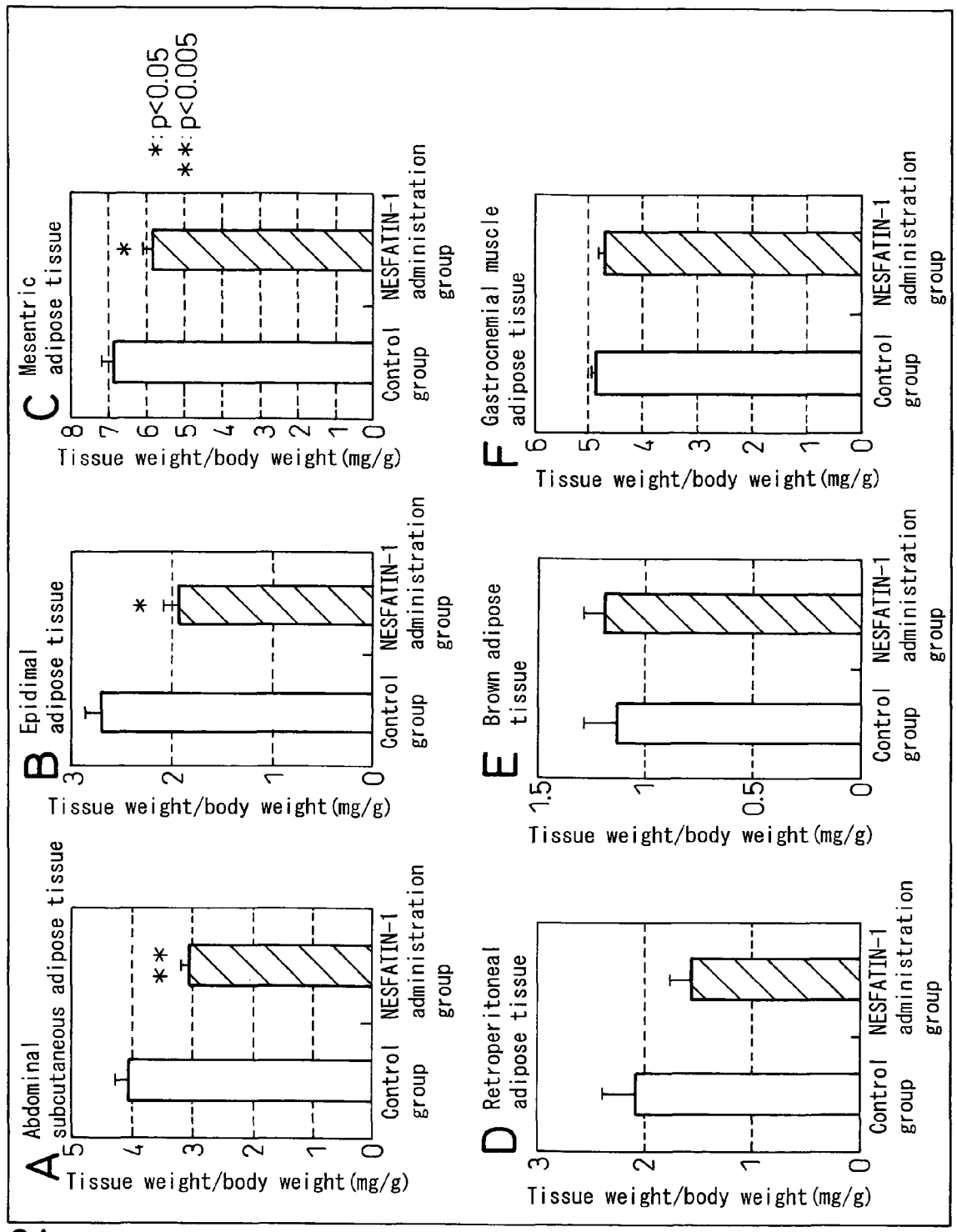

FIG. 32 is a graph of the result showing the ratio (tissue weight/body weight, mg/g) of tissue weight of the abdominal subcutaneous adipose tissue (A), the epididymal adipose tissue (B), the mesenteric adipose tissue (C), the retroperitoneal adipose tissue (D), the brown adipose tissue (E) and the gastrocnemial muscle (F) obtained from the rats that were given nesfatin-1 or physiological saline alone for 10 days relative to the body weight of each individual. In FIG. 32, * and ** represent a significant difference P<0.05 and P<0.005, respectively, relative to the physiological saline-administration group.

Figure 33:
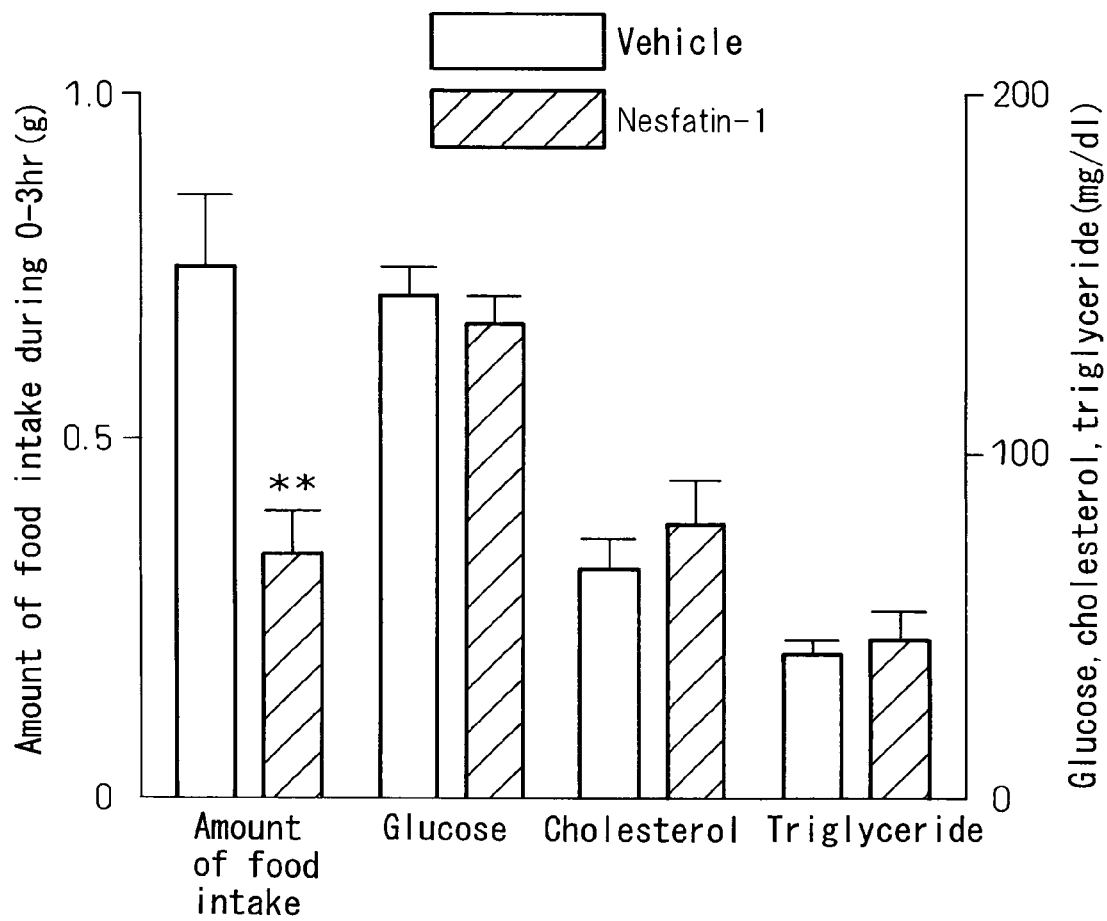

FIG. 33 is a graph of the assay result of the amount of food intake, blood glucose, total cholesterol and triglyceride when nesfatin-1 or physiological saline alone was intraperitoneally given to the mouse. In FIG. 33, the white box and the hatched box represent the physiological saline administration group and the nesfatin-1 administration group, respectively.

In accordance with the present invention, a factor involved in food intake control and body weight control can be obtained by using a PPARγ agonist. Also, by using nesfatin, nesfatin-1, nesfatin-1M30, nesfatin-1M16, nesfatin-1M14, nesfatin-1M10M, NUCB1-M30, NUCB1-M16, NUCB1-M14 and NUCB1-M10M, diseases associated with metabolic and food intake disorders such as obesity or adiposis and nervous hyperphagia, and type 2 diabetes mellitus, impaired glucose tolerance, hypertension, hyperlipidemia, hyperuricemia, fatty liver, cardiac diseases, cerebral vascular diseases, sleep apnea syndrome, orthopedic diseases such as osteoarthritis, menstrual disorders and diseases associated with adiposis such as malignant tumors can be prevented or treated. Furthermore, by using a substance such as antibody that suppresses the activity of nesfatin, nesfatin-1 or nesfatin-1M30, diseases associated with nutritional and food intake disorders such as anorexia and cibophobia in post-surgery and/or cancer patients can be prevented or treated.

BEST MODE FOR CARRYING OUT THE INVENTION

<Method of Obtaining a Factor Involved in Food Intake Control and/or Body Weight Control>

The present invention relates to a method of obtaining a factor that is involved in food intake control and/or body weight control, comprising the steps of reacting a thiazolidine dione compound having a PPARγ agonistic activity to a mammalian cell, and identifying a gene of which expression is induced by said compound.

As used herein "food intake control" refers to the control of the amount of food in animals or meals in humans (both are collectively referred to hereinafter as feeding etc.) during a certain period, or the control of the total calories taken from feeding etc. during a certain period. The control of food intake also includes the control of events such as appetite or the satiety that motivates feeding.

As used herein "the suppression of food intake" refers to the state in which the amount of feeding etc. or the total amount of calories taken in by feeding etc. is decreased compared to when no control of food intake is being done, or the state in which the growing trend of the amount of feeding etc. or the total amount of calories taken in by feeding etc. is being suppressed compared to when no control of food intake is being done. Also, the suppression of food intake includes states such as reduced appetite and enhanced satiety feeling.

On the other hand, "the enhancement of food intake" as used herein refers to the state in which the amount of feeding etc. or the total amount of calories taken in by feeding etc. is increased compared to when no control of food intake is being done, or the state in which the declining trend of the amount of feeding etc. or the total amount of calories taken in by feeding etc. is being suppressed compared to when no control of food intake is being done. Also, enhanced appetite includes states such as an increased appetite and a suppressed feeling of satiety.

"The control of body weight" as used herein refers to controlling the absolute body weight value, the body mass index (an index that employs body weight and body length) or the body fat percentage. As used herein "the suppression of body weight gain" refers to the state in which the absolute body weight value, the body mass index or the body fat percentage are decreased or maintained compared to when no control of body weight is being made, or the state in which the growing trend of the absolute body weight value, the body mass index or the body fat percentage is being suppressed compared to when no control of body weight is being made.

"The suppression of the body fat gain" as used herein refers to the state in which the body fat percentage is decreased or maintained compared to when no control of body weight is being done, or the state in which the growing trend of the body fat percentage is suppressed compared to when no control of body weight is being done. "The enhancement of body weight gain" refers to the state in which the absolute body weight value, the body mass index or the body fat percentage are increased or maintained compared to when no control of body weight is being done, or the state in which the growing trend of the absolute body weight value, the body mass index or the body fat percentage is suppressed compared to when no control of body weight is being done, and it is also called herein "the suppression of body weight reduction". In the case of humans, as the representative body mass index, height BMI (body mass index) is used, which is calculated from body weight (kg)÷height (m)÷height (m), and is expressed in units of Kg/m². Thus, the effect of such a suppression of body weight gain or an enhancement of body weight gain can also be expressed using BMI as an index. Also, the body fat percentage is indicated by a percentage of the weight of body fat in body weight, it can be determined by the body density method, the body moisture method, the body potassium-determining method, the impedance method, the dual X-ray absorption method, the neutron activation method, the near infrared spectroscopic method, the skinfold thickness-determining method, the imaging method and the like (The Japanese Journal of Clinical Medicine (Nippon Rinsho) Vol. 61, Supplement 6, pp. 357-396, 2003, issued by Nippon Rinsho K.K.).

As used herein "thiazolidine dione compounds having a PPARγ agonist activity" include, for example, troglitazone, pioglitazone, rosiglitazone, and roboglitazone etc., and troglitazone was first put into clinical use.

Cells as used in the present invention include a non-small cell lung cancer cell line, an adipose cell and a cerebral nerve-derived cell, but they are not limiting and any cells that express PPARγ can be used.

As the method of reacting said compound to a mammalian cell, as described below, there is a method in which said cell is cultured under stimulation by said compound (Satoh et al., Oncogene, England, 2002, Vol. 21, pp. 2171-2180).

The gene, of which expression is induced by the above compound, can be identified using, for example, a method in which the gene of which expression was specifically induced is subjected to the subtraction method or the DNA array analysis and the like (Satoh et al., Oncogene, England, 2002, Vol. 21, pp. 2171-2180). In order to select a gene encoding a factor that is extracellularly secreted from among the genes that are specifically induced by the activation of PPARγ, the nucleotide sequence of the gene is analyzed and can be selected depending on whether the secretary signal peptide is being encoded or not. Furthermore, as the method of selecting a gene involved in food intake control and/or body weight control among those genes, there can be mentioned immunological detection (illustrated in Working Example 3) or a histochemical method (illustrated in Working Examples 4 and 9) with a tissue extract using a brain sample containing the hypothalamus of a human or an animal, and an antibody that binds to a polypeptide encoded by said gene, and a method of confirming the expression in the hypothalamus using such as the in situ hybridization method (illustrated in Working Example 8) and the RT-PCR method.

For the gene thus obtained that is involved in food intake control and/or body weight control, the nucleotide sequence can be analyzed to identify the amino acid sequence of the encoded polypeptide. A peptide or a polypeptide comprising the amino acid sequence of the polypeptide obtained or a partial amino acid sequence thereof can be prepared using a genetic engineering method or a chemical synthetic method.

By introducing the polypeptide thus obtained or a nucleic acid molecule encoding said peptide introduced in a form that allows in vivo expression locally or systemically into a test animal, and then by examining changes in the amount of food intake by said animal and/or body weight, the polypeptide or the gene involved in food intake control and/or body weight control can be selected from among the polypeptide obtained or the gene encoding said polypeptide. In another method, by introducing an antibody that binds to the polypeptide thus obtained or an antisense oligonucleotide molecule or a RNAi molecule capable of suppressing the expression of the gene encoding said polypeptide locally or systemically into a test animal, and then by examining changes in the amount of food intake by said animal and/or body weight, the polypeptide or the gene involved in food intake control and/or body weight control can be selected from among the polypeptide obtained or the gene encoding said polypeptide.

<A Polypeptide Having an Activity of Suppressing Food Intake and/or Suppressing Body Weight Gain>

The present invention relates to a polypeptide obtained by the above method, said polypeptide having an activity of suppressing food intake and/or suppressing body weight gain. As such a polypeptide, there can be mentioned a polypeptide encoded by the nesfatin gene of which the function had not been identified, and it was found for the first time by the present inventors that said polypeptide has the above function. In accordance with the present invention, it was found that the nesfatin gene is expressed in the hypothalamus of the brain that is said to control appetite (illustrated in Working Examples 4, 8, 9, 24 and 26), and that the nesfatin polypeptide administered into an animal brain causes reduction in the amount of food intake and the body weight of the animal (illustrated in Working Examples 6 and 25). It was further demonstrated that, by suppressing the function of the nesfatin polypeptide or by inhibiting the expression of the nesfatin gene, the enhancement in food intake and body weight gain can be induced in animals (illustrated in Working Example 7 and Working Example 15).

As examples of the nesfatin polypeptide, there can be mentioned those that include amino acid sequences set forth in SEQ ID NOs: 3, 6 and 9. A precursor nesfatin polypeptide containing a human signal peptide is shown in SEQ ID NO: 2. When the precursor nesfatin polypeptide is extracellularly secreted the signal peptide is cleaved, and thus a human matured nesfatin polypeptide, that substantially has an activity, produces a form set forth in SEQ ID NO: 3. As used herein, the nesfatin polypeptide is simply called nesfatin.

Furthermore, the continued intensive and extensive study on the nesfatin polypeptide having said activity of suppressing food intake and/or suppressing body weight gain led to the invention of a polypeptide with a novel structure having an activity of suppressing food intake and/or suppressing body weight gain. The discovery of this polypeptide with a novel structure was based on the investigation on various peptides derived from the nesfatin polypeptide considering a possibility that the nesfatin polypeptide may undergo cleavage by proteolytic enzymes when they are extracellularly secreted. As a result, it was found that a polypeptide comprising 82 amino acids having a sequence corresponding to the amino acids No. 25 to 106 of the nesfatin polypeptide set forth in SEQ ID NO: 5 has an activity of suppressing food intake and/or suppressing body weight gain, and reducing body fat percentage (illustrated in Working Example 12, Working Example 13 and Working Example 34), and that by inhibiting the suppression of function of the nesfatin-1 polypeptide, enhancement in food intake can be induced in animals. Based on the above, said polypeptide was named nesfatin-1 (SEQ ID NO: 14). Though the nesfatin polypeptide has a calcium-binding domain, a DNA-binding domain etc. in its structure, the sequence of nesfatin-1 polypeptide has no such existing domain structures, and thus to obtain this nesfatin-1 polypeptide could not be absolutely expected from the conventional technology. Also, peptide hormones in vivo are known to be expressed in the form of a precursor protein, which then is cleaved by a proteolytic enzyme etc., and there are many reports that a prohormone convertase (or proprotein convertase: PC) is involved in the activity. In the human full-length nesfatin polypeptide set forth in SEQ ID NO: 2, the mouse precursor nesfatin polypeptide set forth in SEQ ID NO: 5 and the rat precursor nesfatin polypeptide set forth in 8, there is a common site (see Working Example 10) that is likely to be cleaved by a subtype of the prohormone convertase, PC1/3 (EC 3.4.21.93, Seidahi et al., DNA and Cell Biology, USA, Vol. 9, 1990, pp. 415-424) or PC2 (EC 3.4.21.94, Seidah et al., DNA and Cell Biology, USA, Vol. 9, 1990, pp. 415-424), and a possibility was demonstrated that nesfatin-1 polypeptides set forth in SEQ ID NO: 13 to SEQ ID NO: 15, respectively, are excised.

Also, when a nesfatin (Mut) having a mutation at the site cleaved with prohormone convertase was given to the ventricle of the rat brain, an unexpected result was obtained that the effect of suppressing food intake could not be noted (Working Example 14). Therefore, this suggested a possibility that the nesfatin-1 polypeptide is a functional molecule involved in food intake control and/or body weight the control in a living body, and that in order for the nesfatin polypeptide to be functional, the process of being processed by a protease such as prohormone convertase is important.

From the foregoing, the fact was not known at all that nesfatin/NEFA functions as a hormone precursor like proinsulin, and thus it was found for the first time in the present invention after the expression site for nesfatin/NEFA and the expression of nesfatin/NEFA in cells that express PC1/3 and PC2 were analyzed and the activity and structure were intensively studied. Also, since there are secretary proteins that are not processed by PC1/3 and PC2 despite the presence of sequences Arg-Arg or Lys-Arg that are recognition sites of the prohormone convertase, it cannot be easily inferred that nesfatin-1 is excised from nesfatin/NEFA and exhibits the activity of suppressing food intake and/or suppressing body weight gain.

From the foregoing, the present invention also relates to nesfatin-1 polypeptides set forth in SEQ ID NOs: 13-15. As described above, said nesfatin-1 polypeptides have an activity of suppressing food intake and/or suppressing body weight gain. The amino acid sequence of mouse nesfatin-1 polypeptide is shown in SEQ ID NO: 14. A nesfatin polypeptide having such a sequence can be obtained by cleaving the nesfatin polypeptide set forth in SEQ ID NO: 14 with the prohormone convertase followed by purification with a technique such as reverse phase chromatography or by performing the step of binding to and releasing from an antibody against the nesfatin-1 polypeptide described below.

Furthermore, after continued intensive investigation on the structure of the nesfatin-1 polypeptide and the activity of suppressing food intake and/or suppressing body weight gain, it was found that a novel polypeptide comprising 30 amino acids having a sequence corresponding to amino acids 24 to 53 of the nesfatin polypeptide set forth in SEQ ID NO: 14 exhibits an activity of suppressing food-intake and/or suppressing body weight gain (illustrated in Working Example 20), and said polypeptide was named nesfatin-1M30 (SEQ ID NO: 41). The discovery of the nesfatin-1M30 polypeptide indicates that when a polypeptide that contains the part corresponding to nesfatin-1M30 is present even after the nesfatin polypeptide or the nesfatin-1 polypeptide was physiologically or artificially cleaved or digested, said polypeptide retains an activity of suppressing food intake and/or suppressing body weight gain.

Furthermore, for the structure of nesfatin-1M30 comprising 30 amino acids, the activity of the site having an activity of suppressing food intake was investigated. The result indicated that nesfatin-1M16 comprising 16 amino acids which is a partial peptide of its peptide, nesfatin-1M14 comprising 14 amino acids, and nesfatin-1M10M comprising 10 amino acids have an activity of suppressing food intake and/or suppressing body weight gain (Working Example 22).

When the sequences of nesfatin-1 comprising 82 amino acids set forth in SEQ ID NO: 13, SEQ ID NO: 14 or SEQ ID NO: 15 was analyzed on homology with the amino acid sequence of a factor having an activity of controlling food intake, no sequences having a high homology were found, and thus it was impossible to estimate that these nesfatin-1M30, nesfatin-1M16, nesfatin-1M14 and nesfatin-1M10M have an activity of suppressing food intake and/or suppressing body weight gain based on the conventional technology. It was also demonstrated that these nesfatin-1M30, nesfatin-1M16, nesfatin-1M14 and nesfatin-1M10M are active even if they are derived from inactive human-derived nesfatin or nesfatin-1.

Thus, the present invention relates to the nesfatin-1M30 polypeptide set forth in SEQ ID NOs: 39-41, the nesfatin-1M16 polypeptide set forth in SEQ ID NO: 65, 68 or 71, the nesfatin-1M14 polypeptide set forth in SEQ ID NO: 66, 69 or 72, or the nesfatin-1M10M polypeptide set forth in SEQ ID NO: 68, 70 or 73. As described above, said nesfatin-1M30 polypeptide, nesfatin-1M16 polypeptide, nesfatin-1M14 polypeptide and nesfatin-1M10M polypeptide have an activity of suppressing food intake and/or suppressing body weight gain. Also, the amino acid sequence of human nesfatin-1M30 polypeptide is shown in SEQ ID NO: 39. Also, the polypeptides comprising an amino acid sequence set forth in SEQ ID NO: 39, SEQ ID NO: 40 or SEQ ID NO: 41 excluding the polypeptides comprising an amino acid sequence set forth in SEQ ID NO: 3, SEQ ID NO: 6 or SEQ ID NO: 9, SEQ ID NO: 13, SEQ ID NO: 14 or SEQ ID NO: 15 are included in the nesfatin-1M30 polypeptide. As examples of such polypeptides, there can be mentioned those polypeptides that were physiologically or artificially cleaved or digested from the nesfatin polypeptide or the nesfatin-1 polypeptide and that contain a sequence corresponding to nesfatin-1M30.

With regard to Nucleobindin I (NUCB1) that has a high homology with NEFA/nesfatin in terms of the amino acid sequence and the nucleotide sequence of the gene and that belongs to the same family, it was investigated whether NUCB1-M30 which is a site corresponding to nesfatin-1M30 of NUCB1 exhibits a similar activity. The result revealed that NUCB1-M30 also has an activity of suppressing food intake and/or suppressing body weight gain (Working Example 23). When human, rat and mouse nesfatins were compared, it was found, the amino acid sequence has been highly conserved at the site corresponding to nesfatin-1 of nesfatin and NUCB1 of each species, specifically at the site corresponding to nesfatin-1M30. From the foregoing, it is inferred that NUCB1-M16 comprising 16 amino acids of NUCB1, NUCB1-M14 comprising 14 amino acids and NUCB1-M10M comprising 10 amino acids of NUCB1 also have an activity of suppressing food intake and/or suppressing body weight gain similarly to the nesfatin-1M16 polypeptide, the nesfatin-1M14 polypeptide and the nesfatin-1M10M polypeptide.

Thus, the present invention relates to the NUCB1-M30 polypeptide set forth in SEQ ID NOs: 101-103, the NUCB1-M16 polypeptide set forth in SEQ ID NO: 107, 110 or 113, the NUCB1-M14 polypeptide set forth in SEQ ID NO: 108, 111 or 114, or the NUCB1-M10M polypeptide set forth in SEQ ID NO: 109, 112 or 115. Said NUCB1-M30 polypeptide, NUCB1-M16 polypeptide, NUCB1-M14 polypeptide and NUCB1-M 10M polypeptide also have an activity of suppressing food intake and/or suppressing body weight gain as described above.

The present invention also relates to a polypeptide that has a homology of at least 60% with any of the amino acid sequences set forth in SEQ ID NOs: 13-15, 39-41, 65-73, 101-103 and 107-115 and that has an activity of suppressing food intake and/or suppressing body weight gain. The homology with the amino acid sequence set forth in SEQ ID NOs: 13-15, 39-41, 65-73, 101-103 and 107-115 is preferably 70% or greater and more preferably 80% or greater. A representative example thereof includes the nesfatin-1M30 polypeptide of a non-human animal. For example, as a polypeptide that has a homology of 60% or greater with the amino acid sequence of the human nesfatin-1M30 polypeptide (SEQ ID NO: 39) and that has an activity of suppressing food intake and/or suppressing body weight gain, there can be mentioned, but not limited to, a mouse nesfatin-1M30 polypeptide (SEQ ID NO: 41) and a rat nesfatin-1M30 polypeptide (SEQ ID NO: 40).

Among the polypeptides comprising an amino acid sequence that has a homology of at least 60% with any of the amino acid sequences set forth in SEQ ID NOs: 13-15, 39-41, 65-73, 101-103 and 107-115, the selection of a polypeptide having an activity of suppressing food intake and/or suppressing body weight gain may be performed by introducing said polypeptide or a nucleic acid molecule encoding said polypeptide locally or systemically into a test animal, and then selecting a polypeptide that suppresses the amount of food intake and/or the body weight of said animal. In an alternative method, the selection may be performed by introducing an antibody against said polypeptide or an antisense oligonucleotide molecule or a RNAi molecule that can suppress the expression of a gene encoding said polypeptide locally or systemically into a test animal, and then selecting a polypeptide that suppresses the amount of food intake and/or the body weight of said animal. Such a polypeptide is referred to hereinafter as altered nesfatin-1M30, altered nesfatin-1M16, altered nesfatin-1M14, altered nesfatin-1M10M, altered NUCB1-M30, altered NUCB1-M16, altered NUCB1-M14 and altered NUCB1-M10M.

Furthermore, the present invention also relates to a polypeptide that comprises an amino acid sequence in which some of the amino acids have been deleted, inserted or substituted in any of the amino acid sequences set forth in SEQ ID NOs: 13-15, 39-41, 65-73, 101-103 and 107-115 and that has an activity of suppressing food intake and/or suppressing body weight gain. Such a polypeptide can be obtained by replacing one or more amino acid residues with amino acids that are chemically or structurally similar to said amino acids in an amino acid sequence set forth in, for example, SEQ ID NOs: 13-15, 39-41, 65-73, 101-103 or 107-115. Specific embodiments of the substitution of amino acids that are chemically or structurally similar, i.e. the substitution of highly conserved amino acids, are well known to a person skilled in the art. For example, chemically or structurally, glycine (Gly) is similar to proline (Pro), alanine (Ala) and valine (Val), leucine (Leu) is similar to isoleucine (Ile), glutamic acid (Glu) is similar to glutamine (Gln), aspartic acid (Asp) is similar to asparagine (Asn), cysteine (Cys) is similar to threonine (Thr), Thr is similar to serine (Ser) and Ala, and lysine (Lys) is similar to arginine (Arg). Further, as alternative method, a person skilled in the art can easily refer to a amino acid matrix method, which represents in what extent can be made substitution of a amino acid, as a matrix, such as PAM (Wilbur, Molecular Biology and Evolution) (USA), 1985, Vol. 2, pp. 434-447), BLOSUM (Henikoff et al., Proceedings of the National Academy of Sciences of the United States of America) (USA) 1992, Vol. 89, pp. 10915-10919, and easily substitute an amino acid, considering height of its score.

Also, among the polypeptides comprising an amino acid sequence in which some of the amino acids have been deleted, inserted or substituted in any of the amino acid sequences set forth in SEQ ID NOs: 13-15, 39-41, 65-73, 101-103 and 107-115, the selection of a polypeptide that has an activity of suppressing food intake and/or suppressing body weight gain can be performed in a manner similar to that described in the selection of the above modified nesfatin. Hereinbelow, such a polypeptide is also referred to as altered nesfatin-1M30.

Furthermore, the present invention also relates to a polypeptide that comprises an amino acid sequence having a homology of at least 60% with any of the amino acid sequences set forth in SEQ ID NOs: 3, 6 and 9; or an amino acid sequence in which some of the amino acids have been deleted, inserted or substituted in any of the amino acid sequences set forth in SEQ ID NOs: 3, 6 and 9, and that has an activity of suppressing food intake and/or suppressing body weight gain. Similarly to the above-mentioned altered products, said polypeptide is also referred to as an altered nesfatin. Said altered nesfatin, similarly to the above-mentioned altered nesfatin-1M30 etc., preferably has a homology of 70% or greater and more preferably 80% or greater with the amino acid sequence set forth in SEQ ID NOs: 3, 6 or 9.

As described above, it was demonstrated by the present invention that for a nesfatin polypeptide to be functional, the step of its being processed by a protease contained in the living body such as prohormone convertase is important. For that purpose, said altered nesfatin preferably is a polypeptide that produces in the living body nesfatin-1, nesfatin-1M30, nesfatin-1M16, nesfatin-1M14, nesfatin-1M10M, NUCB1-M30, NUCB1-M16, NUCB1-M14, or NUCB1-M10M (a polypeptide comprising an amino acid sequence set forth in SEQ ID NOs: 13-15, 39-41, 65-73, 101-103 or 107-115), or an altered product thereof. It is necessary for such an altered nesfatin to have a recognition site, in its amino acid sequence, for a cleaving enzyme such as a protease contained in the living body. As such a cleaving enzyme, there can be mentioned for example prohormone convertase (proprotein convertase: PC), and as such a prohormone convertase, there can be mentioned for example furin, PC1 (also known as PC3), PC2, PACE4, PC4, PC6 (also known as PC5) and LPC (also known as PC7 or PC8) (The FASEB Journal, 1216, vol. 17, July 2003). As long as the protease produces nesfatin-1 etc. in the periphery or the ventricle of the brain, the type of the protease is not specifically limited.

For similar reasons, the position of the recognition site for said cleaving enzyme is not specifically limited. However, based on the experimental results on mouse-derived nesfatin-1, nesfatin-2, nesfatin-3 and nesfatin-2/3 (Working Example 10), altered nesfatin is preferably established so as to contain at least one recognition site for a cleaving enzyme contained in the living body in between the amino acids 82 and 83 (a recognition site for prohormone convertase that produces nesfatin-1) of SEQ ID NO: 3, 6 or 9 and between the amino acids 163 and 164 (another recognition site for prohormone convertase) of SEQ ID NO: 3, 6 or 9, i.e. in an amino acid sequence corresponding to the amino acid numbers 82-162 of SEQ ID NO: 3, 6 or 9, in that it does not affect the activity of the resulting polypeptide.

Also, the confirmation of whether said altered product have an activity of suppressing food intake and/or suppressing body weight gain including an activity of being cleaved and becoming active in vivo can be made, as for the selection of the above-mentioned altered nesfatin-1M30 etc., by introducing said polypeptide or a nucleic acid molecule encoding said polypeptide locally or systemically into a test animal, and then selecting a polypeptide that suppresses the amount of food intake and/or the body weight of said animal. In an alternative method, the selection may be performed by introducing an antibody against said polypeptide or an antisense oligonucleotide molecule or a RNAi molecule that can suppress the expression of a gene encoding said polypeptide locally or systemically into a test animal, and then selecting a polypeptide that suppresses the amount of food intake and/or the body weight of said animal.

The nesfatin polypeptide, nesfatin-1 polypeptide, nesfatin-1M30, nesfatin-1M16, nesfatin-1M14, nesfatin-1M10M, NUCB1-M30, NUCB1-M16, NUCB1-M14, or NUCB1-M10M of the present invention include those in which at least one amino acid has been added to the N terminal or C terminal thereof. Such nesfatin polypeptides include those in which a methionine residue, an acetyl residue or a pyroglutamic acid residue or the like has been added to the N terminal of the amino acid sequence set forth in SEQ ID NO: 3, SEQ ID NO: 6 or SEQ ID NO: 9, and those in which a suitable tag sequence (typically a histidine tag or a FLAG tag) has been added to the N terminal or the C terminal. Nesfatin polypeptides etc. having such construction have an advantage that they can be easily purified using a metal chelate carrier or antibody. Also, when nesfatin has been processed in the living body by prohormone convertase, it is thought, a polypeptide in which the recognition site for prohormone convertase has been added to the C terminal of nesfatin-1 is produced, and such a polypeptide is also encompassed by the present invention.

Also, the nesfatin polypeptide, the nesfatin-1 polypeptide, nesfatin-1M30, nesfatin-1M16, nesfatin-1M14, nesfatin-1M10M, NUCB1-M30, NUCB1-M16, NUCB1-M14, or NUCB1-M10M of the present invention include those in which at least one amino acid residue has been modified by a compound or a peptide. Such a nesfatin polypeptide includes, in addition to the sequence set forth in SEQ ID NO: 3, SEQ ID NO: 6 or SEQ ID NO: 9, polypeptides that are obtained by enzymatically or chemically associating a peptide other than the nesfatin polypeptide or a fluorescent substance etc. by a known method (Hermanson et al., Bioconjugate Techniques, USA, 1996, issued by Academic Press), and includes, for example, one in which the amino acid sequence of an Aequorea-derived fluorescence protein or a secretary alkaline phosphatase has been added (so-called fusion protein). The presence of these fusion proteins can be easily detected; for example, by determining fluorescence intensity for a fusion protein with an Aequorea-derived fluorescence protein, or by determining the intensity of color development, emission or fluorescence resulting from the reaction with said enzyme and its substrate for a fusion protein with a secretary alkaline phosphatase. For such a nesfatin polypeptide, an effect on food intake control and/or body weight control can be identified by investigating the activity by a method described in WOrking Example 6 etc.

The present invention relates to a pharmaceutical composition for suppressing food intake and/or suppressing body weight gain, said composition comprising as an active ingredient any of the nesfatin polypeptide, the nesfatin-1 polypeptide, nesfatin-1M30, nesfatin-1M16, nesfatin-1M14, nesfatin-1M10M, NUCB1-M30, NUCB1-M16, NUCB1-M14, or NUCB1-M10M, or altered products thereof (hereinafter referred to collectively as "the nesfatin polypeptide etc."), or a peptide comprising some of the amino acid sequences of said nesfatin polypeptide etc. The peptide comprising some of the amino acid sequence of said nesfatin polypeptide refers to a peptide in which some of the amino acid sequence of said polypeptide has been deleted within the extent of retaining the activity of suppressing food intake and/or suppressing body weight gain.

<A Pharmaceutical Composition for Treating or Preventing a Disease for which Enhanced Food Intake and Body Weight Gain is a Problem>

The present invention relates to a pharmaceutical composition for treating or preventing a disease for which enhanced food intake and body weight gain is a problem, said composition comprising, as an active ingredient, any of the above nesfatin polypeptide etc., or a peptide comprising some of the amino acid sequence of said polypeptide.

A pharmacological effect of the nesfatin polypeptide etc. of the present invention is demonstrated by the results of the administration of nesfatin polypeptide to the third ventricle of the rat brain (Working Examples 6 and 25), the administration of nesfatin-1 polypeptide into the third ventricle of the rat brain (Working Examples 12, 13, 27 and 34), the administration of nesfatin-1 polypeptide into the abdominal cavity or the subcutaneous of mouse (Working Examples 18 and 19), the administration of nesfatin-1M30 polypeptide to the abdominal cavity of mouse (Working Example 20). A pharmacological effect in pathological model animals is illustrated by the administration of nesfatin-1 polypeptide to the third ventricle of the brain in a model animal indicating leptin resistance, i.e., Zucker (fa/fa) rat (Working Example 17), and a pharmacological effect on pathology of leptin resistance, which is also a problem in human adiposis, is illustrated. Further, it is pharmacologically illustrated that food intake may be controlled through the mechanism different from melanocortine system, which is a known factor related to the control of food intake, by the administration experiment in Agouti yellow mouse (Working Example 18). By the illustrated facts, it is demonstrated that nesfatin polypeptide etc. may be used as a pharmaceutical composition for treating or preventing a disease for which enhanced food intake and body weight gain is a problem.

The diseases for which enhanced food intake and body weight gain is a problem include, for example, obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors. Obesity includes adiposis, a pathological condition that requires body weight reduction when a health problem associated with obesity is complicated or its complication is clinically predicted. Orthopedic diseases include osteoarthritis due to overweight, lumber disorders (spondylosis deformans), low back pain (acute low back pain) etc. Also malignant tumors include breast cancer, uterine cancer, colon cancer, kidney cancer, esophageal cancer, pancreatic cancer, liver cancer and gallbladder cancer.

The pharmaceutical composition of the present invention may contain any pharmaceutically acceptable additives. Formulations using pharmaceutically acceptable additives may be prepared by a method described in "Remington: The Science and Practice of Pharmacy, 20th edition, University of the Sciences in Philadelphia, Williams & Wilkins, issued on Dec. 15, 2000". One dosage form of such a pharmaceutical composition is presented as a liquid prepared by dissolving, suspending or emulsifying them in an aqueous or oleaginous solution. Such solvents used include, for example, distilled water, physiological saline etc. for injection as an aqueous liquid, and in addition, an osmoregulatory agent (for example, D-glucose, D-sorbitol, D-mannitol, and sodium chloride), a suitable solubilizing agent such as alcohols (for example, ethanol), polyalcohols (for example, propylene glycol, and polyethylene glycol), nonionic surfactants (for example, polysorbate 80, polyoxyethylenated hydrogenated castor oil 50) and the like may be used. Also, as the solvents, an oleaginous solution may be used, and said oleaginous solution includes sesame oil, soybean oil etc. and, as the solubilizing agent, benzyl benzoate, benzyl alcohol etc. may be used in combination. In such liquids, there can be used, as appropriate, additives such as buffers (such as phosphate buffers and acetate buffers), soothing agents (such as benzalkonium chloride and procaine hydrochloride), stabilizers (such as human serum albumin and polyethylene glycol), preservatives (such as ascorbic acid, erythorbic acid, and salts thereof), colorants (such as copper chlorophyll, β-carotene, Red No. 2, and Blue No. 1), preservatives (such as ascorbic acid, erythorbic acid, and salts thereof), antiseptics (such as paraoxybenzoate ester, phenol, benzethonium chloride and benzalkonium chloride), thickeners (such as hydroxypropyl cellulose, carboxymethyl cellulose, and salts thereof), stabilizers (such as human serum albumin, mannitol and sorbitol), and corrigents (such as menthol and citrus flagrances). Another dosage form of pharmaceutical compositions (in order to unify the expression with the above several "pharmaceutical compositions") includes solid forms such as powders, tablets, granules, capsules, pills, suppositories, and lozenges. In the case of solid forms that are administered in the form of oral preparations, additives used include excipients (such as crystalline cellulose, lactose and starch), lubricants (such as magnesium stearate and talc), binders (such as hydroxypropyl cellulose, hydroxypropyl methyl cellulose and macrogol), disintegrants (such as starch and carboxymethyl cellulose calcium), and the like. Also, as needed, there can be used antiseptics (such as benzyl alcohol, chlorobutanol, methyl paraoxybenzoate and propyl paraoxybenzoate), antioxidants, colorants, sweeteners and the like. Furthermore, another form also includes pharmaceutical compositions for application to mucosa, and for this form of formulations, in order to impart adsoptivity to mucosa and retentivity, there can be contained additives such as tackifiers, tackiness enhancers, thickener, thickening agent (such as mucin, agar, gelatin, pectin, carrageenan, sodium alginate, locust bean gum, xanthan gum, tragacanth gum, gum arabic, chitosan, pullulan, waxy starch, sucralfate, cellulose and its derivatives (such as hydroxypropyl methyl cellulose, polyglycerin fatty acid esters, acrylic-(meth)acrylic alkyl copolymers or salts thereof, and polyglycerin fatty acid esters). However, dosage forms of pharmaceutical compositions and solvents and additives to be delivered to the living body are not limited to the above, and can be selected, as appropriate, by a person skilled in the art.

For the purpose of ameliorating disease conditions, the above pharmaceutical composition can be administered orally or parenterally. In the case of oral administration, dosage forms such as granules, powders, tablets, capsules, liquids, syrups, emulsions or suspensions, and elixirs can be selected. In the case of parenteral administration, it can be transnasal agents, and liquids, suspensions, solid formulations can be selected. Other agents in the form of parenteral administration, it can be in the form of injections, and injections selected may be hypodermic injections, intravenous injections, drip injections, intramuscular injections, intraventricular injections, or intraperitoneal injections and the like. Other formulations for use in parenteral administration include, for example, transmucosal preparations other than suppositories, sublingual tablets, transdermal preparations, nasal preparations, and the like. Furthermore, intravascular local administration can be performed, in embodiments where they are involved in or applied to stents or anti-intravascular local embolism agents.

The dosage of the above pharmaceutical composition may vary depending on the age, sex, body weight of the patient, condition, therapeutic effect, administration regimen, treatment period, or the types of active ingredients contained in said pharmaceutical composition, but its one dosage is usually in the range of 0.1-500 mg per person for adults, and preferably in the range of 0.5 mg-20 mg. The dosage may vary depending on various conditions, and thus a dosage smaller than that described above may sometimes be sufficient, or at other times a dosage greater than the above may be required.

Also, gene encoding the nesfatin polypeptide or nesfatin-1 polypeptide may be used in embodiments of gene therapy. Said gene therapy, for example, can attain the therapeutic effect by introducing said gene into the living body. Techniques for introducing a gene encoding a protein that provides therapeutic effect and allowing it to be expressed in order to treat a disease is known (Kaneda, Folia Pharmacologica Japonica, 2001, Vol. 117, pp. 299-306).

Furthermore, by administering a transformant in the form in which a gene containing a nesfatin polypeptide or a nesfatin-1 polypeptide has been introduced and that expresses said polypeptide, preferably by administering a transformant that employs a host transplantable into a species into which the gene is to be introduced, treatment with the nesfatin polypeptide or nesfatin-1 polypeptide produced by said transformant can be performed.

<A Nucleic Acid Molecule Encoding a Polypeptide Having an Activity of Suppressing Food Intake and/or Suppressing Body Weight Gain>

The present invention also relates to a nucleic acid molecule encoding any of the above nesfatin polypeptide etc. As the nucleic acid molecule encoding the above nesfatin polypeptide, there can be mentioned a nucleic acid molecule (SEQ ID NO: 1) comprising the nucleotide sequence of a gene encoding the human precursor nesfatin polypeptide, a nucleic acid molecule (SEQ ID NO: 4) comprising the nucleotide sequence of a gene encoding the mouse precursor nesfatin polypeptide, a nucleic acid molecule (SEQ ID NO: 7) comprising the nucleotide sequence of a gene encoding the rat precursor nesfatin polypeptide, a nucleic acid molecule (SEQ ID NO: 10) comprising the nucleotide sequence of a gene encoding a matured nesfatin polypeptide in which a signal peptide portion has been removed, a nucleic acid molecule (SEQ ID NO: 11) comprising the nucleotide sequence of a gene encoding the mouse matured nesfatin polypeptide, a nucleic acid molecule (SEQ ID NO: 12) comprising the nucleotide sequence of a gene encoding the rat matured nesfatin polypeptide, and the like.

As nucleic acid molecules encoding the above nesfatin-1 polypeptides, there can be mentioned a nucleic acid molecule (SEQ ID NO: 18) encoding the human nesfatin-1 polypeptide, a nucleic acid molecule (SEQ ID NO: 19) encoding the mouse nesfatin-1 polypeptide, a nucleic acid molecule (SEQ ID NO: 20) encoding the rat nesfatin-1 polypeptide, and the like.

As nucleic acid molecules encoding the above nesfatin-1M30 polypeptides, there can be mentioned a nucleic acid molecule (SEQ ID NO: 44) encoding the human nesfatin-1M30 polypeptide, a nucleic acid molecule (SEQ ID NO: 46) encoding the mouse nesfatin-1M30 polypeptide, a nucleic acid molecule (SEQ ID NO: 45) encoding the rat nesfatin-1M30 polypeptide, and the like.

As nucleic acid molecules encoding the nesfatin-1M16 polypeptides, there can be mentioned a nucleic acid molecule (SEQ ID NO: 74) encoding the human nesfatin-1M16 polypeptide, a nucleic acid molecule (SEQ ID NO: 80) encoding the mouse nesfatin-1M16 polypeptide, a nucleic acid molecule (SEQ ID NO: 77) encoding the rat nesfatin-1M16 polypeptide, and the like.

As nucleic acid molecules encoding the nesfatin-1M14 polypeptides, there can be mentioned a nucleic acid molecule (SEQ ID NO: 75) encoding the human nesfatin-1M14 polypeptide, a nucleic acid molecule (SEQ ID NO: 81) encoding the mouse nesfatin-1M14 polypeptide, a nucleic acid molecule (SEQ ID NO: 78) encoding the rat nesfatin-1M14 polypeptide, and the like.

As nucleic acid molecules encoding the above nesfatin-1M10M polypeptides, there can be mentioned a nucleic acid molecule (SEQ ID NO: 76) encoding the human nesfatin-1M10M polypeptide, a nucleic acid molecule (SEQ ID NO: 82) encoding the mouse nesfatin-1M10M polypeptide, a nucleic acid molecule (SEQ ID NO: 79) encoding the rat nesfatin-1M10M polypeptide, and the like.

As nucleic acid molecules encoding the NUCB1-M30 polypeptides, there can be mentioned a nucleic acid molecule (SEQ ID NO: 104) encoding the human NUCB1-M30 polypeptide, a nucleic acid molecule (SEQ ID NO: 106) encoding the mouse NUCB1-M30 polypeptide, a nucleic acid molecule (SEQ ID NO: 105) encoding the rat NUCB1-M30 polypeptide, and the like.

As nucleic acid molecules encoding the NUCB1-M16 polypeptides, there can be mentioned a nucleic acid molecule (SEQ ID NO: 116) encoding the human NUCB1-M16 polypeptide, a nucleic acid molecule (SEQ ID NO: 122) encoding the mouse NUCB1-M16 polypeptide, a nucleic acid molecule (SEQ ID NO: 119) encoding the rat NUCB1-M16 polypeptide, and the like.

As nucleic acid molecules encoding the NUCB1-M14 polypeptides, there can be mentioned a nucleic acid molecule (SEQ ID NO: 117) encoding the human NUCB1-M14 polypeptide, a nucleic acid molecule (SEQ ID NO: 123) encoding the mouse NUCB1-M14 polypeptide, a nucleic acid molecule (SEQ ID NO: 120) encoding the rat NUCB1-M14 polypeptide, and the like.

As nucleic acid molecules encoding the above NUCB1-M10M polypeptides, there can be mentioned a nucleic acid molecule (SEQ ID NO: 118) encoding the human NUCB1-M10M polypeptide, a nucleic acid molecule (SEQ ID NO: 124) encoding the mouse NUCB1-M10M polypeptide, a nucleic acid molecule (SEQ ID NO: 121) encoding the rat NUCB1-M10M polypeptide, and the like.

Also, the nesfatin polypeptides etc. of the present invention include, as described above, those in which at least one amino acid has been added to the N terminal or the C terminal, and those in which at least one amino acid residue has been modified by a compound or a peptide. As nucleic acid molecules encoding such nesfatin polypeptides etc., in the case of the nesfatin polypeptide for example, a nucleic acid molecule encoding a polypeptide in which a polypeptide has been added to the N terminal of the sequence of SEQ ID NO: 3, SEQ ID NO: 6 or SEQ ID NO: 9 can be obtained by adding a nucleotide sequence having the nucleotide sequence ATG and a codon encoding an amino acid sequence desired to be added behind it to the 5'-end of SEQ ID NO: 10, SEQ ID NO: 11 or SEQ ID NO: 12. Also, a nucleic acid molecule encoding a polypeptide in which a recognition (cleaving) sequence of protease such as prohormone convertase has been added to the N terminal and/or the C terminal of the amino acid sequence of the nesfatin polypeptide etc. is encompassed by the present invention, but it is not limited to them.

In addition, a nucleic acid molecule is included that comprises a nucleotide sequence in which a gene sequence encoding an Aequorea-derived fluorescence protein or a secretary alkaline phosphatase has been added to the 5'- or 3'-end of the gene sequence encoding a polypeptide comprising an amino acid sequence set forth in SEQ ID NO: 3, SEQ ID NO: 6 or SEQ ID NO: 9 in such a form that the amino acid sequence of each protein can be translated.

Nucleic acid molecules that encode the above altered nesfatin etc. include nucleic acid molecules encoding a polypeptide that comprises an amino acid sequence having a homology of at least 60% with any of the amino acid sequence set forth in SEQ ID NOs: 3, 6, 9, 13-15, 39-41, 65-73, 101-103 or 107-115 and that has an activity of suppressing food intake and/or suppressing body weight gain, and preferably said homology is 70% or greater and more preferably 80% or greater. As the representative example thereof, there can be mentioned, in the case of the nesfatin-1M30 polypeptide for example, a nesfatin-1M30 polypeptide of a non-human animal species. For example, nucleic acid molecules encoding a polypeptide that comprises an amino acid sequence having a homology of 60% or greater with the amino acid sequence (SEQ ID NO: 39) of human nesfatin-1M30 polypeptide etc. and that has an activity of suppressing food intake and/or suppressing body weight gain include a nucleic acid molecule (SEQ ID NO: 46) encoding the mouse nesfatin-1M30 polypeptide, a nucleic acid molecule (SEQ ID NO: 45) encoding the rat nesfatin polypeptide, a nucleic acid molecule (SEQ ID NO: 104) encoding the human NUCB1-M30 polypeptide, a nucleic acid molecule (SEQ ID NO: 106) encoding the mouse NUCB1-M30 polypeptide, and a nucleic acid molecule (SEQ ID NO: 105) encoding the rat NUCB1-M30 polypeptide and the like, but not limited to these nucleic acid molecules.

Also, nucleic acid molecules encoding the above altered nesfatin etc. include those nucleic acid molecules encoding a polypeptide comprising an amino acid sequence in which some of the amino acids have been deleted, inserted or substituted in any of the amino acid sequence set forth in SEQ ID NOs: 6, 9, 13-15, 39-41, 65-73, 101-103 or 107-115 and that has an activity of suppressing food intake and/or suppressing body weight gain.

Furthermore, the present invention also relates to a nucleic acid molecule that hybridizes to a nucleotide sequence set forth in SEQ ID NOs: 4, 7, 11, 12, 18, 19, 20, 44-46, 74-82, 104-106 or 116-124, or a partial sequence thereof under a stringent condition, and that encodes a polypeptide having an activity of suppressing food intake and/or suppressing body weight gain. Such a nucleic acid molecule can be obtained by a hybridization method that employs a nucleotide sequence set forth in SEQ ID NOs: 4, 7, 10, 11, 12, 18, 19, 20, 44-46, 74-82, 104-106 or 116-124, or a partial sequence thereof. Specifically, a library is constructed in which a plasmid vector or a phage vector having inserted therein a cDNA or genomic DNA fragment derived from any type of organism has been introduced into a host such as Escherichia coli (E. coli), and then the library is cultured on an agar medium plate containing a suitable selection drug. Then, the resulting recombinant E. coli clone or a phage clone is transferred to a nitrocellulose membrane etc., and then the cells or phage are lyzed in an alkali- or surfactant-containing condition so as to immobilize DNA contained therein onto the membrane. To the membrane is reacted a suitable hybridization solution at a suitable temperature in which a linearized probe obtained by labelling DNA comprising a nucleotide sequence set forth in SEQ ID NOs: 4, 7, 10, 11, 12, 18, 19, 20, 44-46, 74-82, 104-106 or 116-124, or a partial sequence thereof with $^{32}P$ has been dissolved. After the reaction, the membrane is washed with ×2 SSC to remove the excessive probe, and then washed under a highly stringent condition such as ×0.1 SSC at 65° C., or a medium stringent condition such as ×0.5 SSC at 65° C., and then the membrane is contacted with an X-ray film in the dark for exposure. After an X-ray film that was exposed in a deep freezer for a few hours to a few days is developed to detect the exposed spots, and *E. coli* or phage clones located at positions corresponding to the original plate from which transfer was made to the membrane are harvested and cultured, the sequence of the genes that have been inserted to the vector is analyzed to obtain genes that are highly homologous to the nesfatin gene, the nesfatin-1 gene or the nesfatin-1M30 gene. Also, by obtaining clones by hybridization of cDNA or a genome library using the gene sequence or identifying the surrounding sequences by the primer extension method etc., the gene structure encoding the protein can be elucidated to obtain nucleic acid molecules homologous to nesfatin, nesfatin-1, nesfatin-1M30, nesfatin-1M16, nesfatin-1M14, nesfatin-1M10M, NUCB1-M30, NUCB1-M16, NUCB1-M14 or NUCB1-M10M. Furthermore, among the nucleic acid molecules that hybridize under a stringent condition to the nucleotide sequence set forth in SEQ ID NOs: 4, 7, 10, 11, 12, 18, 19, 20, 44-46, 74-82, 104-106 or 116-124 or the partial sequence of said nucleotide sequence, the nucleic acid molecule encoding a polypeptide having an activity of suppressing food intake and/or suppressing body weight gain can be selected by introducing a polypeptide encoded by said nucleic acid molecule or said nucleic acid molecule locally or systemically to a test animal and by selecting a nucleic acid molecule that suppresses food intake and/or suppresses body weight. In alternative method, it can be performed by introducing an antibody that binds to the polypeptide encoded by said nucleic acid molecule or an antisense oligonucleotide molecule or a RNAi molecule that can suppresses the expression of the gene encoded by said nucleic acid molecule locally or systemically into a test animal, and then selecting a nucleic acid molecule that suppresses the amount of food intake by and/or the body weight of said animal.

<Vector>

The present invention also relates to a vector comprising a nucleic acid molecule encoding any of the above nesfatin polypeptide etc. By constructing a recombinant which is a host cell such as a microorganism having introduced therein the nesfatin gene etc. using a vector comprising a nucleic acid molecule encoding such nesfatin polypeptide etc., said gene can be stably conserved or replicated. The nucleic acid molecule of said gene encoding the nesfatin polypeptide integrated into a vector having a function of being replicated in a host cell can be prepared in large quantities by culturing a recombinant cell in a suitable medium, by cellular growth or by amplifying the copy number of the introduced gene in the cell.

Said nucleic acid molecule may be operably linked under the control of a regulatory nucleic acid molecule that controls the expression of said nucleic acid molecule. As the regulatory nucleic acid molecule that controls the expression of said nucleic acid molecule, there can be mentioned a nucleic acid molecule encoding a regulatory sequence for expressing the integrated gene in the host cell such as a promoter sequence or an enhancer sequence, which can be selected as appropriate by a person skilled in the art. By integrating a nucleic acid molecule encoding the nesfatin polypeptide under the control of a nucleic acid molecule encoding such a regulatory sequence, the nesfatin polypeptide etc. can be produced in large quantities in any host cell (such as a microbial cell, a mammalian cell, an insect cell etc.).

Also as the vector that can be used in the present invention, there can be mentioned a vector that has a promoter upstream to the gene to be expressed, and a polyadenylation site, transcription termination sequence etc. downstream thereto. As such an expression vector for vertebrates, there can be mentioned pSV2dhfr (Mol. Cell. Biol., 854, 1981) having the SV40 early promoter, pcDNA3.1(+) (Invitrogen Corp.), and pCAGGS (Gene 108:193-200, 1991) and the like, but they are not limiting and can be selected as appropriate by a person skilled in the art. Such a vector can also be introduced into a mammalian cell for the treatment of suppressed food intake and/or suppressed body weight gain.

When *E. coli* is used as the host cell, pBR322 and an improved vector thereof can be used, but they are not limiting, and various known microbial strains lines and vectors can also be used. As the promoter, there can be mentioned, but not limited to, promoters such as *E. coli* lactose (lac), *E. coli* trp and the like. Said promoters are those that have already been characterized and known to a person skilled in the art, and can be assembled synthetically or from known plasmids.

Working Example 5 as a specific example demonstrates that by integrating a nucleic acid molecule encoding a nesfatin polypeptide into a vector to construct an *E. coli* recombinant, a nesfatin polypeptide retaining an activity of suppressing food intake and/or suppressing body weight gain could be prepared. Also, Working Example 16 demonstrates that by allowing the amino acid sequences described in SEQ ID NO: 13 to 15 as fusion proteins with glutathione S-transferase (GST) etc, to be expressed. and purifying using the adsorption to and desorption from a glutathione-immobilized carrier followed by cleavage of the GST portion, the nesfatin-1 polypeptide could be produced by a gene recombinant technology.

By introducing the vector of the present invention into a mammalian cell using the technology for gene therapy for the purpose of suppressing food intake and/or suppressing body weight gain, the therapeutic effect can be attained. The method of treating diseases by introducing a gene encoding a protein that provides the therapeutic effect, i.e. the nesfatin polypeptide etc., into a mammalian cell and then allowing it to be expressed is known (Kaneko, Folia Pharmacologica Japonica, issued in 2001, Vol. 117, pp. 299-306).

<Transformant>

The present invention also relates to a transformant comprising a nucleic acid molecule encoding any of the above nesfatin polypeptide etc. Such a transformant can be obtained by introducing the gene encoding said polypeptide into a host cell and transforming it. Methods of transformation include biological methods, physical methods, chemical methods and the like. As biological methods, there can be mentioned a method that employs a virus vector, a method that employs a specific receptor, cell fusion (Sendai virus (HVJ), polyethylene glycol (PEG), electric cell fusion, micronucleate cell fusion (chromosome transfer)), and the like. Physical methods include the microinjection method, an electroporation method, the method that employs a gene particle gun. Chemical methods include the calcium phosphate precipitation method, the liposome method, the DEAE-dextran method, the protoplast method, the erythrocyte ghost method, the erythrocyte membrane ghost method, the microcapsule method, which can be selected and performed as appropriate by a person skilled in the art. The transformant obtained can be cultured according to a standard method, and the nesfatin polypeptide etc. can be produced. As the media used for culturing, various media commonly used can be as appropriate selected depending on the host cell adopted, and culturing can also be performed under a condition suitable for the growth of the host cell.

Various means for expressing the protein of interest in an eukaryotic cell are known per se in said field of art. For example, an expression system in yeast includes "The expression of protein in yeast" described in Japanese Unexamined Patent Publication (Kokai) No. 57-159489, an expression system in plant cells includes "An improved method and equipment for introducing a biological substance into a living cell" described in Patent Publication No. 2517813 or "A method of introducing a gene into a plant cell and a plant cell-treatment equipment for gene introduction" described in Japanese Unexamined Patent Publication (Kokai) No. 2003-274953, an expression system in insect cells includes "A method of producing a recombinant baculovirus expression vector" described in Japanese Unexamined Patent Publication (Kokai) No. 60-37988, and an expression system in mammalian cells includes "Improvement in eukaryotic expression" described in Japanese Unexamined Patent Publication (Kokai) No. 2-171198, but there are many other systems in addition to these.

As host cells for use in transformation, both eukaryotic host cells and prokaryotic host cells can be used. Eukaryotic host cells include vertebrates, yeast, plant cells, insect cells and the like. As plant cells, there can be mentioned tissue sections of dicotyledons and monocotyledons, cells isolated from the tissue, cells derived from callus formed from the tissue and the like. Vertebrate cells include, for example, CHO cells, 293T cells, COS7 cells and the like. Prokaryotic host cells include, for example, *E. coli, Bacillus subtilis, Streptomyces* and the like, and as *E. coli, Escherichia coli* strain K12 is often used. When a vertebrate is used as the host cell, the transformant obtained can be introduced into a mammal for cell therapy of suppressing food intake and/or suppressing body weight gain. As such transformants, those that were confirmed to express the gene encoding the introduced nesfatin polypeptide etc. are preferred. In administering said transformant, it is preferred to administer said transformant by dispersing in various buffers, physiological saline etc. (Japanese Unexamined Patent Publication (Kokai) No. 2003-342201)

<Antibody>

The present invention relates to antibody that binds to any of the above nesfatin polypeptide etc. Such an antibody can be obtained by a method known to a person skilled in the art. The antibody for use in the present invention can be polyclonal antibody or monoclonal antibody (Milstein et al., Nature (England), issued on Oct. 6, 1983, Vol. 305, No. 5934, pp. 537-540). For example, a polyclonal antibody against the nesfatin polypeptide, the nesfatin-1 polypeptide, the nesfatin-1M30 polypeptide, nesfatin-1M16, nesfatin-1M14, nesfatin-1M10M, NUCB1-M30, NUCB1-M16, NUCB1-M14 or NUCB1-M10M can be collected from the serum etc. of a mammal sensitized with the antigen. Furthermore, in another example, it can be collected from the serum etc. of a mammal sensitized with a peptide having a sequence comprising a partial sequence of the nesfatin polypeptide etc. In a more specific example, as shown in Working Example 3, an antibody that binds to the nesfatin polypeptide etc. can be obtained by binding a peptide (SEQ ID NO: 24) having sequence corresponding to amino acids 141-152 of SEQ ID NO: 8 to a carrier protein and using it as the antigen to immunize an animal. When administered to an animal, this antibody exhibits an effect of enhancing food intake and increasing body weight of said animal (Working Example 7). In still another example, a peptide (SEQ ID NO: 32) having a sequence corresponding to amino acids 48-62 of SEQ ID NO: 8 is bound to a carrier protein, which is used as the antigen to immunize an animal so that an antibody that binds to the nesfatin polypeptide etc. can be obtained (Working Example 10). The polypeptide set forth in SEQ ID NO: 32 consists of amino acid sequences common to the nesfatin polypeptide, nesfatin-1 polypeptide and nesfatin-1M30 of human, mouse or rat, and therefore antibodied obtained bind to all of these polypeptides. When administered to an animal, this antibody exhibits an effect of enhancing food intake and increasing body weight of said animal (Working Example 14). In addition to them, it is possible to create antibody by preparing, as appropriate, a peptide to be used as the antigen from the sequence of disclosed nesfatin-1 polypeptide etc.

A monoclonal antibody against the above nesfatin polypeptide etc. can be prepared by collecting immune cells from the animal sensitized with the antigen and subjecting the cells to cell fusion with myeloma cells to collect the antibody from the culture.

Such an antibody can be labelled as appropriate, and can be used to detect the above nesfatin polypeptide etc. Also, instead of labelling this antibody, substances that specifically bind to said antibody, such as Protein A and protein G, can be labelled for indirect detection. As specific methods for detection, for example, ELISA methods can be mentioned.

The antigen used to obtain the antibody of the present invention can be obtained by integrating, for example, a gene encoding the nesfatin polypeptide, the nesfatin-1 polypeptide, nesfatin-1M30, nesfatin-1M16, nesfatin-1M14, nesfatin-1M10M, NUCB1-M30, NUCB1-M16, NUCB1-M14 or NUCB1-M10M mentioned above, or altered products thereof, or part of it into an expression vector, introducing the expression vector into a suitable host cell to construct a transformant, culturing said transformant to express a recombinant protein, and purifying the expressed recombinant protein from the culture or the culture supernatant. Alternatively, an oligopeptide can be chemically synthesized that comprises an amino acid sequence encoded by said gene or a partial amino acid sequence of the amino acid sequence encoded by the full-length cDNA and used as the immunogen. Animals to be immunized include mice, rats, rabbits, goats, horses, hamsters and the like, and can be selected as appropriate by a person skilled in the art.

<A Substance that Suppresses the Activity or Expression of a Polypeptide Having an Activity of Suppressing Food Intake and/or Suppressing Body Weight Control>

In the investigation of the present invention, when an antibody was prepared against a nesfatin polypeptide, a nesfatin-1 polypeptide and a nesfatin-1M30 polypeptide, and administered to the brain of an animal, an increase in the amount of food intake by the animal was noted (Working Examples 7 and 14). Also, when an antisense RNA (oligonucleotide) that suppresses the expression of nesfatin was administered into the brain of an animal, the enhancement of food intake and the increase in the body weight of the animal were noted (Working Example 15). This indicates that the nesfatin polypeptide, the nesfatin-1 polypeptide and the nesfatin-1M30 polypeptide actually operates in the brain for food intake control and/or body weight control. Furthermore, the increased concentration of the nesfatin polypeptide, the nesfatin-1 polypeptide or the nesfatin-1M30 polypeptide in a peripheral (peripheral blood) or a brain caused the suppression of food intake and/or the suppression of body weight gain, and a substance that suppresses the activity or expression of said polypeptide exhibited an activity of enhancing food intake and/or increasing body weight, and therefore the nesfatin polypeptide, the nesfatin-1 polypeptide and/or the nesfatin-1M30 polypeptide was demonstrated to be a central factor responsible for food intake control and/or body weight control. Accordingly, a substance per se that inhibits the activity or expression of the nesfatin polypeptide, the nesfatin-1 polypeptide and/or the nesfatin-1M30 polypeptide can be used in the treatment, diagnosis and/or screening of therapeutic agents for the suppression of food intake and/or the suppression of body weight gain due to diseases and conditions for which decreased food intake and body weight reduction are a problem, such as cibophobia, functional dyspepsia, cancer, inflammatory diseases, decreased functions of the pituitary, the thyroid, the adrenal gland etc., post-surgery, or excessive stress and the like.

Thus, the present invention relates to a substance that inhibits the activity or the production of the nesfatin polypeptide, the nesfatin-1 polypeptide, the nesfatin-1M30 polypeptide, nesfatin-1M16, nesfatin-1M14, nesfatin-1M10M, NUCB1-M30, NUCB1-M16, NUCB1-M14 or NUCB1-M10M. More preferably, it relates to a substance that exhibits an activity of enhancing food intake and/or enhancing body weight gain. Substances that suppress the activity of the nesfatin polypeptide etc. include those characterized by binding to the nesfatin polypeptide etc. and those that do not require binding to these polypeptides. An example of the former is antibody against the nesfatin polypeptide etc., and as the antibody those described above can be used. An example of the latter is a dominant negative polypeptide against the nesfatin polypeptide etc. The "dominant negative" is a mutant that dominantly acts on the wild type both quantitatively and qualitatively so as to inhibit the function of the wild type. The dominant negative can be prepared by deleting or converting part of the amino acids of the wild type.

The present invention also relates to a substance that suppresses the expression of a gene encoding the nesfatin polypeptide, the nesfatin-1 polypeptide, the nesfatin-1M30 polypeptide, nesfatin-1M16, nesfatin-1M14, nesfatin-1M10M, NUCB1-M30, NUCB1-M16, NUCB1-M14 or NUCB1-M10M. Such substances include, for example, an antisense oligonucleotide, a RNAi molecule and the like. The gene encoding the nesfatin polypeptide etc. as used herein refers to a nucleic acid molecule that comprises the entire nucleotide sequence or part thereof of the nucleic acid molecule encoding the nesfatin polypeptide etc. as a contiguous or non-contiguous unit. Also the expression of gene comprises a step of a nucleic acid molecule encoding the nesfatin polypeptide etc. being transcribed from said gene, a step of stabilizing the transcribed nucleic acid molecule, and a step of the nesfatin polypeptide etc. being produced by translation from the transcribed nucleic acid molecule. Thus, the suppression of gene expression refers to suppress any of the steps of transcription from the gene encoding the nesfatin polypeptide etc.; stabilization; and translation.

The above antisense oligonucleotide can be designed by using, for example, a gene sequence encoding the nesfatin polypeptide. As such an antisense oligonucleotide, there can be mentioned a morpholino-type antisense oligonucleotide having the structure of SEQ ID NO: 31. As shown in Working Example 15, by administering this to an animal, said antisense oligonucleotide exhibits an effect of enhancing food intake and enhancing body weight gain. For an antisense oligonucleotides, various modifications or binding formats are known in order to avoid decomposition in the cell, and a person skilled in the art will be able to select the structure of a suitable antisense oligonucleotide (Curreck et al., European Journal of Biochemistry) (UK), 2003, Vol. 270, pp. 1628-486). As the structure, there can be illustrated the natural form (D-oligo), the phosphorothioate type (S-oligo), the methylphosphonate type (M-oligo), the phosphoroamidate type (A-oligo), the 2'-O-methyl type (D-oligo), the morpholidate type (Mo-oligo), a polyamide nucleic acid and the like. The length used is 10 bases to 70 bases, and preferably 15 bases to 30 bases are used.

RNA interference (RNAi) refers to a phenomenon in which a double-stranded RNA of 21-23 residues decomposes a target RNA containing the same sequence thereby to greatly suppress its expression. Thus, RNA containing a double stranded structure having the same nucleotide sequence as mRNA of the gene encoding the nesfatin polypeptide etc. can be used for suppressing the expression of the gene of the nesfatin polypeptide etc. In order to obtain the RNAi effect, it is preferred to use a double stranded RNA having a sequence of at least 20 contiguous nucleotides. The double stranded structure may be composed of different strands, and of two strands provided by the stem loop structure of one RNA. By adding a two-base overhang to the 3'-end of each strand, the effect of suppressing the expression of the gene can be enhanced. For the sequence, length and the structure used in designing RNAi, a person skilled in the art would be able to optimize RNAi having a potent effect of suppressing gene expression through various modification attempts.

The above antisense oligonucleotide molecule and the RNAi molecule can be produced by integrating a nucleic acid molecule comprising a nucleotide sequence complementary to the nucleic acid sequence of said molecule into a vector, introducing this into a host cell for transformation, and culturing the transformant. The host cell used and the method of transformation could be selected as appropriate by a person skilled in the art as described in the above <Transformant>.

<A Pharmaceutical Product for Enhancing Appetite or Enhancing Body Weight Gain>

The present invention also relates to a pharmaceutical composition for enhancing appetite or enhancing body weight gain, said composition comprising as an active ingredient a substance that inhibits the activity or the production of the nesfatin polypeptide etc., or a substance that inhibits the expression of the gene encoding the nesfatin polypeptide etc. Said pharmaceutical composition can be used for diseases and conditions for which the suppression of food intake or body weight gain is a problem. Diseases and conditions for which the suppression of food intake or body weight gain is a problem include, for example, cibophobia, functional dyspepsia, or the suppression of food intake and/or the suppression of body weight gain due to cancer, inflammatory diseases, decreased functions of the pituitary, the thyroid, the adrenal etc., post-surgery, or excessive stress and the like.

The pharmaceutical composition of the present invention may contain any pharmaceutically acceptable additives. Pharmaceutical formulations using pharmaceutically acceptable additives may be prepared by a method described in "Remington: The Science and Practice of Pharmacy, 20th edition, University of the Sciences in Philadelphia, Williams & Wilkins, issued on Dec. 15, 2000". One dosage form of such a pharmaceutical composition is presented as a liquid prepared by dissolving, suspending or emulsifying in an aqueous or oleaginous solution. Such solvents used include, for example, distilled water for injection, physiological saline etc. as an aqueous liquid, and in addition, an osmoregulatory agent (for example, D-glucose, D-sorbitol, D-mannitol, and sodium chloride), a suitable solubilizing agent such as alcohols (for example, ethanol), polyalcohols (for example, propylene glycol and polyethylene glycol), nonionic surfactants (for example, polysorbate 80, polyoxyethylenated hydrogenated castor oil 50) and the like may be used. Also, as the solvents, an oleaginous solution may be used, and said oleaginous solution includes sesame oil, soybean oil etc., and as the solubilizing agent, benzyl benzoate, benzyl alcohol etc. may be used in combination. In such liquids, there can be used, as appropriate, additives such as buffers (such as phosphate buffers and acetate buffers), soothing agents (such as benzalkonium chloride and procaine hydrochloride), stabilizers (such as human serum albumin and polyethylene glycol), preservatives (such as ascorbic acid, erythorbic acid, and salts thereof), colorants (such as copper chlorophyll, β-carotene, Red No. 2, and Blue No. 1), preservatives (such as ascorbic acid, erythorbic acid, and salts thereof), antiseptics (such as paraoxybenzoate ester, phenol, benzethonium chloride and benzalkonium chloride), thickeners (such as hydroxypropyl cellulose, carboxymethyl cellulose, and salts thereof), stabilizers (such as human serum albumin, mannitol and sorbitol), and corrigents (such as menthol and citrus flagrances). Another dosage form of pharmaceutical compositions (in order to unify the expression with the above several "pharmaceutical compositions") includes solid forms such as powders, tablets, granules, capsules, pills, suppositories, and lozenges. In the case of solid forms for administration in the form of oral preparations, additives used include excipients (such as crystalline cellulose, lactose and starch), lubricants (such as magnesium stearate and talc), binders (such as hydroxypropyl cellulose, hydroxypropyl methyl cellulose and macrogol), disintegrants (such as starch and carboxymethyl cellulose calcium), and the like. Also, as needed, there can be used antiseptics (such as benzyl alcohol, chlorobutanol, methyl paraoxybenzoate and propyl paraoxybenzoate), antioxidants, colorants, sweeteners and the like. Furthermore, another form also includes a pharmaceutical composition for application to the mucosa, and for this form of formulations, in order to impart adsoptivity to the mucosa and retentivity, there can be contained additives such as tackifiers, tackiness enhancers, thickeners, thickening agents (such as mucin, agar, gelatin, pectin, caragennan, sodium alginate, locust bean gum, xanthan gum, tragacanth gum, gum arabic, chitosan, pullulan, waxy starch, sucralfate, cellulose and its derivatives (such as hydroxypropyl methyl cellulose), polyglycerin fatty acid esters, acrylic-(meth)acrylic alkyl copolymers or salts thereof, and polyglycerin fatty acid esters). However, dosage forms of pharmaceutical compositions and solvents and additives to be delivered to the living body are not limited to the above, and can be selected, as appropriate, by a person skilled in the art.

For the purpose of ameliorating disease conditions, the above pharmaceutical compositions can be administered orally or parenterally. In the case of oral administration, dosage forms such as granules, powders, tablets, capsules, liquids, syrups, emulsions or suspensions, and elixirs can be selected. In the case of parenteral administration, it can be transnasal agents, and liquids, suspensions or solid formulations can be selected. Other agents in the form of parenteral administration can be in the form of injections, and injections selected may be hypodermic injections, intravenous injections, drip injections, intramuscular injections, intraventricular injections, or intraperitoneal injections and the like. Other formulations for use in parenteral administration include, for example, transmucosal preparations other than suppositories, sublingual tablets, transdermal preparations, transnasal preparations and the like. Furthermore, intravascular local administration can be performed in embodiments wherein they are contained or applied to stents, or anti-intravascular embolism agents.

The dosage of the above pharmaceutical composition may vary depending on the age, sex, body weight of the patient, condition, therapeutic effect, administration regimen, treatment period, or the types of active ingredients contained in said pharmaceutical composition, but its one dosage is usually in the range of 0.1-500 mg per person for adults, and preferably in the range of 0.5 mg-20 mg. The dosage may vary depending on various conditions, and thus a dosage smaller than that described above may sometimes be sufficient, or at other times a dosage greater than the above may be required.

The above antisense oligonucleotide or the RNAi molecule may be integrated downstream to a suitable promoter sequence, and can be administered as the RNA expression vector that provides the effect of antisense oligonucleotide or RNAi. When the expression vector is introduced in a form that can reach the brain of the subject patient, the effect of the antisense oligonucleotide or RNAi effect of the gene allows the expression of a polynucleotide that suppresses the expression of said gene, and the reduced expression level of said gene can attain the therapeutic effect for conditions of suppressed food intake and/or suppressed body weight gain.

<Transgenic Animals, Animal Model of Obese/Adiposis>

The present invention relates to a transgenic non-human animal comprising a gene encoding the above nesfatin polypeptide etc., or a vector containing them. More specifically, it relates to a transgenic non-human animal that exhibits the state of suppressed food intake or the state of suppressed body weight gain wherein the expression of said gene is enhanced systemically, preferably, in the hypothalamus. A transgenic non-human animal in which the expression level of the gene encoding the above polypeptide has been artificially enhanced can be used as an animal model that exhibits suppressed food intake and/or suppressed body weight gain.

The present invention relates to a transgenic non-human animal that has introduced therein the above substance (such as antibody, antisense oligonucleotide, and RNAi molecule) that suppresses the activity or the expression of a polypeptide having an activity of suppressing food intake and/or suppressing body weight control, and that exhibits enhanced appetite or enhanced body weight gain. A non-human transgenic animal produced by introducing a gene encoding such a substance can be used as an animal model that exhibits enhanced food intake or enhanced body weight gain. Also, said transgenic non-human animal can be used as an animal model for diseases such as obesity, diabetes mellitus, hypertension, hyperlipidemia, hyperuricemia, fatty liver, cardiac diseases, cerebral vascular diseases, sleep apnea syndrome, orthopedic diseases such as osteoarthritis, menstrual disorders and malignant tumors.

The method of obtaining transgenic animals with a specific gene as the target is known. Thus, transgenic animals can be obtained by a method in which a gene and an egg are mixed and then treated with calcium phosphate, a method in which a gene is directly introduced into the nucleus of the egg in the pronucleus phase with a micropipette under a phase contrast microscope (the microinjection method, U.S. Pat. No. 4,873, 191), a method of using an embryonic stem cell (ES cell), and the like. In addition, there have been developed a method in which a gene is inserted into a retrovirus vector and then infected to the egg, a sperm-vector method in which a gene is introduced into the egg via the sperm, and the like. The sperm-vector method is a gene recombinant method in which a foreign gene is incorporated into the sperm by adhesion or electroporation and then the sperm is allowed to fertilize the egg to introduce the foreign gene (Lavitranoet M. et al., Cell (1989) 57, 717-723).

Also, if a promoter of which transcription is regulated by a suitable substance such as a drug is used as a promoter for use in the expression vector, the administration of said substance can regulate the expression level of the substance that controls the activity or expression of the gene encoding a foreign nesfatin polypeptide etc. or said polypeptide in a transgenic animal.

Furthermore, the present invention relates to a knock-out animal wherein the entire region or part thereof of the gene encoding the nesfatin polypeptide etc. has been deleted, and a knock-in animal in which said gene has been replaced with another gene is also encompassed in the present invention. For example, a knock-out animal of the nesfatin polypeptide etc. can be used as an animal model that exhibits enhanced food intake and/or enhanced body weight gain.

Furthermore, the present invention also relates to an animal model in which food intake and/or body weight gain has been suppressed comprising a non-human animal in which the above nesfatin polypeptide etc. per se has been administered, or an animal model in which food intake and/or body weight gain has been enhanced comprising a non-human animal in which a substance that suppresses the activity or expression of said polypeptide has been administered. The non-human animal in which food intake and/or body weight gain has been enhanced can be used as an animal model for diseases such as obesity, diabetes mellitus, hypertension, hyperlipidemia, hyperuricemia, fatty liver, cardiac diseases, cerebral vascular diseases, sleep apnea syndrome, orthopedic diseases such as osteoarthritis, menstrual disorders and malignant tumors.

The animal species of the present invention for use as an animal model can be prepared using any vertebrate other than a human. Specifically, for vertebrates such as mice, rats, rabbits, minipigs, goats, sheep, monkeys, dogs, cats, and cattle, animal models can be prepared by the introduction of a gene or the administration of a substance.

<Method of Producing a Polypeptide Having an Activity of Suppressing Food Intake and/or Suppressing Body Weight Gain>

The present invention relates to a method of producing the above nesfatin polypeptide etc., using the above transformant that expresses the gene encoding said nesfatin polypeptide etc., or the above transgenic non-human animal and a transgenic plant comprising the gene encoding said polypeptide or a vector containing the gene.

In the above method of producing said polypeptides of the present invention, various modifications and alterations can be made to the above DNA sequence, the plasmid and the virus in order to be compatible with expression, transcription, translation etc. in the transformant or the transgenic non-human animal. For example, due to degeneracy of the genetic code, nucleotides can be substituted through the entire coding region of protein. Such a sequence can be predicted from the amino acid sequence of the nesfatin polypeptide or nesfatin-1 polypeptide, or from the nucleotide sequence of the gene encoding said polypeptide, and can be assembled by a conventional synthetic method described below. Such a synthetic method can be performed by the method of Itakura et al. (Itakura et al., Science 198:1059, 1977) and the method of Crea et al. (Crea et al., Proc. Natl. Acad. Sci. USA 75:5765, 1978). Thus, the gene encoding the above nesfatin polypeptide etc. for use in the method of producing the polypeptide of the present invention is not limited to those employing the specifically illustrated nucleotide sequence, the plasmid or the virus.

The production of the above polypeptide using a transformant can be performed by culturing said transformant. As the culture medium used for culturing, various media commonly used may be selected as appropriate depending on the host cell adopted, and the culturing may be performed under a condition suitable for the growth of the host cell.

Also, the above polypeptide can be produced in the transformant intracellularly or extracellularly, or on the cell membrane. As other methods of producing polypeptides using a gene encoding the nesfatin polypeptide etc., there can be mentioned a method based on cell-free protein synthesis, a representative of which is an in vitro translation reaction system. In this in vitro translation reaction system, 5' upstream to the gene encoding the nesfatin polypeptide etc., a sequence that controls transcription, preferably SP6 promoter, T3 promoter, T7 promoter etc. may be added, and the gene is transcribed into the cell or in vitro to prepare a RNA molecule encoding the nesfatin polypeptide etc., and a cell extract for in vitro transcription prepared from wheat germ, E. coli, reticulocytes etc. to carry out the production. One example of the production can be accomplished by the method described in Sawazaki et al., Protein, Nucleic acid and Enzyme, 2003, Vol. 48, pp. 549-554. Polypeptides produced by such a transformant or cell-free protein synthesis can be separated and purified as desired by various separation processes using the physical properties, chemical properties etc. [see The Japanese Biochemical Society ed., "Biochemistry Databook II", The First edition, the First print, issued by Tokyo Kagaku Dojin Co., Ltd. on Jun. 23, 1980, pp. 1175-1259; Arakawa et al., Biochemistry (USA), issued on Dec. 16, 1986, Vol. 25, No. 25, pp. 8274-8277 (1986); Langley et al., European Journal of Biochemistry (Germany), issued on Mar. 2, 1987, Vol. 163, No. 2, pp. 313-321]. Said methods specifically include, for example, conventional reconstitution treatment, treatment with a protein precipitating agent (salting out), centrifugation, the osmotic shock method, ultrasonic disruption, ultrafiltration, gel filtration, various chromatographic methods such as adsorption chromatography, ion exchange chromatography, affinity chromatography, and high performance liquid chromatography (HPLC), dialysis, and combinations thereof, and the like. Purification using affinity with the above polypeptide can use, for example, the above-mentioned antibody that binds to the above polypeptide, and can be accomplished by desorption of said polypeptide and said antibody.

The above method of producing the polypeptide of the present invention can also be accomplished by producing a protein in which an affinity tag was fused to said polypeptide in a transformant or a transgenic non-human animal, and then separating and purifying said affinity tag-fused protein. By expressing said affinity tag-fused protein, affinity purification using this tag can be performed. As said affinity tag, there can be mentioned glutathione S-transferase (GST), poly-Histidine (His tag, Sisk et al., J. Virol. (USA), issued in February 1994, Vol. 68, No. 2, pp. 766-775) and FLAG tag (Hopp et al., Biotechnology, issued in 1988, Vol. 6, pp. 1204-1210).

In the case of a GST-fused protein, in which the above polypeptide was fused to GST, the above polypeptide can be produced using a glutathione-immobilized carrier, i.e. said polypeptide can be purified using absorption and desorption of GST and the glutathione bound carrier, and then cleaving the GST portion from the GST-fused protein and purifying it.

In the case of a His tag-fused protein, the above polypeptide can be produced using a metal ion chelate carrier, i.e. said polypeptide can be purified using absorption and desorption of the His tag and said metal ion chelate carrier, and then cleaving the His tag portion from the His tag-fused protein and purifying it.

In the case of a FLAG tag-fused protein, the above polypeptide can be produced using a carrier to which anti-FLAG tag antibody is bound, i.e. said polypeptide can be purified using absorption and desorption of the FLAG tag and said metal ion chelate carrier, and then cleaving the FLAG tag portion from the FLAG tag-fused protein and purifying it.

The nesfatin-1 polypeptide can also be prepared by treating the nesfatin polypeptide obtained in the above-mentioned method with a proteolytic enzyme such as protein convertase, fractionating the digest by a reverse phase chromatography, and confirming and collecting fragments containing the nesfatin-1 polypeptide by mass spectrometry etc. The altered nesfatin-1 can also be obtained in a similar manner.

The thus obtained nesfatin polypeptide etc. of the present invention can also be modified at the N-terminal after translation, and such modified polypeptide molecules are also encompassed in the present invention. For example, a polypeptide of which N-terminal has been converted to pyroglutamine can be obtained by expressing the above nesfatin polypeptide etc. of the present invention etc. so that the N-terminal becomes a glutamine residue, and treating the polypeptide obtained under an acidic condition of a 5-10% acetic acid solution (Park et al., Proceedings of the National Academy of Sciences of the United States of America (USA), issued in March 1991, pp. 2046-2050). A peptide of which N-terminal has been acetylated can be obtained by expressing the above nesfatin polypeptide etc. of the present invention so that the N-terminal becomes any amino acid having an α-amino group, and treating the polypeptide obtained with sulfo-NHS-acetate or acetic anhydride. Such a method of modifying the N-terminal of the polypeptide after translation is well known in the art. In addition, the nesfatin polypeptide etc. of the present invention can also be treated with a fluorescent substance to be modified (Hermanson et al., Bioconjugate Techniques (USA) issued by Academic Press in 1996).

A transgenic non-human animal can also be used to produce the above nesfatin polypeptide etc. According to such a method, for example, fractions containing the peptide of interest can be collected as a liquid component separated from the solid component, or as a liquid component extracted with an aqueous solvent or an organic solvent from processed products obtained by cutting, milling, or fractionating an organ, tissue, blood, milk etc. harvested from a transgenic non-human animal having a gene encoding the above nesfatin polypeptide etc. or a vector comprising said gene. The peptide of interest can be separated and purified from said fractions by various separation procedures using the above-mentioned physical properties, chemical properties etc.

It is also possible to use a transgenic plant to produce the above nesfatin polypeptide etc. The method can be performed referring to Japanese Unexamined Patent Publication (Kokai) No. 2003-116385 "A transgenic plant comprising a gene encoding Japanese encephalitis vaccine". Also, a transgenic plant can produced by referring to Japanese Unexamined Patent Publication (Kokai) No. 2002-17186 "Transgenic Plants". From the tissue of leaves, stems, roots, fruits, rinds, sprouts and petals of such a transgenic plant or callus tissue derived from such a tissue, or optionally from processed products obtained by cutting, peeling, milling, or compressing of said tissue, the polypeptide of interest can be collected in an extract with an aqueous solvent or an organic solvent, a squeeze obtained by the compression or an oil, and furthermore said polypeptide can be separated and purified by various separation procedures using the above-mentioned physical properties, chemical properties etc.

The above polypeptide of the present invention can also be obtained by chemical synthesis. In this case, a commonly used peptide synthetic method such as solid-phase synthesis or liquid-phase synthesis can be used. For the condensation and protection of amino acid protecting groups in peptide synthesis and the elimination of the protecting groups after synthesis, a known method can be used (Izumitani et al., "Basis and Experiment of Peptide Synthesis (PEPUTIDO GOSEINO KISOTO JIKKENN)", issued by Maruzen Co., Ltd. in 1975, Hitoshi Yajima—The Japanese Biochemical Society ed., "Biochemistry Experiment Series (SEIKA-GAKU JIKKENN KOUZA) 1, Chemistry of Protein IV", issued by Tokyo Kagaku Dojin Co., Ltd. in 1977). It is also possible to synthesize the entire peptide sequence at one time, while a method can be used in which partial peptides of said protein are synthesized separately and then the partial peptides are condensed (The Japanese Biochemical Society ed., "New Biochemistry Experiment Series (SINSEIKAGAKU JIKKENN KOUZA), Protein IV, Synthesis and Expression", issued by Tokyo Kagaku Dojin Co., Ltd. in 1991).

Though the α-amine of amino acids commonly used in peptide synthesis is usually protected with a tBoc group or a Fmoc group, the peptide to be finally obtained may retain the protecting group or may be deprotected. As needed, the deprotected amino terminal of the peptide may be modified with pyroglutamic acid, an acetyl group or a formyl group (Hermanson et al., Bioconjugate Techniques (USA) issued by Academic Press in 1996). In a specific example, the above polypeptide of the present invention having glutamine at the N-terminal is synthesized, and said peptide can be cyclized by treating with a dilute acid such as a 5-10% acetic acid to convert to pyroglutamic acid (Park et al., Proceedings of the National Academy of Sciences of the United States of America (USA), issued in March 1991, pp. 2046-2050).

Also, as needed, synthetic peptides in which an amide group or a fluorescent substance has been added at the C-terminal of the polypeptide after synthesis can be prepared. For example, in order to obtain a synthetic peptide having introduced therein an amide group at the C-terminal by solid-phase synthesis, a commercial resin that allows the amidation of the C-terminal can be used in a reaction of cleaving the peptide from the solid-phase carrier (resin). Also, modification with fluorescent substances etc. at the C-terminal can be carried out by a known method (Hermanson et al., Bioconjugate Techniques (USA) issued by Academic Press in 1996).

<Assay Method of Predicting or Diagnosing the State of Food Intake Control and/or Body Weight Control>

The present invention relates to a diagnostic method for use in the judgment of diseases associated with food intake control and/or body weight control in mammals, the monitoring and prediction of severity and progress of disease conditions, the judgment of prognosis and the administration of the above pharmaceutical composition and the like. Thus, the present invention relates to a method of predicting or diagnosing the state of food intake control and/or body weight control using a sample derived from a mammal to be tested, which method comprises comparing the amount contained of a nucleic acid molecule (a nucleic acid molecule comprising a nucleotide sequence set forth in any of SEQ ID NOs: 10-12, 18-20, 44-46, 74-82, 104-106 and 116-124) encoding nesfatin, the nesfatin polypeptide etc. (a polypeptide comprising an amino acid sequence set forth in any of SEQ ID NOs: 3, 6, 9, 13-15, 39-41, 65-73, 101-103 and 107-115) in said sample with that in a sample derived from a normal individual. A normal individual as used herein refers to a normal or untreated individual.

Specifically, the present invention relates to an assay method of predicting or diagnosing the state of food intake control and/or body weight control, which method comprises the steps of comparing the amount contained of a nucleic acid molecule comprising a nucleotide sequence set forth in any of SEQ ID NOs: 10-12, 18-20, 44-46, 74-82, 104-106 and 116-124 in a sample derived from a living body of a mammal to be tested with that in a biological sample derived from a normal individual, and detecting the decreased or the enhanced expression of said gene.

As biological materials to be used, there can be mentioned blood, urine, cerebrospinal fluid, saliva, brain tissues harvested from biopsy etc. with blood being most preferred. Blood for use as a sample includes whole blood, or plasma or serum derived from whole blood. Methods of collecting these biological samples are known. Preparations such as lysates of these biological samples can also be used as the sample. Alternatively, mRNA extracted from the preparations may be used as a sample for determining mRNA corresponding to the above gene. For the extraction of lysates of biological samples or mRNA, commercially available kits can be conveniently used. Alternatively, liquid biological samples such as blood and cerebrospinal fluid can be diluted as needed with a buffer etc. to prepare samples for determining protein or gene.

The amount contained of a nucleic acid molecule comprising a nucleotide sequence set forth in any of SEQ ID NOs: 10-12, 18-20, 44-46, 74-82, 104-106 and 116-124 in a biological sample of a mammal can be determined by using a polynucleotide comprising the nucleotide sequence of said nucleic acid molecule or an oligonucleotide with a length of at least 18 bases comprising a nucleotide sequence complementary to the complementary chain as a PCR primer or a probe. In this case, a skilled in the art can design a primer or a probe suitable for an application, using variety of computer program. Such a polynucleotide or an oligonucleotide may be bound to a suitable label or immobilized to a suitable support depending on the assay format. Such a PCR primer or a probe can be recombinantly or synthetically produced, or may be produced by any means available to a person skilled in the art. For example, the PCR primer that can be used in the present invention include, but not limited to, SEQ ID NO: 22 (forward primer) and SEQ ID NO: 23 (reverse primer). As the probe that can be used in the present invention include, but not limited to, one that is obtained by labelling a fragment amplified using the above primer with the DNA sequence of SEQ ID NO: 21 as the template (see Working Example 2).

The measured values of expression level of a nucleic acid molecule comprising a nucleotide sequence set forth in any of SEQ ID NOs: 10-12, 18-20, 44-46, 74-82, 104-106 and 116-124 can be corrected using a known method. By performing correction, the expression level of a nucleic acid molecule comprising a nucleotide sequence set forth in any of SEQ ID NOs: 10-12, 18-20, 44-46, 74-82, 104-106 and 116-124 can be compared between the biological sample to be tested and the biological sample from a normal individual. The correction of the measured values may be carried out based on the measured value of the expression level of a gene (such as the housekeeping gene) of which expression level does not greatly vary. Examples of the gene of which expression level does not greatly vary include, for example, β-actin and GAPDH.

When mRNA is used in the determination of expression level of a nucleic acid molecule comprising a nucleotide sequence set forth in any of SEQ ID NOs: 10-12, 18-20, 44-46, 74-82, 104-106 and 116-124, a format compatible with the method of diagnosis may be carried out as appropriate. When, for example, mRNA extracted from the biological tissue is used, the RT-PCR method or the Northern blotting method etc. can be selected, and when tissue specimens are used, the in situ hybridization method etc. can be selected. For example, Working Example 8 discloses that in situ hybridization method indicates that an expression of the nesfatin gene is suppressed in rats enhanced appetite by fasting, and the expression is enhanced in a state of suppressed appetite by food intake.

When the expression of a gene comprising a nucleotide sequence set forth in any of SEQ ID NOs: 10-12, 18-20, 44-46, 74-82, 104-106 and 116-124 in a test sample was detected to be decreased compared to that of a biological sample derived from a normal individual, the state of enhanced food intake or enhanced body weight gain is predicted or diagnosed, and furthermore the onset of a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors can be predicted or diagnosed. On the other hand, when the expression of said gene in a biological sample was found to be increased, the mammal tested is in the state of suppressed food intake or suppressed body weight gain is predicted or diagnosed, and furthermore, cibophobia, functional dyspepsia, or the disease conditions of suppressed food intake or suppressed body weight gain resulting from cancer, inflammatory diseases, decreased functions of the pituitary, the thyroid, the adrenal etc., post-surgery, or excessive stress and the like can be predicted or diagnosed.

Furthermore, the present invention relates to a method of predicting or diagnosing the state of food intake control and/or body weight control, which method comprises a step of detecting the decreased state or the enhanced state of the amount contained of the nesfatin polypeptide etc. (a polypeptide comprising an amino acid sequence set forth in SEQ ID NOs: 3, 6, 9, 13-15, 39-41, 65-73, 101-103 or 107-115) by comparing the amount contained of said polypeptide in biological sample of a mammal with that in a biological sample derived from a normal individual. Said method can be carried out by determining the nesfatin polypeptide etc.

As biological samples to be used, there can be mentioned blood, urine, cerebrospinal fluid, saliva, brain tissues harvested from biopsy etc. with blood being most preferred. Blood for use as a sample includes whole blood, or plasma or serum derived from whole blood. Methods of collecting these biological samples are known. Preparations such as lysates of these biological samples can also be used as the sample. For the preparation of lysates of biological samples, commercially available kits can be conveniently used. Alternatively, liquid biological samples such as blood and cerebrospinal fluid can be diluted as needed with a buffer etc. to prepare samples for determining protein or gene.

In order to determine the nesfatin polypeptide etc., an immunological method for said polypeptide can be used in which an antibody that binds to the nesfatin polypeptide etc. can be used. Such an antibody includes those mentioned above, and specifically there can be mentioned an antibody obtained by immunizing a peptide derived from the nesfatin polypeptide obtained in Working Examples 3 and 10, or an antibody obtained by immunizing a peptide derived from the nesfatin-1 polypeptide or the nesfatin-1M30 polypeptide. These antibodies are not limiting, and any polyclonal antibody or monoclonal antibody against the nesfatin polypeptide etc. can be used without specific limitation.

The antibody for use in the present invention may be bound to a suitable label depending on the assay format, or said antibody may be immobilized to a suitable support depending on the assay format.

An immunological method can be carried out as appropriate in a format compatible with the method of diagnosis. For example, when blood samples or lysates are used, the ELISA method, the RIA method, the Western blotting method etc. can be selected, and when tissue specimens are used, immunohistochemical methods etc. may be selected. In a more specific example, the Western blotting method as shown in Examples, the immunohistochemical method as shown in Working Examples 4 and 11 can be mentioned, and it is possible to construct an assay system for the nesfatin polypeptide etc. using appropriate using antibody. For example, the Western blotting method is shown in Working Example 3, immunohistochemical methods in Working Examples 4 and 9, and the ELISA method (competitive EIA method) in Working Example 21.

When the amount contained of the nesfatin polypeptide or the nesfatin polypeptide etc. in a biological sample was found to be decreased compared to that of a biological sample derived from a normal individual, the state of enhanced food intake or enhanced body weight gain is predicted or diagnosed, and furthermore the onset of a disease selected from obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors is predicted or diagnosed. On the other hand, when the amount contained of said polypeptide in a biological sample was found to be increased, the state of suppressed food intake or suppressed body weight gain is predicted or diagnosed, and furthermore, cibophobia, functional dyspepsia, or the disease conditions of suppressed food intake or suppressed body weight gain resulting from cancer, inflammatory diseases, decreased functions of the pituitary, the thyroid, the adrenal etc., post-surgery, or excessive stress and the like can be predicted or diagnosed.

<Kit for Use in the Method of Predicting or Diagnosing the State of Food Intake Control and/or Body Weight Control>

The present invention also relates to a kit for use in the method of predicting or diagnosing the above state of food intake control and/or body weight control. Such a kit includes, for example, a kit for detecting the amount expressed of the gene encoding nesfatin etc. (a gene comprising a nucleotide sequence set forth in any of SEQ ID NOs: 10-12, 18-20, 44-46, 74-82, 104-106 and 116-124) or a kit for detecting the amount contained of the nesfatin polypeptide etc. (a polypeptide comprising an amino acid sequences set forth in any of SEQ ID NOs: 3, 6, 9, 13-15, 39-41, 65-73, 101-103 and 107-115).

The kit for detecting the amount expressed of the gene encoding the nesfatin etc. includes at least one of a PCR primer, a probe or a DNA chip for detecting said gene.

The PCR primer contained in the kit of the present invention refers to an oligonucleotide with a length of at least 18 bases comprising the nucleotide sequence of a gene encoding nesfatin etc. or a nucleotide sequence complementary to the complementary chain thereof, and would be prepared as appropriate based on the base sequence of a gene encoding nesfatin etc. described herein by a person skilled in the art. For example, the PCR primers contained in the kit of the present invention can include, but are not limited to, SEQ ID NO: 22 (forward primer) and SEQ ID NO: 23 (reverse primer). The probe contained in the kit of the present invention includes, but not limited to, one that is obtained by labelling a fragment amplified using the above primer and the DNA sequence of SEQ ID NO: 21 as the template. The DNA chip contained in the kit of the present invention can be prepared by immobilizing the above probe onto a substrate such as glass.

In addition, the kit of the present invention may include, as additional elements, a buffer for diluting reagents and biological samples, positive controls, negative controls, a substrate for determining the label, a reaction vessel, an instruction describing the assay protocol etc. These elements may be mixed in advance as needed. Also, as needed, preservatives and antiseptics may be added to each element.

The kit for determining the amount produced of the nesfatin polypeptide etc. includes an antibody that recognizes said polypeptide, a standard peptide and at least one modified peptide for competitive binding reaction.

The antibody contained in the kit of the present invention, similarly to the antibody used the above method, may be, but is not limited to, an antibody that recognizes the nesfatin polypeptide etc.

The standard peptide contained in the kit of the present invention is used for constructing a calibration curve that demonstrates a dose dependent binding of the above antibody to the nesfatin polypeptide etc. Such a standard polypeptide includes, for example, a polypeptide recognized by the above antibody such as the nesfatin polypeptide etc.

The modified peptide for competitive binding reaction, contained in the kit of the present invention, refers to a peptide recognized by the above antibody, wherein the peptide has an ability of competing with the nesfatin polypeptide or the like in biological samples to be determined for binding to said antibody. Also, the modified peptide for competitive binding reaction is usually used by labelling it as appropriate.

The kit of the present invention can determine the amount of the nesfatin polypeptide etc. contained in a biological sample by, for example, (1) constructing a calibration curve obtained from the standard peptide and the above antibody in the presence of the above modified peptide for competitive binding reaction, (2) adding the above antibody in the presence of the above modified peptide for competitive binding reaction in the biological sample, and (3) determining the amount bound of the modified peptide for competitive binding reaction and the antibody using the standard calibration curve.

It is also possible to determine the amount of the nesfatin polypeptide etc. using two kinds of antibodies that recognize the nesfatin polypeptide or the like and that do not inhibit each other. In this case, the primary antibody is usually immobilized on a solid-phase, and the secondary antibody is suitably labelled for use.

The kit of the present invention can determine the amount of the nesfatin polypeptide etc. contained in a biological sample by, for example, (1) constructing a standard calibration curve by adding the standard peptide to the immobilized primary antibody and reacting the peptide with the primer, and then adding a labelled secondary antibody, (2) adding and reacting the biological sample to the similarly immobilized primary antibody and then adding the labelled secondary antibody, and (3) determining the amount bound of the secondary antibody in the reaction with the biological sample using the calibration curve.

In addition, the kit of the present invention may include, as additional elements, a buffer for diluting reagents and biological samples, positive controls, negative controls, a substrate for determining the label, a reaction vessel, an instruction describing the assay protocol etc. These elements may be mixed in advance as needed. Also, as needed, preservatives and antiseptics may be added to each element.

<Method of Screening a Candidate Therapeutic Compound>

The present invention relates to a method of screening a therapeutic or preventive candidate compound for diseases or conditions associated with food intake control and/or body weight control, said compound having an effect of food intake control and/or body weight control.

Thus, the present invention relates to a method of screening a therapeutic or preventive agent having an effect of suppressing food intake and/or suppressing body weight gain, said method comprising the steps of contacting a test substance with a mammalian cell, and detecting the induced expression of the gene (a gene comprising a nucleotide sequence set forth in any of SEQ ID NOs: 10-12, 18-20, 44-46, 74-82, 104-106 and 116-124) encoding nesfatin etc. in said cell or an increase in the amount of the nesfatin peptide etc. (a polypeptide comprising an amino acid sequence set forth in any of SEQ ID NOs: 3, 6, 9, 13-15, 39-41, 65-73, 101-103 and 107-115) contained in said cell or extracellularly secreted out of the cell. It has been demonstrated that the suppression of food intake or the suppression of body weight gain is required in obesity, diabetes mellitus, hypertension, hyperlipidemia, hyperuricemia, fatty liver, cardiac diseases, cerebral vascular diseases, sleep apnea syndrome, orthopedic diseases, menstrual disorders and malignant tumors. By the above screening method, a therapeutic or preventive agent for said diseases can be obtained.

On the other hand, the present invention also relates to a method of screening a therapeutic or preventive agent having an effect of enhancing food intake and/or enhancing body weight gain, said method comprising the steps of contacting a test substance with a mammalian cell, and detecting the suppressed expression of the gene encoding nesfatin etc. in said cell or a decrease in the amount of the nesfatin peptide etc. contained in said cell or extracellularly secreted out of the cell. It has been demonstrated that the enhancement of food intake or the enhancement of body weight gain is required in cibophobia, functional dyspepsia, or the state of suppressed food intake or suppressed body weight gain resulting from cancer, inflammatory diseases, decreased functions of the pituitary, the thyroid, the adrenal etc., post-surgery, or excessive stress and the like. By the above screening method, a therapeutic or preventive agent for said diseases can be obtained.

Compounds that either increase or decrease the expression level of said polypeptide or a gene encoding it are compounds that act in a promoting or suppressive manner on any step of gene transcription, stabilization or translation, and the secretion, activity expression or stabilization of protein. As used herein, compounds that decrease the expression level of a gene are compounds that have an inhibitory effect on any of these steps.

The method of screening a candidate therapeutic compound of the present invention for diseases or conditions associated with food intake control and/or body weight control may be carried out in vivo or in vitro. This screening in an in vivo case, for example, may be carried out according to the following steps:

(1) a step of administering a candidate compound to a test animal;

(2) a step of determining the expression intensity of the nesfatin polypeptide etc., or the gene encoding said polypeptide in a biological sample from the above test animal; and (3) a step of selecting a compound that enhances, or a compound that decreases, the expression intensity of the nesfatin polypeptide etc., or the gene encoding said polypeptide, as compared to the control that received no candidate compound.

A compound that enhances the production of the nesfatin polypeptide etc. and the expression intensity of the gene encoding said polypeptide can be a candidate of a therapeutic agent for suppressing food intake and/or suppressing body weight gain. Substances having such an activity include, but not limited to, a PPARγ agonist and the like. On the other hand, a compound that suppresses the production of the nesfatin polypeptide etc. or decreases the expression intensity of the gene encoding said polypeptide can be a candidate of a therapeutic agent for enhancing food intake and/or enhancing body weight gain. Substances having such an activity include, but not limited to, an antibody that binds to the nesfatin polypeptide etc., an antisense oligonucleotide against the gene encoding said polypeptide, a PPARγ antagonist and the like.

As the test animal for use in the screening method of the present invention, normal animals can be used and pathological animal models for diseases associated with food intake control and/or body weight control can also be used as appropriate. As the example of such pathological animal models, there can be mentioned the C57BL/6L Ham Slc$^{AY}$ obese mice, the Zucker-fa/fa obese rats and the like. Also the transgenic animals of the present invention or animal models that received the nesfatin polypeptide etc., or a substance that suppresses the activity or the expression of said polypeptide can be used.

The determination of expression intensity of the nesfatin polypeptide etc., or the gene encoding said polypeptide can be carried out by an immunological method or by determining mRNA. In the immunological method, a format compatible with the purpose of determination or the biological sample may be used as appropriate. For example, when blood samples or lysates of biological tissues are used as the biological sample, the ELISA method, the RIA method, the Western blotting method etc. can be selected, and when tissue specimens are used, immunohistochemical methods etc. may be selected. When mRNA is to be determined, a format compatible with the purpose of determination or the biological sample may be used as appropriate. When, for example, mRNA extracted from the biological tissue is used, the RT-PCR method or the Northern blotting method etc. can be selected, and when tissue specimens are used, the in situ hybridization method etc. can be selected.

An example of in vitro screening can be carried out according to the following steps:

(1) a step of contacting a candidate compound with a mammal-derived cell or tissue;

(2) a step of determining the expression intensity of the nesfatin polypeptide etc., or the gene encoding said polypeptide in the above cell sample or the tissue sample; and (3) a step of selecting a compound that enhances, or a compound that decreases, the expression intensity of the nesfatin polypeptide etc., or the gene encoding said polypeptide, as compared to the control that received no candidate compound.

In this case, a compound that enhances the production of the nesfatin polypeptide etc. and the expression intensity of the gene encoding said polypeptide can be a candidate of a therapeutic agent for suppressing food intake and/or suppressing body weight gain. Substances having such an activity include, but not limited to, a PPARγ agonist and the like. On the other hand, a compound that suppresses the production of the nesfatin polypeptide etc. or decreases the expression intensity of the gene encoding said polypeptide can be a candidate of a therapeutic agent for enhancing food intake and/or enhancing body weight gain. Substances having such an activity include, but not limited to, an antibody that binds to the nesfatin polypeptide etc., an antisense oligonucleotide against the gene encoding said polypeptide, a PPARγ antagonist and the like.

As the test cell for use in the screening method of the present invention, a cell separated as appropriate from an animal or an established cell line can be mentioned in the case of cells derived from animals. Their examples include a non-small cell lung cancer cell line, an adipose cell, a brain- or nerve-derived cell, a cell line or the like. As the tissue derived from animals, organs or tissues harvested as appropriate from the animals can be used, and as an example a brain tissue section in the form containing the hypothalamus can be used.

The determination of expression intensity of the nesfatin polypeptide etc., or the gene encoding said polypeptide can be carried out by an immunological method or by determining mRNA. In the immunological method, a format compatible with the purpose of determination or the biological sample may be used as appropriate. For example, when the sample is a cell derived from an animal, flow cytometry or cytoimmunological staining etc. can be used, and when tissue specimens derived from animals are used, immunohistochemical methods etc. may be selected. When preparations such as lysates from samples are used, the ELISA method, the RIA method, the Western blotting method etc. can be selected. When mRNA is to be determined, a format compatible with the purpose of determination, or the biological sample, may be used as appropriate. When, for example, animal-derived cell samples or tissue samples are used as they retain the morphology, the in situ hybridization method etc. can be selected, and when mRNA extracted from said samples is used, the RT-PCR method, the Northern blotting method etc. can be selected.

The present invention discloses that the PPARγ agonist enhances the expression of the nesfatin polypeptide etc. and the gene encoding it. Thus, In the above step of "contacting a candidate compound with a mammal-derived cell or tissue", the compounds that suppresses the expression of the nesfatin polypeptide etc., or the gene encoding of said polypeptide of which expression is enhanced can be screened by contacting PPARγ such as troglitazone with the sample simultaneously with, before or after contact of the candidate compound with the sample, and the compounds that enhance expression of said polypeptide or the gene encoding it, in a mechanism that does not involve PPARγ, can be screened.

The compound can also be screened by determining the reaction of the cell that occurs when the nesfatin polypeptide etc. acts on the cell. As an example of such screening, there can be mentioned those that include the following steps:

(1) a step of contacting a candidate compound with a mammal-derived cell or tissue;

(2) a step of contacting the nesfatin polypeptide etc. with said cell or tissue sample; and (3) a step of determining the presence or absence of the reaction of the cell, or intensity, by the nesfatin polypeptide etc., as compared to the control that was not contacted with the candidate compound.

In this case, a compound that enhances the reactive intensity of the cell by the nesfatin polypeptide etc. can be a candidate of a therapeutic agent for suppressing food intake and/or suppressing body weight gain. Also, a compound that decreases the reactive intensity of the cell by the nesfatin polypeptide etc. can be a candidate of a therapeutic agent for enhancing food intake and/or enhancing body weight gain. Substances having the latter activity include, but are not limited to, an antibody that binds to the nesfatin polypeptide etc.

As the test cell, a cell separated as appropriate from an animal or an established cell line can be mentioned in the case of cells derived from animals. The examples include a non-small cell lung cancer cell line, an adipose cell, a brain- or nerve-derived cell, a cell line or the like. As the tissue derived from animals, organs or tissues harvested as appropriate from the animals can be used, and as an example brain tissue section in a form containing the hypothalamus can be used.

The reaction in the above cell refers to a physical and chemical change induced by the action of the nesfatin polypeptide etc. on the cell, and include, for example, changes in cell morphology, membrane potential, cell growth, intracellular calcium concentration, migration reaction, intracellular secondary messenger molecule (cAMP, dGMP etc.) concentration and the like.

Furthermore, in the screening method of the present invention, a transcription regulatory region that is in a genome of the nesfatin and that controls the expression of said gene is obtained, and can be used in a reporter assay system that employs the nucleic acid molecule of said transcription regulatory region. The reporter assay system refers to an assay system in which a transcription regulatory factor that acts on said transcription regulatory region is screened with the amount expressed of the reporter gene disposed downstream to the transcription regulatory region as an index.

As an example of such screening, there can be mentioned those that include the following steps of (1) to (3):

(1) a step of contacting the candidate compound with a cell having introduced therein a vector comprising the transcription regulatory region of the gene encoding the nesfatin polypeptide and the reporter gene under the control of the transcription regulatory region;

(2) a step of determining the activity of said reporter gene; and (3) a step of selecting a compound that decreases, or a compound that increases, the expression level of said reporter gene as compared to the control that was not contacted with the candidate compound.

In this case, a compound that enhances the expression intensity of the reporter gene can be a candidate of a therapeutic agent for suppressing food intake and/or suppressing body weight gain. Substances having such an activity include, but are not limited to, a PPARγ agonist and the like. Also, a compound that decreases the expression intensity of the reporter gene can be a candidate of a therapeutic agent for enhancing food intake and/or enhancing body weight gain. Substances having such an activity include, but are not limited to, an antibody that binds to the nesfatin polypeptide etc., an antisense oligonucleotide against the gene encoding said polypeptide, a PPARγ antagonist and the like.

As the transcription regulatory region, there can be mentioned a promoter, an enhancer, a CAAT box commonly seen in the promoter region, or a TATA box. As the reporter gene, there can be used the chloramphenicol acetyltransferase (CAT) gene, the luciferase gene, the growth hormone gene and the like.

As the cell into which a reporter gene vector is introduced, there can be mentioned a cell line separated or established from animals, non-mammalian cells such as yeast, and the like.

As the method of introducing the reporter gene vector into the host, there can be illustrated the biological method, the physical method, the chemical method and the like. As the biological method, there can be illustrated a method that employs a virus vector, a method that employs a specific receptor, cell fusion (Sendai virus (HVJ)), polyethylene glycol (PEG), electric cell fusion, micronucleate cell fusion (chromosome transfer)), and the like. The physical method includes a microinjection method, an electroporation method, a method that employs a gene particle gun. The chemical method includes a calcium phosphate precipitation method, a liposome method, a DEAE-dextran method, a protoplast method, an erythrocyte ghost method, an erythrocyte membrane ghost method, and a microcapsule method.

Polynucleotides, antibodies, cell lines, or model animals required for various screening methods of the present invention can be assembled in advance to make kits. These kits may contain, as additional elements, a substrate compound for use in labelling, a medium or a vessel for culturing cells, a positive or negative standard sample, and instructions describing the method of using the kit. The elements may be mixed in advance as needed, and each element may contain preservatives and/or antiseptics as needed.

The present invention will now be explained in more detail hereinbelow with reference to Working Examples, but it should be noted that these Examples do not limit the present invention in any way. In the following Working Examples, unless otherwise specified, each procedure was performed in accordance with the methods described in "Molecular Cloning" (Sambrook, J., Fritsch, E. F. and Maniatis, T., issued by Cold Spring Harbor Laboratory Press in 1989), or when commercially available reagents or kits are used, they were used as described in the instructions attached in the commercially available products. In experiments using animals, unless otherwise specified, animals (male rats) were kept under an illumination cycle of 12 hours of the light period from 6 a.m. to 6 p.m. and 12 hours of the dark period from 6 p.m. to 6 a.m. the next morning at 22° C., and the experiment was carried out under the authority of the animal experiment facility of Gunma University.

WORKING EXAMPLES

Working Example 1

Cloning of the Gene Induced by Stimulation with the PPARγ Agonist

In order to identify the gene that acts on food intake control and/or body weight control among the genes of which expression is regulated by PPARγ, genes that are specifically induced when SQ-5 cells (mainly derived from humans) are stimulated with the PPARγ agonist were cloned, and from them, genes that are likely to function as a secretary factor were selected.

The method of obtaining genes of which expression is specifically induced by PPARγ in non-small cell lung cancer was carried out according to the method of Satoh et al., Oncogene (England), 2002, Vol. 21, pp. 2171-2180. The method is briefly described below. From each of SQ-5 (Riken BioResource Center RBC0110) cultured for 48 hours under stimulation with $10^{-4}$ M of troglitazone (Sankyo Co., Ltd.), a PPARγ agonist, and SQ-5 cells not stimulated with troglitazone, poly(A)+RNA (mRNA) was prepared, and was subjected to a reverse transcription reaction to prepare double stranded cDNA. A subtraction method was carried out in which the gene expressing in common cDNA (driver) using the cells being expressed in the non-stimulated cells is subtracted from cDNA (tester) prepared from the cells stimulated with troglitazone using the double stranded cDNA obtained. The subtraction method was carried out using fragments obtained by cleaving the tester and driver cDNA with a restriction enzyme RsaI and by the Clontech's PCR-based cloning kit according to the attached protocol. The residual cDNA after subtraction was subjected to electrophoresis on a 1% agarose gel in TAE buffer (40 mM Tris-acetate, 1 mM EDTA), and then cDNA with a length corresponding to 0.5-2.0 kb was collected and ligated to the PGEM®-T Easy vector using the PGEM®-T Easy Vector System I (Promega Corp., Cat. No. A1360) according to the attached protocol. The ligated vector was introduced into a E. coli strain DH5α and allowed to form colonies on an agar medium prepared with a LB medium containing 50 μg/ml ampicillin, and the colonies obtained were picked up to obtain clones containing cDNA of the gene of which expression is specifically induced by troglitazone stimulation.

Each clone was identified by analyzing the nucleotide sequence of the cloned cDNA. E. coli of each clone obtained was cultured overnight in a 10 mL of the LB medium containing 50 μg/ml ampicillin, and a plasmid was prepared from the cells using the QIAGEN's QIAprep®Spin Miniprep kit according to the attached protocol.

For the plasmid of each clone obtained, a reactant for nucleotide sequence analysis was prepared using the T7 primer (Promega Corp., Cat. No. Q5021) and the BigDye Terminator Cycle Sequencing FS Ready Reaction kit (Cat. No. 4303149) of Applied Biosystems according to the attached protocol, and its nucleotide sequence was analyzed using the ABI337 type DNA Sequencer (Perkin-Elmer).

By subjecting the nucleotide sequence of cDNA of each clone as a query to the BLAST method with the sequences on the EMBL and the Genbank nucleic acid database, a sequence was obtained for which the full-length cDNA sequence was known.

From the full-length cDNA sequence obtained in the above process, cDNA encoding a protein having a signal peptide was analyzed by the Signal P software in order to select secretary factors.

<Result>

Clones obtained by the subtraction of cDNA of the SQ-5 cells not stimulated with troglitazone using the cDNA obtained from the SQ-5 cells stimulated with troglitazone were 596 clones. For 213 clones among them, remarkable homology was noted with the registered sequences in the nucleic acid sequences in EMBL and Genbank. Furthermore, by the analysis of signal peptides, 9 clones were suggested to have a signal peptide sequence. One of the 9 clones was the human NEFA gene for which a function had not been identified (SEQ ID NO: 1).

Working Example 2

Induction of the NEFA Gene Expression in a Cultured Cell Line by PPARγ Agonist Stimulation In order to confirm the induction of the NEFA gene expression by troglitazone, cell lines HTB185 and SQ5 expressing PPARγ and an adipose cell line 3T3-L1 were analyzed for the expression of the NEFA gene by Northern blotting.

SQ-5 (Riken BioResource Center RBC0110) was subcultured in a RPMI 1640 medium (Invitrogen-BRL, Cat. No. 11875-085) containing 10% bovine fetal serum (Invitrogen-GIBCO). Human cerebrospinal blastocytoma cell line HTB185 cells (D283 Med: ATCC HTB185) and mouse fetal fibroblast cell line (precursor adipose cell line) 3T3-L1 cells (ATCC CL-173) of which differentiation was induced with insulin, dexamethasone and IBMX were subcultured in a DMEM medium (Invitrogen-GIBCO, Cat. No. 11955-040) containing 10% bovine fetal serum. $10^6$ cells from each cell suspended in 10 ml of the medium were plated in a dish with a diameter of 10 cm. After the cells adhered to the substrate, DMSO alone (control) or troglitazone (Sankyo Co., Ltd.) were added to a concentration of $10^{-4}$ M, $10^{-4.5}$ M or $10^{-5}$ M, and cultured under the condition of 5% $CO_2$ at 37° C. for 24 hours or 48, hours. For each experiment group, cells treated in 5 dishes were scraped from the substrate after a certain period, and total RNA was extracted and collected using ISOGEN (Nippon Gene, Cat. No. 317-02503) according to the method described in the protocol.

A probe for detecting the NEFA gene was prepared using a 565 bp DNA fragment set forth in SEQ ID NO: 21 by labelling with in vitro transcription using a SP6 polymerase. Using a plasmid extracted from the mouse brain cDNA library (Invitrogen Corp., Cat. No. 10655-25) as the template and the following-primers at a concentration of 0.2 μM, amplified DNA was prepared by 35 cycles of reaction comprising denaturation at 94° C. for 1.5 minute, annealing at 58° C. for one minute and amplification at 72° C. for 2 minutes (Takara Bio Inc., Takara Ex Taq™ polymerase, Cat. No. RR001A 2.5U was used).

PCR primers for preparing the NEFA probe:

```
                                          (SEQ ID NO: 22)
Forward primer: 5-CCAGTGGAAAATGCAAGGAT-3

(SEQ ID NO: 23)
Reverse primer: 5-TCTTTGCTTCCGGGATGATTA-3
```

After the purity of the amplified DNA product obtained was confirmed by a 2% agarose gel electrophoresis using the TAE buffer, it was subcloned into the pGEM®-T Easy vector using the pGEM®-T Easy Vector System I (Promega Corp., Cat. No. A1360) according to the attached protocol, and introduced into the E. coli DH5α to form colonies on an agar medium prepared with the LB medium containing 50 μg/ml ampicillin. Several colonies obtained were each picked up, and the E. coli was cultured overnight in 10 ml of the LB medium containing 50 μg/ml ampicillin. From the cells, plasmid was prepared using the QIAGEN's QIAprep® Spin Miniprep kit according to the attached protocol. A reactant for nucleotide sequence analysis was prepared using the T7 primer (Promega Corp., Cat. No. Q5021) or the SP6 primer (Promega Corp., Cat. No. Q5011) and the BigDye Terminator Cycle Sequencing FS Ready Reaction kit (Cat. No. 4303149) of Applied Biosystems according to the attached protocol, and its nucleotide sequence was analyzed using the ABI337 DNA Sequencer (Perkin-Elmer). A clone that has a sequence corresponding to the predicted sequence and in which the 5'-end of the amplified NEFA-derived gene faces the T7 promoter side of the vector was made a clone for obtaining a plasmid for preparing the probe. The clone obtained was cultured overnight in a 10 mL of the LB medium containing 50 μg/ml ampicillin, and a plasmid was prepared from the cells using the QIAGEN's Plasmid Mini kit according to the attached protocol. The prepared plasmid was cleaved with a restriction enzyme NcoI, extracted with phenol, purified with phenol/CIAA extraction, and after precipitating with ethanol, it was dissolved at 1 μg/ml in a ribonuclease-free TE buffer (10 mM Tris-HCl, 1 mM EDTA, pH 8.0) to prepare a template plasmid DNA for preparing the probe. A labelled RNA probe was prepared from 1 μg of the template plasmid DNA using Promega's Riboprobe® System-SP6 with 2.5 μM [α-$^{32}$P] UTP (Amersham Biosciences Inc., Cat. No. PB10203, 3000 Ci/mM, 10 mCi/ml) and 20U of RNA synthase SP6 (contained in the kit) according to the protocol attached to the kit.

For electrophoresis for Northern blotting, total RNA obtained from each cell was subjected to electrophoresis using a 1.2% agarose gel prepared in a MOPS buffer (20 mM 3-(N-morpholino)-propanesulfonic acid, 5 mM sodium acetate, 0.5 mM EDTA) containing 0.66 M deionized formaldehyde at 100 V for 2 hours. Using a 10-fold concentration of SSC (150 mM NaCl, 15 mM sodium acetate), RNA was transferred from the gel after electrophoresis to a nylon membrane (Perkin-Elmer Inc., Gene Screen Plus® Hybridization Transfer Membrane). To the transferred membrane, RNA was immobilized by UV using Stratagene's Stratalinker. Then, the nylon membrane was subjected to prehybridization in a prehybridization solution (0.25 M NaCl, 20 mM Tris-HCl, pH 7.5, 2.5 mM EDTA, 1% SDS, 0.5% bovine serum albumin, 0.5% polyvinyl pyrrolidone, 0.5% Ficoll, 50% deionized formamide) at 43° C. for 3 hours, and to hybridization in a hybridization solution (0.25 M NaCl, 20 mM Tris-HCl, pH 7.5, 2.5 mM EDTA, 1% SDS, 0.5% bovine serum albumin, 0.5% polyvinyl pyrrolidone, 0.5% Ficoll, 50% deionized formamide, 10% dextran sulfate) containing 1,000,000 cpm/ml of the labelled RNA probe at 43° C. overnight. After rinsing the nylon membrane after hybridization with a two-fold concentration of SSC, it was washed twice under a stringent condition of 0.2-fold concentration of SSC containing 0.1% SDS at 60° C. for 30 minutes. The nylon membrane after washing was exposed overnight to an X-ray film (Kodak, XAR film) in the presence of an intensifying screen (Cronex, Lightining Plus), and the labelled RNA probe that hybridized was detected.

<Result>

The result of Northern blotting analysis of the induction of the NEFA gene with troglitazone (TGZ) in a cell line is shown in FIG. 1. Lanes 1-4 represent results for the human medulloblastoma cell line HTB185 cells that are expressing PPARγ. Lanes 1 and 3 show the detection of the NEFA gene expression with the RNA of cells cultured (24 hours and 48 hours, respectively) without the TGZ stimulation of the HTB185 cells, while lanes 2 and 4 show the detection of the NEFA gene expression with the RNA of cells stimulated $10^{-4}$ M troglitazone for 24 and 48 hours, respectively. As a result, only a slight expression of the NEFA gene was noted in the cells not stimulated with TGZ (lanes 1 and 3), whereas marked induction was noted in the cells stimulated with TGZ for 48 hours (lane 4). Lanes 5 and 6 in the Figure represent the result obtained with SQ-5 that is expressing PPARγ. Lane 5 shows the detection of the NEFA gene expression with the RNA of the SQ-5 cells cultured without TGZ stimulation, while lane 6 shows the detection of the NEFA gene expression with the RNA of cells stimulated $10^{-4}$ M TGZ for 24 hours. As a result, a low level of expression was noted in the cells not stimulated with TGZ (lane 5), whereas marked induction of expression of the NEFA gene was noted in the cells stimulated with TGZ for 24 hours (lane 6). Furthermore, lanes 7-10 in FIG. 1 represent results for the mouse fetal fibroblast cell line (precursor adipose cell line) 3T3-L1 cells that are expressing PPARγ. Lane 7 shows the detection of the NEFA gene expression with the RNA of the 3T3-L1 cells cultured without TGZ stimulation, while lanes 8-10 show the detection of the NEFA gene expression with the RNA of the 3T3-L1 cells stimulated with $10^{-5}$ M, $10^{-4.5}$ M and $10^{-4}$ M of TGZ, respectively, for 48 hours. As a result, a considerable amount of expression of the NEFA gene was noted even in the absence of TGZ stimulation (lane 7), and similar expression was obtained when stimulated with $10^{-5}$ M to $10^{-4}$ M of TGZ, indicating that the NEFA gene is being constantly expressed irrespective of the stimulation of PPARγ.

Working Example 3

Preparation of Antibody Against NEFA and the Demonstration of Expression in the Rat Brain The secretary protein expressed in the adipose cells is also expressed in the brain, and thus has been proposed as the Brain-Adipose Axis that is likely to have an effect of controlling food intake (Masatomo Mori: Adipose Research (Shibou Kenkyu), 2004, Vol. 10, pp. 117-119, Shimizu H. and Mori M.: Nutritional Neurosci 8:7-20, 2005). Thus, an antibody against NEFA that is expressed in the adipose cells and the brain tumor cells to investigate the localized expression of NEFA in the hypothalamus.

For the preparation of the antibody against NEFA, a synthetic peptide (SEQ ID NO: 24: synthesized at ATP K.K.) in which Cys was attached to the C-terminal of a sequence from His at position 141 to Ser at position 152 of the amino acid sequence (SEQ ID NO: 8) of the rat precursor NEFA polypeptide (said peptide is hereinafter referred to as the NAP peptide) was used as the antigen. NAP peptide: N-HisLeuAsn-HisGlnAsnProAspThrPheGluSerCys-C (SEQ ID NO: 24).

Said synthetic NAP peptide was conjugated to keyhole limpet hemocyanin (KLH) using the Imject® Maleimide Activated Mariculture Keyhole Limpet Hemocyanin of Pierce Inc. according to the attached protocol. 0.2 mg of the peptide obtained was used for one immunization per rabbit. For immunization, 0.25 ml of the conjugate solution (conjugate concentration: 1 mg/ml) and an equal amount of Freund's complete adjuvant H-37 Ra (Wako Pure Chemical—Difco, Cat. No. 528-00031) were mixed, and 50 μl each was intradermally injected at 8 different places on the shaved back of New Zealand White rabbits (purchased from Imai Experimental Animal Testing Site). Similar immunization was performed further 4 times every two weeks. One week after the last immunization, part of the blood was collected, and antibody titer in the serum was confirmed by the ELISA method employing the immobilized peptide conjugate. On the next day, the animals were sacrificed to collect whole blood. From the blood obtained, serum was prepared. From the serum rabbit IgG was purified using the DEAE Sepharose FF (Amersham Biosciences Inc., Cat. No. 17-0709-10) according to a standard method. The purified rabbit IgG was affinity-purified using a peptide-immobilized column that was prepared from 1 mg of the NAP peptide using the SulfoLink kit (Pierce Inc., Cat. No. 44895), according to the protocol attached to the kit.

Using the obtained antibody (anti-NAP polyclonal antibody) against the NAP peptide, the expression of the NEFA polypeptide in the rat brain was analyzed by Western blotting.

Protein extracts from the rat brain was prepared by homogenizing the hypothalamus (1.7 g) of 8 week-old Wistar rats (Nippan Charles River) in 5 ml of the extraction buffer (50 mM Tris-HCl, pH8.0, 150 mM NaCl, 5 mM EDTA, 1% Nonidet P-40). The rat brain lysate obtained was mixed with an equal amount of the Laemmli sample buffer (Bio-Rad Inc., Cat. No. 161-0737) containing 5% β-mercaptoethanol for SDS-polyacrylamide gel electrophoresis (SDS-PAGE) and heated to 100° C. for 5 minutes, and then centrifuged in a microcentrifuge at an ordinary temperature at 15,000 rpm for 10 minutes to collect the supernatant. 20 μl of the supernatant was electrophoresed on a polyacrylamide gel (Bio-Rad Inc., Ready gel 10-20%, Cat. No. 161-J390V) using the Tris-glycine/SDS buffer (25 mM Tris, 192 mM glycine, 0.1% SDS, pH 8.3) at 100V for 1 hour, and then transferred to a nitrocellulose membrane. The membrane was blocked in 3% gelatin/TBS at room temperature for 1 hour, and washed three times in TBS-0.05% Tween and once in TBS. It was then allowed to react overnight at room temperature in a 1% gelatin/TBS solution containing 1 μg/ml of anti-NAP polyclonal antibody. On the next day, it was washed three times in TBS-0.05% Tween and once in TBS, and then was reacted with anti-rabbit IgG goat polyclonal antibody-peroxidase conjugate (Cappel Inc., Cat. No. 674371) diluted to about 1 μg/ml in 1% gelatin/TBS solution at room temperature for 1 hour. It was then washed for three times in TBS-0.05% Tween and twice in TBS, and was allowed to develop color using the HRP color development kit (Bio-Rad Inc., Cat. No. 170-64631) at room temperature for five minutes, and the bands were detected <Result>
FIG. 2 A shows the schematic diagram of the structure of the NEFA polypeptide and the position of the peptide, which was used for preparing the antibody, on NEFA, and FIG. 2 B shows the result of Western blotting of the protein extracts from the rat brain with a polyclonal antibody prepared by immunization with the NAP peptide. In the Western blotting of the protein extracts from the rat brain with a polyclonal antibody prepared against the NAP peptide, a single band was observed at a molecular weight of about 47.5 kd (FIG. 2 B). This revealed that the antibody against NAP recognizes the full-length NEFA and that NEFA is being expressed in the rat brain.

Working Example 4

Study on the Expression Site of nesfatin in the Rat Brain Hypothalamus

In order to analyze the expression site of NEFA in the rat brain hypothalamus associated with the control of food intake, an immunohistochemical analysis of the sections of the rat brain was carried out. Eight week-old Wistar rats (purchased from Nippon SLC) were anesthetized by an intraperitoneal injection of 40 mg/kg of pentobarbital sodium, and then thoracotomy was performed to inject 50 ml of physiological saline (0.85% NaCl) into the heart, and then PBS containing 4% paraformaldehyde (20 mM phosphate buffer, 150 mM NaCl, pH 7.2) was injected and circulated using a 400 ml peristatic pump to perfusion fix the brain. The brain was then extracted, and the portion containing the hypothalamus was excised, and was fixed overnight at 4° C. in PBS containing 4% paraformaldehyde. The fixed brain sample was immersed in PBS containing 10% sucrose for 4 hours, PBS containing 10% sucrose for 4 hours, and PBS containing 20% sucrose overnight at 4° C. Then the brain sample was immersed in an OCT compound and frozen in dry ice-acetone to prepare the embedded block. From the block prepared, sections of 6 μm in thickness were prepared at −20° C. using a cryostat, and then were air-dried on a silane-coated slide (MAS coat slide prepared by Matsunami). Tissue sections on the slide were treated with 3% hydrogen peroxide for 5 minutes, and then washed twice in PBS for 5 minutes. Furthermore, the tissue sections were blocked by treating with 10% goat normal serum (Nichirei Corp., Cat. No. 426042) at room temperature for 10 minutes, and then were reacted to 1 μg/ml of a polyclonal antibody (Working Example 3) against the NAP peptide diluted in PBS containing 0.5% BSA at room temperature for 1 hour (Ab group). After washing the slide in PBS, the slide was reacted with the Histofine Simple Stain Rat MAX PO (Nichirei Corp., Cat. No. 414181), and after three times-washing in PBS for 5 minutes per each, color was developed using the Simple Stain DAB solution (Nichirei Corp., Cat. No. 415172). The slide after color development was washed in water, and then stained with the Meyer-Hematoxylin (Muto Pure Chemicals Co., Ltd., Cat. No. 3000), washed in water, dehydrated in alcohol and cleared in xylene, and mounted using a non-aqueous mounting agent (Nichirei Corp., Cat. No. 415141) with a cover slip. The brain section on the slide after mounting was examined with a microscope.

<Result>
FIG. 3 shows a micrograph (200× magnification) of histoimmunochemical staining with the anti-NAP peptide in the tissue section at the hypothalamus and the third ventricle (3V) regions of the rat's brain. Specific staining was seen in Arc: arcuate nucleus, PVN: paraventricular nucleus, LH: lateral hypothalamic area, SON: supraoptic nucleus of the hypothalamus in the figure, indicating the expression of NEFA in these sites. From the foregoing, it was demonstrated that the NEFA polypeptide is expressed in the rat hypothalamus, specifically in the arcuate nucleus, the paraventricular nucleus, the lateral hypothalamic area and the supraoptic nucleus.

Since the expression of the NEFA polypeptide encoded by the NEFA gene was noted at sites associated with the control of food intake in the hypothalamus, said polypeptide was named nesfatin.

Working Example 5

Preparation of Recombinant nesfatin

In order to confirm the properties of nesfatin expressed in the nerve nucleus of the hypothalamus associated with food intake, recombinant nesfatin was prepared in *E. coli*. The recombinant matured mouse nesfatin (SEQ ID NO: 26) was purified by expressing a fusion protein (recombinant mouse GST-NEFA: SEQ ID NO: 25) in which glutathione S-transferase (GST) was bound to the N-terminal of mouse matured mouse nesfatin (SEQ ID NO: 6), and treating the fusion protein with a protease. The level of homology on the amino acid level of the rat nesfatin and the mouse nesfatin is as high as 96.5%.

A gene for expressing recombinant mouse GST-NEFA was prepared using a plasmid extracted from the mouse brain cDNA library (Invitrogen Corp., Cat. No. 10655-25) as the template and using the primers described below (0.25 µM each) in a denaturation reaction at 94° C. for 1.5 minute, followed by five cycles of reaction comprising denaturation at 94° C. for 0.5 minute, annealing at 60° C. for 0.5 minute, and extension at 72° C. for 2 minutes and then 30 cycles of reaction comprising denaturation at 94° C. for 0.5 minute, annealing and extension at 72° C. for 2 minutes, to prepare the amplified DNA (Stratagene's PfuTurbo® polymerase, Cat. No. 600250 was used).

PCR primers for preparing recombinant matured mouse NEFA cDNA

```
Forward primer:
                                        (SEQ ID NO: 27)
5-TTGGATCCGTTCCTATCGATGTGGACAAGAC-3

Reverse primer: 5
                                        (SEQ ID NO: 28)
5-TTGCGGCCGCTTATGTGTGTGGCTCAAACTTCAG-3
```

The PCR product obtained was purified by QIAGEN's MinElute PCR Purification Kit, cleaved with restriction enzymes BamHI and NotI, and an about 1.3 kb band was excised by a 2% agarose gel-TAE electrophoresis and the DNA fragment was collected (QIAGEN's MinElute Gel Extraction Kit, Cat. No. 28604 was used). The 1.3 kb DNA fragment was ligated to pGEM-11Zf(+) vector (Promega, P2411) that had been cleaved with restriction enzymes BamHI and NotI, which was transformed to *E. coli* strain DH5α (Takara Bio Inc., Cat. No. 9057) and was allowed to form colonies on an agar medium comprising an LB medium containing 50 µg/ml ampicillin.

Several of the colonies obtained were picked up, and for the plasmid prepared from each clone the nucleotide sequence was analyzed using pUC/M13 forward primer (Promega Corp., Cat. No. Q5391), pUC/M13 reverse primer (Promega Corp., Cat. No. Q5401), two kinds of primers mSQ1 (5-CCT-GAACCACCAGAATCC-3: SEQ ID NO: 29) and mSQ2 (5-AGACTGATGGATTGGACC-3: SEQ ID NO: 30) in the sequence of the mouse NEFA gene, and using the BigDye Terminator Cycle Sequencing FS Ready Reaction kit (Cat. No. 4303149) of Applied Biosystems and the ABI337 type DNA Sequencer (Perkin-Elmer). Clones that were shown to have a nucleotide sequence corresponding to SEQ ID NO: 11 by the nucleotide sequence analysis were cultured overnight in 10 ml of the LB medium containing 50 µg/ml ampicillin, and plasmid was prepared from the cells using the QIAGEN's QIAprep®Spin Miniprep kit according to the attached protocol.

The plasmid was cleaved with restriction enzymes BamHI and NotI, was electrophoresed on a 2% agarose TAE gel, and the 1.2 kb band was excised to collect DNA. The collected DNA fragments were ligated to the pGEX-4T-1 vector (Amersham Biosciences Inc., Cat. No. 27-4580-01) that had been cleaved with restriction enzymes BamHI and NotI, and which was transformed to *E. coli* strain BL21 (Amersham Biosciences Inc., Cat. No. 27-1542-01) using the Gene Pulser Xcell electroporation system (Bio-Rad Inc., Cat. No. 165-2660J1) so as to allow colonies to be formed on an agar medium prepared with the LB medium containing 50 µg/ml ampicillin. Recombinant *E. coli* obtained by transformation was confirmed for the presence or absence of an insert by PCR using the pGEX5' Sequencing Primer and the pGEX3' Sequencing Primer (Amersham Biosciences Inc., Cat. No. 27-1410-01 and 27-1411-01), and the insertion of the NEFA gene was confirmed by PCR using the PCR primer set for preparing the NEFA probe used in Working Example 2. Clones for which the matured NEFA cDNA was confirmed to be integrated into the pGEX-4T-1 vector were used to express the recombinant mouse GST-NEFA protein. The clones were cultured overnight at 37° C. with 10 ml of a LB medium containing 100 µg/ml ampicillin, and 5 ml of it was added to 500 ml of a LB medium containing 100 µg/ml ampicillin and cultured by shaking at 37° C. until the absorbance at a wavelength of 600 nm became 0.6 (some of the bacteria were sampled out: Preinduced bacteria). To the medium was added isopropyl-β-D-thiogalacto-pyranoside (IPTG: Gibco BRL) to a final concentration of 1 mM, and was further cultured by shaking at 37° C. for 3 hours. After culturing, the medium containing the cells were centrifuged at 5,000 g at 4° C. for 15 minutes to collect the cells, which were suspended in 25 ml of PBS. The suspension was frozen at −80° C. for about 1 hour, and then thawed quickly at 37° C., and the cells were subjected to sonication for 30 seconds× five times to disrupt the cells. It was followed by centrifugation at 10,000 g at 4° C. for 30 minutes to collect the supernatant (the precipitated fraction was sampled out: Post-sonicated pellet).

The supernatant was applied to a 5 ml-scale GSTrapFF column (Amersham Biosciences Inc., Cat. No. 17-5131-01) equilibrated with PBS using the AKTA-FPLC liquid chromatography system (Amersham Biosciences Inc.), and then the column was washed with 50 ml of PBS (flow rate: 1 ml/min). Then the elution buffer (10 mM reduced glutathione, 0.4 M Tris-HCl, pH 8.0, 0.2 M NaCl) was run at a flow rate of 1 ml/min to collect 1 ml fractions, and fractions containing protein as determined by absorbance at a wavelength of 280 nm were collected (the fraction having the highest absorbance at 280 nm: Purified GST-NEFA). A portion of each of the Preincubation bacteria fraction, the Post-sonicated pellet fraction, and the Purified GST-NEFA fraction was dissolved in the Laemmli sample buffer (Bio-Rad Inc., Cat. No. 161-0737) containing 5% β-mercaptoethanol, treated at 100° C. for 5 minutes, and centrifuged in a microfuge at 15,000 rpm for 5 minutes to obtain a supernatant, which was subjected to a polyacrylamide gel electrophoresis (Bio-Rad Inc., Ready gel 10-20%, Cat. No. 161-J390V) at 100 V for 1 hour using a Tris-glycine/SDS buffer and then stained in a Coomassie brilliant blue stain (Bio-Rad Inc., Bio-Safe CBB G-250, Cat. No. 161-0786). For most of the Purified GST-NEFA fraction, reduced glutathione was removed from the sample using liquid chromatography with the HITrap Desalting column (Amersham Biosciences Inc., Cat. No. 17-1408-01) equilibrated with PBS, and the sample was applied again to a 5 ml-scale GSTrapFF column equilibrated with PBS. After the column was washed with 25 ml of PBS at a flow rate of 1 ml/min, 15 ml of the protease reaction buffer (50 mM Tris-HCl, pH7.5, 150 mM NaCl, 1 mM EDTA, 1 mM DTT) was run into the column, and 4.6 ml of the protease reaction buffer containing 20 U/ml thrombin (Amersham Biosciences Inc., Cat. No. 27-0846-01) was applied to the column. When the entire volume entered the column, the pump of the liquid chromatography was stopped, and reaction with protease was carried out at room temperature (22° C.) overnight. On the next day, 15 ml of PBS was run through the column at a flow rate of 1 ml/min to collect fractions, and the fractions collected were run through the HiTrap Benzamidine FF column (Amersham Biosciences Inc., Cat. No. 17-5143-02) to obtain a fraction in which thrombin was removed (Prepurified sample). The fraction was fractionated by chromatography with an anion exchange resin to purify the recombinant matured mouse NEFA polypeptide. The Prepurified sample (20 ml) was diluted 5-fold with the Buffer A (20 mM bis-Tris, pH 6.5, 0.1 M NaCl, 0.1% CHAPS), and applied to the HiTrap Q HP column (Amersham Biosciences Inc., Cat. No. 17-1153-01) equilibrated with the Buffer A, and then washed with the Buffer A at a flow rate of 1 ml/min (1 ml fractions were collected: Washed sample). The washed column was eluted using the Buffer A and the Buffer B (20 mM bis-Tris, pH 6.5, 1M NaCl, 0.1% CHAPS) in a linear concentration gradient of 0-50%/60 minutes of the Buffer B at a flow rate of 0.5 ml/min. At this time, 0.5 ml fractions were collected, and fractions containing protein as determined by absorbance at a wavelength of 280 nm were collected (Purified sample). A portion of each of the samples (Prepurified sample, Washed sample, Purified sample) obtained in this purification process was taken, and was mixed with an equal amount of the Laemmli sample buffer containing 5% β-mercaptoethanol followed by heating at 100° C. for 5 minutes, and then was subjected to Western blotting in a manner similar to that described in Working Example 3. The fraction was dialyzed against PBS to obtain a purified matured mouse NEFA polypeptide.

<Result>

A of FIG. 4 shows a stained image of SDS-PAGE of a sample obtained by expressing the GST-NEFA fusion protein in recombinant E. coli and purifying the GST-NEFA fusion protein with the GSTrapFF column. B shows the result of Western blotting using anti-NAP polyclonal antibody of a sample obtained by excising the matured mouse NEFA polypeptide from the GST-NEFA fusion protein with thrombin and purifying with the HiTrap Q HP column. In A of FIG. 4, a marked increase in the product with a molecular weight 65 kd was noted in the Post-sonicated pellet wherein the cells were disrupted after the expression induction with IPTG in lane 3 relative to the Preincubated bacteria sample in lane 2. As the major 65 kd product was also noted in the fraction (Purified sample) purified with the GSTrapFF column, it was demonstrated that the recombinant mouse GST-NEFA fusion protein was expressed in the recombinant E. coli. In B of FIG. 4, several bands were noted in the sample before purification (Prepurified sample) in addition to the band of the matured mouse NEFA polypeptide with a molecular weight of 47.5 kd cleaved with thrombin and the band of the recombinant mouse GST-NEFA fusion protein with a molecular weight of 65 kd. On the other hand, in the Purified sample, a major band with a molecular weight of 47.5 kd and a weaker band with a molecular weight of 65 kd were noted, indicating that an almost pure recombinant matured mouse NEFA polypeptide was obtained.

Working Example 6

Study on the Effect of Intraventricular Administration of nesfatin on Feeding Behavior In order to demonstrate the effect of recombinant nesfatin obtained on the feeding behavior of animals, an experiment was carried out in which unanesthetized rats received intracerebroventricular administration into the third ventricle.

Rats used were Wistar rats (purchased from Nippon SLC), and the animals were housed under a cycle of 12 hours of the light period from 6 a.m. to 6 p.m. and 12 hours of the dark period from 6 p.m. to 6 a.m. the next morning and fed a powder chew (Nippon Clea, CE-2), and kept at 22° C., and housing was continued under a similar condition during the experiment. For the experiment, among 8-9 week-old male Wistar rats, those individuals weighing 200-250 g were used. For administration, 5 μl of saline (control) or recombinant nesfatin prepared in Working Example 5 dissolved to 0.2 pmol, 0.6 pmol and 3.0 pmol in 5 μl of PBS was administered per individual (N=5 for each group). The rats received intraperitoneal administration of 40 mg/kg body weight of pentobarbital sodium for anesthesia. After the hair was removed from the head, they were fixed in a brain stereotaxic apparatus (David Kopf Instruments, Model 962) and the scalp was incised and a 23G needle (guide cannula) was implanted so as to reach the third ventricle (2.5 mm behind the bregma, 9.5 mm from the surface). One week after implanting the guide cannula, the animals were subjected to the experiment. After recovering from the surgery, a 29G cannula for injection was inserted into the guide cannula under no anesthesia, and 5 μl of PBS or the matured mouse nesfatin solution in PBS was administered at a rate of 1 μl/second. After fixing the cannula as it was for 2-3 minutes after the administration, the cannula was extracted, and the animals were returned to the individual cages. One, three, and six hours thereafter, the weight of the food was determined to record the amount of food intake, which was used as an index of feeding behavior. For the test of significant difference, analysis of variance was used.

<Result>

The amount of food intake at 0-1 hour after the administration of 0 (PBS alone), 1, 4 and 20 pmol of recombinant nesfatin into the third ventricle is graphically shown in A of FIG. 5, the amount of food intake at 1-3 hours after administration is graphically shown in B of FIG. 5, and the amount of food intake at 3-6 hours after administration is graphically shown in C of FIG. 5. For any of 0-1, 1-3 and 3-6 hours, a reduction in the amount of food intake was noted in a dose dependent manner in the recombinant nesfatin administration group compared to the rats that only received saline. Specifically, in the 20 pmol recombinant nesfatin-administration group, a significant activity of suppressing food intake was noted in any of 0-1 hour/1-3 hours/3-6 hours (each P<0.01) as compared to the control group. These data suggested that nesfatin in the brain has an effect of suppressing feeding behavior.

Working Example 7

Study on the Effect of Intraventricular Administration of Anti-nesfatin Antibody on Feeding Behavior In order to demonstrate the effect of nesfatin on the control of food intake, the effect of administration of an antibody against nesfatin into the third ventricular on feeding behavior was investigated.

The antibody used was the anti-NAP peptide antibody (NAP IgG) prepared in Working Example 4, and 5 µl of antibody diluted in saline was administered to rats (dose 5 µg). As the control, the same amount and concentration of IgG (control IgG) purified from non-immunized rabbits was administered. Rats used were Wistar rats (purchased from Nippon SLC), and were housed as in Working Example 6. Among 8-9 week-old male Wistar rats, those individuals weighing 200-250 g were selected. The time of administration was before beginning the light period when there is little feeding behavior, and the method of administration was similar to that in Working Example 6. During the period of 0-3 hours, 3-6 hours, or 6-9 hours after the intra-celebroventricular administration, the weight of the powder food was determined. For the test of significant difference, analysis of variance was used.

<Result>

For rats that received the intraventricular administration of control IgG or the anti-nesfatin antibody (NAP IgG), the amount of food intake at 0-3 hours after the administration is graphically shown in A of FIG. 6, the amount of food intake at 3-6 hours after administration is graphically shown in B of FIG. 6, and the amount of food intake at 6-12 hours after administration is graphically shown in C of FIG. 6. It was demonstrated that in individuals that received the intra-celebroventricular administration of anti-nesfatin antibody, food intake during 0-3 hours (Fig. A of 6) and 3-6 hours (B of FIG. 6) was promoted in a statistically significant manner (each $P<0.001$). The feeding amount of the rat from the anti-nesfatin antibody-administration group increased about 9 times during 0-3 hours (A of FIG. 6), and about 10 times during 3-6 hours, respectively, compared to that of the control IgG-administration group during the corresponding periods. However, since the period of 6-9 hours was in the dark period and food intake was started in the control IgG-administration group, no significant difference was noted. Thus, as the administration of the anti-nesfatin antibody promoted food intake by rats, it was demonstrated that the anti-nesfatin antibody suppresses the effect of endogenous nesfatin and that nesfatin is involved in feeding behavior.

Working Example 8

Study on the Expression of the NEFA Gene in the Rat Hypothalamus and the Effect of Fasting on the Expression An in situ hybridization was carried out to determine the effect of fasting on changes in the expression of endogenous NEFA gene.

The probe used for in situ hybridization in the brain tissue was the plasmid for preparing the NEFA probe that was prepared in Working Example 2. Using 1 µg of said plasmid cleaved with a restriction enzyme NcoI and purified, a DIG-labelled cRNA probe was prepared by a reaction of the SP6-RNA transcriptase using the digoxygenin (DIG) RNA labelling kit (Roche Diagnostics K.K., Cat. No. 1175025). The reaction with the SP6-RNA transcriptase was carried out at 40° C. for 2 hours. After the reaction, 2 µl of 0.2 M EDTA (pH 7.0) was added to 20 µl of the reaction mixture to stop the reaction. After 2.5 µl of 3M LiCl and 75 µl of ethanol cooled to −20° C. were added thereto and mixed, it was allowed to stand at −20° C. overnight. On the next day, the reaction mixture was centrifuged in a microfuge at 4° C. and 15,000 rpm for 20 minutes and the supernatant was removed. After adding 50 µl of 70% ethanol to the precipitate and centrifuging again, the supernatant was removed and the precipitate was dried. The precipitate was dissolved in the DEPC-treated water (Nippon Gene K.K., Cat. No. 314-90205), and the amount of RNA was determined by agarose gel electrophoresis, and was diluted in the DEPC-treated water to a RNA concentration of about 0.1 mg/ml. In order to shorten the length (about 450 bases) of the cRNA probe obtained, 10 µl of the DEPC-treated water and 40 µl of carbonate buffer (60 mM sodium carbonate, 40 mM sodium bicarbonate, pH 10.2) were added to 10 µl of the RNA solution at 0.1 mg/ml, and reacted at 60° C. for 30 minutes. To the reaction mixture, 60 µl of the neutralization solution (3 M sodium acetate, 1% acetic acid, pH 6.0) was added, and 360 µl of ethanol that had been cooled to −20° C. was further added and mixed, and then centrifuged in a microfuge at 4° C. and 15,000 rpm for 20 minutes, which was precooled at −70° C. for 30 minutes to be set at 4° C., and the supernatant was removed to obtain the precipitate. After adding 100 µl of 70% ethanol (−20° C.) to the precipitate and centrifuging again, the supernatant was removed and the precipitate was dried. The dried precipitate was dissolved in 100 µl of the DEPC-treated water, and the concentration was determined by agarose gel electrophoresis. The concentration of the probe obtained was about 50 µg/ml. The DIG-labelled NEFAcRNA probe thus obtained was used for in situ hybridization.

About 8 week-old male Wistar rats (purchased from Nippon SLC) (body weight 220-250 g) were grouped into the individuals (Normal) that can take the powder food ad libitum, the individuals (Starvation) that were kept 48 hours with drinking water alone without any food, the individuals (Re-feeding) that were kept without food for 36 hours and then were given the food ad libitum for 12 hours, and each brain was perfusion fixed with PBS containing 4% paraformaldehyde in a method similar to that described in Working Example 5 and the brain was extracted. From the extracted brain, a portion that contains the hypothalamus was excised, which was further fixed in PBS containing 4% paraformaldehyde at 4° C. overnight. The fixed brain tissue was treated with a cryostat in a method similar to that described in Working Example 4 to prepare sections of 10 µm in thickness, which were placed on a silane-coated glass slide. The slide glass having a brain tissue section placed thereon was placed in an incubator and treated at 50° C. for 2 minutes, and then the sections were dried at room temperature for 30 minutes. The sections were fixed again in PBS containing 4% paraformaldehyde at room temperature for 7 minutes, and then washed in PBS for 3 minutes and in 2-fold concentrated SSC twice for 5 minutes.

An in situ hybridization solution (4-fold concentrated SSC, 10% dextran sulfate, 1-fold concentrated Denhardt's solution, 2 mM EDTA, 50% deionized formamide, 500 µg/ml trout sperm DNA) was delivered so as to cover the brain tissue section on the slide glass, and was prehybridized at 37° C. for 1 hour. After the completion of prehybridization, the delivered liquid was discarded, and an in situ hybridization solution containing 200 ng/ml of DIG-labelled NEFA cRNA probe was delivered so as to cover the tissue, and was hybridized in a humid chamber at 37° C. for 16 hours. The slide glass having the brain tissue section placed thereon after hybridization was washed in 2-fold concentrated SSC at 37° C. for 5 minutes, and then washed at 37° C. three times for 5 minutes each in 0.2-fold concentrated SSC containing 60% formamide, and then at room temperature twice for 5 minutes each in 2-fold concentrated SSC.

The probe that hybridized in the brain tissue after washing was detected using the DIG Nucleic Acid Detection kit (Roche Diagnostics K.K., Cat. No. 11175041), and the outline of the method is as follows. The slide glass having the brain tissue placed thereon was washed in 100 mM Tris-HCl (pH 7.5) buffer containing 150 mM NaCl at room temperature for 5 minutes, and blocked using the same buffer (blocking buffer) saturated with the blocking reagent contained in the kit at room temperature for 30 minutes. On the slide glass was placed anti-DIG-alkaline phosphatase conjugate contained in the kit diluted to a concentration of 1/200 in the blocking buffer, and it was reacted at room temperature for 2 hours. The slide glass after the reaction was washed twice in 100 mM Tris-HCl (pH 7.5) buffer containing 150 mM NaCl for 5 minutes, and then washed in the detection buffer (100 Tris-HCl, pH 7.5, 100 mM NaCl, 50 mM $MgCl_2$) for 10 minutes. Then, the detection buffer containing 0.18 mg/ml BCIP and 0.34 mg/ml NBT was placed and was reacted at room temperature for 16 hours to develop color. The slide glass was washed in 10 mM Tris-HCl (ph 8.0) containing 1 mM EDTA for minutes to stop the color development reaction.

Then the slide glass was washed in distilled water for 5 minutes, and stained in 1% methylene green for 5 minutes, washed in distilled water, dehydrated in alcohol and cleared in xylene, and mounted using a non-aqueous mounting agent (Nichirei Corp., Cat. No. 415141) with a cover slip. It was then examined with a microscope.

<Result>

Relative to the control group shown in A of FIG. 7, there was a marked decrease in the expression of nesfatin mRNA in the paraventricular nucleus (PVN) in the case of 48-hour fasting shown in B of FIG. 7, and as shown in C of FIG. 7, it was demonstrated that the expression of the nesfatin mRNA gene was restored by re-feeding after fasting. These results revealed that endogenous nesfatin is involved in the control of food intake.

Working Example 9

Study on nesfatin Expression in the Brain of Starvated Rats

Changes in endogenous nesfatin at fasting were studied by the immunohistological stain method.

About 8 week-old male Wistar rats (purchased from Nippon SLC) (body weight 220-250 g) were grouped into the control group that can take the powder food ad libitum and the fasting group that was fasted for 24 hours, and the brain tissue section of these rats were prepared for the analysis by immunohistological chemistry using anti-nesfatin antibody. The preparation of tissue sections and the immunohistological stain method were carried out in a manner similar to that described in Working Example 4. Furthermore, in order to study the state of activation of nerve cells in the regions of the brain related to food intake, the immunohistochemical analysis was carried out at the brain tissue of the fasting group using an antibody against c-Fos. The method was carried out using a 500-fold diluted c-Fos (K-25) antibody (Santa Cruz Biotechnology, sc-253) instead of anti-nesfatin antibody in a manner similar to that described above.

<Result>

A micrograph (200× magnification) of immunohistochemical staining with the anti-nesfatin antibody (NAP Ab) at the hypothalamus of the control group is shown in A of FIG. 8, a micrograph (the same magnification as A) of immunohistochemical staining with the anti-nesfatin antibody (NAP Ab) at the hypothalamus of the fasting group is shown in B of FIG. 8, and a micrograph (the same magnification as A) of immunohistochemical staining with the anti-c-Fos antibody at the hypothalamus of the fasting group is shown in C of FIG. 8. The upper half of the figure shows the image of the paraventricular nucleus, and the lower half shows the image of the arcuate nucleus. In the hypothalamus of the fasting group as compared the control group, staining properties at the paraventricular nucleus (upper half of the figure) and the arcuate nucleus (the lower half of the figure) are markedly decreased, indicating that the expression of nesfatin is decreased in fasting. In a state in which appetite is enhanced, the expression of the c-Fos protein was noted. From this, it is believed, in a state in which appetite is enhanced due to fasting, the expression of nesfatin, thought to exhibit the effect of a suppressed appetite, is decreased and is responsible for the control of appetite.

Working Example 10

Preparation of nesfatin-1, nesfatin-2, nesfatin-3 and nesfatin-2/3 polypeptide, and Preparation of Antibody Against nesfatin-1, nesfatin-3 and nesfatin-2/3 peptide In Working Examples 3-9, it was demonstrated that nesfatin has an effect the expression in the brain hypothalamus and on food intake control and body weight control. Also, as the precursor of nesfatin has a signal peptide, nesfatin is likely to be secreted extracellularly out of the cell. Some active proteins are known to be cleaved with the prohormone convertase (PC) in a post-translational process. Thus, it was investigated whether or not the Arg-Arg sequence or the Lys-Arg sequence that are the sequence at the cleavage site of the prohormone convertase are present in the mouse, rat and human NEFA sequence. As a result, it was found that in common with mouse, rat and human NEFA sequence, the Lys-Arg sequence was present at the amino acid positions 107 and 108 from the N-terminal and the positions 199 and 200, and the Arg-Arg sequence is present at positions 188 and 189 (FIG. 9A). Thus, among the nesfatin sequence, a peptide comprising 82 residues corresponding to amino acid Nos. 25 to 106 was named nesfatin-1 (SEQ ID NO: 15), a peptide comprising 79 residues corresponding to amino acid Nos. 109 to 187 was named nesfatin-2 (SEQ ID NO: 16), and a peptide comprising 231 residues corresponding to amino acid Nos. 190 to 420 was named nesfatin-3 (SEQ ID NO: 17). In this case, the DNA-binding region (amino acid Nos. 171-223) which is a known domain structure, is divided into nesfatin-2 and nesfatin-3, the nectin-binding region (amino acid Nos. 213-420), the calcium-binding region (amino acid Nos. 254-265 and 306-317) and Asp/GLu-rich region (amino acid Nos. 306-317) are contained in the sequence of nesfatin-3, but no known domains are contained in the sequence of nesfatin-1 (FIG. 9B). Therefore, the portion of the sequence consisting of the nesfatin-2 and the nesfatin-3 was named nesfatin-2/3 (SEQ ID NO: 47). The synthesis of the rat nesfatin-1 peptide (SEQ ID NO: 15) and the nesfatin-2 peptide (SEQ ID NO: 16) was referred to Yanaihara Institute Inc., where they were synthesized by solid-phase synthesis and purified by reverse phase liquid chromatography. The cDNA prepared from rat brain was amplified, using primers set forth in SEQ ID NO: 48 and SEQ ID NO: 49, to obtain DNA (SEQ ID NO: 50), and then the DNA was used to prepare nesfatin-3 peptide (SEQ ID NO: 17), by Post Genome Institute Co., Ltd. (Shimizu Y. et al.: Nature Biotech 19: 751-755, 2001), by the cell-free protein synthesis.

The PCR primers used:

```
                                            (SEQ ID NO: 48)
Forward Primer: 5'-ATGGAGTATTTAAAAACGCTGAGTGAG-3'

(SEQ ID NO: 49)
Reverse Primer: 5'-TTATGTGTGTGGCTCAAACTTCA-3'
```

The nesfatin-3 prepared in this manner has a sequence in which Met is added to the N-terminal (SEQ ID NO: 51).

By the same manner, the cDNA derived from rat brain was amplified, using primers set forth in SEQ ID NOs: 52 and 53 to obtain DNA (SEQ ID NO: 50), to obtain DNA (SEQ ID NO: 54), and then the DNA was used to prepare nesfatin-2/3 (SEQ ID NO: 47), by the cell-free protein synthesis.

The PCR primers used:

```
                                            (SEQ ID NO: 52)
Forward Primer: 5'-ATGGAAGAAGTAGGAAGACTGAGAA-3'

(SEQ ID NO: 53)
Reverse Primer: 5'-TTATGTGTGTGGCTCAAACTTCA-3'
```

Also, in order to prepare antibodies for regions other than those for anti-NAP peptide antibodies prepared in Working Example 3, a sequence in which Cys was added to the C-terminal of a sequence corresponding to the amino acid Nos. 24-38 (corresponding to the amino acid Nos. 48-62 of the mouse precursor NEFA polypeptide of SEQ ID NO: 5) of NAP-1 peptide (NAP-1Ab: SEQ ID NO: 32), a sequence corresponding to the amino acid Nos. 1-9 (corresponding to the amino acid Nos. 190-198 of the mouse precursor NEFA polypeptide of SEQ ID NO: 5) of NAP-3, and a sequence in which Cys was added to the C-terminal of a sequence corresponding to the amino acid Nos. 136-149 (corresponding to the amino acid Nos. 325-338 of the mouse precursor NEFA polypeptide of SEQ ID NO: 5) of NAP3 peptide (NAP-1 Ab: SEQ ID NO: 33 and NAP-1 Ab: SEQ ID NO: 34) were prepared.

```
NAP-1 Ab:
                                            (SEQ ID NO: 32)
N-ProAspThrGlyLeuTyrTyrAspGluTyrLeuLysGlnValIle
Cys-C

NAP-C1 Ab:
                                            (SEQ ID NO: 33)
N-GluTyrLeuLysThrLeuSerGluGluCys-C

NAP-C2 Ab:
                                            (SEQ ID NO: 22)
N-LysGluPheLeuGluProAspSerTrpGluThrLeuAspGlnCys-C
```

The preparation of each peptide of NAP-1 Ab, NAP-C1 Ab and NAP-C2 Ab was referred to ATP Co., Ltd. in which they were synthesized by solid-phase synthesis and purified by reverse phase liquid chromatography. Each peptide of NAP-1 Ab, NAP-C1 Ab and NAP-C2 Ab thus obtained was conjugated to KLH in a manner similar to that described in Working Example 3, and then immunized to rabbits to prepared serum containing antibody to each peptide. From the serum, rabbit IgG was purified using the DEAE column, and named NAP-1 IgG (nesfatin-1 IgG), NAP-C1 IgG (nesfatin-C1 IgG), and NAP-C2 IgG (nesfatin C2 IgG).

Each of the prepared nesfatin-1 and nesfatin-3 peptide were subjected to SDS-polyacrylamide gel electrophoresis (12%), and then Western blotting was carried out for each peptide, by in a manner similar to that described in Working Example 3, using the nesfatin-1 IgG antibody and the nesfatin-C2 IgG antibody, respectively.

<Result>

The nesfatin-1 peptide, nesfatin-2 peptide, nesfatin-3 peptide and nesfatin-2/3 peptide that were synthesized by solid-phase synthesis and purified by reverse phase liquid chromatography were purified by an analytical C18 reverse phase chromatography to a purity of almost a single peak. By collecting a portion of the peaks and analyzing with mass spectrometry (nesfatin-1 and nesfatin-2) or SDS-polyacrylamide gel electrophoresis (12% gel) (nesfatin-3 and nesfatin-2/3), it was demonstrated that peptides estimated to be approximately the molecular weight of each peptide of predicted nesfatin-1, nesfatin-2, nesfatin-3 and nesfatin-2/3 was synthesized. In rabbits that were immunized with the conjugate of each peptide of NAP-1 IgG, NAP-C1 IgG and NAP-C2 IgG and KLH, increased in the titer of antibody against these 3 peptides were observed, and antibody (IgG) against each peptide was obtained.

As the results of the Western blotting with the nesfatin-1 IgG after electrophoresis of the nesfatin-1 peptide, a 9.7 kd single band was observed, and as the results of the Western blotting with the nesfatin-C2 IgG after electrophoreisis of the nesfatin-3 peptide, a 27.9 kd single band was observed (FIG. 9C). Herefrom, it is shown that the nesfatin-1 IgG antibody and the nesfatin-C2 IgG antibody, bond to the nesfatin-1 peptide, the nesfatin-3 (nesfatin-2/3), respectively.

Working Example 11

Immunohistochemical Analysis with NAP-1 IgG and Anti-PC Antibody

In order to demonstrate that nesfatin is processed to produce nesfatin-1, the localization of nesfatin and PC was first analyzed by a double immunohistological stain of the rat hypothalamus with NAP-1 IgG (nesfatin-1 IgG) prepared in Working Example 10 and anti-prohormone convertase antibody (anti-PC).

Brain tissue sections were prepared in the following method. Eight week-old Wistar rats (purchased from CHARLES RIVER LABORATORIES Japan, Inc.) were anesthetized by an intraperitoneal injection of 40 mg/kg of pentobarbital sodium, and then thoracotomy was performed to inject 50 ml of physiological saline (0.85% NaCl) into the heart, and then PBS containing 4% paraformaldehyde (20 mM phosphate buffer, 150 mM NaCl, pH 7.2) was injected and circulated using a 400 ml peristatic pump to perfusion fix the brain. The brain was then extracted, and the portion containing the hypothalamus was excised, and was fixed overnight at 4° C. in PBS containing 4% paraformaldehyde. The fixed brain sample was immersed in PBS containing 10% sucrose for 4 hours, PBS containing 15% sucrose for 4 hours, and PBS containing 20% sucrose overnight at 4° C. Then the brain sample was immersed in an OCT compound and frozen in dry ice-acetone to prepare the embedded block. From the block prepared, sections of 6 μm in thickness were prepared at −20° C. using a cryostat, and then were air-dried on a silane-coated slide (MAS coat slide prepared by Matsunami). Tissue sections on the slide were treated with 3% hydrogen peroxide for 5 minutes, and then washed twice in PBS for 5 minutes.

The slide glass having a brain tissue section placed thereon was blocked by treating with 10% goat normal serum (Nichirei Corp., Cat. No. 426042) at room temperature for 10 minutes, and then was reacted to NAP-1 IgG (nesfatin-1 IgG: Working Example 10) diluted 1/500 in PBS containing 5% BSA at room temperature for 1 hour. The slide glass to which antibody was reacted was washed in PBS three times for 5 minutes, and the Histofine Simple Stain Rat MAX PO (Nichirei Corp., Cat. No. 414181) was reacted thereto, and after washing in PBS, color was developed using 4-chloro-1-naphthol (ICN, Cat. No. 980611: 4-chloro-1-naphthol stabilized chromogen). The slide glass after color development was washed in PBS three times for 5 minutes, and then immersed in 0.1M glycine buffer (pH 2.2) for 1.5 hours (said buffer was changed every 30 minutes), and washed in PBS three times for 5 minutes. The slide glass was further blocked with 10% goat normal serum (Nichirei Corp., Cat. No. 426042) at room temperature for 10 minutes. The slide glasses that were treated to this point were divided into two groups: one was reacted to an antibody (PC-1/3: Chemicon, Cat. No. AB1260) that recognizes prohormone convertase subtypes PC1 and PC3, and the other was reacted to antibody (PC-2: Chemicon, Cat. No. AB1262) that recognizes prohormone convertase subtype PC2 as an antibody solution diluted in PBS containing 0.5% BSA at room temperature for 1 hour. The slide glass was then washed in PBS three times for 5 minutes, and to the slide glass was reacted to goat anti-rabbit IgG-Alexa594 conjugate (Molecular Probes, Cat. No. A11008) diluted 1/200 in PBS containing 0.5% BSA at room temperature for 30 minutes. Then the slide glass was washed in PBS three times for 5 minutes and slightly air-dried, and then mounted with glycerol and a cover slip, and the perimeter was sealed with clear manicure to prepare a specimen. The specimen was examined as a phase contrast image of 4-chloro-1-naphthol stain by a cofocal laser microscope (Bio-Rad Inc. MRC-1024 cofocal laser scanning equipment+Nikon's Eclipse E800 upright microscope) and fluorescence with Alexa 594 was examined as a fluorescent image by an excitation beam with the Krypton-Argon laser using a 605±30 nm band filter.

<Result>

In the immunohistochemical image for the rat hypothalamus tissue, a stained image with nesfatin-1 IgG is shown in an upper panel and a lower panel in A of FIG. 10, a fluorescence image with PC-1/3 in the upper panel in B of FIG. 10, and a fluorescence image with PC-2 in the lower panel in B of FIG. 10. The upper panel in A of FIG. 10 and the lower panel in B of FIG. 10, and lower panel in A of FIG. 10 and the lower panel in B of FIG. 10 represent a color image and a fluorescence image at the same field. As shown in the upper panel and the lower panel in A of FIG. 10, cells stained with nesfatin-1 IgG was observed in the neural cells in the rat brain. Many of cells which were stained with anti-PC-1/3 and anti-PC-2 antibody also corresponded to the nesfatin-1 IgG positive cells. This indicated that in cells expressing nesfatin prohormone convertases PC1/3 and PC2 are simultaneously expressed suggesting the possibility that nesfatin undergoes processing by prohormone convertase.

Working Example 12

Study on the Effect of Intracerebral Administration of nesfatin-1, nesfatin-2, nesfatin-3 and nesfatin-2/3 on Food Intake Control The site of nesfatin of which the activity of food intake suppression is present was investigated.

Samples used for intracerebral administration were PBS alone (vehicle group), or nesfatin-1, nesfatin-2, nesfatin-3 or nesfatin-2/3 prepared in Working Example 10 each dissolved in PBS, and 25 pmol was administered per individual into the third ventricle immediately before the dark period. Rats used were Wistar rats (purchased from Nippon SLC) and were housed as in Working Example 6, and among 8-9 week-old male Wistar rats, those individuals weighing 200-250 g were selected and used (N=5). The technique of intraventricular administration and the measurement of the amount of food intake in rats were carried out in a method similar to those in Working Example 6. In the measurement of the amount of food intake, the reduced amount of food at 1 hour after administration (0-1 hr) and 2 hours after administration (1-3 hrs) was determined as food intake.

In the same condition above, 1, 5 or 25 pmol of nesfatin-1 as a sample was administered per rat individual into the third ventricle immediately before the dark period. In this experiment, the amount of food intake was determined at 1 hour after administration (0-1 hr).

<Result>

Compared to the control group (Cont), as shown in A of FIG. 11, the intraventricular administration of nesfatin-2, nesfatin-3 and nesfatin 2/3 did not exhibit any significant changes in the amount of food intake (0-1 hr: a-1 in A of FIG. 11; 1-3 hr: a-2 in A of FIG. 11A). On the contrary, the intra-celebroventricular administration of 25 pmol of nesfatin-1 exhibits marked effect on the suppression of feeding. As shown in B of FIG. 11, the intraventricular administration of 1, 5 or 25 pmpl of nesfatin-1 per rat individual did exhibit the decreased amount of food intake, with the increased amount of the administered nesfatin-1, compared to the saline group (0). In particular, a significant decreased amount of food intake was observed in the administration of 5 pmol or 25 pmpl of nesfatin-1. These results revealed that the activity of suppressing food intake by nesfatin is localized in nesfatin-1.

Working Example 13

Changes in the Amount of Food Intake and Body Weight in the Intraventricular Continuous Administration of nesfatin-1

Effect of intraventricular continuous administration of nesfatin-1 on changes in the amount of food intake and body weight was investigated.

The administration of nesfatin-1 was carried out into the ventricle by an osmotic pump for 10 consecutive days. Among 8 week-old male Wistar rats (purchased from Nippon SLC), those individuals weighing 200-250 g were used. The rats received intraperitoneal administration of 40 mg/kg body weight of pentobarbital sodium for anesthesia. After the hair was removed from the head, they were fixed in a brain stereotaxic apparatus (David Kopf Instruments, Model 962) and the scalp was incised and a 23G needle (guide cannula) was implanted so that the tip reaches the third ventricle (2.5 mm behind the bregma, 9.5 mm from the surface). One week after implanting the guide cannula, the animals were subjected to the experiment. The osmotic pump used was Alzet's Model 2002. Nesfatin-1 (nesfatin-1 administration group) dissolved in physiological saline that was filter-sterilized with a 0.22 μm Millex GV filter (Millpore Co. Ltd.), or sterilized physiological saline alone (control group) were injected into the osmotic pump immediately before use, and were primed in sterilized physiological saline from the day before use. The osmotic pump to which each sample was connected to a tube connected to the injection cannula, and through the guide cannula previously implanted the injection cannula was fixed so that the tip of the cannula reaches the third ventricle of the rat. In this form of use, the sample is injected to the third ventricle at a flow rate of 12 μl per 24 hours, and in the nesfatin-1 administration group, it is equivalent to 5 pmol of nesfatin-1 per day administered to the ventricle. After confirming the rats into which the osmotic pump was implanted recovered from anesthesia, they were placed in individual cages where they were kept under the condition that they can take the powder chew and water at libitum. The measurement of the amount of food intake started from the day after the cannula and the osmotic pump were implanted, and the weight of the residual food was measured at 9 a.m. every day, and by determining the difference from the weight of the food on the previous day, the amount of food intake of the day (24 hours) was calculated. From day 6 after the start of administration, body weight was measured at the time of measuring the amount of food intake, and changes in body weight were also recorded.

<Result>

As shown in A of FIG. 12, in the nesfatin-1 administration group, a decrease in the amount of food intake was noted from day 1 after the start of administration, and the decrease was maintained during the period of measurement as compared to the control group. Also as shown in B of FIG. 12, the rate of increase in body weight in the nesfatin-1 administration group has significantly declined as compared to the control group.

Working Example 14

Study on Food Intake Control by the Intraventricular Administration of Anti-nesfatin-1 Antibody or Anti-nesfatin-3 Antibody In Working Examples 12 and 13, the effect of decreasing the amount of food intake by the intraventricular administration of nesfatin-1 peptide was found. In order to further confirm this fact, NAP-1 IgG (nesfatin-1 IgG) that recognizes nesfatin-1, NAP-C1 IgG (nesfatin-C1 IgG), or NAP-C2 IgG (nesfatin-C2 IgG) that recognizes nesfatin-3 were intraventricularly administered to rat to study its effect on the amount of food intake. To study the relationship between the nesfatin cleaved by prohormone convertase to generate nesfatin-1, and the food intake control, a mutant (KR-AA mutant: Mut) in which a Lys-Arg sequence corresponding to amino acid numbers 84 and 85, among a sequence set forth in SEQ ID NO: 26, is replaced with a Ala-Ala sequence was prepared and investigated effect on the intraventricular administration in rats.

Samples used for intraventricular administration were IgG (control IgG group) purified from unimmunized rabbits with PBS, NAP-1 IgG (nesfatin-1 IgG), NAP-C1 IgG (nesfatin-C1 IgG) or NAP-C2 IgG (nesfatin-C2 IgG) prepared in Working Example 11, which was dissolved in PBS, and 5 μl (5 μg) of them was administered to the third ventricle. The rats used were Wistar rats (purchased from Nippon SLC) and were housed as in Working Example 6, and among 8-9 week-old male Wistar rats, those individuals weighing 200-250 g were selected and used. The technique of intraventricular administration and the measurement of the amount of food intake were carried out in a method similar to those in Working Example 7. In the measurement of the amount of food intake, the reduced amount of food at 3 hours after administration (0-3 hr) and 3 hours over 3 hours after administration (3-6 hrs) was determined as food intake.

The preparation of the KA-AA mutant was carried out by altering a nesfatin gene from the mature mouse prepared in Working Example 5 and by expressing the gene. Two fragments were prepared using the plasmide in which the nesfatin gene from the mature mouse obtained in Working Example 5 was cloned to pGEM-11Zf(+), by PCR method. The first fragment was prepared using 5 ng of the plasmid and by carrying out PCR reaction with a set of mNucB2-F360-[Sac2Thr] primer and mNucB2-[KR-AA] R583 primer.

mNucB2-F360 [Sac2Thr]:
(SEQ ID NO: 56)
5'-GGTTCCGCGGGTCTGGTTCCGCGTGGTTCTGTTCCTATCGATGTGGA

CAAGACCAA-3' mNucB2 [KR-AA] R583:
(SEQ ID NO: 57)
5'-CTTCTTGAGCAGCCAGCTCATCCAGTCTCGTCCTCA-3'

The PCR reaction comprised a denaturation reaction at 90° C. for 1 minute, followed by 20 cycles of reaction comprising denaturation at 98° C. for 10 seconds, annealing at 60° C. for 30 seconds, and extension at 68° C. for 1 minute, to prepare the amplified DNA (Stratagene's PfuTurbo® polymerase, Cat. No. 600250 was used).

The second fragment was prepared using 5 ng of DNA fragment of the plasmid and by carrying out PCR reaction with a set of mNucB2[KR-AA] F612 primer and mNucB2-R1527[NotI] primer.

mNucB2 [KR-AA] F612:
(SEQ ID NO: 58)
5'-GAGCTGGCTGCTCAAGAAGTAGGAAGACTGCGGGATGCT-3' mNucB2-R1527 [NotI :
(SEQ ID NO: 59)
5'-GGTTGCGGCCGCACTTTATGTGTGTGGCTCAAAC-3'

The PCR condition is the same as the amplification condition for the first DNA fragment.

To prepare 2 DNA fragments, the samples obtained by two PCR reactions were added to a reaction mixture so that a concentration of the reaction mixture is 5 μl each per 50 μl. Using 0.25 μM each of His-Thr-For[SpeI] primer and the above mNucB2-R1527-[NotI] primer, and a reaction mixture of 1× concentrated Pfu buffer, 2.5 units of PfuTurbo DNA polymerase (stated above: Strategene) and 0.2 mM of dNTPs (Promega: C1141), a denaturation reaction was carried out at 90° C. for 1 minute, followed by 20 cycles of reaction comprising denaturation at 98° C. for 10 seconds, annealing at 60° C. for 30 seconds, and extension at 68° C. for 1 minute, to prepare the amplified DNA.

His-Thr-For[SpeI]:
(SEQ ID NO: 60)
5'-GGTTACTAGTGGTTCTGGTCATCACCATCACCATCACTCCGCGGGTC

TGGTTCCGCGT-3'.

The PCR product obtained was subjected to 1% agarose gel electrophoresis to excise an amplified band, which was purified with QIAEX-II kit (QIAGEN). The amplified DNA excised was cleaved with restriction enzymes SpeI and NotI, and ligated to pET41a(+) plasmid vector (Novagen) cleaved with restriction enzymes SpeI and NotI, using the Quick DNA ligase kit (New England Biolabs). From the cloned DNA, a clone, which has no errors in mutant portions introduced after analyzing DNA sequences in a similar manner to Working Example 5 and other nucleotide sequences, can be selected to obtain a vector for expressing the KR-AA mutant. The expression and purification were carried out in a similar manner to Working Example 5. The amino acid sequence of the KR-AA mutant obtained is set forth in SEQ ID NO: 61. Wt (normal nesfatin), which was prepared in Working Example 5, was used. 5 pmol each of the KR-AA mutant (Mut) peptide and the normal nesfatin (Wt) peptide were administered to the third ventricle of rats in a similar manner to Working Example 6. One, three, six and 12 hours thereafter, the weight of the food was determined to record the amount of food intake, which was used as an index of feeding behavior.

<Result>

In each of the administration into the third intraventricular administration group of control IgG, NAP-1 IgG (nesfatin-1 IgG), NAP-C1 IgG (nesfatin-C1 IgG) or NAP-C2 IgG (nesfatin-2 IgG), the amount of food intake during 0-1 hour after the administration is graphically shown in a-1 of FIG. 13A, the amount of food intake during 3-6 hours is graphically shown in a-2 of FIG. 13A, and the amount of food intake during 6-9 hours is graphically shown in a-3 of FIG. 13A. In 0-3 hour (a-1 of FIG. 13A) and 3-6 hours (a-2 of FIG. 13A), as compared to the control IgG administration rats, individuals that received NAP-1 IgG (nesfatin-1 IgG) exhibited a significant increase in the amount of food intake ($P<0.01$ for 0-3 hour, $P<0.05$ for the 3-6 hours), but in the groups that received NAP-C1 IgG (nesfatin-C1 IgG) or NAP-C2 IgG (nesfatin-C2 IgG), no significant difference was noted as compared to the vehicle group. In the results for 6-9 hours, no significant difference was noted in each of the control IgG group, the NAP-1 IgG (nesfatin-1 IgG) group, the NAP-C1 IgG (nesfatin-C1 IgG) group and NAP-C2 IgG (nesfatin-C2 IgG) group. This result indicated that the function of endogenous nesfatin-1 is inhibited by antibody against nesfatin-1, resulting in the increase of amount of food intake. This demonstrated that a substance that inhibits the function of nesfatin-1 has an effect of enhancing the amount of food intake, in addition to the effect of suppressing food intake by the intraventricular administration of the nesfatin-1 polypeptide as demonstrated in Working Example 13.

Further, the results of an effect on the amount of food intake in rats, in which 5 pmol each of a recombinant mouse nesfatin (Wt) and the mutant (KR-AA mutant: Mut) in which a Lys-Arg sequence corresponding to amino acid numbers 84 and 85 was replaced with an Ala-Ala sequence, was administered to intraventricular in the rats, are shown in FIG. 13B. In FIG. 13B, the amount of food intake at 0-1 hour, 1-3 hour and 3-6 hours after the administration were graphically shown in b-1, b-2, b-3, respectively. As shown in b-1 to b-3, in the rats in which 5 pmol of Wt (normal nesfatin) was administered, a significant control activity of food intake was observed at each of the period, while no control activity of food intake was observed in the nesfatin (Mut) in which a mutation was introduced into the site cleaved by prohormone convertase. Herefrom, it was demonstrated that the step of nesfatin-1 processed by prohormone convertase is important for nesfatin to functionate.

Working Example 15

Study on the Effect of Continuous Intraventricular Administration of Antisense RNA Against the NEFA Gene on Food Intake and Body Weight In order to further investigate the relationship between the expression of the nesfatin (NEFA) gene and the control of food intake and body weight, antisense RNA that suppresses the expression of nesfatin gene was continuously administered into the third ventricle and its effect was investigated.

As the antisense RNA against nesfatin-1 gene, was used a morpholino RNA which sandwiches a translational start site, as follows.

```
Nesfatin-1 antisense RNA:
5-ATGGTCCTCCACCTCATCTTCAGAG-3      (SEQ ID NO: 31)
```

The administration of nesfatin antisense RNA was carried out into the ventricle by an osmotic pump for 12 consecutive days using an osmotic pump. Among 8 week-old male Wistar rats (purchased from Nippon SLC), those individuals weighing 200-250 g were selected and used. The rats received intraperitoneal administration of 40 mg/kg body weight of pentobarbital sodium for anesthesia. After the hair was removed from the head, they were fixed in a brain stereotaxic apparatus (David Kopf Instruments, Model 962) and the scalp was incised and a 23G needle (guide cannula) was implanted so that the tip reaches the third ventricle (2.5 mm behind the bregma, 9.5 mm from the surface). One week after implanting the guide cannula, the animals were subjected to the experiment. The osmotic pump used was Alzet's Model 2002 that was primed in sterilized physiological saline from the day before use. Nesfatin antisense RNA (antisense administration group) dissolved in physiological saline that was filter-sterilized with 0.22 μm Millex GV filter, or missence RNA (ATcGTgCTCCACgTCATCTaCAcAG) sterilized in the same manner that dissolved in sterilized physiological saline (control group) were injected into the osmotic pump immediately before use. The osmotic pump to which each sample was connected to a tube connected to the injection cannula, and through the guide cannula previously implanted the injection cannula was fixed so that the tip of the cannula reaches the third ventricle of the rat. In this form of use, the sample is injected to the third ventricle at a flow rate of 12 μl per 24 hours, and 40 μg each of antisense RNA and missense RNA were injected. After confirming the rats into which the osmotic pump was implanted recovered from anesthesia, they were placed in individual cages where they were kept under the condition that they can take the powder food and water at libitum. The measurement of the amount of food intake started from the day after the cannula and the osmotic pump were implanted, and the weight of the residual food was measured at 9 a.m. every day and, by determining the difference from the weight of the food on the previous day, the amount of food intake of the day (24 hours) was calculated. From day 6 after the start of administration, body weight was measured at the time of measuring the amount of food intake, and changes in body weight were also recorded.

On day 12 after the start of administration, the individuals in each group were sacrificed, and the hypothalamus in the brain was removed. Using the sample extracted, the expression of nesfatin was confirmed by Western blotting with nesfatin-1 Ab. Western blotting was carried out in a manner similar to those described in Working Examples 13 and 12. The concentration of bands stained in Western blotting was determined by densitometry.

<Result>

Changes in the amount of food intake during 24 hours for the control group and the antisense administration group to which nesfatin antisense RNA was administered are shown in A of FIG. 14 and changes in body weight are shown in B of FIG. 14. As compared to the control group, an increase in the amount of food intake (A of FIG. 14) was noted in the antisense administration group from the day 1 after the start of administration, and the amount of food intake was always greater than the control group during the measurement period (until day 12 after the start of administration). For changes in body weight (B of FIG. 14), no difference was noted on day 6 after the start of administration between the control group and the antisense administration group, but on day 7 and after a significant increase in body weight (P<0.05) was noted in the antisense administration group as compared to the control group, and the difference expanded from day 9 to day 11 of the measurement period. In the Western blotting analysis of nesfatin-1 using the rat hypothalamus sacrificed on day 12, the expression of nesfatin-1 was significantly decreased in the antisense administration group (the band intensity by densitometry was 8.5±0.7 AU) compared to the control group (the band intensity indicated 14.3±1.2 AU, which was determined using densitometry). From the result, it was revealed that the intraventricular administration of nesfatin antisense RNA has an effect of suppressing the expression of nesfatin-1 and of enhancing the amount of food intake and body weight gain.

Working Example 16

Production of Recombinant nesfatin-1 by a Recombinant

In order to prepare nesfatin-1 in large quantities, a method of producing recombinant nesfatin-1 using a recombinant was investigated.

A gene encoding mouse nesfatin-1 was obtained, and an expression vector was constructed by binding the gene of glutathione S-transferase (GST) and histidine tag to the N-terminal of the nesfatin-1 gene, so that a cleavage site (-Leu-Val-Pro-Arg-Gly-Ser-) cleaved using thrombin mediates the amino acid sequence of histidine tag and the amino acid sequence of mouse nesfatin-1 in the protein after translation. The gene of mouse nesfatin-1 was obtained using mouse brain cDNA (Clontech) by two runs of PCR (nested PCR). The first PCR used a forward primer (mNucB2-F337: SEQ ID NO: 35) and a reverse primer (mNucB2-R712: SEQ ID NO: 36) at 100 µM each, Pyrobest DNA polymerase (Takarabio K.K. R005A), the reaction buffer attached and dNTP and was carried out according to the attached protocol. The PCR reaction comprised, after reaction of 90° C. for 1 minute, a temperature condition of 30 cycles of 98° C. for 10 seconds and 68° C. for 1 minute, and then a reaction at 68° C. for 2 minutes.

```
Forward primer (mNucB2-F337):
5'-GCACGCTGAC CGCTCTGGAAG-3'      (SEQ ID NO: 35)

Reverse primer (mNucB2-R712):
5'-CAAATGTGTT AGGATTCTGGTGGTTCA-3'  (SEQ ID NO: 36)
```

Using 0.5 µl of the PCR product obtained, the second run of PCR was carried out using a forward primer (mNucB2-N3-[SacI-Thr]) and a reverse primer (mNucB2-R389-[NotI]) at 100 µM each, and using Pyrobest DNA polymerase as in the first PCR. The PCR reaction comprised, after reaction of 90° C. for 1 minute, a temperature condition of 20 cycles of 98° C. for 10 seconds, 60° C. for 30 seconds and 68° C. for 1 minute, and then a reaction at 68° C. for 2 minutes.

```
Forward primer (mNucB2-N3 [SacI-Thr]):
                                   (SEQ ID NO: 37)
5'-GGTTCCGCGGGTCTGGTTCCGCGTGG TTCTCCTATCGATGTGGACA

AGACCAA-3'
```

```
Reverse primer (mNucB2-R589[NotI]):
                                   (SEQ ID NO: 38)
5'-GGTTGCGGCCGCTTACCTCT TCAGCTCA TCCAGTCTCG-3'
```

PCR reaction samples that were subjected to two runs of PCR were purified with phenol/chloroform extraction, cleaved with restriction enzymes SacII and NotI, and then subjected to agarose gel electrophoresis to excise a band corresponding to a length of about 300 bp, which was purified with QIAEX-II kit (QIAGEN). The purified PCR product of about 300 bp was ligated to pET41a(+) plasmid vector (Novagen) cleaved with restriction enzymes SacII and NotI using the Quick DNA ligase kit (New England Biolabs). The ligated vector was introduced into an E. coli strain J409 and the 8 transformants thus obtained were subjected to plasmid extraction on a small scale. The plasmids thus obtained were analyzed for the nucleotide sequence of the sequence of the nesfatin-1 gene integrated, using the BigDye Terminator Cycle Sequencing FS Ready Reaction kit and ABI377 type DNA sequencer (Perkin-Elmer Inc.). As a result, an expression vector having a gene in which the correct sequence of nesfatin-1 has been integrated was obtained, and this was named pET41a(+)GST-His-LVPRGS-mNAP1.

By introducing the pET41a(+)GST-His-LVPRGS-mNAP1 into E. coli BL21 (DE3) Codon Plus RIPL and expressing, a fusion protein (GST-His-LVPRGS-mNAP1) of GST-Histidine tag-thrombin cleavage sequence-nesfatin-1 was expressed. Clones obtained by introducing the pET41a(+) GST-His-LVPRGS-mNAP1 into E. coli BL21 (DE3) Codon Plus RIPL and selecting in a LB medium containing kanamycin was cultured in 10 ml of the LB medium containing kanamycin at 37° C. Culturing was stopped when the absorbance at a wavelength of 600 nm became 0.8. 3 ml of the culture liquid was inoculated into 100 ml of the LB medium containing kanamycin, which was cultured at 37° C. When the absorbance at a wavelength of 600 nm became 0.8, 1 ml of 100 mM IPTG was added to induce the expression of protein. After adding IPTG, a shaking culture was carried out at 37° C. for 3 hours. The culture liquid was centrifuged at 8000 rpm for 20 minutes (4° C.) to collect the cells of E. coli.

From the cells of E. coli thus obtained, the GST-His-LVPRGS-mNAP1 fusion protein was extracted, and purified with a nickel chelate column (Ni-NTA agarose). The cells were suspended in 20 ml of the Sonication buffer (50 mM KH2PO4, 50 mM NaCl, 2 mM DTT, pH 7.5) containing one-fold concentration of Complete-EDTA free (Roche Diagnostics K.K.) and 0.5-fold concentration of BugBuster (Merck Ltd., Novagen, Cat. No. 70584), and were disrupted by sonication in ice water for 10 minutes. The sonicated sample was centrifuged at 15,000 rpm for 20 minutes, and the supernatant was collected. 10 ml of the supernatant obtained was applied to 1 ml Ni-NTA agarose column equilibrated with the Lysis buffer (50 mM NaH2PO4, 300 mM NaCl, 10 mM imidazole, pH 8.0), and washed twice in 10 ml of the Wash buffer (50 mM NaH2PO4, 300 mM NaCl, 20 mM imidazole, pH 8.0). The column after washing was eluted twice with 2.5 ml of the Elution buffer (50 mM Na2HPO4, 300 mM NaCl, 250 mM imidazole, pH 8.0), and a fraction containing the eluted GST-His-LVPRGS-mNAP1 fusion protein was collected. The extraction supernatant from the residual cells was similarly treated, and a fraction containing GST-His-LVPRGS-mNAP1 fusion protein was collected.

From the GST-His-LVPRGS-mNAP1 fusion protein, the portion of GST and histidine tag was removed, and further purification, GST-His-LVPRGS-mNAP1 fusion protein bound to the GST resin was subjected to thrombin treatment and to purification with reverse phase chromatography in order to remove E. coli-derived lipopolysaccharide (LPS) that may act as an inflammatory substance. The buffers at this stage and after were those confirmed to be LPS-free. 7.2 ml of the fraction containing the GST-His-LVPRGS-mNAP1 fusion protein was washed one-fold concentration of GST Bind/Wash buffer (Merck Ltd., Novagen, Cat. No. 70571), which was finally added to the GST resin (Merck Ltd., Novagen, Cat. No. 70541) (equivalent to 7.2 ml) suspended in 3 ml of the GST Bind/Wash buffer, and gently stirred at 20° C. for 1 hour. After collecting the resin by centrifugation, said resin was washed twice in 36 ml of the GST Bind/Wash buffer. To the washed resin, 3.6 ml of a solution of 20 units/ml of thrombin in PBS was added and suspended, and reacted at 20° C. for 20 hours under gentle stirring. The resin after the reaction was delivered in 1.8 ml in a filter-attached cup (Millipore) with a pore size of 0.22 µm, centrifuged at 3,000 rpm for 2 minutes, and the filtered thrombin-treated sample was collected. To 450 µl of the thrombin-treated sample was added 50 µl of acetic acid to prepare a sample for C18 reverse phase chromatography. The reverse phase chromatography comprised the elution with a gradient of acetonitrile in 0.1% trifluoroacetic acid, and the gradient was set at 10% acetonitrile:10 minutes/10-20% acetonitrile gradient:60 minutes/30-40% acetonitrile gradient:40 minutes/40-60% acetonitrile gradient:5 minutes. Protein eluted from the column was monitored by measuring absorbance at a wavelength of 280 nm. By examining the fractions eluted with acetonitrile gradient by SDS-PAGE and Western blotting, nesfatin-1 was found to be eluted at an acetonitrile concentration of 36.2%. Thus, this fraction was collected, lyophilized, and dissolved again in distilled water for injection, which was used to determine protein concentration by absorbance and LPS content by Endospacy assay (Seikagaku Kogyo).

<Result>

From 100 ml of the culture liquid, about 7 mg of crude GST-His-LVPRGS-mNAP1 was purified with Ni-NTA-agarose, and the recovery of nesfatin-1 that was thrombin-treated or highly purified by C18 reverse phase chromatography was 472.5 µg. The amount of LPS contained in the highly purified nesfatin-1 was about 4 µg relative to 1 µg of nesfatin-1. Furthermore, when the highly purified nesfatin-1 was intraventricularly administered to rats in a method similar to that in Working Example 13, the effect of suppressing food intake and/or suppressing body weight gain was noted. This indicated that the production of active nesfatin-1 is possible by expression and purification using a recombinant.

Working Example 17

Study on the Effect of nesfatin-1 Administration into the Third Ventricle of Zucker fa/fa Rats on Food Intake Control As described in the conventional technology, many of obese people or patients with adiposis exhibit resistance to leptin, which poses a problem in the pathology and treatment. Thus, using Zucker fa/fa rats (Michael et al., Nature Genetics, Vol. 13, pp. 18-19, 1996), an animal pathological model of leptin-resistance, the effect of nesfatin-1 on the control of the amount of food intake was investigated.

As rats, 8 week-old male Zucker fa/fa (Zucker) rats and Zucker +/+(Lean) rats as the control animal were purchased from Nippon Charles River, and were housed in a cycle of 12 hours of the light period from 6 a.m. to 6 p.m. and 12 hours of the dark period from 6 p.m. to 6 a.m. the next morning and fed a powder food (Nippon Clea, CE-2), and kept at 22° C., and throughout the experiment period, a similar condition was continued in housing. After preliminary housing of the purchased rats for over one week, individuals weighing 200-250 g were selected from among 9 to 10 week-old individuals.

The sample used for administration was one in which the recombinant mouse nesfatin-1 prepared in Working Example 16 was dissolved to 5 pmol in 5 µl of PBS, and as the control sample physiological saline (Saline) was used. Five µl of the samples prepared were administered into the third ventricle of each rat for the group of five each of Zucker rats and the Lean rats per group (the Zucker/nesfatin-1 group, the Lean/nesfatin-1 group, the Zucker/Saline group, the Lean/Saline group). The timing of administration was immediately before beginning the dark period when food intake behavior is enhanced, and the method of administration was similar to that described in Working Example 6.

After intraventricular administration, the amount of food intake was determined by measuring the amount decreased of the powder food for each rat during 0-1 hour, 1-3 hours and 3-6 hours. For test of significant difference, analysis of variance was used.

<Result>

A of FIG. 15 shows the result measured of food intake for the group (the Lean/nesfatin-1 group) in which nesfatin-1 was administered and for the group (the Lean/Saline group) in which physiological saline was administered to the Lean rats, and B of FIG. 15 shows the result measured of food intake for the group (the Zucker/nesfatin-1 group) in which nesfatin-1 was administered and the group (the Zucker/Saline group) in which physiological saline was administered to the Zucker rats. In a result (A of FIG. 15) for the control animal, Lean rats, the amount of food intake during 0-1 hour and during 1-3 hours was decreased in the nesfatin-1 administration group relative to the Saline administration group ($P<0.001$). No difference was noted in the amount of food intake during 3-6 hours. In Zucker, a leptin-resistant animal, as in Lean, a significant reduction in the amount of food intake during 0-1 hour and during 1-3 hours was noted in the nesfatin-1 administration group relative to the Saline administration group ($P<0.001$). During 3-6 hours, a significant reduction ($P<0.05$) was also noted (B in FIG. 15). The above suggests that the effect of suppressing food intake by nesfatin-1 was exhibited without the effect of leptin and it is considered effective under a leptin-resistant condition.

Working Example 18

Study on the Effect of Intraperitoneal Administration of nesfatin-1 on the Control of the Amount of Food Intake in Mice It was demonstrated in the experiment of intraventricular administration in rats that nesfatin and nesfatin-1 are involved in controlling the amount of food intake. In order to study the effect on other animal species, the administration experiment on mice was carried out. Considering practical utility as a pharmaceutical, it was thought to be important that the peripheral administration is also effective, and thus an intraperitoneal administration was selected as an administration route. Furthermore, an administration experiment was also carried out on the Agouti-yellow (c57BL/6J-$A^y$/a) mice which are animal model of obesity in which the function of suppressing food intake by MC3R/MC4R has been inhibited by the excessive expression of the Agouti protein.

The experimental animal was 7 week-old male ICR mice purchased from Japan SLC, Inc., and were housed after purchase in a cycle of 12 hours of the light period from 6 a.m. to 6 p.m. and 12 hours of the dark period from 6 p.m. to 6 a.m. the next morning with free access to a pellet food (Nippon Clea, CE-2), kept at 22° C., and housing was continued in a similar condition during the experiment period. The mice purchased were subjected to preliminary housing for over one week, individuals weighing 35-40 g were selected among 8 to 9 week-old individuals and were used in the experiment.

The sample used in the administration was the recombinant mouse nesfatin-1 prepared in Working Example 16 dissolved in 200 µl of physiological saline so as to contain 2 nmol, 10 nmol or 50 nmol, and as the control sample, physiological saline (Saline) alone was used. Using a tuberculin syringe equipped with a 25G needle, 200 µl each of the sample was administered once into the abdominal cavity of each mouse (5 animals per group), and the time of administration was immediately before the start (6 p.m.) of the dark period.

In the experiment on the animal model of obesity, C57BL/6J mice were used as the control group and Agouti-yellow mice were used as the animal model of obesity, and these animals were purchased from Nippon Charles River (Jackson Lab.). The housing condition and the week age of the mice used were similar to those for the ICR mice, whereas individuals weighing 25-28 g for the control group mice and individuals weighing 31-38 g for the Agouti-yellow mice were selected and used. The sample used in the administration was recombinant mouse nesfatin-1 dissolved in 200 µl of physiological saline so as to contain 10 nmol, and as the control sample, physiological saline (Saline) alone was used (16 animals per group). Other conditions were similar to those in the above.

Each mouse that received administration was placed in an individual cage, and during 0-3 hours after the administration the weight decreased of the pellet food was measured to determine the amount of food intake. For testing of significant difference, analysis of variance was used.

<Result>

The result measured of the amount of food intake during 0-3 hours after administration when nesfatin-1 or physiological saline was intraperitoneally administered into ICR mice is shown in A of FIG. 16. In the result of A of FIG. 16, a decreases in the amount of food intake was noted in the mice that received 2 nmol, 10 nmol and 50 nmol of nesfatin-1 per mouse relative to the control (Saline group), and statistically significant decreases in the amount of food intake were noted in 10 nmol ($p<0.05$) and 50 nmol ($p<0.005$). This indicated that since nesfatin-1 exhibits an activity of suppressing food intake in mice as well as in rats, it has an effect of controlling food intake in many species, and administration from not only via the brain but via the periphery such as the abdominal cavity is effective in suppressing food intake. Also, it was demonstrated that the intraperitoneally administered nesfatin-1 is has an effect of suppressing food intake in the early stage after administration.

Also, in the experiment on the mouse model of obesity, the result measured of the amount of food intake when physiological saline (Cont) or nesfatin-1 (10 pmol) was administered to the mice (c57BL/6J) of the control group is shown in B of FIG. 16, and the result measured of the amount of food intake when physiological saline (Cont) or nesfatin-1 (10 pmol) was administered to the Agouti-yellow mice, the mouse model of obesity, is shown in C of FIG. 16. As a result, both in the mice of the control group and the mice of the Agouti-yellow mice, the amount of food intake was significantly decreased in the mice that received the intraperitoneal administration of nesfatin-1 relative to the control. Since Agouti-yellow mice is a model of obesity in which the function of suppressing food intake by melanocortin, a ligand of MC3R/MC4R, does not work due to the over expression of the Agouti protein, it was suggested, a pharmacological activity was demonstrated in a leptin-resistant model in the result for the Zucker (fa/fa) rats in Working Example 17, and similarly food intake was controlled by a mechanism independent of that of food intake suppression in the existing Agouti/melanocortin system.

Working Example 19

Study on the Effect of the Intraperitoneal and Subcutaneous Administration Of nesfatin-1 On Controlling the Amount of Food Intake in Mice In Working Example 18, it was disclosed that the intraperitoneal administration of nesfatin-1 into mice is also effective in suppressing food intake, and thus as an example of another peripheral administration, the effect of subcutaneous administration of nesfatin-1 was also examined.

The sample used in the administration was the recombinant mouse nesfatin-1 prepared in Working Example 16 dissolved in 200 µl of physiological saline so as to contain 10 nmol, and as the control sample, physiological saline (Saline) alone was used. Using a tuberculin syringe equipped with a 25G needle, 200 µl each of the samples was administered once into the abdominal cavity or the hypodermis of the back of each mouse, and the time of administration was immediately before the start (6 p.m.) of the dark period. Other conditions were similar to those in Working Example 18.

<Result>

The result measured of the amount of food intake during 0-3 hours after administration when nesfatin-1 (10 nmol) or physiological saline (0) was intraperitoneally (ip) or subcutaneously (sc) administered into the mice is shown in A of FIG. 17, and that during 0-14 hours is shown in B of FIG. 17. In A of FIG. 17, the amount of food intake tended to decrease in the groups in which 10 nmol of nesfatin-1 was intraperitoneally (ip) and subcutaneously (sc) administered relative to the physiological saline-administration group (O), and specifically for the intraperitoneal administration, a statistically significant decrease ($P<0.05$) was noted. In B of FIG. 17 as well, the amount of food intake tended to decrease in the group in which 10 nmol of nesfatin-1 was intraperitoneally (ip) and subcutaneously (sc) administered relative to the physiological saline-administration group (O), but in the intraperitoneal administration group (ip) the decrease in the amount of food intake was not significant and in the subcutaneous administration group (sc) the decrease was significant ($P<0.005$) relative to the physiological saline-administration group. In the results of both A and B of FIG. 17, the intraperitoneal administration of nesfatin-1 tended to exhibit the effect of suppressing food intake early and the effect by the subcutaneous administration tended to lag behind. The above suggests that for the peripheral administration, nesfatin-1, whether intraperitoneally or subcutaneously administered, is effective in suppressing food intake. For drugs that act in the brain, the presence of effect by the peripheral administration is important in practical use, and in this regard nesfatin-1 was shown to be useful as a pharmaceutical based on the results of Working Examples 18 and 19.

Working Example 20

Study on the Effect of the Intraperitoneal Administration of a Partial Peptide (nesfatin-1n23, nesfatin-1M30, nesfatin-1C29) of nesfatin-1 on the Control of Food Intake in Mice In Working Examples 10 and 12, nesfatin-1 was found from the cleavage sites in nesfatin of prohormone convertase. In the analyzing the function of nesfatin-1, however, it is important to identify the functional site of said peptide, and also in its application into pharmaceuticals, the short amino acid length of the peptide is considered advantageous in terms of production, dosage, antigenicity and the like. Thus, in order to examine in further detail the sites having an activity of suppressing food intake, partial peptides were prepared from the structure of nesfatin-1 comprising a 82-amino acid length, and an experiment was carried out to measure the amount of food intake when they were intraperitoneally administered to mice.

Of the amino acid sequence (SEQ ID NO: 14) of mouse nesfatin-1 derived from the sequence of mouse nesfatin, a sequence of amino acid numbers 1 to 23 from the amino terminal was termed as nesfatin-1N23, that of amino acid numbers 23 to 53 as nesfatin-1M30, and that of amino acid numbers 54 to 82 as nesfatin-1C29.

```
nesfatin-1N23:
                                    (SEQ ID NO: 42)
ValProIleAspValAspLysThrLysValHisAsnThrGluProVal GluAsnAlaArgIleGluPro nesfatin-1M30:
                                    (SEQ ID NO: 41)
ProAspThrGlyLeuTyrTyrAspGluTyrLeuLysGlnValIleGlu ValLeuGluThrAspProHisPheArgGluLysLeuGlnLys nesfatin-1C29:
                                    (SEQ ID NO: 43)
AlaAspIleGluGluIleArgSerGlyArgLeuSerGlnGluLeuAsp LeuValSerHisLysValArgThrArgLeuAspGluLeu
```

Each peptide of nesfatin-1N23, nesfatin-1M30 and nesfatin-1C29 used was a synthetic peptide of which production was referred to Biologica Co., Ltd. and was purified by HPLC to a purity of 95% or higher. Each peptide was prepared in physiological saline so as to contain 50 nmol per 200 µl, which was used as the sample, and as the control sample physiological saline (Vehicle) alone was used. Using a tuberculin syringe equipped with a 25G needle, 200 µl each of the samples was administered once into the abdominal cavity of each mouse (5 animals per group), and the time of administration was immediately before the start (6 p.m.) of the dark period. Mice used were male ICR mice (Nippon SLC) and the housing condition was similar to those in Working Example 18.

Each mouse that received administration was placed in an individual cage, and during 0-3 hours after the administration the weight decreased of the pellet food was measured to determine the amount of food intake. For testing of significant difference, analysis of variance was used.

Comparison by the alignment of the amino acid sequences of human, rat and mouse nesfatin-1 was also carried out. Using the amino acid sequence of human nesfatin-1 (SEQ ID NO: 13), mouse nesfatin-1 (SEQ ID NO: 14) and rat nesfatin-1 (SEQ ID NO: 15), alignment was carried out using the CLUSTAL-W method (Higgins et al., Nucleic Acids Research, Vol. 22, pp. 4673-4680, 1994).

<Result>

The result measured of the amount of food intake during 0-3 hours after administration when physiological saline (Vehicle), nesfatin-1N23 (-N23), nesfatin-1M30 (-M30) and nesfatin-1C29 (-C29) was intraperitoneally administered into mice is shown in A of FIG. 18. In the nesfatin-1M30-administration group (N-1b) relative to the control group (Vehicle) that received physiological saline, a significant decrease ($P<0.02$) in the amount of food intake was noted. However, in the nesfatin-1N23-administration group (N-1a) and the nesfatin-1C29-administration group (N-1c), no significant decrease or enhancement in the amount of food intake was noted. The above indicated that nesfatin-1M30 is the most important functional site for the activity of nesfatin-1 (and nesfatin) of suppressing food intake. Also, since the intraperitoneal administration of nesfatin-1M30 exhibited an activity of suppressing food intake, the possible use of said polypeptide as a pharmaceutical was indicated.

The result of amino acid alignment of human, mouse and rat nesfatin-1, and the sites of nesfatin-1N23, nesfatin-1M30 and nesfatin-1C29 are shown in B of FIG. 18. It was shown that the amino acid sequences of the sites of nesfatin-1M30 are highly conserved among species.

Working Example 21

Construction of an EIA System and the Detection of the nesfatin-1 Peptide in the Hypothalamus Tissue From the result with an antibody (nesfatin-1 IgG) against nesfatin-1 and an antibody (PC1/3 and PC2) against prohormone convertase in the cells of the rat hypothalamus in Working Example 11, it was demonstrated, nesfatin and prohormone convertase were expressed in the same cells and nesfatin-1 is likely to be produced therein. In order to further investigate this, a competitive EIA system that detects nesfatin or nesfatin-1 was constructed, and a fractionation pattern by the reverse phase HPLC of a sample extracted from the tissue of the rat hypothalamus and a pattern of nesfatin-1 prepared by synthesis were compared.

The competitive EIA system was created using nesfatin-1 IgG prepared in Working Example 10 and a biotin-labelled nesfatin-1 polypeptide. Nesfatin-1 IgG dissolved in PBS at 10 µg/ml was aliquoted into a 96-well ELISA plate (SUMITOMO BAKELITE Co., Ltd.: MS-8596F) at 50 µl/well, which was sealed with a plate seal and allowed to stand at 4° C. overnight in order to immobilize the antibody. After washing each well of the antibody-immobilized plate with PBS, PBS containing 10% bovine serum albumin (BSA) was dispensed at 250 µl/well and the plate was allowed to stand at room temperature for 2 hours. Then, after each well of the plate was washed three times with PBS, the antibody-immobilized plate was prepared.

In order to prepare a labelled nesfatin-1, a cysteine residue was added to the C terminal of nesfatin-1 (nesfatin-1 Cys: SEQ ID NO: 62). Though the method of preparation was similar to that of Working Example 16, PCR in order to obtain a nucleic acid encoding nesfatin-1 Cys was carried out using the following primer set:

```
Forward primer:
                                    (SEQ ID NO: 63)
5'-GGTTCCGCGGGTCTGGTTCCGCGTGGTTCTCCTATCGATGTGGACAA

GACCAA-3'
```

-continued

Reverse primer:
(SEQ ID NO: 64)
5'-GGTTGCGGCCGCTTAACACCTCTTCAGCTCATCCAGTCTCG-3'

Nesfatin-1 Cys expressed and purified as in the method of Working Example 16 was dissolved in 0.1M phosphate buffer (pH 6.0) containing 50 mM 2-mercaptoethanolamine and 1 mM EDTA and treated at 37° C. for 90 minutes. Then trifluoroacetic acid (TFA) was added to 0.1%, which was placed on a Sep-Pak C18 column (Waters). After washing the column with 10 ml of aqueous solution of 0.1% TFA and 10% acetonitrile, it was eluted with 3 ml of an aqueous solution of 0.1% TFA and 60% acetonitrile. After the eluate was lyophilized, it was dissolved in 0.1 M phosphate buffer (pH 7.0) to 5 mg/ml, and 20 mg/ml of biotin (Long Arm) maleimide (VECTRO Lab.) dissolved in 1/40 volume of dimethylformamide (DMF) was added and reacted at room temperature for 3 hours. To biotin (Long Arm) maleimide-reacted nesfatin-1 Cys, TFA was added to 0.1%, and was applied to HPLC equipped with a reverse phase C18 column (Nacalai Tesque Inc.: COSMOSIL (trade mark) 5C18-AR-300 20.0 mm I.D.× 150 mm). While monitoring absorbance at a wavelength of 210 nm, it was washed with an aqueous solution of 0.1% TFA and then an aqueous solution of 20% acetonitrile containing 0.1% TFA until the absorbance of the eluate cannot be observed. Subsequently, an aqueous solution of acetonitrile at a 20-60% gradient was run to obtain a fraction having the highest peak of absorbance at 210 nm. The fraction obtained was lyophilized and then dissolved in PBS, which was used as the labelled nesfatin-1.

The labelled nesfatin-1 was dissolved to 1 μg/ml in PBS containing 2% BSA. For the creation of a standard curve, the recombinant nesfatin-1 prepared in Working Example 16 was diluted to a concentration of 6000 ng/ml in PBS containing 2% BSA, which was then diluted in PBS containing 2% BSA at a common ratio of 2 and used (standard samples: 6000, 3000, 1500, 750.0, 375.0, 187.5, 93.8 ng/ml). Fifty μl each of the prepared labelled nesfatin-1 and the standard samples were placed into a microtest tube and mixed, and 50 μl each of them was dispensed in a well of the antibody-immobilized plate. As an example of a biological sample, 50 μl of the cerebrospinal fluid as it is collected or the sample diluted 2-fold in PBS containing 2% BSA was mixed with 50 μl of the labelled nesfatin-1 solution in a microtest tube, and 50 μl thereof was aliquoted in wells of the antibody-immobilized plate (test sample). After the aliquoted antibody-immobilize plate was allowed to stand at room temperature for 1 hour, the reaction sample in the well was discarded, and washed three times in PBS containing 0.2% Tween 20. Then 50 μl of avidin-peroxidase (Sigma, A7419-2mL) diluted 1/1,000 with PBS containing 2% BSA and 0.2% Tween 20 was dispensed in each well and was allowed to stand at room temperature for 30 minutes. After the reaction, the solution in each well was removed, and after washing four times in PBS containing 0.2% Tween 20, it was washed twice in TBS (50 mM Tris-HCl, 0.15 M NaCl, pH 8.0). To each well of the antibody-immobilized plate after washing, 50 μl of a peroxidase substrate, TMB (PIERCE: 1-Step (TM) Turbo TMB), was added and reacted at room temperature for 30 minutes. Then to each well, 50 μl of 0.5 N sulfuric acid was added to stop the reaction, absorbance at a wavelength of 450 nm and that at a wavelength of 620 nm were measured by an absorbance plate reader, and the absorbance at a wavelength of 620 nm was subtracted from that at a wavelength of 450 nm (450 (Δ620) nm) to obtain the measured value.

The analysis of nesfatin-1 expression at the hypothalamus was carried out by fractionation using HPLC with the peptide extracted from the tissue as the sample. The hypothalamus was excised from the brains of eight rats, homogenized in 4 ml of an aqueous solution of 0.1% TFA by a Teflon (trade mark) homogenizer, and centrifuged at 10,000 rpm for 10 minutes to collect the supernatant. After the collected supernatant was filtered with a filter (Millipore) having a pore size of 0.45 μm, it was run through the Sep-Pak C18 column (Waters), and the column was washed in 5 ml of an aqueous solution of 0.1% TFA. Then, to the column 3 ml of an aqueous solution of 60% acetonitrile was added for elution, and the eluate was dried in an evaporator. The dried product was dissolved in 0.8 ml of an aqueous solution of 0.1% TFA, centrifuged at 10,000 rpm for 10 minutes, and 500 μl of the supernatant was injected to a HPLC instrument equipped with a C18 reverse phase chromatocolumn (Nacalai Tesque Inc.: COSMOSIL % C18-AR-II, 4.6 mm I.D.×250 mm). After injecting the sample, an aqueous solution of 0.1% TFA was run through the column at a flow rate of 1 ml/min while monitoring the absorbance of the eluate at a wavelength of 224 nM. After washing, while keeping the flow rate, acetonitrile at a 0-60% concentration gradient (A1%/min) was run in the presence of 0.1% TFA to collect the eluate as 1 ml fractions. After freezing the fractions obtained at −80° C., they were lyophilized, and the samples after drying were each dissolved in 200 μl of PBS containing 2% BSA, and nesfatin and nesfatin/nesfatin-1 were measured by a competitive EIA method. Similarly, from the samples obtained by drying 600 μl of the cerebrospinal fluid collected from eight rats, peptide samples were prepared, fractionated by HPLC, and the eluated fractions were examined by the competitive EIA system. Also, as the control, 80 μg of the recombinant nesfatin-1 peptide prepared in Working Example 16 was dissolved in 100 μl an aqueous solution of 0.1% TFA, which was injected into HPLC, and the fractions in which nesfatin-1 was eluated were detected.

<Result>

A standard reaction curve obtained by measuring the standard samples in the competitive EIA system is shown in FIG. 19A-1. It was demonstrated that with increased concentrations of the reacted nesfatin-1, the binding of the labelled nesfatin-1 is competitively inhibited and the absorbance at 450 (A620) decreases, indicating that nesfatin-1 concentrations in samples can be determined in this system. The sensitivity of this system corresponds to 4.6 ng/tube (93 ng/ml) of nesfatin-1. The result of the concentration of nesfatin-1 (nesfatin) in the cerebrospinal fluid determined by this competitive EIA system is shown in FIG. 19A-2. The values obtained by measuring the cerebrospinal fluid as it is or after diluting ½ (converted by the dilution factor after measurement) are almost the same and indicated that about 230 ng/ml of nesfatin-1 (nesfatin) is present.

b-1 of FIG. 19B shows a result in which a peptide sample extracted from the rat hypothalamus was fractionated by HPLC and the presence of nesfatin-1 in the fractions were determined, and b-2 of FIG. 19B shows a result in which a similar study was carried out using a peptide sample extracted from the rat cerebrospinal fluid. In both b-1 of FIG. 19B and b-2 of FIG. 19B, a reaction peak which is likely to be nesfatin-1 was noted in the fractions from No. 44 and 45. In a result when the recombinant nesfatin-1 was fractionated by HPLC under a similar condition, nesfatin-1 was eluted at No. 44 fraction, the factor of which presence was indicated from HPLC fractions of the hypothalamus and the cerebrospinal fluid by the competitive EIA system is believed to be nesfatin-1.

Working Example 22

Study on the Effect of the Intraperitoneal Administration of the Partial Peptide (nesfatin-1M16, nesfatin-1M14, nesfatin-1M10M) of nesfatin-1M30 on Food Intake Control in Mice In Working Example 20, the study on the effect of suppressing food intake of a partial peptide derived from nesfatin-1 led to the invention of nesfatin-1M30. Furthermore, in order to examine in further detail the sites having an activity of suppressing food intake, a partial peptide of nesfatin-1M30 was prepared from the structure of nesfatin-1M30 comprising a 30-amino acid length, and an experiment was carried out to measure the amount of food intake when it was intraperitoneally administered to mice.

For nesfatin-1M16 comprising a 16-amino acid length, nesfatin-1M14 comprising a 14-amino acid length and nesfatin-1M10M comprising a 10-amino acid length which are partial peptides of mouse nesfatin-1M30, the preparation of synthetic peptides having the following sequences was referred to Biologica Co., Ltd. and were purified by HPLC to a purity of 95% or higher.

nesfatin-1M16:
(SEQ ID NO: 71)
N-ProAspThrGlyLeuTyrTyrAspGluTyrLeuLysGlnValIle

Glu-C nesfatin-1M14:
(SEQ ID NO: 72)
N-ValLeuGluThrAspProHisPheArgGluLysLeuGlnLys-C nesfatin-1M10M:
(SEQ ID NO: 73)
N-LysGlnValIleGluValLeuGluThrAsp-C Each peptide was prepared in physiological saline so as to contain 10 pmol per 100 µl, which was used as the sample for administration, and as the control sample physiological saline (Vehicle) alone was used. The physiological saline as the control and the peptide samples prepared were intraperitoneally administered at 100 µl per mouse (6 animals per group). Mice used were male ICR mice (Nippon SLC) and the housing condition and the experimental condition were similar to those in Working Example 18.

Each mouse that received administration was placed in an individual cage, and during 0-3 hours after the administration the weight decreased of the pellet food was measured to determine the amount of food intake. For testing of significant difference, analysis of variance was used.

<Result>

FIG. 20 shows the amount of food intake during 0-3 hours after administration when a partial peptide of nesfatin-1M30, nesfatin-1M16 (M16), nesfatin-1M10M (M10M) or nesfatin-M14 (M14), was intraperitoneally administered into mice. In all of the group that received nesfatin-1M16 (M16), nesfatin-1M10M (M10M) or nesfatin-M14 (M14) relative to the control group (Cont.) that received physiological saline alone, a significant effect of suppressing food intake was noted.

Working Example 23

Study on the Effect of Human nesfatin-1M30 and Mouse NUCB1-M30 on Food Intake Control Working Example 20 demonstrated that mouse nesfatin-1M30 has an effect of suppressing food intake. Based on this, human nesfatin-1M30 was prepared and studied on its effect on the food intake behavior when administered on mice. Nucleobindin-1 (NUCB1) is a factor that forms a family having a high homology with NEFA/nesfatin in the amino acid sequence of peptides and the nucleotide sequence of the genes. Thus, NUCB1-M30 which is a site corresponding to nesfatin-1M30 of NUCB1 was created and was administered to mice to examine the effect on food intake.

The preparation of human nesfatin-1M30 (SEQ ID NO: 39) and mouse NUCB1-M30 by chemical synthesis was referred to Biologica Co., Ltd. and was purified by HPLC to a purity of 95% or higher.

Human nesfatin-1M30:
(SEQ ID NO: 39)
N-ProAspThrGlyLeuTyrTyrAspGluTyrLeuLysGlnValIleAsp ValLeuGluThrAspLysHisPheArgGluLysLeuGlnLys-C Mouse NUCB1-M30:
(SEQ ID NO: 103)
N-ProAspThrGlyLeuTyrTyrHisArgTyrLeuGlnGluValIleAsn ValLeuGluThrAspGlyHisPheArgGluLysLeuGlnAla-C Each of the prepared human nesfatin-1M30 and mouse NUCB1-M30 was prepared in physiological saline so as to contain 10 pmol per 100 µl, which was used as the sample for administration. For nesfatin-1M30 that exhibited an activity of suppressing food intake, one prepared in Working Example 20 was used as the comparative sample at similar amounts as nesfatin-1M30 and NUCB1-M30, and as the control sample physiological saline (Vehicle) alone was used.

The physiological saline as the control and the peptide sample prepared were intraperitoneally administered at 100 µl per mouse (n=6 per group). Mice used were male ICR mice (Nippon SLC) and the housing condition and the experimental condition were similar to those in Working Example 18.

Each mouse that received administration was placed in an individual cage, and during 0-3 hours after the administration the weight decreased of the pellet food was measured to determine the amount of food intake. For testing of significant difference, analysis of variance was used.

The alignment of amino acid sequence was performed for human, rat and mouse nesfatin and human, rat and mouse NUCB1. The method used the amino acid sequences of human, mouse and rat nesfatin of SEQ ID NO: 2, SEQ ID NO: 5 and SEQ ID NO: 8, respectively, and the amino acid sequences of human, mouse and rat NUCB1 of SEQ ID NO: 84, SEQ ID NO: 88 and SEQ ID NO: 92, respectively, and analyzed by the Clustal-W method.

<Result>

The result measured of the amount of food intake during 0-3 hours after administration when human nesfatin-1M30 (human/nesfatin-1M30), mouse nesfatin-1M30 (mouse/nesfatin-1M30) or mouse NUCB1-M30 (mouse NUCB1) was administered is shown in FIG. 21A. FIG. 21A indicates that in all of the groups that received human nesfatin-1M30 (human/nesfatin-1M30), mouse nesfatin-1M30 (mouse/nesfatin-1M30) or mouse NUCB1-M30 (mouse NUCB1) relative to the control group (Vehicle) that received physiological saline alone, a significant effect of suppressing food intake was noted.

Also, the results of alignment of amino acid sequence for human, rat and mouse nesfatin and for human, rat and mouse NUCB1 and sites corresponding to nesfatin-1 and nesfatin-1M30 are shown in FIGS. 21B to 21C. It was shown that amino acid sequences are highly conserved in sites corresponding to nesfatin and nesfatin-1 of NUCB2, in particular the site corresponding to nesfatin-1M30.

Working Example 24

Study on the Expression Site of the nesfatin Gene in the Rat Hypothalamus

The expression of nesfatin mRNA in the brain hypothalamus was analyzed by an in situ hybridization method in Working Example 8. In order to further analyze the site where the nesfatin gene is being expressed, a study by an in situ hybridization method using radioisotope was carried out.

Using eight week-old male Wistar rats (purchased from Nippon SLC) (body weight: 220-250 g) that were housed with free access to the food, the rats were deeply anesthetized by pentobarbital in the light period, and the brain was fixed by perfusing 4% paraformaldehyde dissolved in ice-cold 0.1M borate buffer (pH 9.5) from the heart. The brain was extracted, and was immersed in 0.1M borate buffer (pH 9.5) containing 10% sucrose and 4% paraformaldehyde for 2 days. The fixed brain was frozen in dry ice-acetone, and sliced with a cryostat to sections 20 µm thick, which were placed on a slide glass (MAS coat slide S-9116 prepared by Matsunami Glass).

For the preparation of the radioisotope-labelled probe, a plasmid was used which was obtained by cleaving a plasmid for the preparation of the NEFA probe that was used in Working Example 2 with a restriction enzyme NcoI and then purifying it. To 0.1 µg of the plasmid, 20 U (1 µl) of SP6 RNA polymerase (Promega, P1085) was added at a condition of 19 µl of a solution containing 36 mM Tris-HCl buffer (pH 7.5), 6 mM magnesium chloride, 2 mM spermidine, 8 mM dithiothreitol, 25 mM adenosine triphosphate/guanosine triphosphate/cytosine triphosphate, 5 mM uracil triphosphate and 5 mM [α-35S]-uracil triphosphate, and 1U of RNAsin™ ribonuclease inhibitor (Promega, N2111), reacted at 37° C. for 60 minutes to prepare a 35S-labelled NEFA cRNA probe. After the reaction, 20 µl of the TNE buffer (10 mM Tris-C1, pH 8.0, 0.5 M NaCl, and 0.25 mM EDTA, pH 8.0) was added to stop the reaction, and then the probe was purified using the NEN-SORB™ PREP Nucleic Acid Purification Cartridges (Perkin-Elmer, Inc., NLP028001EA) according to the attached protocol.

The slide glass of the prepared section sample was dried overnight under vacuum before hybridization, treated with PBS containing 10 µg/ml of Protease K (Sigma, P2308) at 37° C. for 30 minutes, and washed twice with PBS, and furthermore treated by immersing in 0.1 M triethylamine-hydrochloric acid buffer (pH 8.0) containing 0.25% acetic anhydride at room temperature for 10 minutes, followed by washing twice with 2× concentrated SSC. The washed section sample was dehydrated by immersing in 75% ethanol, 95% ethanol and 99% ethanol in this order, dried in the air, and further dried under vacuum.

On to the dried slide glass of the section sample, an in situ hybridization solution (10 mM Tris-HCl buffer, pH 8.0, 30 mM NaCl, 10% dextran sulfate, 1× concentrated Denhardt's solution, 12 mM EDTA, 50% deionized formamide, 0.5 mg/ml yeast rRNA) was placed so as to cover the brain tissue section, and prehybridized at 65° C. for 1 hour. After discarding the prehybridization solution, 80 µl, per slide glass, of a hybridization solution containing $10^6$ cpm/ml 35S-labelled NEFA cRNA probe and 10 mM dithiothreitol was placed, and a cover slip was placed thereon, which was placed in a wet chamber and hybridized overnight at 65° C. After the slide glass after hybridization was washed four times with 4× concentrated SSC, it was treated with the TNE buffer (10 mM Tris-HCl, pH 8.0, 0.5 M NaCl, and 0.25 mM EDTA, pH 8.0) containing 20 µg/ml of RNAase A at 37° C. for 30 minutes, washed twice with 2× concentrated SSC at room temperature, and further washed twice with 0.1× concentrated SSC at 65° C. for 30 minutes. The slide glass after washing was dehydrated by immersing in 75% ethanol, 95% ethanol and 99% ethanol in this order, and then dried in the air. After the slide glass having the tissue section thereon was exposed to X-ray film for 7 days, it was immersed in a 2× diluted light-sensitive emulsion (Kodak, NTB3) and exposed to light for 3 weeks. After exposure the slide glass was washed with water, stained with Thionine, and black spots resulted from the exposure were examined under microscope.

The position of each part in the rat brain was identified according to The Rat Brain in Stereotaxic Coordinates by Paxinos G. and Watoson C. (Academic Press) (USA) 1986.

<Result>

A of FIG. 22 shows an image of in situ hybridization of a tissue section containing paraventricular nucleus (PVN) and supraoptic nucleus (SON), B of FIG. 22 shows that of a tissue section containing zona incerta (Zi) and arcuate nucleus (Arc), and C of FIG. 22 shows that of a tissue section containing lateral hypothalamic area (LHA). At each area of PVN, SON, Zi, Arc and LHA, spots that were light-sensitized by the hybridization of the radioisotope-labelled NEFA cRNA probe, indicating the expression of the NEFA gene.

Working Example 25

Study on the Effect of Intraventricular Administration of nesfatin on Food Intake Behavior While the amount of food intake during 0-1 hour/1-3 hours/3-6 hours after the administration of nesfatin to rats was studied in Working Example 6, the effect on food intake behavior during 6-12 hours after the administration was further studied herein.

In order to demonstrate the reproducibility of Working Example 6, the amount of food intake during 0-1 hour after administration was determined when 0 (PBS alone), 1, 4 and 20 pmol of recombinant nesfatin was administered to the third ventricle of brain, as in Working Example 6. Also, in the same manner as in Working Example 6, after 5 pmol of nesfatin was administered into the rat ventricle, the amount of food intake was determined during 0-1 hour/1-3 hours/3-6 hours after the administration. The control group used was the one that only received physiological saline (0 pmol). For testing of significant difference, analysis of variance was used.

<Result>

As shown in A of FIG. 23, the amount of food intake at 0-1 hour after the administration of 4 pmol or 20 pmol of nesfatin into the brain ventricle was significantly reduced as compared to the control group (0 pmol) ($p<0.01$). Also, as shown in B of FIG. 23, a significant reduction in the amount of food intake was noted in the individual that received the intraventricular administration of 5 pmol of nesfatin during 0-1 hour ($p<0.01$), 1-3 hours ($p<0.05$) and 3-6 hours ($p<0.001$) as compared to the control group (0 pmol). However, in the amount of food intake during 6-12 hours, no difference was noted between the group that received 5 pmol of nesfatin and the control group.

Working Example 26

Study on the Amount Expressed of nesfatin mRNA and the nesfatin Polypeptide in the Rat Hypothalamus During Starvation In order to study the expression of the nesfatin gene during starvation, in situ hybridization was carried out in the brain hypothalamus region of the rats that had free access to the food and the fasted rats, and increases or decreases in the amount of nesfatin mRNA at arcuate nucleus, paraventricular nucleus, lateral hypothalamic area and supraoptic nucleus from the tissue were determined. Also, in order to study the amount expressed of the nesfatin-1 peptide at paraventricular nucleus, the hypothalamus region of the rats that had free access to the food and the fasted rats was excised, and the extracted peptides were determined by competitive EIA system.

As in Working Example 8, rats used were individuals (the control group) that were allowed free access to the powder food, and individuals (the fasting group) that were housed on water alone without any food for 48 hours. For the determination of the amount expressed of nesfatin mRNA at each region of the hypothalamus, tissue sections were prepared in a manner similar to Working Example 24, which was subjected to in situ hybridization, and the image obtained by exposing to X-ray film was measured using an image analyzer (Imaging Research Inc., MCID™ Elite) (Imaki et al., Brain Research, Netherlands, 1993, Vol. 623, pp. 223-228). Density of the exposed image at each region of arcuate nucleus, paraventricular nucleus, lateral hypothalamic area and supraoptic nucleus was determined, and the values were changed into numerical values as relative optical values on a 256-stage gray scale from white to black, which were then changed into numerical values as relative optical densities according to the following equation to obtain the absolute values for mRNA expression:

Relative optical density=log 10(256/relative optical value).

Each region of arcuate nucleus, paraventricular nucleus, lateral hypothalamic area and supraoptic nucleus in the rat brain was identified according to The Rat Brain in Stereotaxic Coordinates by Paxinos G. and Watoson C. (Academic Press) (USA) 1986.

The nesfatin-1 peptide at the paraventricular nucleus of the rat brain was determined as follows. Rats that were allowed free access to the food and that were fasted as described above were sacrificed by decapitation, and the brain was immediately frozen in dry ice-ethanol, and sliced by a cryostat into sections 60 μm thick. The tissue was Nissl stained, and the parts corresponding to paraventricular nucleus on both sides of the brain were excised and recovered. The recovered tissue was homogenized in 100 μl of 0.1 N hydrochloric acid in a 1.5 ml microtube using the microtube pestle (Scientific Specialties, 1005-39). The homogenized solution was centrifuged in a microfuge at 15,000 rpm for 20 minutes, the supernatant was collected and the solvent was removed by lyophilization. The lyophilized sample was dissolved in 100 μl of PBS, and the amount of the nesfatin-1 peptide was determined at a condition of 50 μl/well by the competitive EIA described in Working Example 21.

<Result>

A of FIG. 24 shows the result of image analysis by in situ hybridization of nesfatin mRNA expression at various hypothalamus regions of arcuate nucleus (Arc), paraventricular nucleus (PVN), lateral hypothalamic area (LHA) and supraoptic nucleus (SON) in the rat brain in the feeding ad libitum group (control group) and the fasting group. In arcuate nucleus (Arc), lateral hypothalamic area (LHA) and supraoptic nucleus (SON), no difference in the value (relative optical density) of nesfatin mRNA expression was noted in the fasting group relative to that in the feeding ad libitum group (control group). In contrast, in the result for paraventricular nucleus (PVN), the amount expressed of nesfatin mRNA in the fasting group was significantly reduced relative to the feeding ad libitum group (control group).

B of FIG. 24 shows the result of image analysis by a competitive EIA method of the expression of the nesfatin-1 peptide at paraventricular nucleus (PVN) among the hypothalamic regions of the rat brain in the feeding ad libitum group (control group) and the fasting group. It was demonstrated that the expression of the nesfatin-1 peptide at paraventricular nucleus is significantly decreased in the fasting group relative to the feeding ad libitum group (control group).

The above result shows that fasting markedly reduces the expression of the nesfatin (NEFA) gene and nesfatin-1 at paraventricular nucleus of the hypothalamus that is important in the control of food intake.

Working Example 27

Study on the Effect of Intraventricular Administration of nesfatin-1 into the Rat Brain on Food Intake Behavior It was shown in Working Example 12 that the part of nesfatin-1 alone had an activity of suppressing food intake in the experiment of the administration of partial peptides of nesfatin. In order to further validate the experiment, changes in the activity of suppressing food intake with time after administration was investigated.

The experimental condition was similar to that in Working Example 12, and 5 pmol of nesfatin-1 was administered into the third ventricle of the rat brain immediately before the start of the dark period, the amount decreased of the food (the amount of food intake) during 1 hour immediately after administration (0-1 hr), during 2 hours from 1 hour after the administration (1-3 hr), during 3 hours from 3 hours after the administration (3-6 hr), and during 6 hours from 6 hours after the administration (6-12 hr) was measured as the amount of food intake. As the control group, the amount of food intake by individuals that received physiological saline alone was measured.

<Result>

FIG. 25 shows the amount of food intake during 0-1 hr, 1-3 hr, 3-6 hr and 6-12 hr when nesfatin-1 was administered to the third ventricle of the rat brain. Significant decreases in the amount of food intake in 0-1 hr, 1-3 hr and 3-6 hr were noted in the nesfatin-1-administration group relative to the control group ($p<0.01$). In contrast, in 6-12 hr, an increase in the amount of food intake was noted in the nesfatin-1-administration group relative to the control group ($p<0.01$). The above results demonstrated that the suppression of food intake by the intraventricular administration of nesfatin-1 is temporary, and the disappearance of the pharmacological effect of nesfatin with the passage of time and the resultant recovery of food intake can be noted.

Working Example 28

Study on the Specificity of Effect of Intraventricular Administration of Anti-nesfatin-1 Antibody on Enhancing Food Intake It was shown in Working Example 14 that the effect of enhancing food intake is noted when an antibody against nesfatin-1 is administered into the rat ventricle. In order to validate that the effect is due to the inhibition of the effect of nesfatin-1, a study was carried out to determine whether the suppression of food intake by the intraventricular administration of nesfatin-1 can be inhibited by the simultaneous administration of anti-nesfatin-1 antibody.

The experimental condition was similar to that in Working Example 12, and for a group that received 5 pmol of nesfatin-1 alone into the third ventricle of the rat brain immediately before the start of the dark period and a group that received 5 pmol of nesfatin-1 and 8 µg of anti-nesfatin-1 antibody (nesfatin-1 IgG), the amount of food intake for 1 hour after administration was measured and compared to that for the control group (physiological saline alone was administered). Also, for a group that received only leptin (Rat leptin: R & D Systems, 598-LP-01M) (1 µg) which is known to have an activity of suppressing food intake by intraventricular administration and a group that received leptin and anti-nesfatin-1 antibody, its effect on food intake was also studied.

<Result>

FIG. 26 is a graph showing the amount of food intake for 1 hour after administration for a group that received nesfatin-1 alone (nesfatin-1 IgG/nesfatin-1/leptin: −/+/−), a group that received nesfatin-1 and anti-nesfatin-1 antibody (nesfatin-1 IgG/nesfatin-1/leptin: +/+/−), a group that received leptin (nesfatin-1 IgG/nesfatin-1/leptin: −/−/+), and a group that received leptin and anti-nesfatin-1 antibody (nesfatin-1 IgG/nesfatin-1/leptin: +/−/+). The amount of food intake significantly decreased in the group that received nesfatin alone relative to the control group (nesfatin-1 IgG/nesfatin-1/leptin: −/−/−), whereas in the group that received nesfatin-1 and anti-nesfatin-1 antibody, the effect of enhancing the amount of food intake to about the same degree as the control group was noted. In contrast, in the group that received leptin, the amount of food intake also decreased, whereas in the group that received leptin and anti-nesfatin-1 antibody, no effect of enhancing the suppression of the amount of food intake by leptin was noted. This result suggests that the effect of enhancing food intake by anti-nesfatin-1 antibody results from the specific suppression of the effect of nesfatin-1.

Working Example 29

Study on the Binding Specificity of Anti-nesfatin-1 Antibody

It was shown in Working Example 28 that the intraventricular administration of anti-nesfatin-1 antibody specifically inhibits the effect of nesfatin-1. Its binding property with other factors known at present to have an activity of controlling food intake was further studied by the Western blotting method using extracts of the rat brain.

Western blotting analysis was carried out by the method described in Working Example 3 with the primary antibody being changed from anti-NAP polyclonal antibody to anti-nesfatin-1 antibody. Before reacting anti-nesfatin-1 antibody to the membrane in Western blotting as an experiment for investigating the binding specificity of anti-nesfatin-1 antibody, 5 µg of each peptide of NAP1-Ab (Working Example 10), and leptin (Rat leptin: R & D Systems, 598-LP-01M), αMSH (Melanocyte Stimulating Hormone; Peptide Institute, Inc., 4057-v), CART (Rat Cocaine- and Amphetamine-Regulated Transcript 55-102; Peptide Institute, Inc., 4351-s), NPY (Human, Rat Neuropeptide Y; Peptide Institute, Inc., 4158-v), MCH (Human Melanin-Concentrating Hormone; Peptide Institute, Inc., 4369-v) and Orexin-A (Human, Rat, Mouse, Bovine Orexin-A; Peptide Institute, Inc., 4346-s) per 1 µg of anti-nesfatin-1 antibody was added, and reacted at room temperature for 1 hour, and then Western blotting was carried out in the method described above to examine whether or not the bands disappear.

<Result>

A of FIG. 27 shows an image of Western blotting carried out with anti-nesfatin-1 antibody using protein extracts from the rat brain. As a result, a band was noted at a position of molecular weight corresponding to 47.5 kd nesfatin polypeptide. B of FIG. 27 shows an image at about 47.5 kd of Western blotting carried out after anti-nesfatin-1 antibody and various peptides were previously reacted. When anti-nesfatin-1 antibody was reacted to NAP1-Ab, the 47.5 kd band disappeared, indicating that the previous binding of NAP-1 Ab to NAP1-Ab peptide blocked the binding site of nesfatin. In contrast, when it was reacted to letptin, αMSH, CART, NPY, MCH and Orexin-A, and when the peptide was not subjected to the anti-nesfatin-1 antibody reaction, the 47.5 kb band did not disappear. These results demonstrated that anti-nesfatin-1 antibody specifically binds to nesfatin, but not to other food intake-related peptides such as letptin, αMSH, CART, NPY, MCH and Orexin-A.

Working Example 30

Study on the Expression Site of nesfatin in the Rat Medulla Oblongata

In Working Example 4, expression in the vicinity of the hypothalamus of a rat brain was studied by immunohistochemical analysis. In order to further study the expression of nesfatin in the vicinity of the rat medulla oblongata, a similar immunohistochemical analysis was carried out.

Using eight week-old Wistar rats (purchased from Nippon SLC), brain tissue sections of the part containing the medulla oblongata were prepared from samples similarly to Working Example 4. The method of immunohistochemical stain was also similar to that in Working Example 4. Furthermore, the NAP peptide (Working Example 3) was added to an antibody (1 µg/ml) against the NAP peptide to 100 µg/ml, reacted at room temperature for 1 hour, and then immunohistochemical stain was also carried out using the antibody.

<Result>

A of FIG. 28 shows an image of immunohistochemical stain in the brain tissue containing the medulla oblongata. In the immunohistochemical stain in the brain tissue containing the medulla oblongata, stain was noted at STN: the nucleus of solitary tract, and the expression of the nesfatin polypeptide was noted. B of FIG. 28 shows an image of immunohistochemical stain carried out after an antibody against the NAP peptide and the NAP peptide were previously reacted. Since the stain observed in A of FIG. 28 disappeared by reacting the anti-NAP antibody to the NAP peptide in advance, it was demonstrated, the nesfatin polypeptide has been specifically stained in this immunohistochemical stain. The results revealed that nesfatin is also expressed in the nucleus of solitary tract which is a viceral sensory nerve nucleus and is though to be involved in the mechanism of food intake control.

Working Example 31

Effect of Troglitazone Administration on Blood Leptin and the Intracerebral Expression of nesfatin in the Normal and Leptin-Resistant Obese Rats In Working Example 2, the induction of the nesfatin (NEFA) gene in cultured cells by troglitazone, a PPARγ agonist that was used as an antidiabetic drug, was studied. In order to further study the induced expression of nesfatin by troglitazone, troglitazone was given to rats to study the induction of nesfatin in the brain. Similarly, blood levels of leptin which is known to be responsible for control of food intake were studied. In the study, normal Zucker rats (Zucker +/+: Lean) and Zucker fa/fa, an animal model of leptin-resistant obese rats, were used.

As animals, 8 week-old male Zucker fa/fa (Zucker) rats and Zucker +/+(Lean) rats as the control animal were purchased from Nippon Charles River, and were housed in a cycle of 12 hours of the light period from 6 a.m. to 6p.m. and 12 hours of the dark period from 6 p.m. to 6 a.m. the next morning and fed a powder food (Nippon Clea, CE-2), and kept at 22° C. After preliminary housing for over one week, individuals weighing 200-250 g were selected among 9 to 10 week-old individuals from the rats purchased and 6 animals per group were used in the experiment. Troglitazone (TGZ; Sankyo Co., Ltd.) was administered at a concentration of 0.2% blended in the powder food, to which the animals were allowed free access. As the control that did not receive troglitazone, rats that were housed on the normal powder food alone were used. After housing on the troglitazone-containing food or the normal food for 10 days on end, the animals were weighed and sacrificed to collect whole blood. From the rat's blood collected, serum was separated, and leptin concentration in the serum was determined using a commercial ELISA kit (Yanaihara Institute Inc., YK050) according to the attached protocol. Furthermore, the brain was harvested from the rats sacrificed, and was subjected to Western blotting in a similar manner to Working Example 3, the density of the bands was analyzed by an image analyzer (Imaging Research Inc., MCID™ Basic), and the degree of color development of the band was expressed as relative units.

<Result>

A of FIG. 29 is a graph showing the body weight of the group (TGZ: +) in which the troglitazone-containing food was given to the normal rats (Lean) and the Zucker fa/fa rats (Zucker), and the group (TGZ: −) in which the troglitazone-free food was given thereto. In the normal rats and the Zucker fa/fa rats as well, no marked difference in body weight due to troglitazone administration was noted. Also, irrespective of the administration of troglitazone, the Zucker fa/fa rats weighed significantly heavily ($p<0.01$) relative to the normal rats.

B of FIG. 29 is a graph showing the concentration of leptin in the blood of the group (TGZ: −) in which the troglitazone-containing food was given to the normal rats (Lean) and the Zucker fa/fa rats, and the group (TGZ: −) in which the troglitazone-free food was given thereto. In the normal rats and the Zucker fa/fa rats, the concentration of leptin in the blood significantly decreased ($p<0.05$) due to troglitazone administration. Also, irrespective of the administration of troglitazone, the concentration of leptin in the blood was significantly high in the Zucker fa/fa rats ($p<0.01$) relative to the normal rats.

C of FIG. 29 is a graph showing, as relative values, the density of bands obtained by Western blotting of protein-extracted samples of the brains from the group (TGZ: +) in which the troglitazone-containing food was given to the normal rats (Lean) and the Zucker fa/fa rats and the group (TGZ: −) in which the troglitazone-free food was given thereto. In the normal rats, no difference in the amount expressed of nesfatin in the brain was noted between the group (TGZ: +) in which the troglitazone-containing food was given and the group (TGZ: −) in which the troglitazone-free food was given. In contrast, in the Zucker fa/fa rats, the amount expressed of nesfatin in the brain significantly increased ($p<0.01$). Also, irrespective of the administration of troglitazone, the amount expressed of nesfatin in the brain was significantly high in the Zucker fa/fa rats ($p<0.01$) relative to the normal rats.

The above results suggest that troglitazone that was used as an antidiabetic drug does not induce nesfatin in the brain of the normal animals, whereas it can induce the expression of nesfatin in the brain of the animal model that exhibits a leptin-resistant pathology. In contrast, it is suggested, the enhanced blood concentrations of leptin cannot be obtained by troglitazone in both the normal animals and the pathogenic animals, and conversely blood concentrations are decreased.

Working Example 32

Detection of the nesfatin-1 Peptide in the HPLC Fractions of the Hypothalamus Tissue Extract The peptide extracted from the hypothalamus tissue in Working Example 21 as the sample was subjected to HPLC fractionation, and the fractions were examined for the presence of nesfatin-1 by the competitive EIA assay system. Furthermore, in order to investigate the peptide detected in the fractions is a molecule corresponding to nesfatin-1, the HPLC fractions of the hypothalamus tissue extract were analyzed by the Western blotting method.

HPLC fractions of the hypothalamus tissue extract was prepared in a similar manner to Working Example 21, and the fractions of No. (Fraction #) 43-47 were lyophilized. Samples after lyophilization were dissolved in 100 μl of PBS, and 20 μl of it was subjected to SDS-PAGE on a 12% polyacrylamide gel, and then to Western blotting with anti-nesfatin-1 antibody in a similar manner to Working Example 3.

<Result>

A of FIG. 30 shows an image of Western blotting of the fraction No. 45 obtained by fractionating a peptide extract from the rat hypothalamus by HPLC. The molecular weight of the band detected by Western blotting is about 9.7 kd, which almost agreed with that of the recombinantly prepared nesfatin-1 peptide (Working Example 10, FIG. 9C). B of FIG. 30 shows an image of the region at a molecular weight of about 9.7 kd in the image of Western blotting of the fraction Nos. 43-47 obtained by fractionating the peptide extract from the rat hypothalamus by HPLC. The 9.7 kd band is most strongly observed in fraction No. 45, which result agreed with the pattern obtained by determining by a competitive EIA method the fractions obtained by fractionating the peptide extract from the rat hypothalamus by HPLC (b-1 of FIG. 19B).

The above result indicated that a molecule corresponding to nesfatin-1 is present in the rat hypothalamus, and that a molecule corresponding to nesfatin-1 can be detected by fractionating it according to the method in Working Example 21 and then by detecting by a competitive EIA method and/or the Western blotting method.

Working Example 33

Study on the Specificity of Immunohistochemical Stain of the Regions of the Rat Hypothalamus In Working Example 4, in order to analyze the NEFA expression site in the hypothalamus of the rat brain which is related to food intake the control, an immunohistochemical analysis using rat brain sections was carried out. In order to study whether the stain is nesfatin-specific, an immunohistochemical analysis was carried out again taking into consideration the binding property of a peptide known to control food intake to an antibody.

In a method similar to that in Working Example 4, immunohistochemical stain was carried out on tissue sections of the rat brain each containing arcuate nucleus and paraventricular nucleus, in which anti-nesfatin-1 antibody (nesfatin-1 IgG; Working Example 10) was used in stead of a anti-NAP polyclonal antibody as the primary antibody. Also, before reacting the primary antibody with the tissue sample, 5 µg of each peptide of anti-nesfatin-1 antibody (Working Example 10), and leptin (Rat leptin: R & D Systems, 598-LP-01M), αMSH (Melanocyte Stimulating Hormone; Peptide Institute, Inc., 4057-v), CART (Rat Cocaine- and Amphetamine-Regulated Transcript 55-102; Peptide Institute, Inc., 4351-s) and NPY (Human, Rat Neuropeptide Y; Peptide Institute, Inc., 4158-v), known for the effect of controlling food intake, per 1 µg of anti-nesfatin-1 antibody was added, and reacted at room temperature for 1 hour, and then used in the immunohistochemical stain to validate the reaction specificity of the antibody.

<Result>

A of FIG. 31 shows the result of immunohistochemical stain section using an anti-nesfatin-1 antibody in the rat brain tissue containing the arcuate nucleus, and the result of immunohistochemical stain carried out after the primary antibody and various peptides were previously reacted. In A of FIG. 31, since a-1 shows that the arcuate nucleus of the rat brain is immunologically stained with the anti-nesfatin-1 antibody and a-2 shows that when the anti-nesfatin-1 antibody is previously reacted with the nesfatin-1 peptide the stain disappears, it was demonstrated that the anti-nesfatin-1 antibody detects nesfatin being expressed in the arcuate nucleus. In contrast, when the anti-nesfatin-1 antibody was previously reacted with leptin (a-3 in A of FIG. 31), αMSH (a-4 in A of FIG. 31), CART (a-5 in A of FIG. 31) and NPY (a-6 in A of FIG. 31), the immunological stain in the arcuate nucleus does not disappear, indicating that these peptides do not bind to the anti-nesfatin-1 antibody, and thus it was demonstrated that in the immunohistochemical stain said antibody does not react to these peptides.

B of FIG. 31 shows the result of immunohistochemical stain using an anti-nesfatin-1 antibody in the rat brain tissue section containing the paraventricular nucleus, and the result of immunohistochemical stain carried out after the primary antibody and various peptides were previously reacted. In B of FIG. 31, since b-1 shows that the arcuate nucleus of the rat brain is immunologically stained with the anti-nesfatin-1 antibody and a-2 shows that when the anti-nesfatin-1 antibody is previously reacted with the nesfatin-1 peptide the stain disappears, it was demonstrated that the anti-nesfatin-1 antibody detects nesfatin being expressed in the paraventricular nucleus. In contrast, when the anti-nesfatin-1 antibody was previously reacted with leptin (b-3 in B of FIG. 31), αMSH (b-4 in B of FIG. 31), CART (b-5 in B of FIG. 31) and NPY (b-6 in B of FIG. 31), the immunological stain in the arcuate nucleus does not disappear, indicating that these peptides do not bind to the anti-nesfatin-1 antibody, and thus it was demonstrated that in the immunohistochemical stain said antibody does not react to these peptides.

In the above result, the expression of nesfatin is specifically detected in the immunohistochemical stain using the anti-nesfatin-1 antibody, indicating that in the rat brain nesfatin is being expressed in the arcuate nucleus and the paraventricular nucleus.

Working Example 34

Study on the Effect of Continuous Administration of nesfatin-1 into the Rat Ventricle on the Weight of the Adipose Tissue In order to study the effect of nesfatin-1 on the amount of the adipose tissue, nesfatin-1 was continuously administered into the rat ventricle to analyze changes in the weight of the adipose tissue etc.

Nesfatin-1 (5 pmol per day) or physiological saline alone (the control group) was administered into the third ventricle of a rat using an osmotic pump for 10 consecutive days (5 and 4 rats were used per group). Intraventricular administration into rats by the osmotic pump was carried out in a manner similar to that in Working Example 13.

After the administration of nesfatin-1 or physiological saline alone for 10 days, each rat was sacrificed, dissected to excise all of the abdominal subcutaneous adipose tissue, the epididymal adipose tissue (these are white adipose tissue) and the retroperitoneal brown adipose tissue, and the weight of them was measured. Also, the gastrocnemial muscles of the bilateral hind legs were harvested and the weight of them was measured. From the weight of the tissues measured, their ratio to the body weight of each individual was determined (tissue weight/body weight, mg/g). For testing of significant difference, analysis of variance was used.

<Result>

FIG. 32 is a graph of the result showing the ratio of tissue weight of each adipose tissue (A-E) and the gastrocnemial muscle (F) obtained from the rats that were given nesfatin-1 or physiological saline alone for 10 days relative to the body weight. In the abdominal subcutaneous adipose tissue (A of FIG. 32), the epididymal adipose tissue (B of FIG. 32) and the mesenteric adipose tissue (C of FIG. 32), significant decreases in the ratio of tissue weight to body weight were noted in the nesfatin-1-administration group relative to the control group that received physiological saline alone. In the retroperitoneal adipose tissue (D of FIG. 32), the ratio of tissue weight to body weight tended to decrease but no significant difference was noted relative to the control group. Furthermore, in the brown adipose tissue (E of FIG. 32) and the gastrocnemial muscle (F of FIG. 32), no significant difference in the total tissue weight to the body weight was noted between the control group and the nesfatin-1-administration group.

The above result indicated that nesfatin-1 has an effect of decreasing the ratio of tissue weight of the white adipose tissue to body weight, i.e. body fat percentage. It was also shown that it does not affect the ratio of tissue weight of the brown adipose tissue and the muscle tissue to body weight.

Working Example 35

Study on the Effect of Intraperitoneal Administration of nesfatin-1 into the Rat on Blood Biochemical Parameters It was investigated whether the activities of suppressing food intake, suppressing body weight gain or reducing the amount of the adipose tissue are associated with changes in blood sugar (blood glucose values) and lipid-related parameters (cholesterol values, triglyceride values).

As experimental animals, 7 week-old male c57BL/6J mice were purchased from Nippon Clea, and were housed in a cycle of 12 hours of the light period from 6 a.m. to 6 p.m. and 0.12 hours of the dark period from 6 p.m. to 6 a.m. the next morning and were allowed free access to a pellet food (Nippon Clea, CE-2), and kept at 22° C.

Into the abdominal cavity of the c57BL/6J mice, 10 nmol of recombinant mouse nesfatin-1 prepared in Working Example 16 dissolved in 100 μl of physiological saline was administered, and as the control sample physiological saline alone was used. Using a tuberculin syringe equipped with a 26G needle, 100 μl each of the sample was administered once into the abdominal cavity of each mouse (5 animals per group), and the time of administration was immediately before the start (6 p.m.) of the dark period.

Each mouse that received administration was placed in an individual cage, and during 0-3 hours after the administration the weight decreased of the pellet food was measured to determine the amount of food intake. Also, 3 hours after the administration each mouse was sacrificed by decapitation to collect whole blood, and serum was collected therefrom. For the serum, the contents of glucose, total cholesterol and triglyceride were measured using commercial reagents for determination (KYOWA MEDEX, Determiner L GLUII, Determiner L TCII, Determiner L TGII).

For testing of significant difference, analysis of variance was used.

<Result>

FIG. 33 is a graph of the assay result of the amount of food intake, glucose, total cholesterol and triglyceride in the blood when nesfatin-1 or physiological saline alone was intraperitoneally given to the mice.

Nesfatin-1 administration significantly reduced the amount of food intake as compared to the control group. In contrast, little difference was noted between the nesfatin-1-administration group and the control group in glucose content in the blood (glucose in the figure) which represents a blood sugar level, or lipid-related parameters such as total cholesterol content (cholesterol in the figure), triglyceride content (triglyceride in the figure).

The above result suggests that the effect of nesfatin-1 is to suppress food intake, suppress body weight gain and reduce the amount of the adipose tissue without causing changes in blood sugar levels and blood levels of lipid-related parameters.

In accordance with the present invention, a factor involved in food intake control and/or body weight control can be obtained by using a PPARγ agonist. Also by using nesfatin and/or nesfatin-1, diseases associated with metabolic and food intake disorders such as obesity or adiposis and nervous hyperphagia, and diseases associated with adiposis such as type 2 diabetes mellitus, impaired glucose tolerance, hypertension, hyperlipidemia, hyperuricemia, fatty liver, cardiac diseases, cerebral vascular diseases, sleep apnea syndrome, orthopedic diseases such as osteoarthritis, menstrual disorders and malignant tumors can be prevented or treated. Furthermore, by using a substance such as antibody that suppresses the activity of nesfatin or nesfatin-1, anorexia in post-surgery and/or cancer patients, and diseases associated with nutritional and feeding disorders such as cibophobia can be prevented or treated.

What is claimed is:

1. An isolated polypeptide consisting of the amino acid sequence of SEQ ID NO:13, or a fragment thereof having an activity of suppressing food intake or suppressing body weight gain.

2. An isolated polypeptide having an activity of suppressing food intake or suppressing body weight gain, wherein said polypeptide consists of an amino acid sequence at least 80% identical to SEQ ID NO: 13.

3. A pharmaceutical composition comprising the polypeptide according to claim 1 or 2, and a pharmaceutically acceptable carrier.

4. An isolated polypeptide having an activity of suppressing food intake or suppressing body weight gain, wherein said polypeptide comprises the amino acid sequence of SEQ ID NO: 13, with the proviso that said polypeptide is not NUCB2.

5. An isolated polypeptide having an activity of suppressing food intake or suppressing body weight gain, wherein said polypeptide comprises an amino acid sequence having at least 80% identity with the amino acid sequence of SEQ ID NO: 13, with the proviso that said polypeptide is not NUCB2.

6. An isolated polypeptide having an activity of suppressing food intake or suppressing body weight gain, wherein said polypeptide comprises the amino acid sequence of SEQ ID NO: 13, and wherein said polypeptide does not contain a prohormone convertase cleavage site.

7. An isolated polypeptide having an activity of suppressing food intake or suppressing body weight gain, wherein said polypeptide comprises an amino acid sequence having at least 80% identity with the amino acid sequence of SEQ ID NO: 13, and wherein said polypeptide does not contain a prohormone convertase cleavage site.

* * * * *

SEQUENCE LISTING

```
<160> NUMBER OF SEQ ID NOS: 124

<210> SEQ ID NO 1
<211> LENGTH: 1263
<212> TYPE: DNA
<213> ORGANISM: Homo sapiens
<220> FEATURE:
<221> NAME/KEY: CDS
<222> LOCATION: (1)..(1263)

<400> SEQUENCE: 1 atg agg tgg agg acc atc ctg cta cag tat tgc ttt ctc ttg att aca        48
Met Arg Trp Arg Thr Ile Leu Leu Gln Tyr Cys Phe Leu Leu Ile Thr
1               5                   10                  15 tgt tta ctt act gct ctt gaa gct gtg cct att gac ata gac aag aca        96
Cys Leu Leu Thr Ala Leu Glu Ala Val Pro Ile Asp Ile Asp Lys Thr
                20                  25                  30 aaa gta caa aat att cac cct gtg gaa agt gcg aag ata gaa cca cca       144
Lys Val Gln Asn Ile His Pro Val Glu Ser Ala Lys Ile Glu Pro Pro
            35                  40                  45 gat act gga ctt tat tat gat gaa tat ctc aag caa gtg att gat gtg       192
Asp Thr Gly Leu Tyr Tyr Asp Glu Tyr Leu Lys Gln Val Ile Asp Val
        50                  55                  60 ctg gaa aca gat aaa cac ttc aga gaa aag ctc cag aaa gca gac ata       240
Leu Glu Thr Asp Lys His Phe Arg Glu Lys Leu Gln Lys Ala Asp Ile
65                  70                  75                  80 gag gaa ata aag agt ggg agg cta agc aaa gaa ctg gat tta gta agt       288
Glu Glu Ile Lys Ser Gly Arg Leu Ser Lys Glu Leu Asp Leu Val Ser
                85                  90                  95
```

-continued

| | | |
|---|---|---|
| cac cat gtg agg aca aaa ctt gat gaa ctg aaa agg caa gaa gta gga<br>His His Val Arg Thr Lys Leu Asp Glu Leu Lys Arg Gln Glu Val Gly<br>              100                           105                      110 | 336 |
| agg tta aga atg tta att aaa gct aag ttg gat tcc ctt caa gat ata<br>Arg Leu Arg Met Leu Ile Lys Ala Lys Leu Asp Ser Leu Gln Asp Ile<br>             115                     120                     125 | 384 |
| ggc atg gac cac caa gct ctt cta aaa caa ttt gat cac cta aac cac<br>Gly Met Asp His Gln Ala Leu Leu Lys Gln Phe Asp His Leu Asn His<br>   130                     135                     140 | 432 |
| ctg aat cct gac aag ttt gaa tcc aca gat tta gat atg cta atc aaa<br>Leu Asn Pro Asp Lys Phe Glu Ser Thr Asp Leu Asp Met Leu Ile Lys<br>145                    150                     155                 160 | 480 |
| gcg gca aca agt gat ctg gaa cac tat gac aag act cgt cat gaa gaa<br>Ala Ala Thr Ser Asp Leu Glu His Tyr Asp Lys Thr Arg His Glu Glu<br>             165                     170                     175 | 528 |
| ttt aaa aaa tat gaa atg atg aag gaa cat gaa agg aga gaa tat tta<br>Phe Lys Lys Tyr Glu Met Met Lys Glu His Glu Arg Arg Glu Tyr Leu<br>                 180                     185                 190 | 576 |
| aaa aca ttg aat gaa gaa aag aga aaa gaa gaa gag tct aaa ttt gaa<br>Lys Thr Leu Asn Glu Glu Lys Arg Lys Glu Glu Glu Ser Lys Phe Glu<br>             195                     200                     205 | 624 |
| gaa atg aag aaa aag cat gaa aat cac cct aaa gtt aat cac cca gga<br>Glu Met Lys Lys Lys His Glu Asn His Pro Lys Val Asn His Pro Gly<br>210                    215                     220 | 672 |
| agc aaa gat caa cta aaa gag gta tgg gaa gag act gat gga ttg gat<br>Ser Lys Asp Gln Leu Lys Glu Val Trp Glu Glu Thr Asp Gly Leu Asp<br>225                    230                     235                 240 | 720 |
| cct aat gac ttt gac ccc aag aca ttt ttc aaa tta cat gat gtc aat<br>Pro Asn Asp Phe Asp Pro Lys Thr Phe Phe Lys Leu His Asp Val Asn<br>                   245                     250                 255 | 768 |
| agt gat gga ttc ctg gat gaa caa gaa tta gaa gcc cta ttt act aaa<br>Ser Asp Gly Phe Leu Asp Glu Gln Glu Leu Glu Ala Leu Phe Thr Lys<br>             260                     265                 270 | 816 |
| gag ttg gag aaa gta tat gac cct aaa aat gaa gag gat gat atg gta<br>Glu Leu Glu Lys Val Tyr Asp Pro Lys Asn Glu Glu Asp Asp Met Val<br>                 275                     280                 285 | 864 |
| gaa atg gaa gaa gaa agg ctt aga atg agg gaa cat gta atg aat gag<br>Glu Met Glu Glu Glu Arg Leu Arg Met Arg Glu His Val Met Asn Glu<br>   290                     295                     300 | 912 |
| gtt gat act aac aaa gac aga ttg gtg act ctg gag gag ttt ttg aaa<br>Val Asp Thr Asn Lys Asp Arg Leu Val Thr Leu Glu Glu Phe Leu Lys<br>305                    310                     315                 320 | 960 |
| gcc aca gaa aaa aaa gaa ttc ttg gag cca gat agc tgg gag aca tta<br>Ala Thr Glu Lys Lys Glu Phe Leu Glu Pro Asp Ser Trp Glu Thr Leu<br>             325                     330                 335 | 1008 |
| gat cag caa cag ttc ttc aca gag gaa gaa cta aaa gaa tat gaa aat<br>Asp Gln Gln Gln Phe Phe Thr Glu Glu Glu Leu Lys Glu Tyr Glu Asn<br>                 340                     345                 350 | 1056 |
| att att gct tta caa gaa aat gaa ctt aag aag aag gca gat gag ctt<br>Ile Ile Ala Leu Gln Glu Asn Glu Leu Lys Lys Lys Ala Asp Glu Leu<br>             355                     360                 365 | 1104 |
| cag aaa caa aaa gaa gag cta caa cgt cag cat gat caa ctg gag gct<br>Gln Lys Gln Lys Glu Glu Leu Gln Arg Gln His Asp Gln Leu Glu Ala<br>370                    375                     380 | 1152 |
| cag aag ctg gaa tat cat cag gtc ata cag cag atg gaa caa aaa aaa<br>Gln Lys Leu Glu Tyr His Gln Val Ile Gln Gln Met Glu Gln Lys Lys<br>385                    390                     395                 400 | 1200 |
| tta caa caa gga att cct cca tca ggg cca gct gga gaa ttg aag ttt<br>Leu Gln Gln Gly Ile Pro Pro Ser Gly Pro Ala Gly Glu Leu Lys Phe | 1248 |

```
                        405                 410                 415
gag cca cac att taa                                                       1263
Glu Pro His Ile
        420

<210> SEQ ID NO 2
<211> LENGTH: 420
<212> TYPE: PRT
<213> ORGANISM: Homo sapiens

<400> SEQUENCE: 2

Met Arg Trp Arg Thr Ile Leu Leu Gln Tyr Cys Phe Leu Leu Ile Thr
1               5                   10                  15

Cys Leu Leu Thr Ala Leu Glu Ala Val Pro Ile Asp Ile Asp Lys Thr
            20                  25                  30

Lys Val Gln Asn Ile His Pro Val Glu Ser Ala Lys Ile Glu Pro Pro
        35                  40                  45

Asp Thr Gly Leu Tyr Tyr Asp Glu Tyr Leu Lys Gln Val Ile Asp Val
    50                  55                  60

Leu Glu Thr Asp Lys His Phe Arg Glu Lys Leu Gln Lys Ala Asp Ile
65                  70                  75                  80

Glu Glu Ile Lys Ser Gly Arg Leu Ser Lys Glu Leu Asp Leu Val Ser
                85                  90                  95

His His Val Arg Thr Lys Leu Asp Glu Leu Lys Arg Gln Glu Val Gly
            100                 105                 110

Arg Leu Arg Met Leu Ile Lys Ala Lys Leu Asp Ser Leu Gln Asp Ile
        115                 120                 125

Gly Met Asp His Gln Ala Leu Leu Lys Gln Phe Asp His Leu Asn His
    130                 135                 140

Leu Asn Pro Asp Lys Phe Glu Ser Thr Asp Leu Asp Met Leu Ile Lys
145                 150                 155                 160

Ala Ala Thr Ser Asp Leu Glu His Tyr Asp Lys Thr Arg His Glu Glu
                165                 170                 175

Phe Lys Lys Tyr Glu Met Met Lys Glu His Glu Arg Arg Glu Tyr Leu
            180                 185                 190

Lys Thr Leu Asn Glu Glu Lys Arg Lys Glu Glu Ser Lys Phe Glu
        195                 200                 205

Glu Met Lys Lys Lys His Glu Asn His Pro Lys Val Asn His Pro Gly
    210                 215                 220

Ser Lys Asp Gln Leu Lys Glu Val Trp Glu Glu Thr Asp Gly Leu Asp
225                 230                 235                 240

Pro Asn Asp Phe Asp Pro Lys Thr Phe Phe Lys Leu His Asp Val Asn
                245                 250                 255

Ser Asp Gly Phe Leu Asp Glu Gln Glu Leu Glu Ala Leu Phe Thr Lys
            260                 265                 270

Glu Leu Glu Lys Val Tyr Asp Pro Lys Asn Glu Glu Asp Asp Met Val
        275                 280                 285

Glu Met Glu Glu Glu Arg Leu Arg Met Arg Glu His Val Met Asn Glu
    290                 295                 300

Val Asp Thr Asn Lys Asp Arg Leu Val Thr Leu Glu Glu Phe Leu Lys
305                 310                 315                 320

Ala Thr Glu Lys Lys Glu Phe Leu Glu Pro Asp Ser Trp Glu Thr Leu
                325                 330                 335

Asp Gln Gln Gln Phe Phe Thr Glu Glu Glu Leu Lys Glu Tyr Glu Asn
            340                 345                 350
```

-continued

Ile Ile Ala Leu Gln Glu Asn Glu Leu Lys Lys Lys Ala Asp Glu Leu
        355                 360                 365

Gln Lys Gln Lys Glu Glu Leu Gln Arg Gln His Asp Gln Leu Glu Ala
    370                 375                 380

Gln Lys Leu Glu Tyr His Gln Val Ile Gln Gln Met Glu Gln Lys Lys
385                 390                 395                 400

Leu Gln Gln Gly Ile Pro Pro Ser Gly Pro Ala Gly Glu Leu Lys Phe
                405                 410                 415

Glu Pro His Ile
            420

<210> SEQ ID NO 3
<211> LENGTH: 396
<212> TYPE: PRT
<213> ORGANISM: Homo sapiens
<220> FEATURE:
<221> NAME/KEY: mat_peptide
<222> LOCATION: (1)..(396)

<400> SEQUENCE: 3

Val Pro Ile Asp Ile Asp Lys Thr Lys Val Gln Asn Ile His Pro Val
1               5                   10                  15

Glu Ser Ala Lys Ile Glu Pro Pro Asp Thr Gly Leu Tyr Tyr Asp Glu
            20                  25                  30

Tyr Leu Lys Gln Val Ile Asp Val Leu Glu Thr Asp Lys His Phe Arg
        35                  40                  45

Glu Lys Leu Gln Lys Ala Asp Ile Glu Glu Ile Lys Ser Gly Arg Leu
    50                  55                  60

Ser Lys Glu Leu Asp Leu Val Ser His His Val Arg Thr Lys Leu Asp
65                  70                  75                  80

Glu Leu Lys Arg Gln Glu Val Gly Arg Leu Arg Met Leu Ile Lys Ala
            85                  90                  95

Lys Leu Asp Ser Leu Gln Asp Ile Gly Met Asp His Gln Ala Leu Leu
            100                 105                 110

Lys Gln Phe Asp His Leu Asn His Leu Asn Pro Asp Lys Phe Glu Ser
        115                 120                 125

Thr Asp Leu Asp Met Leu Ile Lys Ala Ala Thr Ser Asp Leu Glu His
    130                 135                 140

Tyr Asp Lys Thr Arg His Glu Glu Phe Lys Lys Tyr Glu Met Met Lys
145                 150                 155                 160

Glu His Glu Arg Arg Glu Tyr Leu Lys Thr Leu Asn Glu Glu Lys Arg
            165                 170                 175

Lys Glu Glu Glu Ser Lys Phe Glu Glu Met Lys Lys Lys His Glu Asn
            180                 185                 190

His Pro Lys Val Asn His Pro Gly Ser Lys Asp Gln Leu Lys Glu Val
        195                 200                 205

Trp Glu Glu Thr Asp Gly Leu Asp Pro Asn Asp Phe Asp Pro Lys Thr
    210                 215                 220

Phe Phe Lys Leu His Asp Val Asn Ser Asp Gly Phe Leu Asp Glu Gln
225                 230                 235                 240

Glu Leu Glu Ala Leu Phe Thr Lys Glu Leu Glu Lys Val Tyr Asp Pro
            245                 250                 255

Lys Asn Glu Glu Asp Asp Met Val Glu Met Glu Glu Glu Arg Leu Arg
            260                 265                 270

Met Arg Glu His Val Met Asn Glu Val Asp Thr Asn Lys Asp Arg Leu

```
                275                 280                 285
Val Thr Leu Glu Glu Phe Leu Lys Ala Thr Glu Lys Lys Glu Phe Leu
    290                 295                 300

Glu Pro Asp Ser Trp Glu Thr Leu Asp Gln Gln Gln Phe Phe Thr Glu
305                 310                 315                 320

Glu Glu Leu Lys Glu Tyr Glu Asn Ile Ile Ala Leu Gln Glu Asn Glu
                325                 330                 335

Leu Lys Lys Lys Ala Asp Glu Leu Gln Lys Gln Lys Glu Glu Leu Gln
                340                 345                 350

Arg Gln His Asp Gln Leu Glu Ala Gln Lys Leu Glu Tyr His Gln Val
                355                 360                 365

Ile Gln Gln Met Glu Gln Lys Lys Leu Gln Gln Gly Ile Pro Pro Ser
    370                 375                 380

Gly Pro Ala Gly Glu Leu Lys Phe Glu Pro His Ile
385                 390                 395

<210> SEQ ID NO 4
<211> LENGTH: 1263
<212> TYPE: DNA
<213> ORGANISM: Mus musculus
<220> FEATURE:
<221> NAME/KEY: CDS
<222> LOCATION: (1)..(1263)

<400> SEQUENCE: 4 atg agg tgg agg atc atc caa gta cag tac tgt ttt ctc ttg gtt ccg        48
Met Arg Trp Arg Ile Ile Gln Val Gln Tyr Cys Phe Leu Leu Val Pro
1               5                   10                  15 tgc acg ctg acc gct ctg gaa gct gtt cct atc gat gtg gac aag acc        96
Cys Thr Leu Thr Ala Leu Glu Ala Val Pro Ile Asp Val Asp Lys Thr
                20                  25                  30 aaa gta cac aac act gag cca gtg gaa aat gca agg ata gag cca cca       144
Lys Val His Asn Thr Glu Pro Val Glu Asn Ala Arg Ile Glu Pro Pro
            35                  40                  45 gat act gga ctt tat tat gat gaa tac ctc aag caa gtg att gaa gtc       192
Asp Thr Gly Leu Tyr Tyr Asp Glu Tyr Leu Lys Gln Val Ile Glu Val
        50                  55                  60 ttg gaa aca gat cca cat ttc aga gaa aag ctc cag aaa gca gac ata       240
Leu Glu Thr Asp Pro His Phe Arg Glu Lys Leu Gln Lys Ala Asp Ile
65                  70                  75                  80 gag gag ata agg agc ggg agg ctg agt caa gag ctg gac tta gta agt       288
Glu Glu Ile Arg Ser Gly Arg Leu Ser Gln Glu Leu Asp Leu Val Ser
                85                  90                  95 cac aaa gtg agg acg aga ctg gat gag ctg aag agg caa gaa gta gga       336
His Lys Val Arg Thr Arg Leu Asp Glu Leu Lys Arg Gln Glu Val Gly
            100                 105                 110 aga ctg cgg atg ctc atc aaa gct aag ctg gat gcc ctt caa gac act       384
Arg Leu Arg Met Leu Ile Lys Ala Lys Leu Asp Ala Leu Gln Asp Thr
        115                 120                 125 ggc atg aat cac cac ctt ctt ctg aag cag ttt gaa cac ctg aac cac       432
Gly Met Asn His His Leu Leu Leu Lys Gln Phe Glu His Leu Asn His
    130                 135                 140 cag aat cct aac aca ttt gaa tcc aga gat ttg gat atg cta atc aaa       480
Gln Asn Pro Asn Thr Phe Glu Ser Arg Asp Leu Asp Met Leu Ile Lys
145                 150                 155                 160 gca gct acc gcg gat ctg gag caa tat gac cgg act cgg cat gaa gag       528
Ala Ala Thr Ala Asp Leu Glu Gln Tyr Asp Arg Thr Arg His Glu Glu
                165                 170                 175 ttt aag aag tac gag atg atg aag gaa cac gag cgg aga gag tat tta       576
```

-continued

| | | |
|---|---|---|
| | Phe Lys Lys Tyr Glu Met Met Lys Glu His Glu Arg Arg Glu Tyr Leu<br>180                    185                    190 | |
| aaa acg ctg agt gag gag aag agg aaa gaa gaa gag tct aag ttt gaa<br>Lys Thr Leu Ser Glu Glu Lys Arg Lys Glu Glu Glu Ser Lys Phe Glu<br>        195                    200                    205 | | 624 |
| gag atg aag agg aag cac gaa gac cac ccc aaa gtt aat cat ccc gga<br>Glu Met Lys Arg Lys His Glu Asp His Pro Lys Val Asn His Pro Gly<br>210                    215                    220 | | 672 |
| agc aaa gat caa cta aaa gag gtt tgg gaa gag act gat gga ttg gac<br>Ser Lys Asp Gln Leu Lys Glu Val Trp Glu Glu Thr Asp Gly Leu Asp<br>225                    230                    235                    240 | | 720 |
| cct aat gac ttt gac ccc aag aca ttt ttc aaa tta cat gat gtt aac<br>Pro Asn Asp Phe Asp Pro Lys Thr Phe Phe Lys Leu His Asp Val Asn<br>                245                    250                    255 | | 768 |
| aac gat gga ttc ctg gat gaa caa gaa tta gaa gca cta ttc aca aga<br>Asn Asp Gly Phe Leu Asp Glu Gln Glu Leu Glu Ala Leu Phe Thr Arg<br>        260                    265                    270 | | 816 |
| gag ttg gag aaa gtg tat aac cca caa aat gca gag gac gat atg ata<br>Glu Leu Glu Lys Val Tyr Asn Pro Gln Asn Ala Glu Asp Asp Met Ile<br>275                    280                    285 | | 864 |
| gaa atg gaa gag gag agg ctc agg atg aga gaa cac gtc atg agt gag<br>Glu Met Glu Glu Glu Arg Leu Arg Met Arg Glu His Val Met Ser Glu<br>290                    295                    300 | | 912 |
| att gat aac aac aaa gac cga ttg gtg act ctg gag gaa ttc ctg aga<br>Ile Asp Asn Asn Lys Asp Arg Leu Val Thr Leu Glu Glu Phe Leu Arg<br>305                    310                    315                    320 | | 960 |
| gct aca gag aag aaa gaa ttc ctg gag cct gat agc tgg gag aca ctg<br>Ala Thr Glu Lys Lys Glu Phe Leu Glu Pro Asp Ser Trp Glu Thr Leu<br>                325                    330                    335 | | 1008 |
| gac cag caa cag tta ttc acc gag gac gag ctt aaa gag tat gaa agc<br>Asp Gln Gln Gln Leu Phe Thr Glu Asp Glu Leu Lys Glu Tyr Glu Ser<br>        340                    345                    350 | | 1056 |
| att att gct atc caa gag aac gag ctt aag aag agg gcg gaa gag ctg<br>Ile Ile Ala Ile Gln Glu Asn Glu Leu Lys Lys Arg Ala Glu Glu Leu<br>355                    360                    365 | | 1104 |
| cag aaa cag aag gag gat ctg cag cgg cag cac gac cac ctc gag gcg<br>Gln Lys Gln Lys Glu Asp Leu Gln Arg Gln His Asp His Leu Glu Ala<br>370                    375                    380 | | 1152 |
| cag aag cag gag tat cat cag gcc gtc cag cac ctg gaa cag aag aaa<br>Gln Lys Gln Glu Tyr His Gln Ala Val Gln His Leu Glu Gln Lys Lys<br>385                    390                    395                    400 | | 1200 |
| ctt caa caa ggc att gct cca tca ggg cca gcg gga gag ctg aag ttt<br>Leu Gln Gln Gly Ile Ala Pro Ser Gly Pro Ala Gly Glu Leu Lys Phe<br>                405                    410                    415 | | 1248 |
| gag cca cac aca taa<br>Glu Pro His Thr<br>        420 | | 1263 |

<210> SEQ ID NO 5
<211> LENGTH: 420
<212> TYPE: PRT
<213> ORGANISM: Mus musculus

<400> SEQUENCE: 5

Met Arg Trp Arg Ile Ile Gln Val Gln Tyr Cys Phe Leu Leu Val Pro
1               5                   10                  15

Cys Thr Leu Thr Ala Leu Glu Ala Val Pro Ile Asp Val Asp Lys Thr
            20                  25                  30

Lys Val His Asn Thr Glu Pro Val Glu Asn Ala Arg Ile Glu Pro Pro
        35                  40                  45

-continued

```
Asp Thr Gly Leu Tyr Tyr Asp Glu Tyr Leu Lys Gln Val Ile Glu Val
     50                  55                  60
Leu Glu Thr Asp Pro His Phe Arg Glu Lys Leu Gln Lys Ala Asp Ile
 65                  70                  75                  80
Glu Glu Ile Arg Ser Gly Arg Leu Ser Gln Glu Leu Asp Leu Val Ser
                 85                  90                  95
His Lys Val Arg Thr Arg Leu Asp Glu Leu Lys Arg Gln Glu Val Gly
                100                 105                 110
Arg Leu Arg Met Leu Ile Lys Ala Lys Leu Asp Ala Leu Gln Asp Thr
            115                 120                 125
Gly Met Asn His His Leu Leu Leu Lys Gln Phe Glu His Leu Asn His
130                 135                 140
Gln Asn Pro Asn Thr Phe Glu Ser Arg Asp Leu Asp Met Leu Ile Lys
145                 150                 155                 160
Ala Ala Thr Ala Asp Leu Glu Gln Tyr Asp Arg Thr Arg His Glu Glu
                165                 170                 175
Phe Lys Lys Tyr Glu Met Met Lys Glu His Glu Arg Arg Glu Tyr Leu
            180                 185                 190
Lys Thr Leu Ser Glu Glu Lys Arg Lys Glu Glu Ser Lys Phe Glu
            195                 200                 205
Glu Met Lys Arg Lys His Glu Asp His Pro Lys Val Asn His Pro Gly
210                 215                 220
Ser Lys Asp Gln Leu Lys Glu Val Trp Glu Glu Thr Asp Gly Leu Asp
225                 230                 235                 240
Pro Asn Asp Phe Asp Pro Lys Thr Phe Phe Lys Leu His Asp Val Asn
                245                 250                 255
Asn Asp Gly Phe Leu Asp Glu Gln Glu Leu Glu Ala Leu Phe Thr Arg
            260                 265                 270
Glu Leu Glu Lys Val Tyr Asn Pro Gln Asn Ala Glu Asp Asp Met Ile
            275                 280                 285
Glu Met Glu Glu Glu Arg Leu Arg Met Arg Glu His Val Met Ser Glu
290                 295                 300
Ile Asp Asn Asn Lys Asp Arg Leu Val Thr Leu Glu Glu Phe Leu Arg
305                 310                 315                 320
Ala Thr Glu Lys Lys Glu Phe Leu Glu Pro Asp Ser Trp Glu Thr Leu
                325                 330                 335
Asp Gln Gln Gln Leu Phe Thr Glu Asp Glu Leu Lys Glu Tyr Glu Ser
            340                 345                 350
Ile Ile Ala Ile Gln Glu Asn Glu Leu Lys Lys Arg Ala Glu Glu Leu
            355                 360                 365
Gln Lys Gln Lys Glu Asp Leu Gln Arg Gln His Asp His Leu Glu Ala
370                 375                 380
Gln Lys Gln Glu Tyr His Gln Ala Val Gln His Leu Glu Gln Lys Lys
385                 390                 395                 400
Leu Gln Gln Gly Ile Ala Pro Ser Gly Pro Ala Gly Glu Leu Lys Phe
                405                 410                 415
Glu Pro His Thr
            420

<210> SEQ ID NO 6
<211> LENGTH: 395
<212> TYPE: PRT
<213> ORGANISM: Mus musculus
<220> FEATURE:
```

```
<221> NAME/KEY: mat_peptide
<222> LOCATION: (1)..(395)

<400> SEQUENCE: 6

Pro Ile Asp Val Asp Lys Thr Lys Val His Asn Thr Glu Pro Val Glu
1               5                   10                  15

Asn Ala Arg Ile Glu Pro Pro Asp Thr Gly Leu Tyr Tyr Asp Glu Tyr
            20                  25                  30

Leu Lys Gln Val Ile Glu Val Leu Glu Thr Asp Pro His Phe Arg Glu
        35                  40                  45

Lys Leu Gln Lys Ala Asp Ile Glu Glu Ile Arg Ser Gly Arg Leu Ser
50                  55                  60

Gln Glu Leu Asp Leu Val Ser His Lys Val Arg Thr Arg Leu Asp Glu
65                  70                  75                  80

Leu Lys Arg Gln Glu Val Gly Arg Leu Arg Met Leu Ile Lys Ala Lys
                85                  90                  95

Leu Asp Ala Leu Gln Asp Thr Gly Met Asn His His Leu Leu Leu Lys
            100                 105                 110

Gln Phe Glu His Leu Asn His Gln Asn Pro Asn Thr Phe Glu Ser Arg
        115                 120                 125

Asp Leu Asp Met Leu Ile Lys Ala Ala Thr Ala Asp Leu Glu Gln Tyr
130                 135                 140

Asp Arg Thr Arg His Glu Glu Phe Lys Lys Tyr Glu Met Met Lys Glu
145                 150                 155                 160

His Glu Arg Arg Glu Tyr Leu Lys Thr Leu Ser Glu Glu Lys Arg Lys
                165                 170                 175

Glu Glu Glu Ser Lys Phe Glu Glu Met Lys Arg Lys His Glu Asp His
            180                 185                 190

Pro Lys Val Asn His Pro Gly Ser Lys Asp Gln Leu Lys Glu Val Trp
        195                 200                 205

Glu Glu Thr Asp Gly Leu Asp Pro Asn Asp Phe Asp Pro Lys Thr Phe
210                 215                 220

Phe Lys Leu His Asp Val Asn Asn Asp Gly Phe Leu Asp Glu Gln Glu
225                 230                 235                 240

Leu Glu Ala Leu Phe Thr Arg Glu Leu Glu Lys Val Tyr Asn Pro Gln
                245                 250                 255

Asn Ala Glu Asp Asp Met Ile Glu Met Glu Glu Arg Leu Arg Met
            260                 265                 270

Arg Glu His Val Met Ser Glu Ile Asp Asn Asn Lys Asp Arg Leu Val
        275                 280                 285

Thr Leu Glu Glu Phe Leu Arg Ala Thr Glu Lys Lys Glu Phe Leu Glu
290                 295                 300

Pro Asp Ser Trp Glu Thr Leu Asp Gln Gln Gln Leu Phe Thr Glu Asp
305                 310                 315                 320

Glu Leu Lys Glu Tyr Glu Ser Ile Ile Ala Ile Gln Glu Asn Glu Leu
                325                 330                 335

Lys Lys Arg Ala Glu Glu Leu Gln Lys Gln Glu Asp Leu Gln Arg
            340                 345                 350

Gln His Asp His Leu Glu Ala Gln Lys Gln Glu Tyr His Gln Ala Val
        355                 360                 365

Gln His Leu Glu Gln Lys Lys Leu Gln Gln Gly Ile Ala Pro Ser Gly
370                 375                 380

Pro Ala Gly Glu Leu Lys Phe Glu Pro His Thr
385                 390                 395
```

<210> SEQ ID NO 7
<211> LENGTH: 1263
<212> TYPE: DNA
<213> ORGANISM: Rattus norvegicus
<220> FEATURE:
<221> NAME/KEY: CDS
<222> LOCATION: (1)..(1263)

<400> SEQUENCE: 7

| | | | | | | | | | | | | | | | | |
|---|---|---|---|---|---|---|---|---|---|---|---|---|---|---|---|---|
| atg | agg | tgg | agg | acc | atc | caa | gca | cgg | tac | tgt | ttt | ctc | ttg | gtt | ccg | 48 |
| Met | Arg | Trp | Arg | Thr | Ile | Gln | Ala | Arg | Tyr | Cys | Phe | Leu | Leu | Val | Pro | |
| 1 | | | | 5 | | | | | 10 | | | | | 15 | | |
| tgc | gtg | ctc | act | gcg | ctg | gaa | gct | gtt | cct | att | gat | gtg | gac | aag | acc | 96 |
| Cys | Val | Leu | Thr | Ala | Leu | Glu | Ala | Val | Pro | Ile | Asp | Val | Asp | Lys | Thr | |
| | | | 20 | | | | | 25 | | | | | 30 | | | |
| aaa | gtg | cac | aac | gtc | gag | ccg | gtg | gaa | agt | gca | agg | ata | gaa | ccg | cca | 144 |
| Lys | Val | His | Asn | Val | Glu | Pro | Val | Glu | Ser | Ala | Arg | Ile | Glu | Pro | Pro | |
| | | 35 | | | | | 40 | | | | | 45 | | | | |
| gac | acg | gga | ctt | tat | tat | gat | gaa | tac | ctc | aag | caa | gtg | att | gaa | gtc | 192 |
| Asp | Thr | Gly | Leu | Tyr | Tyr | Asp | Glu | Tyr | Leu | Lys | Gln | Val | Ile | Glu | Val | |
| | 50 | | | | | 55 | | | | | 60 | | | | | |
| ttg | gaa | aca | gat | ccg | cat | ttc | aga | gaa | aag | ctc | cag | aaa | gca | gac | ata | 240 |
| Leu | Glu | Thr | Asp | Pro | His | Phe | Arg | Glu | Lys | Leu | Gln | Lys | Ala | Asp | Ile | |
| 65 | | | | | 70 | | | | | 75 | | | | | 80 | |
| gag | gag | ata | agg | agc | ggg | agg | ctg | agt | caa | gag | ctg | gac | tta | gta | agt | 288 |
| Glu | Glu | Ile | Arg | Ser | Gly | Arg | Leu | Ser | Gln | Glu | Leu | Asp | Leu | Val | Ser | |
| | | | 85 | | | | | 90 | | | | | 95 | | | |
| cac | aaa | gtg | agg | acg | aga | ctg | gat | gaa | ctg | aag | agg | caa | gaa | gta | gga | 336 |
| His | Lys | Val | Arg | Thr | Arg | Leu | Asp | Glu | Leu | Lys | Arg | Gln | Glu | Val | Gly | |
| | | 100 | | | | | 105 | | | | | 110 | | | | |
| aga | ctg | aga | atg | ctc | atc | aaa | gcc | aag | ctg | gat | gcc | ctt | caa | gac | act | 384 |
| Arg | Leu | Arg | Met | Leu | Ile | Lys | Ala | Lys | Leu | Asp | Ala | Leu | Gln | Asp | Thr | |
| | 115 | | | | | 120 | | | | | 125 | | | | | |
| ggc | atg | aat | cac | cac | ctt | ctt | ctt | aag | cag | ttt | gaa | cac | ctg | aac | cac | 432 |
| Gly | Met | Asn | His | His | Leu | Leu | Leu | Lys | Gln | Phe | Glu | His | Leu | Asn | His | |
| 130 | | | | | 135 | | | | | 140 | | | | | | |
| cag | aat | cct | gac | aca | ttt | gaa | tcc | aaa | gac | ttg | gat | atg | cta | atc | aag | 480 |
| Gln | Asn | Pro | Asp | Thr | Phe | Glu | Ser | Lys | Asp | Leu | Asp | Met | Leu | Ile | Lys | |
| 145 | | | | | 150 | | | | | 155 | | | | | 160 | |
| gcg | gcc | acc | gcg | gat | ctg | gag | cag | tat | gac | cgg | act | cgg | cat | gag | gag | 528 |
| Ala | Ala | Thr | Ala | Asp | Leu | Glu | Gln | Tyr | Asp | Arg | Thr | Arg | His | Glu | Glu | |
| | | | 165 | | | | | 170 | | | | | 175 | | | |
| ttt | aag | aag | tat | gag | atg | atg | aag | gaa | cat | gaa | cgc | aga | gaa | tat | tta | 576 |
| Phe | Lys | Lys | Tyr | Glu | Met | Met | Lys | Glu | His | Glu | Arg | Arg | Glu | Tyr | Leu | |
| | | | 180 | | | | | 185 | | | | | 190 | | | |
| aaa | acg | ctg | agt | gag | gag | aag | agg | aaa | gag | gaa | gaa | gcc | aag | ttt | gca | 624 |
| Lys | Thr | Leu | Ser | Glu | Glu | Lys | Arg | Lys | Glu | Glu | Glu | Ala | Lys | Phe | Ala | |
| | | 195 | | | | | 200 | | | | | 205 | | | | |
| gag | atg | aag | agg | aag | cat | gaa | gac | cac | ccc | aaa | gtt | aat | cac | ccc | gga | 672 |
| Glu | Met | Lys | Arg | Lys | His | Glu | Asp | His | Pro | Lys | Val | Asn | His | Pro | Gly | |
| | 210 | | | | | 215 | | | | | 220 | | | | | |
| agc | aaa | gat | caa | cta | aaa | gag | gtt | tgg | gaa | gag | act | gat | gga | ttg | gac | 720 |
| Ser | Lys | Asp | Gln | Leu | Lys | Glu | Val | Trp | Glu | Glu | Thr | Asp | Gly | Leu | Asp | |
| 225 | | | | | 230 | | | | | 235 | | | | | 240 | |
| cct | aat | gac | ttt | gac | ccc | aag | aca | ttt | ttc | aaa | tta | cat | gat | gtt | aac | 768 |
| Pro | Asn | Asp | Phe | Asp | Pro | Lys | Thr | Phe | Phe | Lys | Leu | His | Asp | Val | Asn | |
| | | | 245 | | | | | 250 | | | | | 255 | | | |
| aac | gat | gga | ttc | ctg | gat | gaa | caa | gaa | ttg | gaa | gca | ctg | ttc | aca | aaa | 816 |
| Asn | Asp | Gly | Phe | Leu | Asp | Glu | Gln | Glu | Leu | Glu | Ala | Leu | Phe | Thr | Lys | |
| | | 260 | | | | | 265 | | | | | 270 | | | | |

-continued

```
gag ttg gac aaa gtg tat aac ccg cag aat gca gag gat gat atg ata         864
Glu Leu Asp Lys Val Tyr Asn Pro Gln Asn Ala Glu Asp Asp Met Ile
        275                 280                 285 gaa atg gaa gag gag agg ctc agg atg aga gag cac gtc atg aat gag         912
Glu Met Glu Glu Glu Arg Leu Arg Met Arg Glu His Val Met Asn Glu
    290                 295                 300 att gat aac aac aaa gac cga ttg gtg act ctg gag gaa ttc ttg aga         960
Ile Asp Asn Asn Lys Asp Arg Leu Val Thr Leu Glu Glu Phe Leu Arg
305                 310                 315                 320 gcc aca gag aag aaa gaa ttc ttg gag ccc gat agc tgg gag aca ctg        1008
Ala Thr Glu Lys Lys Glu Phe Leu Glu Pro Asp Ser Trp Glu Thr Leu
                325                 330                 335 gac cag cag cag tta ttc acc gag gaa gag ctc aaa gag tat gaa agt        1056
Asp Gln Gln Gln Leu Phe Thr Glu Glu Glu Leu Lys Glu Tyr Glu Ser
            340                 345                 350 atc att gct atc caa gag agt gaa ctt aag aag aag gca gat gaa ctg        1104
Ile Ile Ala Ile Gln Glu Ser Glu Leu Lys Lys Lys Ala Asp Glu Leu
        355                 360                 365 cag aag cag aag gag gag ctg cag cgc cag cac gac cac ctt gag gcc        1152
Gln Lys Gln Lys Glu Glu Leu Gln Arg Gln His Asp His Leu Glu Ala
    370                 375                 380 cag aag cag gag tat cag cag gct gta cag cag ctg gaa cag aag aaa        1200
Gln Lys Gln Glu Tyr Gln Gln Ala Val Gln Gln Leu Glu Gln Lys Lys
385                 390                 395                 400 ttc caa caa ggg att gct cca tca ggg ccg gca gga gag ctg aag ttt        1248
Phe Gln Gln Gly Ile Ala Pro Ser Gly Pro Ala Gly Glu Leu Lys Phe
                405                 410                 415 gag cca cac aca taa                                                    1263
Glu Pro His Thr
            420

<210> SEQ ID NO 8
<211> LENGTH: 420
<212> TYPE: PRT
<213> ORGANISM: Rattus norvegicus

<400> SEQUENCE: 8

Met Arg Trp Arg Thr Ile Gln Ala Arg Tyr Cys Phe Leu Leu Val Pro
1               5                   10                  15

Cys Val Leu Thr Ala Leu Glu Ala Val Pro Ile Asp Val Asp Lys Thr
            20                  25                  30

Lys Val His Asn Val Glu Pro Val Glu Ser Ala Arg Ile Glu Pro Pro
        35                  40                  45

Asp Thr Gly Leu Tyr Tyr Asp Glu Tyr Leu Lys Gln Val Ile Glu Val
    50                  55                  60

Leu Glu Thr Asp Pro His Phe Arg Glu Lys Leu Gln Lys Ala Asp Ile
65                  70                  75                  80

Glu Glu Ile Arg Ser Gly Arg Leu Ser Gln Glu Leu Asp Leu Val Ser
                85                  90                  95

His Lys Val Arg Thr Arg Leu Asp Glu Leu Lys Arg Gln Glu Val Gly
            100                 105                 110

Arg Leu Arg Met Leu Ile Lys Ala Lys Leu Asp Ala Leu Gln Asp Thr
        115                 120                 125

Gly Met Asn His His Leu Leu Lys Gln Phe Glu His Leu Asn His
    130                 135                 140

Gln Asn Pro Asp Thr Phe Glu Ser Lys Asp Leu Asp Met Leu Ile Lys
145                 150                 155                 160
```

```
Ala Ala Thr Ala Asp Leu Glu Gln Tyr Asp Arg Thr Arg His Glu Glu
            165                 170                 175

Phe Lys Lys Tyr Glu Met Met Lys Glu His Glu Arg Arg Glu Tyr Leu
            180                 185                 190

Lys Thr Leu Ser Glu Lys Arg Lys Glu Glu Ala Lys Phe Ala
        195                 200                 205

Glu Met Lys Arg Lys His Glu Asp His Pro Lys Val Asn His Pro Gly
            210                 215                 220

Ser Lys Asp Gln Leu Lys Glu Val Trp Glu Thr Asp Gly Leu Asp
225                 230                 235                 240

Pro Asn Asp Phe Asp Pro Lys Thr Phe Phe Lys Leu His Asp Val Asn
                245                 250                 255

Asn Asp Gly Phe Leu Asp Glu Gln Glu Leu Glu Ala Leu Phe Thr Lys
                260                 265                 270

Glu Leu Asp Lys Val Tyr Asn Pro Gln Asn Ala Glu Asp Met Ile
            275                 280                 285

Glu Met Glu Glu Glu Arg Leu Arg Met Arg Glu His Val Met Asn Glu
            290                 295                 300

Ile Asp Asn Asn Lys Asp Arg Leu Val Thr Leu Glu Glu Phe Leu Arg
305                 310                 315                 320

Ala Thr Glu Lys Lys Glu Phe Leu Glu Pro Asp Ser Trp Glu Thr Leu
                325                 330                 335

Asp Gln Gln Gln Leu Phe Thr Glu Glu Leu Lys Glu Tyr Glu Ser
            340                 345                 350

Ile Ile Ala Ile Gln Glu Ser Glu Leu Lys Lys Ala Asp Glu Leu
        355                 360                 365

Gln Lys Gln Lys Glu Glu Leu Gln Arg Gln His Asp His Leu Glu Ala
370                 375                 380

Gln Lys Gln Glu Tyr Gln Gln Ala Val Gln Leu Glu Gln Lys Lys
385                 390                 395                 400

Phe Gln Gln Gly Ile Ala Pro Ser Gly Pro Ala Gly Glu Leu Lys Phe
                405                 410                 415

Glu Pro His Thr
            420

<210> SEQ ID NO 9
<211> LENGTH: 396
<212> TYPE: PRT
<213> ORGANISM: Rattus norvegicus
<220> FEATURE:
<221> NAME/KEY: mat_peptide
<222> LOCATION: (1)..(396)

<400> SEQUENCE: 9

Val Pro Ile Asp Val Asp Lys Thr Lys Val His Asn Val Glu Pro Val
1               5                   10                  15

Glu Ser Ala Arg Ile Glu Pro Pro Asp Thr Gly Leu Tyr Tyr Asp Glu
            20                  25                  30

Tyr Leu Lys Gln Val Ile Glu Val Leu Glu Thr Asp Pro His Phe Arg
        35                  40                  45

Glu Lys Leu Gln Lys Ala Asp Ile Glu Glu Ile Arg Ser Gly Arg Leu
    50                  55                  60

Ser Gln Glu Leu Asp Leu Val Ser His Lys Val Arg Thr Arg Leu Asp
65                  70                  75                  80

Glu Leu Lys Arg Gln Glu Val Gly Arg Leu Arg Met Leu Ile Lys Ala
                85                  90                  95
```

```
Lys Leu Asp Ala Leu Gln Asp Thr Gly Met Asn His Leu Leu Leu
            100                 105                 110

Lys Gln Phe Glu His Leu Asn His Gln Asn Pro Asp Thr Phe Glu Ser
        115                 120                 125

Lys Asp Leu Asp Met Leu Ile Lys Ala Ala Thr Ala Asp Leu Glu Gln
    130                 135                 140

Tyr Asp Arg Thr Arg His Glu Glu Phe Lys Lys Tyr Glu Met Met Lys
145                 150                 155                 160

Glu His Glu Arg Arg Glu Tyr Leu Lys Thr Leu Ser Glu Glu Lys Arg
                165                 170                 175

Lys Glu Glu Glu Ala Lys Phe Ala Glu Met Lys Arg Lys His Glu Asp
            180                 185                 190

His Pro Lys Val Asn His Pro Gly Ser Lys Asp Gln Leu Lys Glu Val
        195                 200                 205

Trp Glu Glu Thr Asp Gly Leu Asp Pro Asn Asp Phe Asp Pro Lys Thr
    210                 215                 220

Phe Phe Lys Leu His Asp Val Asn Asn Asp Gly Phe Leu Asp Glu Gln
225                 230                 235                 240

Glu Leu Glu Ala Leu Phe Thr Lys Glu Leu Asp Lys Val Tyr Asn Pro
                245                 250                 255

Gln Asn Ala Glu Asp Asp Met Ile Glu Met Glu Glu Arg Leu Arg
            260                 265                 270

Met Arg Glu His Val Met Asn Glu Ile Asp Asn Asn Lys Asp Arg Leu
    275                 280                 285

Val Thr Leu Glu Glu Phe Leu Arg Ala Thr Glu Lys Lys Glu Phe Leu
290                 295                 300

Glu Pro Asp Ser Trp Glu Thr Leu Asp Gln Gln Gln Leu Phe Thr Glu
305                 310                 315                 320

Glu Glu Leu Lys Glu Tyr Glu Ser Ile Ile Ala Ile Gln Glu Ser Glu
                325                 330                 335

Leu Lys Lys Lys Ala Asp Glu Leu Gln Lys Gln Lys Glu Glu Leu Gln
            340                 345                 350

Arg Gln His Asp His Leu Glu Ala Gln Lys Gln Glu Tyr Gln Gln Ala
        355                 360                 365

Val Gln Gln Leu Glu Gln Lys Lys Phe Gln Gln Gly Ile Ala Pro Ser
    370                 375                 380

Gly Pro Ala Gly Glu Leu Lys Phe Glu Pro His Thr
385                 390                 395

<210> SEQ ID NO 10
<211> LENGTH: 1188
<212> TYPE: DNA
<213> ORGANISM: Homo sapiens
<220> FEATURE:
<221> NAME/KEY: gene
<222> LOCATION: (1)..(1188)

<400> SEQUENCE: 10
cctattgaca tagacaagac aaaagtacaa aatattcacc ctgtggaaag tgcgaagata      60
gaaccaccag atactggact ttattatgat gaatatctca agcaagtgat tgatgtgctg     120
gaaacagata acacttcag agaaaagctc cagaaagcag acatagagga aataaagagt      180
gggaggctaa gcaaagaact ggatttagta agtcaccatg tgaggacaaa acttgatgaa     240
ctgaaaaggc aagaagtagg aaggttaaga atgttaatta agctaagtt ggattccctt     300
```

```
caagatatag gcatggacca ccaagctctt ctaaaacaat tgatcacct aaaccacctg      360 aatcctgaca agtttgaatc cacagattta gatatgctaa tcaaagcggc aacaagtgat      420
ctggaacact atgacaagac tcgtcatgaa gaatttaaaa aatatgaaat gatgaaggaa      480
catgaaagga gagaatattt aaaaacattg aatgaagaaa agagaaaaga agaagagtct      540
aaatttgaag aaatgaagaa aaagcatgaa aatcacccta agttaatca cccaggaagc      600 aaagatcaac taaaagaggt atgggaagag actgatggat tggatcctaa tgactttgac      660
cccaagacat ttttcaaatt acatgatgtc aatagtgatg gattcctgga tgaacaagaa      720
ttagaagccc tatttactaa agagttggag aaagtatatg accctaaaaa tgaagaggat      780
gatatggtag aaatggaaga agaaaggctt agaatgaggg aacatgtaat gaatgaggtt      840
gatactaaca agacagatt ggtgactctg gaggagtttt tgaaagccac agaaaaaaaa      900
gaattcttgg agccagatag ctgggagaca ttagatcagc aacagttctt cacagaggaa      960
gaactaaaag aatatgaaaa tattattgct ttacaagaaa atgaacttaa gaagaaggca     1020
gatgagcttc agaaacaaaa agaagagcta caacgtcagc atgatcaact ggaggctcag     1080
aagctggaat atcatcaggt catacagcag atggaacaaa aaaaattaca acaaggaatt     1140
cctccatcag ggccagctgg agaattgaag tttgagccac acatttaa              1188

<210> SEQ ID NO 11
<211> LENGTH: 1191
<212> TYPE: DNA
<213> ORGANISM: Mus musculus
<220> FEATURE:
<221> NAME/KEY: gene
<222> LOCATION: (1)..(1191)

<400> SEQUENCE: 11
gttcctatcg atgtggacaa gaccaaagta cacaacactg agccagtgga aaatgcaagg       60
atagagccac cagatactgg actttattat gatgaatacc tcaagcaagt gattgaagtc      120
ttggaaacag atccacattt cagagaaaag ctccagaaag cagacataga ggagataagg      180
agcgggaggc tgagtcaaga gctggactta gtaagtcaca aagtgaggac gagactggat      240
gagctgaaga ggcaagaagt aggaagactg cggatgctca tcaaagctaa gctggatgcc      300
cttcaagaca ctggcatgaa tcaccacctt cttctgaagc agtttgaaca cctgaaccac      360
cagaatccta acacatttga atccagagat ttggatatgc taatcaaagc agctaccgcg      420
gatctggagc aatatgaccg gactcggcat gaagagttta agaagtacga gatgatgaag      480
gaacacgagc ggagagagta tttaaaaacg ctgagtgagg agaagaggaa agaagaagag      540
tctaagtttg aagagatgaa gaggaagcac gaagaccacc ccaaagttaa tcatcccgga      600
agcaaagatc aactaaaaga ggtttgggaa gagactgatg gattggaccc taatgacttt      660
gaccccaaga cattttttcaa attacatgat gttaacaacg atggattcct ggatgaacaa      720
gaattagaag cactattcac aagagagttg gagaaagtgt ataaccccaca aaatgcagag      780 gacgatatga tagaaatgga gaggagagg ctcaggatga gagaacacgt catgagtgag      840
attgataaca acaaagaccg attggtgact ctggaggaat tcctgagagc tacagagaag      900
aaagaattcc tggagcctga tagctgggag acactggacc agcaacagtt attcaccgag      960
gacgagctta agagtatga aagcattatt gctatccaag agaacgagct taagaagagg     1020
gcggaagagc tgcagaaaca gaaggaggat ctgcagcggc agcacgacca cctcgaggcg     1080
cagaagcagg agtatcatca ggccgtccag cacctggaac agaagaaact tcaacaaggc     1140
```
attgctccat cagggccagc gggagagctg aagtttgagc cacacacata a        1191

<210> SEQ ID NO 12
<211> LENGTH: 1191
<212> TYPE: DNA
<213> ORGANISM: Rattus norvegicus
<220> FEATURE:
<221> NAME/KEY: gene
<222> LOCATION: (1)..(1191)

<400> SEQUENCE: 12
gttcctattg atgtggacaa gaccaaagtg cacaacgtcg agccggtgga aagtgcaagg        60
atagaaccgc cagacacggg actttattat gatgaatacc tcaagcaagt gattgaagtc       120
ttggaaacag atccgcattt cagagaaaag ctccagaaag cagacataga ggagataagg       180
agcgggaggc tgagtcaaga gctggactta gtaagtcaca aagtgaggac gagactggat       240
gaactgaaga ggcaagaagt aggaagactg agaatgctca tcaaagccaa gctggatgcc       300
cttcaagaca ctggcatgaa tcaccacctt cttcttaagc agtttgaaca cctgaaccac       360
cagaatcctg acacatttga atccaaagac ttggatatgc taatcaaggc ggccaccgcg       420
gatctggagc agtatgaccg gactcggcat gaggagttta agaagtatga gatgatgaag       480
gaacatgaac gcagagaata tttaaaaacg ctgagtgagg agaagaggaa agaggaagaa       540
gccaagtttg cagagatgaa gaggaagcat gaagaccacc ccaaagttaa tcaccccgga       600
agcaaagatc aactaaaaga ggtttgggaa gagactgatg gattggaccc taatgacttt       660
gaccccaaga cattttttcaa attacatgat gttaacaacg atggattcct ggatgaacaa       720
gaattggaag cactgttcac aaaagagttg gacaaagtgt ataacccgca gaatgcagag       780
gatgatatga tagaaatgga agaggagagg ctcaggatga gagagcacgt catgaatgag       840
attgataaca acaaagaccg attggtgact ctggaggaat tcttgagagc cacagagaag       900
aaagaattct tggagcccga tagctgggag acactggacc agcagcagtt attcaccgag       960
gaagagctca agagtatga aagtatcatt gctatccaag agagtgaact taagaagaag      1020
gcagatgaac tgcagaagca gaaggaggag ctgcagcgcc agcacgacca ccttgaggcc      1080
cagaagcagg agtatcagca ggctgtacag cagctggaac agaagaaatt ccaacaaggg      1140
attgctccat cagggccggc aggagagctg aagtttgagc cacacacata a              1191

<210> SEQ ID NO 13
<211> LENGTH: 82
<212> TYPE: PRT
<213> ORGANISM: Homo sapiens
<220> FEATURE:
<221> NAME/KEY: PEPTIDE
<222> LOCATION: (1)..(82)

<400> SEQUENCE: 13

Val Pro Ile Asp Ile Asp Lys Thr Lys Val Gln Asn Ile His Pro Val
1               5                   10                  15

Glu Ser Ala Lys Ile Glu Pro Pro Asp Thr Gly Leu Tyr Tyr Asp Glu
            20                  25                  30

Tyr Leu Lys Gln Val Ile Asp Val Leu Glu Thr Asp Lys His Phe Arg
        35                  40                  45

Glu Lys Leu Gln Lys Ala Asp Ile Glu Glu Ile Lys Ser Gly Arg Leu
    50                  55                  60

Ser Lys Glu Leu Asp Leu Val Ser His His Val Arg Thr Lys Leu Asp
65                  70                  75                  80

Glu Leu

<210> SEQ ID NO 14
<211> LENGTH: 82
<212> TYPE: PRT
<213> ORGANISM: Mus musculus
<220> FEATURE:
<221> NAME/KEY: PEPTIDE
<222> LOCATION: (1)..(82)

<400> SEQUENCE: 14

Val Pro Ile Asp Val Asp Lys Thr Lys Val His Asn Thr Glu Pro Val
1               5                   10                  15

Glu Asn Ala Arg Ile Glu Pro Pro Asp Thr Gly Leu Tyr Tyr Asp Glu
            20                  25                  30

Tyr Leu Lys Gln Val Ile Glu Val Leu Glu Thr Asp Pro His Phe Arg
        35                  40                  45

Glu Lys Leu Gln Lys Ala Asp Ile Glu Glu Ile Arg Ser Gly Arg Leu
    50                  55                  60

Ser Gln Glu Leu Asp Leu Val Ser His Lys Val Arg Thr Arg Leu Asp
65                  70                  75                  80

Glu Leu

<210> SEQ ID NO 15
<211> LENGTH: 82
<212> TYPE: PRT
<213> ORGANISM: Rattus norvegicus
<220> FEATURE:
<221> NAME/KEY: PEPTIDE
<222> LOCATION: (1)..(82)

<400> SEQUENCE: 15

Val Pro Ile Asp Val Asp Lys Thr Lys Val His Asn Val Glu Pro Val
1               5                   10                  15

Glu Ser Ala Arg Ile Glu Pro Pro Asp Thr Gly Leu Tyr Tyr Asp Glu
            20                  25                  30

Tyr Leu Lys Gln Val Ile Glu Val Leu Glu Thr Asp Pro His Phe Arg
        35                  40                  45

Glu Lys Leu Gln Lys Ala Asp Ile Glu Glu Ile Arg Ser Gly Arg Leu
    50                  55                  60

Ser Gln Glu Leu Asp Leu Val Ser His Lys Val Arg Thr Arg Leu Asp
65                  70                  75                  80

Glu Leu

<210> SEQ ID NO 16
<211> LENGTH: 79
<212> TYPE: PRT
<213> ORGANISM: Rattus norvegicus
<220> FEATURE:
<221> NAME/KEY: PEPTIDE
<222> LOCATION: (1)..(79)

<400> SEQUENCE: 16

Gln Glu Val Gly Arg Leu Arg Met Leu Ile Lys Ala Lys Leu Asp Ala
1               5                   10                  15

Leu Gln Asp Thr Gly Met Asn His His Leu Leu Lys Gln Phe Glu
            20                  25                  30

His Leu Asn His Gln Asn Pro Asp Thr Phe Glu Ser Lys Asp Leu Asp
        35                  40                  45

Met Leu Ile Lys Ala Ala Thr Ala Asp Leu Glu Gln Tyr Asp Arg Thr

```
                      50                  55                  60
Arg His Glu Glu Phe Lys Lys Tyr Glu Met Met Lys Glu His Glu
65                  70                  75

<210> SEQ ID NO 17
<211> LENGTH: 231
<212> TYPE: PRT
<213> ORGANISM: Rattus norvegicus
<220> FEATURE:
<221> NAME/KEY: PEPTIDE
<222> LOCATION: (1)..(231)

<400> SEQUENCE: 17

Glu Tyr Leu Lys Thr Leu Ser Glu Glu Lys Arg Lys Glu Glu Ala
1               5                   10                  15

Lys Phe Ala Glu Met Lys Arg Lys His Glu Asp His Pro Lys Val Asn
                20                  25                  30

His Pro Gly Ser Lys Asp Gln Leu Lys Glu Val Trp Glu Thr Asp
            35                  40                  45

Gly Leu Asp Pro Asn Asp Phe Asp Pro Lys Thr Phe Phe Lys Leu His
    50                  55                  60

Asp Val Asn Asn Asp Gly Phe Leu Asp Glu Gln Glu Leu Glu Ala Leu
65                  70                  75                  80

Phe Thr Lys Glu Leu Asp Lys Val Tyr Asn Pro Gln Asn Ala Glu Asp
                85                  90                  95

Asp Met Ile Glu Met Glu Glu Glu Arg Leu Arg Met Arg Glu His Val
            100                 105                 110

Met Asn Glu Ile Asp Asn Asn Lys Asp Arg Leu Val Thr Leu Glu Glu
        115                 120                 125

Phe Leu Arg Ala Thr Glu Lys Lys Glu Phe Leu Glu Pro Asp Ser Trp
    130                 135                 140

Glu Thr Leu Asp Gln Gln Gln Leu Phe Thr Glu Glu Glu Leu Lys Glu
145                 150                 155                 160

Tyr Glu Ser Ile Ile Ala Ile Gln Glu Ser Glu Leu Lys Lys Lys Ala
                165                 170                 175

Asp Glu Leu Gln Lys Gln Lys Glu Glu Leu Gln Arg Gln His Asp His
            180                 185                 190

Leu Glu Ala Gln Lys Gln Glu Tyr Gln Gln Ala Val Gln Gln Leu Glu
        195                 200                 205

Gln Lys Lys Phe Gln Gln Gly Ile Ala Pro Ser Gly Pro Ala Gly Glu
    210                 215                 220

Leu Lys Phe Glu Pro His Thr
225                 230

<210> SEQ ID NO 18
<211> LENGTH: 246
<212> TYPE: DNA
<213> ORGANISM: Homo sapiens
<220> FEATURE:
<221> NAME/KEY: gene
<222> LOCATION: (1)..(246)

<400> SEQUENCE: 18
gtgcctattg acatagacaa gacaaaagta caaatatttc accctgtgga aagtgcgaag      60
atagaaccac cagatactgg acttttattat gatgaatatc tcaagcaagt gattgatgtg    120
ctggaaacag ataaacactt cagagaaaag ctccagaaag cagacataga ggaaataaag     180
agtgggaggc taagcaaaga actggattta gtaagtcacc atgtgaggac aaaacttgat     240
``` gaactg                                                                        246

<210> SEQ ID NO 19
<211> LENGTH: 246
<212> TYPE: DNA
<213> ORGANISM: Mus musculus
<220> FEATURE:
<221> NAME/KEY: gene
<222> LOCATION: (1)..(246)

<400> SEQUENCE: 19
gttcctatcg atgtggacaa gaccaaagta cacaacactg agccagtgga aaatgcaagg      60
atagagccac cagatactgg actttattat gatgaatacc tcaagcaagt gattgaagtc     120
ttggaaacag atccacattt cagagaaaag ctccagaaag cagacataga ggagataagg     180
agcgggaggc tgagtcaaga gctggactta gtaagtcaca aagtgaggac gagactggat     240
gagctg                                                                246

<210> SEQ ID NO 20
<211> LENGTH: 246
<212> TYPE: DNA
<213> ORGANISM: Rattus norvegicus
<220> FEATURE:
<221> NAME/KEY: gene
<222> LOCATION: (1)..(246)

<400> SEQUENCE: 20
gttcctattg atgtggacaa gaccaaagtg cacaacgtcg agccggtgga aagtgcaagg      60
atagaaccgc cagacacggg actttattat gatgaatacc tcaagcaagt gattgaagtc     120
ttggaaacag atccgcattt cagagaaaag ctccagaaag cagacataga ggagataagg     180
agcgggaggc tgagtcaaga gctggactta gtaagtcaca aagtgaggac gagactggat     240
gaactg                                                                246

<210> SEQ ID NO 21
<211> LENGTH: 566
<212> TYPE: DNA
<213> ORGANISM: Mus musculus
<220> FEATURE:
<221> NAME/KEY: gene
<222> LOCATION: (1)..(566)

<400> SEQUENCE: 21
ccagtggaaa atgcaaggat agagccacca gatactggac tttattatga tgaatacctc      60
aagcaagtga ttgaagtctt ggaaacagat ccacatttca gagaaaagct ccagaaagca     120
gacatagagg agataaggag cgggaggctg agtcaagagc tggacttagt aagtcacaaa     180
gtgaggacga gactggatga gctgaagagg caagaagtag aagactgcg gatgctcatc      240 aaagctaagc tggatgccct tcaagacact ggcatgaatc accaccttct tctgaagcag     300
tttgaacacc tgaaccacca gaatcctaac acatttgaat ccagagattt ggatatgcta     360
atcaaagcag ctaccgcgga tctggagcaa tatgaccgga ctcggcatga agagtttaag     420
aagtacgaga tgatgaagga acacgagcgg agagagtatt taaaaacgct gagtgaggag     480
aagaggaaaa aagaagagtc taagtttgaa gagatgaaga ggaagcacga agaccacccc     540
aaagttaatc atcccggaag caaaga                                          566

<210> SEQ ID NO 22
<211> LENGTH: 20

```
<212> TYPE: DNA
<213> ORGANISM: Mus musculus
<220> FEATURE:
<221> NAME/KEY: gene
<222> LOCATION: (1)..(20)

<400> SEQUENCE: 22
ccagtggaaa atgcaaggat                                                     20

<210> SEQ ID NO 23
<211> LENGTH: 21
<212> TYPE: DNA
<213> ORGANISM: Mus musculus
<220> FEATURE:
<221> NAME/KEY: gene
<222> LOCATION: (1)..(21)

<400> SEQUENCE: 23
tctttgcttc cgggatgatt a                                                   21

<210> SEQ ID NO 24
<211> LENGTH: 13
<212> TYPE: PRT
<213> ORGANISM: Artificial Sequence
<220> FEATURE:
<223> OTHER INFORMATION: Chemically-synthesized peptide antigen

<400> SEQUENCE: 24
```

His Leu Asn His Gln Asn Pro Asp Thr Phe Glu Ser Cys
1               5                   10

```
<210> SEQ ID NO 25
<211> LENGTH: 621
<212> TYPE: PRT
<213> ORGANISM: Artificial Sequence
<220> FEATURE:
<223> OTHER INFORMATION: Chemically-synthesized recombinant mouse
      GST-NEFA

<400> SEQUENCE: 25
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

-continued

```
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly Ser Pro Ile Asp Val Asp Lys Thr Lys Val His Asn Thr Glu Pro
225                 230                 235                 240
Val Glu Asn Ala Arg Ile Glu Pro Pro Asp Thr Gly Leu Tyr Tyr Asp
                245                 250                 255
Glu Tyr Leu Lys Gln Val Ile Glu Val Leu Glu Thr Asp Pro His Phe
            260                 265                 270
Arg Glu Lys Leu Gln Lys Ala Asp Ile Glu Ile Arg Ser Gly Arg
        275                 280                 285
Leu Ser Gln Glu Leu Asp Leu Val Ser His Lys Val Arg Thr Arg Leu
    290                 295                 300
Asp Glu Leu Lys Arg Gln Glu Val Gly Arg Leu Arg Met Leu Ile Lys
305                 310                 315                 320
Ala Lys Leu Asp Ala Leu Gln Asp Thr Gly Met Asn His His Leu Leu
                325                 330                 335
Leu Lys Gln Phe Glu His Leu Asn His Gln Asn Pro Asn Thr Phe Glu
            340                 345                 350
Ser Arg Asp Leu Asp Met Leu Ile Lys Ala Ala Thr Ala Asp Leu Glu
        355                 360                 365
Gln Tyr Asp Arg Thr Arg His Glu Glu Phe Lys Lys Tyr Glu Met Met
    370                 375                 380
Lys Glu His Glu Arg Arg Glu Tyr Leu Lys Thr Leu Ser Glu Glu Lys
385                 390                 395                 400
Arg Lys Glu Glu Glu Ser Lys Phe Glu Glu Met Lys Arg Lys His Glu
                405                 410                 415
Asp His Pro Lys Val Asn His Pro Gly Ser Lys Asp Gln Leu Lys Glu
            420                 425                 430
Val Trp Glu Glu Thr Asp Gly Leu Asp Pro Asn Asp Phe Asp Pro Lys
        435                 440                 445
Thr Phe Phe Lys Leu His Asp Val Asn Asn Asp Gly Phe Leu Asp Glu
    450                 455                 460
Gln Glu Leu Glu Ala Leu Phe Thr Arg Glu Leu Glu Lys Val Tyr Asn
465                 470                 475                 480
Pro Gln Asn Ala Glu Asp Asp Met Ile Glu Met Glu Glu Arg Leu
                485                 490                 495
Arg Met Arg Glu His Val Met Ser Glu Ile Asp Asn Asn Lys Asp Arg
            500                 505                 510
Leu Val Thr Leu Glu Glu Phe Leu Arg Ala Thr Glu Lys Lys Glu Phe
        515                 520                 525
Leu Glu Pro Asp Ser Trp Glu Thr Leu Asp Gln Gln Gln Leu Phe Thr
    530                 535                 540
Glu Asp Glu Leu Lys Glu Tyr Glu Ser Ile Ile Ala Ile Gln Glu Asn
545                 550                 555                 560
Glu Leu Lys Lys Arg Ala Glu Glu Leu Gln Lys Gln Lys Glu Asp Leu
                565                 570                 575
Gln Arg Gln His Asp His Leu Glu Ala Gln Lys Gln Glu Tyr His Gln
            580                 585                 590
```

```
Ala Val Gln His Leu Glu Gln Lys Lys Leu Gln Gln Gly Ile Ala Pro
            595                 600                 605

Ser Gly Pro Ala Gly Glu Leu Lys Phe Glu Pro His Thr
610                 615                 620

<210> SEQ ID NO 26
<211> LENGTH: 397
<212> TYPE: PRT
<213> ORGANISM: Artificial Sequence
<220> FEATURE:
<223> OTHER INFORMATION: Chemically-synthesized nesfatin mutant protein

<400> SEQUENCE: 26

Gly Ser Pro Ile Asp Val Asp Lys Thr Lys Val His Asn Thr Glu Pro
1               5                   10                  15

Val Glu Asn Ala Arg Ile Glu Pro Asp Thr Gly Leu Tyr Tyr Asp
            20                  25                  30

Glu Tyr Leu Lys Gln Val Ile Glu Val Leu Glu Thr Asp Pro His Phe
        35                  40                  45

Arg Glu Lys Leu Gln Lys Ala Asp Ile Glu Glu Ile Arg Ser Gly Arg
    50                  55                  60

Leu Ser Gln Glu Leu Asp Leu Val Ser His Lys Val Arg Thr Arg Leu
65                  70                  75                  80

Asp Glu Leu Lys Arg Gln Glu Val Gly Arg Leu Arg Met Leu Ile Lys
                85                  90                  95

Ala Lys Leu Asp Ala Leu Gln Asp Thr Gly Met Asn His His Leu Leu
            100                 105                 110

Leu Lys Gln Phe Glu His Leu Asn His Gln Asn Pro Asn Thr Phe Glu
        115                 120                 125

Ser Arg Asp Leu Asp Met Leu Ile Lys Ala Ala Thr Ala Asp Leu Glu
    130                 135                 140

Gln Tyr Asp Arg Thr Arg His Glu Glu Phe Lys Lys Tyr Glu Met Met
145                 150                 155                 160

Lys Glu His Glu Arg Arg Glu Tyr Leu Lys Thr Leu Ser Glu Glu Lys
                165                 170                 175

Arg Lys Glu Glu Glu Ser Lys Phe Glu Glu Met Lys Arg Lys His Glu
            180                 185                 190

Asp His Pro Lys Val Asn His Pro Gly Ser Lys Asp Gln Leu Lys Glu
        195                 200                 205

Val Trp Glu Glu Thr Asp Gly Leu Asp Pro Asn Asp Phe Asp Pro Lys
    210                 215                 220

Thr Phe Phe Lys Leu His Asp Val Asn Asn Asp Gly Phe Leu Asp Glu
225                 230                 235                 240

Gln Glu Leu Glu Ala Leu Phe Thr Arg Glu Leu Glu Lys Val Tyr Asn
                245                 250                 255

Pro Gln Asn Ala Glu Asp Asp Met Ile Glu Met Glu Glu Glu Arg Leu
            260                 265                 270

Arg Met Arg Glu His Val Met Ser Glu Ile Asp Asn Asn Lys Asp Arg
        275                 280                 285

Leu Val Thr Leu Glu Glu Phe Leu Arg Ala Thr Glu Lys Lys Glu Phe
    290                 295                 300

Leu Glu Pro Asp Ser Trp Glu Thr Leu Asp Gln Gln Gln Leu Phe Thr
305                 310                 315                 320

Glu Asp Glu Leu Lys Glu Tyr Glu Ser Ile Ile Ala Ile Gln Glu Asn
                325                 330                 335
```

```
Glu Leu Lys Lys Arg Ala Glu Glu Leu Gln Lys Gln Lys Glu Asp Leu
            340                 345                 350

Gln Arg Gln His Asp His Leu Glu Ala Gln Lys Gln Glu Tyr His Gln
        355                 360                 365

Ala Val Gln His Leu Glu Gln Lys Lys Leu Gln Gln Gly Ile Ala Pro
    370                 375                 380

Ser Gly Pro Ala Gly Glu Leu Lys Phe Glu Pro His Thr
385                 390                 395

<210> SEQ ID NO 27
<211> LENGTH: 31
<212> TYPE: DNA
<213> ORGANISM: Artificial Sequence
<220> FEATURE:
<223> OTHER INFORMATION: Chemically-synthesized PCR primer

<400> SEQUENCE: 27
ttggatccgt tcctatcgat gtggacaaga c                              31

<210> SEQ ID NO 28
<211> LENGTH: 34
<212> TYPE: DNA
<213> ORGANISM: Artificial Sequence
<220> FEATURE:
<223> OTHER INFORMATION: Chemically-synthesized PCR primer

<400> SEQUENCE: 28
ttgcggccgc ttatgtgtgt ggctcaaact tcag                           34

<210> SEQ ID NO 29
<211> LENGTH: 18
<212> TYPE: DNA
<213> ORGANISM: Mus musculus
<220> FEATURE:
<221> NAME/KEY: gene
<222> LOCATION: (1)..(18)

<400> SEQUENCE: 29
cctgaaccac cagaatcc                                             18

<210> SEQ ID NO 30
<211> LENGTH: 18
<212> TYPE: DNA
<213> ORGANISM: Mus musculus
<220> FEATURE:
<221> NAME/KEY: gene
<222> LOCATION: (1)..(18)

<400> SEQUENCE: 30
agactgatgg attggacc                                             18

<210> SEQ ID NO 31
<211> LENGTH: 25
<212> TYPE: DNA
<213> ORGANISM: Artificial Sequence
<220> FEATURE:
<223> OTHER INFORMATION: Chemically-synthesized Nesfatin-1 antisense RNA

<400> SEQUENCE: 31
atggtcctcc acctcatctt cagag                                     25

<210> SEQ ID NO 32
<211> LENGTH: 16
<212> TYPE: PRT
<213> ORGANISM: Artificial Sequence
```

```
<220> FEATURE:
<223> OTHER INFORMATION: Chemically-synthesized peptide antigen

<400> SEQUENCE: 32

Pro Asp Thr Gly Leu Tyr Tyr Asp Glu Tyr Leu Lys Gln Val Ile Cys
1               5                   10                  15

<210> SEQ ID NO 33
<211> LENGTH: 10
<212> TYPE: PRT
<213> ORGANISM: Artificial Sequence
<220> FEATURE:
<223> OTHER INFORMATION: Chemically-synthesized peptide antigen

<400> SEQUENCE: 33

Glu Tyr Leu Lys Thr Leu Ser Glu Glu Cys
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Chemically-synthesized peptide antigen

<400> SEQUENCE: 34

Lys Glu Phe Leu Glu Pro Asp Ser Trp Glu Thr Leu Asp Gln Cys
1               5                   10                  15

<210> SEQ ID NO 35
<211> LENGTH: 21
<212> TYPE: DNA
<213> ORGANISM: Artificial Sequence
<220> FEATURE:
<223> OTHER INFORMATION: Chemically-synthesized PCR primer

<400> SEQUENCE: 35
gcacgctgac cgctctggaa g                                          21

<210> SEQ ID NO 36
<211> LENGTH: 27
<212> TYPE: DNA
<213> ORGANISM: Artificial Sequence
<220> FEATURE:
<223> OTHER INFORMATION: Chemically-synthesized PCR primer

<400> SEQUENCE: 36
caaatgtgtt aggattctgg tggttca                                    27

<210> SEQ ID NO 37
<211> LENGTH: 53
<212> TYPE: DNA
<213> ORGANISM: Artificial Sequence
<220> FEATURE:
<223> OTHER INFORMATION: Chemically-synthesized PCR primer

<400> SEQUENCE: 37
ggttccgcgg gtctggttcc gcgtggttct cctatcgatg tggacaagac caa         53

<210> SEQ ID NO 38
<211> LENGTH: 38
<212> TYPE: DNA
<213> ORGANISM: Artificial Sequence
<220> FEATURE:
<223> OTHER INFORMATION: Chemically-synthesized PCR primer

<400> SEQUENCE: 38
```

```
ggttgcggcc gcttacctct tcagctcatc cagtctcg                                    38
```

<210> SEQ ID NO 39
<211> LENGTH: 30
<212> TYPE: PRT
<213> ORGANISM: Homo sapiens

<400> SEQUENCE: 39

Pro Asp Thr Gly Leu Tyr Tyr Asp Glu Tyr Leu Lys Gln Val Ile Asp
1               5                   10                  15

Val Leu Glu Thr Asp Lys His Phe Arg Glu Lys Leu Gln Lys
            20                  25                  30

<210> SEQ ID NO 40
<211> LENGTH: 30
<212> TYPE: PRT
<213> ORGANISM: Rattus norvegicus

<400> SEQUENCE: 40

Pro Asp Thr Gly Leu Tyr Tyr Asp Glu Tyr Leu Lys Gln Val Ile Glu
1               5                   10                  15

Val Leu Glu Thr Asp Pro His Phe Arg Glu Lys Leu Gln Lys
            20                  25                  30

<210> SEQ ID NO 41
<211> LENGTH: 30
<212> TYPE: PRT
<213> ORGANISM: Mus musculus

<400> SEQUENCE: 41

Pro Asp Thr Gly Leu Tyr Tyr Asp Glu Tyr Leu Lys Gln Val Ile Glu
1               5                   10                  15

Val Leu Glu Thr Asp Pro His Phe Arg Glu Lys Leu Gln Lys
            20                  25                  30

<210> SEQ ID NO 42
<211> LENGTH: 23
<212> TYPE: PRT
<213> ORGANISM: Mus musculus

<400> SEQUENCE: 42

Val Pro Ile Asp Val Asp Lys Thr Lys Val His Asn Thr Glu Pro Val
1               5                   10                  15

Glu Asn Ala Arg Ile Glu Pro
            20

<210> SEQ ID NO 43
<211> LENGTH: 29
<212> TYPE: PRT
<213> ORGANISM: Mus musculus

<400> SEQUENCE: 43

Ala Asp Ile Glu Glu Ile Arg Ser Gly Arg Leu Ser Gln Glu Leu Asp
1               5                   10                  15

Leu Val Ser His Lys Val Arg Thr Arg Leu Asp Glu Leu
            20                  25

<210> SEQ ID NO 44
<211> LENGTH: 90
<212> TYPE: DNA
<213> ORGANISM: Homo sapiens -continued

<400> SEQUENCE: 44
ccagatactg gactttatta tgatgaatat ctcaagcaag tgattgatgt gctggaaaca    60
gataaacact tcagagaaaa gctccagaaa                                    90

<210> SEQ ID NO 45
<211> LENGTH: 90
<212> TYPE: DNA
<213> ORGANISM: Rattus norvegicus

<400> SEQUENCE: 45
ccagacacag gactttatta tgatgaatac ctcaagcaag tgattgaagt cttggaaaca    60
gatccgcatt tcagagaaaa gctccagaaa                                    90

<210> SEQ ID NO 46
<211> LENGTH: 90
<212> TYPE: DNA
<213> ORGANISM: Mus musculus

<400> SEQUENCE: 46
ccagatactg gactttatta tgatgaatac ctcaagcaag tgattgaagt cttggaaaca    60
gatccacatt tcagagaaaa gctccagaaa                                    90

<210> SEQ ID NO 47
<211> LENGTH: 312
<212> TYPE: PRT
<213> ORGANISM: Rattus norvegicus

<400> SEQUENCE: 47

Gln Glu Val Gly Arg Leu Arg Met Leu Ile Lys Ala Lys Leu Asp Ala
1               5                   10                  15

Leu Gln Asp Thr Gly Met Asn His His Leu Leu Lys Gln Phe Glu
            20                  25                  30

His Leu Asn His Gln Asn Pro Asp Thr Phe Glu Ser Lys Asp Leu Asp
        35                  40                  45

Met Leu Ile Lys Ala Ala Thr Ala Asp Leu Glu Gln Tyr Asp Arg Thr
    50                  55                  60

Arg His Glu Glu Phe Lys Lys Tyr Glu Met Met Lys Glu His Glu Arg
65                  70                  75                  80

Arg Glu Tyr Leu Lys Thr Leu Ser Glu Glu Lys Arg Lys Glu Glu Glu
                85                  90                  95

Ala Lys Phe Ala Glu Met Lys Arg Lys His Glu Asp His Pro Lys Val
            100                 105                 110

Asn His Pro Gly Ser Lys Asp Gln Leu Lys Glu Val Trp Glu Glu Thr
        115                 120                 125

Asp Gly Leu Asp Pro Asn Asp Phe Asp Pro Lys Thr Phe Phe Lys Leu
    130                 135                 140

His Asp Val Asn Asn Asp Gly Phe Leu Asp Glu Gln Glu Leu Glu Ala
145                 150                 155                 160

Leu Phe Thr Lys Glu Leu Asp Lys Val Tyr Asn Pro Gln Asn Ala Glu
                165                 170                 175

Asp Asp Met Ile Glu Met Glu Glu Arg Leu Arg Met Arg Glu His
            180                 185                 190

Val Met Asn Glu Ile Asp Asn Asn Lys Asp Arg Leu Val Thr Leu Glu
        195                 200                 205

Glu Phe Leu Arg Ala Thr Glu Lys Lys Glu Phe Leu Glu Pro Asp Ser
    210                 215                 220

```
Trp Glu Thr Leu Asp Gln Gln Gln Leu Phe Thr Glu Glu Leu Lys
225                 230                 235                 240

Glu Tyr Glu Ser Ile Ile Ala Ile Gln Glu Ser Glu Leu Lys Lys Lys
            245                 250                 255

Ala Asp Glu Leu Gln Lys Gln Lys Glu Leu Gln Arg Gln His Asp
            260                 265                 270

His Leu Glu Ala Gln Lys Gln Tyr Gln Ala Val Gln Leu
        275                 280                 285

Glu Gln Lys Lys Phe Gln Gln Gly Ile Ala Pro Ser Gly Pro Ala Gly
    290                 295                 300

Glu Leu Lys Phe Glu Pro His Thr
305                 310
```

<210> SEQ ID NO 48
<211> LENGTH: 27
<212> TYPE: DNA
<213> ORGANISM: Artificial Sequence
<220> FEATURE:
<223> OTHER INFORMATION: Chemically-synthesized PCR primer

<400> SEQUENCE: 48
atggaatatt taaaaacgct gagtgag                                    27

<210> SEQ ID NO 49
<211> LENGTH: 23
<212> TYPE: DNA
<213> ORGANISM: Rattus norvegicus
<220> FEATURE:
<223> OTHER INFORMATION: Chemically-synthesized PCR primer

<400> SEQUENCE: 49
ttatgtgtgt ggctcaaact tca                                       23

<210> SEQ ID NO 50
<211> LENGTH: 699
<212> TYPE: DNA
<213> ORGANISM: Artificial Sequence
<220> FEATURE:
<223> OTHER INFORMATION: Chemically-synthesized nesfatin-3 coding
      sequence

<400> SEQUENCE: 50
atggaatatt taaaaacgct gagtgaggag aagaggaaag aagaagagtc taagtttgaa      60
gagatgaaga ggaagcacga agaccacccc aaagttaatc atcccggaag caaagatcaa     120
ctaaaagagg tttgggaaga gactgatgga ttggacccta atgactttga ccccaagaca     180
tttttcaaat tacatgatgt taacaacgat ggattcctgg atgaacaaga attagaagca     240
ctattcacaa gagagttgga gaaagtgtat aacccacaaa atgcagagga cgatatgata     300
gaaatggaag aggagaggct caggatgaga gaacacgtca tgagtgagat tgataacaac     360
aaagaccgat tggtgactct ggaggaattc ctgagagcta cagagaagaa agaattcctg     420
gagcctgata gctgggagac actgaccag caacagttat tcaccgagga cgagcttaaa     480
gagtatgaaa gcattattgc tatccaagag aacgagctta agaagagggc ggaagagctg     540
cagaaacaga aggaggatct gcagcggcag cacgaccacc tcgaggcgca agcaggag       600 tatcatcagg ccgtccagca cctggaacag aagaaacttc aacaaggcat tgctccatca     660
gggccagcgg gagagctgaa gtttgagcca cgtatgtaa                            699

<210> SEQ ID NO 51
<211> LENGTH: 232
<212> TYPE: PRT
<213> ORGANISM: Artificial Sequence
<220> FEATURE:
<223> OTHER INFORMATION: Chemically-synthesized nesfatin-3

<400> SEQUENCE: 51

```
Met Glu Tyr Leu Lys Thr Leu Ser Glu Glu Lys Arg Lys Glu Glu
1               5                   10                  15

Ala Lys Phe Ala Glu Met Lys Arg Lys His Glu Asp His Pro Lys Val
            20                  25                  30

Asn His Pro Gly Ser Lys Asp Gln Leu Lys Glu Val Trp Glu Glu Thr
                35                  40                  45

Asp Gly Leu Asp Pro Asn Asp Phe Asp Pro Lys Thr Phe Phe Lys Leu
    50                  55                  60

His Asp Val Asn Asn Asp Gly Phe Leu Asp Glu Gln Glu Leu Glu Ala
65                  70                  75                  80

Leu Phe Thr Lys Glu Leu Asp Lys Val Tyr Asn Pro Gln Asn Ala Glu
                85                  90                  95

Asp Asp Met Ile Glu Met Glu Glu Arg Leu Arg Met Arg Glu His
            100                 105                 110

Val Met Asn Glu Ile Asp Asn Asn Lys Asp Arg Leu Val Thr Leu Glu
                115                 120                 125

Glu Phe Leu Arg Ala Thr Glu Lys Lys Glu Phe Leu Glu Pro Asp Ser
    130                 135                 140

Trp Glu Thr Leu Asp Gln Gln Gln Leu Phe Thr Glu Glu Glu Leu Lys
145                 150                 155                 160

Glu Tyr Glu Ser Ile Ile Ala Ile Gln Glu Ser Glu Leu Lys Lys Lys
                165                 170                 175

Ala Asp Glu Leu Gln Lys Gln Lys Glu Glu Leu Gln Arg Gln His Asp
            180                 185                 190

His Leu Glu Ala Gln Lys Gln Glu Tyr Gln Gln Ala Val Gln Gln Leu
        195                 200                 205

Glu Gln Lys Lys Phe Gln Gln Gly Ile Ala Pro Ser Gly Pro Ala Gly
    210                 215                 220

Glu Leu Lys Phe Glu Pro His Thr
225                 230
```

<210> SEQ ID NO 52
<211> LENGTH: 25
<212> TYPE: DNA
<213> ORGANISM: Artificial Sequence
<220> FEATURE:
<223> OTHER INFORMATION: Chemically-synthesized PCR primer

<400> SEQUENCE: 52
atgcaagaag taggaagact gagaa        25

<210> SEQ ID NO 53
<211> LENGTH: 23
<212> TYPE: DNA
<213> ORGANISM: Rattus norvegicus
<220> FEATURE:
<223> OTHER INFORMATION: Chemically-synthesized PCR primer

<400> SEQUENCE: 53
ttatgtgtgt ggctcaaact tca        23

```
<210> SEQ ID NO 54
<211> LENGTH: 699
<212> TYPE: DNA
<213> ORGANISM: Artificial Sequence
<220> FEATURE:
<223> OTHER INFORMATION: Chemically-synthesized nesfatin-2/3 coding
      sequence

<400> SEQUENCE: 54
atggagtatt taaaaacgct gagtgaggag aagaggaaag aagaagagtc taagtttgaa    60
gagatgaaga ggaagcacga agaccacccc aaagttaatc atcccggaag caaagatcaa   120
ctaaaagagg tttgggaaga gactgatgga ttggacccta atgactttga ccccaagaca   180
tttttcaaat tacatgatgt taacaacgat ggattcctgg atgaacaaga attagaagca   240
ctattcacaa agagttgga gaaagtgtat aacccacaaa atgcagagga cgatatgata   300
gaaatggaag aggagaggct caggatgaga gaacacgtca tgagtgagat tgataacaac   360
aaagaccgat tggtgactct ggaggaattc ctgagagcta cagagaagaa agaattcctg   420
gagcctgata gctgggagac actggaccag caacagttat tcaccgagga cgagcttaaa   480
gagtatgaaa gcattattgc tatccaagag aacgagctta agaagagggc ggaagagctg   540
cagaaacaga aggaggatct gcagcggcag cacgaccacc tcgaggcgca aagcaggag   600 tatcatcagg ccgtccagca cctggaacag aagaaacttc aacaaggcat tgctccatca   660
gggccagcgg gagagctgaa gtttgagcca cgtatgtaa                          699

<210> SEQ ID NO 55
<211> LENGTH: 313
<212> TYPE: PRT
<213> ORGANISM: Artificial Sequence
<220> FEATURE:
<223> OTHER INFORMATION: Chemically-synthesized nesfatin-2/3

<400> SEQUENCE: 55

Met Gln Glu Val Gly Arg Leu Arg Met Leu Ile Lys Ala Lys Leu Asp
  1               5                  10                  15

Ala Leu Gln Asp Thr Gly Met Asn His His Leu Leu Lys Gln Phe
             20                  25                  30

Glu His Leu Asn His Gln Asn Pro Asp Thr Phe Glu Ser Lys Asp Leu
         35                  40                  45

Asp Met Leu Ile Lys Ala Ala Thr Ala Asp Leu Glu Gln Tyr Asp Arg
     50                  55                  60

Thr Arg His Glu Glu Phe Lys Lys Tyr Glu Met Met Lys Glu His Glu
 65                  70                  75                  80

Arg Arg Glu Tyr Leu Lys Thr Leu Ser Glu Glu Lys Arg Lys Glu Glu
                 85                  90                  95

Glu Ala Lys Phe Ala Glu Met Lys Arg Lys His Glu Asp His Pro Lys
            100                 105                 110

Val Asn His Pro Gly Ser Lys Asp Gln Leu Lys Glu Val Trp Glu Glu
        115                 120                 125

Thr Asp Gly Leu Asp Pro Asn Asp Phe Asp Pro Lys Thr Phe Phe Lys
    130                 135                 140

Leu His Asp Val Asn Asn Asp Gly Phe Leu Asp Glu Gln Glu Leu Glu
145                 150                 155                 160

Ala Leu Phe Thr Lys Glu Leu Asp Lys Val Tyr Asn Pro Gln Asn Ala
                165                 170                 175

Glu Asp Asp Met Ile Glu Met Glu Glu Glu Arg Leu Arg Met Arg Glu
            180                 185                 190
```

```
His Val Met Asn Glu Ile Asp Asn Asn Lys Asp Arg Leu Val Thr Leu
            195                 200                 205

Glu Glu Phe Leu Arg Ala Thr Glu Lys Lys Glu Phe Leu Glu Pro Asp
        210                 215                 220

Ser Trp Glu Thr Leu Asp Gln Gln Gln Leu Phe Thr Glu Glu Glu Leu
225                 230                 235                 240

Lys Glu Tyr Glu Ser Ile Ile Ala Ile Gln Glu Ser Glu Leu Lys Lys
                245                 250                 255

Lys Ala Asp Glu Leu Gln Lys Gln Lys Glu Glu Leu Gln Arg Gln His
            260                 265                 270

Asp His Leu Glu Ala Gln Lys Gln Glu Tyr Gln Gln Ala Val Gln Gln
        275                 280                 285

Leu Glu Gln Lys Lys Phe Gln Gln Gly Ile Ala Pro Ser Gly Pro Ala
    290                 295                 300

Gly Glu Leu Lys Phe Glu Pro His Thr
305                 310

<210> SEQ ID NO 56
<211> LENGTH: 56
<212> TYPE: DNA
<213> ORGANISM: Artificial Sequence
<220> FEATURE:
<223> OTHER INFORMATION: Chemically-synthesized PCR primer

<400> SEQUENCE: 56
ggttccgcgg gtctggttcc gcgtggttct gttcctatcg atgtggacaa gaccaa        56

<210> SEQ ID NO 57
<211> LENGTH: 36
<212> TYPE: DNA
<213> ORGANISM: Artificial Sequence
<220> FEATURE:
<223> OTHER INFORMATION: Chemically-synthesized PCR primer

<400> SEQUENCE: 57
cttcttgagc agccagctca tccagtctcg tcctca                              36

<210> SEQ ID NO 58
<211> LENGTH: 38
<212> TYPE: DNA
<213> ORGANISM: Artificial Sequence
<220> FEATURE:
<223> OTHER INFORMATION: Chemically-synthesized PCR primer

<400> SEQUENCE: 58
gagctggctg ctcaagaagt aggaagactg cggatgct                            38

<210> SEQ ID NO 59
<211> LENGTH: 39
<212> TYPE: DNA
<213> ORGANISM: Artificial Sequence
<220> FEATURE:
<223> OTHER INFORMATION: Chemically-synthesized PCR primer

<400> SEQUENCE: 59
ggttgcggcc gcactttatg tgtgtggctc aaacttcag                           39

<210> SEQ ID NO 60
<211> LENGTH: 58
<212> TYPE: DNA
<213> ORGANISM: Artificial Sequence
<220> FEATURE:
```

-continued

<223> OTHER INFORMATION: Chemically-synthesized PCR primer

<400> SEQUENCE: 60
ggttactagt ggttctggtc atcaccatca ccatcactcc gcgggtctgg ttccgcgt    58

<210> SEQ ID NO 61
<211> LENGTH: 397
<212> TYPE: PRT
<213> ORGANISM: Artificial Sequence
<220> FEATURE:
<223> OTHER INFORMATION: Chemically-synthesized KR-AA mutant polypeptide

<400> SEQUENCE: 61

```
Gly Ser Pro Ile Asp Val Asp Lys Thr Lys Val His Asn Thr Glu Pro
1               5                   10                  15

Val Glu Asn Ala Arg Ile Glu Pro Asp Thr Gly Leu Tyr Tyr Asp
            20                  25                  30

Glu Tyr Leu Lys Gln Val Ile Glu Val Leu Glu Thr Asp Pro His Phe
        35                  40                  45

Arg Glu Lys Leu Gln Lys Ala Asp Ile Glu Glu Ile Arg Ser Gly Arg
    50                  55                  60

Leu Ser Gln Glu Leu Asp Leu Val Ser His Lys Val Arg Thr Arg Leu
65                  70                  75                  80

Asp Glu Leu Ala Ala Gln Glu Val Gly Arg Leu Arg Met Leu Ile Lys
                85                  90                  95

Ala Lys Leu Asp Ala Leu Gln Asp Thr Gly Met Asn His His Leu Leu
            100                 105                 110

Leu Lys Gln Phe Glu His Leu Asn His Gln Asn Pro Asn Thr Phe Glu
        115                 120                 125

Ser Arg Asp Leu Asp Met Leu Ile Lys Ala Ala Thr Ala Asp Leu Glu
    130                 135                 140

Gln Tyr Asp Arg Thr Arg His Glu Glu Phe Lys Lys Tyr Glu Met Met
145                 150                 155                 160

Lys Glu His Glu Arg Arg Glu Tyr Leu Lys Thr Leu Ser Glu Glu Lys
                165                 170                 175

Arg Lys Glu Glu Glu Ser Lys Phe Glu Glu Met Lys Arg Lys His Glu
            180                 185                 190

Asp His Pro Lys Val Asn His Pro Gly Ser Lys Asp Gln Leu Lys Glu
        195                 200                 205

Val Trp Glu Glu Thr Asp Gly Leu Asp Pro Asn Asp Phe Asp Pro Lys
    210                 215                 220

Thr Phe Phe Lys Leu His Asp Val Asn Asn Asp Gly Phe Leu Asp Glu
225                 230                 235                 240

Gln Glu Leu Glu Ala Leu Phe Thr Arg Glu Leu Glu Lys Val Tyr Asn
                245                 250                 255

Pro Gln Asn Ala Glu Asp Asp Met Ile Glu Met Glu Glu Glu Arg Leu
            260                 265                 270

Arg Met Arg Glu His Val Met Ser Glu Ile Asp Asn Asn Lys Asp Arg
        275                 280                 285

Leu Val Thr Leu Glu Glu Phe Leu Arg Ala Thr Glu Lys Lys Glu Phe
    290                 295                 300

Leu Glu Pro Asp Ser Trp Glu Thr Leu Asp Gln Gln Leu Phe Thr
305                 310                 315                 320

Glu Asp Glu Leu Lys Glu Tyr Glu Ser Ile Ile Ala Ile Gln Glu Asn
                325                 330                 335
```

-continued

```
Glu Leu Lys Lys Arg Ala Glu Glu Leu Gln Lys Gln Lys Glu Asp Leu
            340                 345                 350

Gln Arg Gln His Asp His Leu Glu Ala Gln Lys Gln Glu Tyr His Gln
        355                 360                 365

Ala Val Gln His Leu Glu Gln Lys Lys Leu Gln Gln Gly Ile Ala Pro
    370                 375                 380

Ser Gly Pro Ala Gly Glu Leu Lys Phe Glu Pro His Thr
385                 390                 395

<210> SEQ ID NO 62
<211> LENGTH: 86
<212> TYPE: PRT
<213> ORGANISM: Artificial Sequence
<220> FEATURE:
<223> OTHER INFORMATION: Chemically-synthesized nesfatin-1 Cys
      polypeptide

<400> SEQUENCE: 62

Gly Ser Pro Ile Asp Val Asp Lys Thr Lys Val His Asn Thr Glu Pro
1               5                   10                  15

Val Glu Asn Ala Arg Ile Glu Pro Pro Asp Thr Gly Leu Tyr Tyr Asp
            20                  25                  30

Glu Tyr Leu Lys Gln Val Ile Glu Val Leu Glu Thr Asp Pro His Phe
        35                  40                  45

Arg Glu Lys Leu Gln Lys Ala Asp Ile Glu Glu Ile Arg Ser Gly Arg
    50                  55                  60

Leu Ser Gln Glu Leu Asp Leu Val Ser His Lys Val Arg Thr Arg Leu
65                  70                  75                  80

Asp Glu Leu Lys Arg Cys
                85

<210> SEQ ID NO 63
<211> LENGTH: 53
<212> TYPE: DNA
<213> ORGANISM: Artificial Sequence
<220> FEATURE:
<223> OTHER INFORMATION: Chemically-synthesized PCR primer

<400> SEQUENCE: 63
ggttccgcgg gtctggttcc gcgtggttct cctatcgatg tggacaagac caa      53

<210> SEQ ID NO 64
<211> LENGTH: 41
<212> TYPE: DNA
<213> ORGANISM: Artificial Sequence
<220> FEATURE:
<223> OTHER INFORMATION: Chemically-synthesized PCR primer

<400> SEQUENCE: 64
ggttgcggcc gcttaacacc tcttcagctc atccagtctc g            41

<210> SEQ ID NO 65
<211> LENGTH: 16
<212> TYPE: PRT
<213> ORGANISM: Homo sapiens

<400> SEQUENCE: 65

Pro Asp Thr Gly Leu Tyr Tyr Asp Glu Tyr Leu Lys Gln Val Ile Asp
1               5                   10                  15

<210> SEQ ID NO 66
<211> LENGTH: 14
```

```
<212> TYPE: PRT
<213> ORGANISM: Homo sapiens

<400> SEQUENCE: 66

Val Leu Glu Thr Asp Lys His Phe Arg Glu Lys Leu Gln Lys
1               5                   10

<210> SEQ ID NO 67
<211> LENGTH: 10
<212> TYPE: PRT
<213> ORGANISM: Homo sapiens

<400> SEQUENCE: 67

Lys Gln Val Ile Asp Val Leu Glu Thr Asp
1               5                   10

<210> SEQ ID NO 68
<211> LENGTH: 16
<212> TYPE: PRT
<213> ORGANISM: Rattus norvegicus

<400> SEQUENCE: 68

Pro Asp Thr Gly Leu Tyr Tyr Asp Glu Tyr Leu Lys Gln Val Ile Glu
1               5                   10                  15

<210> SEQ ID NO 69
<211> LENGTH: 14
<212> TYPE: PRT
<213> ORGANISM: Rattus norvegicus

<400> SEQUENCE: 69

Val Leu Glu Thr Asp Pro His Phe Arg Glu Lys Leu Gln Lys
1               5                   10

<210> SEQ ID NO 70
<211> LENGTH: 10
<212> TYPE: PRT
<213> ORGANISM: Rattus norvegicus

<400> SEQUENCE: 70

Lys Gln Val Ile Glu Val Leu Glu Thr Asp
1               5                   10

<210> SEQ ID NO 71
<211> LENGTH: 16
<212> TYPE: PRT
<213> ORGANISM: Mus musculus

<400> SEQUENCE: 71

Pro Asp Thr Gly Leu Tyr Tyr Asp Glu Tyr Leu Lys Gln Val Ile Glu
1               5                   10                  15

<210> SEQ ID NO 72
<211> LENGTH: 14
<212> TYPE: PRT
<213> ORGANISM: Mus musculus

<400> SEQUENCE: 72

Val Leu Glu Thr Asp Pro His Phe Arg Glu Lys Leu Gln Lys
1               5                   10

<210> SEQ ID NO 73
<211> LENGTH: 10
<212> TYPE: PRT
<213> ORGANISM: Mus musculus
```

-continued

```
<400> SEQUENCE: 73

Lys Gln Val Ile Glu Val Leu Glu Thr Asp
1               5                   10

<210> SEQ ID NO 74
<211> LENGTH: 48
<212> TYPE: DNA
<213> ORGANISM: Homo sapiens

<400> SEQUENCE: 74
ccagatactg gactttatta tgatgaatat ctcaagcaag tgattgat            48

<210> SEQ ID NO 75
<211> LENGTH: 42
<212> TYPE: DNA
<213> ORGANISM: Homo sapiens

<400> SEQUENCE: 75
gtgctggaaa cagataaaca cttcagagaa aagctccaga aa                  42

<210> SEQ ID NO 76
<211> LENGTH: 30
<212> TYPE: DNA
<213> ORGANISM: Homo sapiens

<400> SEQUENCE: 76
aagcaagtga ttgatgtgct ggaaacagat                                30

<210> SEQ ID NO 77
<211> LENGTH: 48
<212> TYPE: DNA
<213> ORGANISM: Rattus norvegicus

<400> SEQUENCE: 77
ccagacacag gactttatta tgatgaatac ctcaagcaag tgattgaa            48

<210> SEQ ID NO 78
<211> LENGTH: 42
<212> TYPE: DNA
<213> ORGANISM: Rattus norvegicus

<400> SEQUENCE: 78
gtcttggaaa cagatccgca tttcagagaa aagctccaga aa                  42

<210> SEQ ID NO 79
<211> LENGTH: 30
<212> TYPE: DNA
<213> ORGANISM: Rattus norvegicus

<400> SEQUENCE: 79
aagcaagtga ttgaagtctt ggaaacagat                                30

<210> SEQ ID NO 80
<211> LENGTH: 48
<212> TYPE: DNA
<213> ORGANISM: Mus musculus

<400> SEQUENCE: 80
ccagatactg gactttatta tgatgaatac ctcaagcaag tgattgaa            48

<210> SEQ ID NO 81
<211> LENGTH: 42
```

-continued

```
<212> TYPE: DNA
<213> ORGANISM: Mus musculus

<400> SEQUENCE: 81
gtcttggaaa cagatccaca tttcagagaa aagctccaga aa                            42

<210> SEQ ID NO 82
<211> LENGTH: 30
<212> TYPE: DNA
<213> ORGANISM: Mus musculus

<400> SEQUENCE: 82
aagcaagtga ttgaagtctt ggaaacagat                                          30

<210> SEQ ID NO 83
<211> LENGTH: 1386
<212> TYPE: DNA
<213> ORGANISM: Homo sapiens
<220> FEATURE:
<221> NAME/KEY: CDS
<222> LOCATION: (1)..(1383)

<400> SEQUENCE: 83 atg cct ccc tct ggg ccc cga gga acc ctc ctt ctg ttg ccg ctg ctg           48
Met Pro Pro Ser Gly Pro Arg Gly Thr Leu Leu Leu Leu Pro Leu Leu
1               5                   10                  15 ctg ctg ctc ctg ctt cgc gcc gtg ctg gct gtc ccc ctg gag cga ggg           96
Leu Leu Leu Leu Leu Arg Ala Val Leu Ala Val Pro Leu Glu Arg Gly
                20                  25                  30 gcg ccc aac aag gag gag acc cct gcg act gag agt ccc gac aca ggc          144
Ala Pro Asn Lys Glu Glu Thr Pro Ala Thr Glu Ser Pro Asp Thr Gly
            35                  40                  45 ctg tac tac cac cgg tac ctc cag gag gtc atc gat gta ctg gag acg          192
Leu Tyr Tyr His Arg Tyr Leu Gln Glu Val Ile Asp Val Leu Glu Thr
        50                  55                  60 gat ggg cat ttc cga gag aag ctg cag gct gcc aat gcg gag gac atc          240
Asp Gly His Phe Arg Glu Lys Leu Gln Ala Ala Asn Ala Glu Asp Ile
65                  70                  75                  80 aag agc ggg aag ctg agc cga gag ctg gac ttt gtc agc cac cac gtc          288
Lys Ser Gly Lys Leu Ser Arg Glu Leu Asp Phe Val Ser His His Val
                85                  90                  95 cgc acc aag ctg gat gag ctc aag cga cag gag gtg tca cgg ctg cgg          336
Arg Thr Lys Leu Asp Glu Leu Lys Arg Gln Glu Val Ser Arg Leu Arg
            100                 105                 110 atg ctg ctc aag gcc aag atg gac gcc gag cag gat ccc aat gta cag          384
Met Leu Leu Lys Ala Lys Met Asp Ala Glu Gln Asp Pro Asn Val Gln
        115                 120                 125 gtg gat cat ctg aat ctc ctg aaa cag ttt gaa cac ctg gac cct cag          432
Val Asp His Leu Asn Leu Leu Lys Gln Phe Glu His Leu Asp Pro Gln
    130                 135                 140 aac cag cat aca ttc gag gcc cgc gac ctg gag ctg ctg atc cag acg          480
Asn Gln His Thr Phe Glu Ala Arg Asp Leu Glu Leu Leu Ile Gln Thr
145                 150                 155                 160 gcc acc cgg gac ctt gcc cag tac gac gca gcc cat cat gaa gag ttc          528
Ala Thr Arg Asp Leu Ala Gln Tyr Asp Ala Ala His His Glu Glu Phe
                165                 170                 175 aag cgc tac gag atg ctt aag gaa cac gag aga cgg cgt tat ctg gag          576
Lys Arg Tyr Glu Met Leu Lys Glu His Glu Arg Arg Arg Tyr Leu Glu
            180                 185                 190 tca ctg gga gag gag cag aga aag gag gcg gag agg aag ctg gaa gag          624
Ser Leu Gly Glu Glu Gln Arg Lys Glu Ala Glu Arg Lys Leu Glu Glu
        195                 200                 205
```

```
caa cag cgc cgg cac cgc gag cac cct aaa gtc aac gtg cct ggc agc        672
Gln Gln Arg Arg His Arg Glu His Pro Lys Val Asn Val Pro Gly Ser
    210                 215                 220 caa gcc cag ttg aag gag gtg tgg gag gag ctg gat gga ctg gac ccc        720
Gln Ala Gln Leu Lys Glu Val Trp Glu Glu Leu Asp Gly Leu Asp Pro
225                 230                 235                 240 aac agg ttt aac ccc aag acc ttc ttc ata ctg cat gat atc aac agt        768
Asn Arg Phe Asn Pro Lys Thr Phe Phe Ile Leu His Asp Ile Asn Ser
                245                 250                 255 gat ggt gtc ctg gat gag cag gag ctg gag gca ctc ttc acc aag gag        816
Asp Gly Val Leu Asp Glu Gln Glu Leu Glu Ala Leu Phe Thr Lys Glu
            260                 265                 270 ctg gag aaa gtg tac gac cca aag aat gag gag gac gac atg cgg gag        864
Leu Glu Lys Val Tyr Asp Pro Lys Asn Glu Glu Asp Asp Met Arg Glu
        275                 280                 285 atg gag gag gag cga ctg cgc atg cgg gag cat gtg atg aag aat gtg        912
Met Glu Glu Glu Arg Leu Arg Met Arg Glu His Val Met Lys Asn Val
    290                 295                 300 gac acc aac cag gac cgc ctc gtg acc ctg gag gag ttc ctc gca tcc        960
Asp Thr Asn Gln Asp Arg Leu Val Thr Leu Glu Glu Phe Leu Ala Ser
305                 310                 315                 320 act cag agg aag gag ttt ggg gac acc ggg gag ggc tgg gag aca gtg       1008
Thr Gln Arg Lys Glu Phe Gly Asp Thr Gly Glu Gly Trp Glu Thr Val
                325                 330                 335 gag atg cac cct gcc tac acc gag gaa gag ctg agg cgc ttt gaa gag       1056
Glu Met His Pro Ala Tyr Thr Glu Glu Glu Leu Arg Arg Phe Glu Glu
            340                 345                 350 gag ctg gct gcc cgg gag gca gag ctg aat gcc aag gcc cag cgc ctc       1104
Glu Leu Ala Ala Arg Glu Ala Glu Leu Asn Ala Lys Ala Gln Arg Leu
        355                 360                 365 agc cag gag aca gag gct cta ggg cgg tcc cag ggc cgc ctg gag gcc       1152
Ser Gln Glu Thr Glu Ala Leu Gly Arg Ser Gln Gly Arg Leu Glu Ala
    370                 375                 380 cag aag aga gag ctg cag cag gct gtg ctg cac atg gag cag cgg aag       1200
Gln Lys Arg Glu Leu Gln Gln Ala Val Leu His Met Glu Gln Arg Lys
385                 390                 395                 400 cag cag cag cag cag cag caa ggc cac aag gcc ccg gct gcc cac cct       1248
Gln Gln Gln Gln Gln Gln Gln Gly His Lys Ala Pro Ala Ala His Pro
                405                 410                 415 gag ggg cag ctc aag ttc cac cca gac aca gac gat gta cct gtc cca       1296
Glu Gly Gln Leu Lys Phe His Pro Asp Thr Asp Asp Val Pro Val Pro
            420                 425                 430 gct cca gcc ggt gac cag aag gag gtg gac act tca gaa aag aaa ctt       1344
Ala Pro Ala Gly Asp Gln Lys Glu Val Asp Thr Ser Glu Lys Lys Leu
        435                 440                 445 ctc gag cgg ctc cct gag gtt gag gtg ccc cag cat ctg tga              1386
Leu Glu Arg Leu Pro Glu Val Glu Val Pro Gln His Leu
    450                 455                 460

<210> SEQ ID NO 84
<211> LENGTH: 461
<212> TYPE: PRT
<213> ORGANISM: Homo sapiens

<400> SEQUENCE: 84

Met Pro Pro Ser Gly Pro Arg Gly Thr Leu Leu Leu Pro Leu Leu
1               5                   10                  15

Leu Leu Leu Leu Leu Arg Ala Val Leu Ala Val Pro Leu Glu Arg Gly
                20                  25                  30
```

-continued

```
Ala Pro Asn Lys Glu Glu Thr Pro Ala Thr Glu Ser Pro Asp Thr Gly
        35                  40                  45

Leu Tyr Tyr His Arg Tyr Leu Gln Glu Val Ile Asp Val Leu Glu Thr
    50                  55                  60

Asp Gly His Phe Arg Glu Lys Leu Gln Ala Ala Asn Ala Glu Asp Ile
65                  70                  75                  80

Lys Ser Gly Lys Leu Ser Arg Glu Leu Asp Phe Val Ser His His Val
                85                  90                  95

Arg Thr Lys Leu Asp Glu Leu Lys Arg Gln Glu Val Ser Arg Leu Arg
            100                 105                 110

Met Leu Leu Lys Ala Lys Met Asp Ala Glu Gln Asp Pro Asn Val Gln
            115                 120                 125

Val Asp His Leu Asn Leu Leu Lys Gln Phe Glu His Leu Asp Pro Gln
        130                 135                 140

Asn Gln His Thr Phe Glu Ala Arg Asp Leu Glu Leu Ile Gln Thr
145                 150                 155                 160

Ala Thr Arg Asp Leu Ala Gln Tyr Asp Ala Ala His His Glu Glu Phe
                165                 170                 175

Lys Arg Tyr Glu Met Leu Lys Glu His Glu Arg Arg Tyr Leu Glu
            180                 185                 190

Ser Leu Gly Glu Glu Gln Arg Lys Glu Ala Glu Arg Lys Leu Glu Glu
        195                 200                 205

Gln Gln Arg Arg His Arg Glu His Pro Lys Val Asn Val Pro Gly Ser
    210                 215                 220

Gln Ala Gln Leu Lys Glu Val Trp Glu Glu Leu Asp Gly Leu Asp Pro
225                 230                 235                 240

Asn Arg Phe Asn Pro Lys Thr Phe Phe Ile Leu His Asp Ile Asn Ser
                245                 250                 255

Asp Gly Val Leu Asp Glu Gln Glu Leu Glu Ala Leu Phe Thr Lys Glu
            260                 265                 270

Leu Glu Lys Val Tyr Asp Pro Lys Asn Glu Glu Asp Asp Met Arg Glu
        275                 280                 285

Met Glu Glu Glu Arg Leu Arg Met Arg Glu His Val Met Lys Asn Val
    290                 295                 300

Asp Thr Asn Gln Asp Arg Leu Val Thr Leu Glu Glu Phe Leu Ala Ser
305                 310                 315                 320

Thr Gln Arg Lys Glu Phe Gly Asp Thr Gly Glu Gly Trp Glu Thr Val
                325                 330                 335

Glu Met His Pro Ala Tyr Thr Glu Glu Leu Arg Arg Phe Glu Glu
            340                 345                 350

Glu Leu Ala Ala Arg Glu Ala Glu Leu Asn Ala Lys Ala Gln Arg Leu
        355                 360                 365

Ser Gln Glu Thr Glu Ala Leu Gly Arg Ser Gln Gly Arg Leu Glu Ala
    370                 375                 380

Gln Lys Arg Glu Leu Gln Gln Ala Val Leu His Met Glu Gln Arg Lys
385                 390                 395                 400

Gln Gln Gln Gln Gln Gln Gly His Lys Ala Pro Ala His Pro
                405                 410                 415

Glu Gly Gln Leu Lys Phe His Pro Asp Thr Asp Val Pro Val Pro
            420                 425                 430

Ala Pro Ala Gly Asp Gln Lys Glu Val Asp Thr Ser Glu Lys Lys Leu
        435                 440                 445

Leu Glu Arg Leu Pro Glu Val Glu Val Pro Gln His Leu
```

-continued

```
          450                 455                 460

<210> SEQ ID NO 85
<211> LENGTH: 1308
<212> TYPE: DNA
<213> ORGANISM: Homo sapiens
<220> FEATURE:
<221> NAME/KEY: CDS
<222> LOCATION: (1)..(1308)

<400> SEQUENCE: 85 gtc ccc ctg gag cga ggg gcg ccc aac aag gag gag acc cct gcg act      48
Val Pro Leu Glu Arg Gly Ala Pro Asn Lys Glu Glu Thr Pro Ala Thr
1               5                   10                  15 gag agt ccc gac aca ggc ctg tac tac cac cgg tac ctc cag gag gtc      96
Glu Ser Pro Asp Thr Gly Leu Tyr Tyr His Arg Tyr Leu Gln Glu Val
                20                  25                  30 atc gat gta ctg gag acg gat ggg cat ttc cga gag aag ctg cag gct     144
Ile Asp Val Leu Glu Thr Asp Gly His Phe Arg Glu Lys Leu Gln Ala
            35                  40                  45 gcc aat gcg gag gac atc aag agc ggg aag ctg agc cga gag ctg gac     192
Ala Asn Ala Glu Asp Ile Lys Ser Gly Lys Leu Ser Arg Glu Leu Asp
        50                  55                  60 ttt gtc agc cac cac gtc cgc acc aag ctg gat gag ctc aag cga cag     240
Phe Val Ser His His Val Arg Thr Lys Leu Asp Glu Leu Lys Arg Gln
65                  70                  75                  80 gag gtg tca cgg ctg cgg atg ctg ctc aag gcc aag atg gac gcc gag     288
Glu Val Ser Arg Leu Arg Met Leu Leu Lys Ala Lys Met Asp Ala Glu
                85                  90                  95 cag gat ccc aat gta cag gtg gat cat ctg aat ctc ctg aaa cag ttt     336
Gln Asp Pro Asn Val Gln Val Asp His Leu Asn Leu Leu Lys Gln Phe
                100                 105                 110 gaa cac ctg gac cct cag aac cag cat aca ttc gag gcc cgc gac ctg     384
Glu His Leu Asp Pro Gln Asn Gln His Thr Phe Glu Ala Arg Asp Leu
            115                 120                 125 gag ctg ctg atc cag acg gcc acc cgg gac ctt gcc cag tac gac gca     432
Glu Leu Leu Ile Gln Thr Ala Thr Arg Asp Leu Ala Gln Tyr Asp Ala
        130                 135                 140 gcc cat cat gaa gag ttc aag cgc tac gag atg ctt aag gaa cac gag     480
Ala His His Glu Glu Phe Lys Arg Tyr Glu Met Leu Lys Glu His Glu
145                 150                 155                 160 aga cgg cgt tat ctg gag tca ctg gga gag gag cag aga aag gag gcg     528
Arg Arg Arg Tyr Leu Glu Ser Leu Gly Glu Glu Gln Arg Lys Glu Ala
                165                 170                 175 gag agg aag ctg gaa gag caa cag cgc cgg cac cgc gag cac cct aaa     576
Glu Arg Lys Leu Glu Glu Gln Gln Arg Arg His Arg Glu His Pro Lys
                180                 185                 190 gtc aac gtg cct ggc agc caa gcc cag ttg aag gag gtg tgg gag gag     624
Val Asn Val Pro Gly Ser Gln Ala Gln Leu Lys Glu Val Trp Glu Glu
            195                 200                 205 ctg gat gga ctg gac ccc aac agg ttt aac ccc aag acc ttc ttc ata     672
Leu Asp Gly Leu Asp Pro Asn Arg Phe Asn Pro Lys Thr Phe Phe Ile
        210                 215                 220 ctg cat gat atc aac agt gat ggt gtc ctg gat gag cag gag ctg gag     720
Leu His Asp Ile Asn Ser Asp Gly Val Leu Asp Glu Gln Glu Leu Glu
225                 230                 235                 240 gca ctc ttc acc aag gag ctg gag aaa gtg tac gac cca aag aat gag     768
Ala Leu Phe Thr Lys Glu Leu Glu Lys Val Tyr Asp Pro Lys Asn Glu
                245                 250                 255 gag gac gac atg cgg gag atg gag gag gag cga ctg cgc atg cgg gag     816
Glu Asp Asp Met Arg Glu Met Glu Glu Glu Arg Leu Arg Met Arg Glu
```

```
                    260                 265                 270
cat gtg atg aag aat gtg gac acc aac cag gac cgc ctc gtg acc ctg       864
His Val Met Lys Asn Val Asp Thr Asn Gln Asp Arg Leu Val Thr Leu
        275                 280                 285 gag gag ttc ctc gca tcc act cag agg aag gag ttt ggg gac acc ggg       912
Glu Glu Phe Leu Ala Ser Thr Gln Arg Lys Glu Phe Gly Asp Thr Gly
290                 295                 300 gag ggc tgg gag aca gtg gag atg cac cct gcc tac acc gag gaa gag       960
Glu Gly Trp Glu Thr Val Glu Met His Pro Ala Tyr Thr Glu Glu Glu
305                 310                 315                 320 ctg agg cgc ttt gaa gag gag ctg gct gcc cgg gag gca gag ctg aat      1008
Leu Arg Arg Phe Glu Glu Glu Leu Ala Ala Arg Glu Ala Glu Leu Asn
                325                 330                 335 gcc aag gcc cag cgc ctc agc cag gag aca gag gct cta ggg cgg tcc      1056
Ala Lys Ala Gln Arg Leu Ser Gln Glu Thr Glu Ala Leu Gly Arg Ser
        340                 345                 350 cag ggc cgc ctg gag gcc cag aag aga gag ctg cag cag gct gtg ctg      1104
Gln Gly Arg Leu Glu Ala Gln Lys Arg Glu Leu Gln Gln Ala Val Leu
355                 360                 365 cac atg gag cag cgg aag cag cag cag cag cag caa ggc cac aag           1152
His Met Glu Gln Arg Lys Gln Gln Gln Gln Gln Gln Gly His Lys
370                 375                 380 gcc ccg gct gcc cac cct gag ggg cag ctc aag ttc cac cca gac aca      1200
Ala Pro Ala Ala His Pro Glu Gly Gln Leu Lys Phe His Pro Asp Thr
385                 390                 395                 400 gac gat gta cct gtc cca gct cca gcc ggt gac cag aag gag gtg gac      1248
Asp Asp Val Pro Val Pro Ala Pro Ala Gly Asp Gln Lys Glu Val Asp
                405                 410                 415 act tca gaa aag aaa ctt ctc gag cgg ctc cct gag gtt gag gtg ccc      1296
Thr Ser Glu Lys Lys Leu Leu Glu Arg Leu Pro Glu Val Glu Val Pro
        420                 425                 430 cag cat ctg tga                                                       1308
Gln His Leu
        435

<210> SEQ ID NO 86
<211> LENGTH: 435
<212> TYPE: PRT
<213> ORGANISM: Homo sapiens

<400> SEQUENCE: 86

Val Pro Leu Glu Arg Gly Ala Pro Asn Lys Glu Glu Thr Pro Ala Thr
1               5                   10                  15

Glu Ser Pro Asp Thr Gly Leu Tyr Tyr His Arg Tyr Leu Gln Glu Val
                20                  25                  30

Ile Asp Val Leu Glu Thr Asp Gly His Phe Arg Glu Lys Leu Gln Ala
            35                  40                  45

Ala Asn Ala Glu Asp Ile Lys Ser Gly Lys Leu Ser Arg Glu Leu Asp
        50                  55                  60

Phe Val Ser His His Val Arg Thr Lys Leu Asp Glu Leu Lys Arg Gln
65                  70                  75                  80

Glu Val Ser Arg Leu Arg Met Leu Leu Lys Ala Lys Met Asp Ala Glu
                85                  90                  95

Gln Asp Pro Asn Val Gln Val Asp His Leu Asn Leu Leu Lys Gln Phe
            100                 105                 110

Glu His Leu Asp Pro Gln Asn Gln His Thr Phe Glu Ala Arg Asp Leu
        115                 120                 125

Glu Leu Leu Ile Gln Thr Ala Thr Arg Asp Leu Ala Gln Tyr Asp Ala
```

```
                    130                 135                 140
Ala His His Glu Glu Phe Lys Arg Tyr Glu Met Leu Lys Glu His Glu
145                 150                 155                 160

Arg Arg Arg Tyr Leu Glu Ser Leu Gly Glu Glu Gln Arg Lys Glu Ala
                165                 170                 175

Glu Arg Lys Leu Glu Glu Gln Gln Arg Arg His Arg Glu His Pro Lys
            180                 185                 190

Val Asn Val Pro Gly Ser Gln Ala Gln Leu Lys Glu Val Trp Glu Glu
                195                 200                 205

Leu Asp Gly Leu Asp Pro Asn Arg Phe Asn Pro Lys Thr Phe Phe Ile
210                 215                 220

Leu His Asp Ile Asn Ser Asp Gly Val Leu Asp Glu Gln Glu Leu Glu
225                 230                 235                 240

Ala Leu Phe Thr Lys Glu Leu Glu Lys Val Tyr Asp Pro Lys Asn Glu
                245                 250                 255

Glu Asp Asp Met Arg Glu Met Glu Glu Arg Leu Arg Met Arg Glu
            260                 265                 270

His Val Met Lys Asn Val Asp Thr Asn Gln Asp Arg Leu Val Thr Leu
            275                 280                 285

Glu Glu Phe Leu Ala Ser Thr Gln Arg Lys Glu Phe Gly Asp Thr Gly
290                 295                 300

Glu Gly Trp Glu Thr Val Glu Met His Pro Ala Tyr Thr Glu Glu Glu
305                 310                 315                 320

Leu Arg Arg Phe Glu Glu Glu Leu Ala Ala Arg Glu Ala Glu Leu Asn
                325                 330                 335

Ala Lys Ala Gln Arg Leu Ser Gln Glu Thr Glu Ala Leu Gly Arg Ser
            340                 345                 350

Gln Gly Arg Leu Glu Ala Gln Lys Arg Glu Leu Gln Gln Ala Val Leu
        355                 360                 365

His Met Glu Gln Arg Lys Gln Gln Gln Gln Gln Gln Gly His Lys
            370                 375                 380

Ala Pro Ala Ala His Pro Glu Gly Gln Leu Lys Phe His Pro Asp Thr
385                 390                 395                 400

Asp Asp Val Pro Val Pro Ala Pro Ala Gly Asp Gln Lys Glu Val Asp
                405                 410                 415

Thr Ser Glu Lys Lys Leu Leu Glu Arg Leu Pro Glu Val Glu Val Pro
            420                 425                 430

Gln His Leu
        435

<210> SEQ ID NO 87
<211> LENGTH: 1380
<212> TYPE: DNA
<213> ORGANISM: Rattus norvegicus
<220> FEATURE:
<221> NAME/KEY: CDS
<222> LOCATION: (1)..(1380)

<400> SEQUENCE: 87 atg cct acc tct gtg ccc cgc ggg gcg cct ttc ctt ctc cta cca cct    48
Met Pro Thr Ser Val Pro Arg Gly Ala Pro Phe Leu Leu Leu Pro Pro
1               5                   10                  15 tta ctg atg ctg tct gct gtg ctg gca gtg cct gtg gac cgc gca gca    96
Leu Leu Met Leu Ser Ala Val Leu Ala Val Pro Val Asp Arg Ala Ala
            20                  25                  30 cct cat cag gag gac aac cag gcc act gag acc ccg gac aca ggc ctg   144
```

```
                  -continued

Pro His Gln Glu Asp Asn Gln Ala Thr Glu Thr Pro Asp Thr Gly Leu
        35                  40                  45 tac tac cat cgg tac ctc cag gag gtc atc aac gtg cta gag aca gat      192
Tyr Tyr His Arg Tyr Leu Gln Glu Val Ile Asn Val Leu Glu Thr Asp
 50                  55                  60 ggg cac ttc cgg gag aag ctg caa gct gcc aac gct gag gac att aag      240
Gly His Phe Arg Glu Lys Leu Gln Ala Ala Asn Ala Glu Asp Ile Lys
65                  70                  75                  80 agt gga aag ctg agt caa gag ctg gac ttc gtc agc cac aac gtc cgc      288
Ser Gly Lys Leu Ser Gln Glu Leu Asp Phe Val Ser His Asn Val Arg
                 85                  90                  95 acc aag ctg gat gag ctc aag cga cag gag gta tca agg ctt cgg atg      336
Thr Lys Leu Asp Glu Leu Lys Arg Gln Glu Val Ser Arg Leu Arg Met
            100                 105                 110 ctg ctc aag gcc aag atg gat gca aag cag gag cct aac ttg cag gtg      384
Leu Leu Lys Ala Lys Met Asp Ala Lys Gln Glu Pro Asn Leu Gln Val
        115                 120                 125 gac cac atg aac ctt ctg aag cag ttt gaa cac ctg gac cct cag aac      432
Asp His Met Asn Leu Leu Lys Gln Phe Glu His Leu Asp Pro Gln Asn
    130                 135                 140 cag cac acg ttt gag gct cgg gac cta gag ctg ctg atc cag acg gcc      480
Gln His Thr Phe Glu Ala Arg Asp Leu Glu Leu Leu Ile Gln Thr Ala
145                 150                 155                 160 acc cga gac ctc gcc cag tat gac gct gca cac cat gaa gag ttc aaa      528
Thr Arg Asp Leu Ala Gln Tyr Asp Ala Ala His His Glu Glu Phe Lys
                165                 170                 175 cgc tac gag atg ctc aag gaa cat gag cga aga cgt tac ctg gag tct      576
Arg Tyr Glu Met Leu Lys Glu His Glu Arg Arg Arg Tyr Leu Glu Ser
            180                 185                 190 ctg gga gag gag cag cgg aag gag gct gag agg aag cta caa gag cag      624
Leu Gly Glu Glu Gln Arg Lys Glu Ala Glu Arg Lys Leu Gln Glu Gln
        195                 200                 205 cag cgc aga cac cgg gaa cac ccc aaa gtc aat gtt cct ggc agc caa      672
Gln Arg Arg His Arg Glu His Pro Lys Val Asn Val Pro Gly Ser Gln
    210                 215                 220 gcc cag ttg aag gag gtg tgg gag gag cta gat gga ttg gac ccc aac      720
Ala Gln Leu Lys Glu Val Trp Glu Glu Leu Asp Gly Leu Asp Pro Asn
225                 230                 235                 240 agg ttc aac ccc aag acc ttc ttc ata ctg cat gac atc aac agc gat      768
Arg Phe Asn Pro Lys Thr Phe Phe Ile Leu His Asp Ile Asn Ser Asp
                245                 250                 255 ggt gtc cta gat gag caa gaa ctg gaa gct ctg ttt acc aag gag ctg      816
Gly Val Leu Asp Glu Gln Glu Leu Glu Ala Leu Phe Thr Lys Glu Leu
            260                 265                 270 gag aag gtg tac gac ccg aag aac gag gag gac gac atg agg gag atg      864
Glu Lys Val Tyr Asp Pro Lys Asn Glu Glu Asp Asp Met Arg Glu Met
        275                 280                 285 gag gag gag cgg ctg cgc atg cgg gag cat gtg atg aag aac gtg gac      912
Glu Glu Glu Arg Leu Arg Met Arg Glu His Val Met Lys Asn Val Asp
    290                 295                 300 acc aac cag gac cga ctt gtg acc ctg gag gaa ttc ctg gca tcc aca      960
Thr Asn Gln Asp Arg Leu Val Thr Leu Glu Glu Phe Leu Ala Ser Thr
305                 310                 315                 320 cag agg aag gag ttt ggg gaa act gcg gag gga tgg aag aca gtg gaa      1008
Gln Arg Lys Glu Phe Gly Glu Thr Ala Glu Gly Trp Lys Thr Val Glu
                325                 330                 335 atg tat cca gcc tac aca gag gaa gag ctg aag cgt ttt gaa gag gag      1056
Met Tyr Pro Ala Tyr Thr Glu Glu Glu Leu Lys Arg Phe Glu Glu Glu
            340                 345                 350
```

```
ctt gct gcc cgg gag gct gag cta aat gcc aga gcc cag cgc ctc agc    1104
Leu Ala Ala Arg Glu Ala Glu Leu Asn Ala Arg Ala Gln Arg Leu Ser
        355                 360                 365 cag gag aca gag gcc ctg ggg cgc tcc cag gac cgc cta gag gct cag    1152
Gln Glu Thr Glu Ala Leu Gly Arg Ser Gln Asp Arg Leu Glu Ala Gln
370                 375                 380 aag aga gag ctg cag cag gcc gtt ctg cag atg gag caa agg aag cag    1200
Lys Arg Glu Leu Gln Gln Ala Val Leu Gln Met Glu Gln Arg Lys Gln
385                 390                 395                 400 caa cag caa gag cag agc gct ccg cct tcc caa cct gat ggg cag ctg    1248
Gln Gln Gln Glu Gln Ser Ala Pro Pro Ser Gln Pro Asp Gly Gln Leu
                405                 410                 415 cag ttc cgt gca gac aca ggg gat gct cct gtc cca gct cca gca ggt    1296
Gln Phe Arg Ala Asp Thr Gly Asp Ala Pro Val Pro Ala Pro Ala Gly
            420                 425                 430 gac cag aaa gac gtg cct gct tct gaa aag aag gtt cca gag cag ccc    1344
Asp Gln Lys Asp Val Pro Ala Ser Glu Lys Lys Val Pro Glu Gln Pro
        435                 440                 445 cct gtg ctg cca cag ctg gat tct cag cat tta taa                    1380
Pro Val Leu Pro Gln Leu Asp Ser Gln His Leu
    450                 455

<210> SEQ ID NO 88
<211> LENGTH: 459
<212> TYPE: PRT
<213> ORGANISM: Rattus norvegicus

<400> SEQUENCE: 88

Met Pro Thr Ser Val Pro Arg Gly Ala Pro Phe Leu Leu Leu Pro Pro
1               5                   10                  15

Leu Leu Met Leu Ser Ala Val Leu Ala Val Pro Val Asp Arg Ala Ala
            20                  25                  30

Pro His Gln Glu Asp Asn Gln Ala Thr Glu Thr Pro Asp Thr Gly Leu
        35                  40                  45

Tyr Tyr His Arg Tyr Leu Gln Glu Val Ile Asn Val Leu Glu Thr Asp
    50                  55                  60

Gly His Phe Arg Glu Lys Leu Gln Ala Ala Ala Glu Asp Ile Lys
65                  70                  75                  80

Ser Gly Lys Leu Ser Gln Glu Leu Asp Phe Val Ser His Asn Val Arg
                85                  90                  95

Thr Lys Leu Asp Glu Leu Lys Arg Gln Glu Val Ser Arg Leu Arg Met
            100                 105                 110

Leu Leu Lys Ala Lys Met Asp Ala Lys Gln Glu Pro Asn Leu Gln Val
        115                 120                 125

Asp His Met Asn Leu Leu Lys Gln Phe Glu His Leu Asp Pro Gln Asn
    130                 135                 140

Gln His Thr Phe Glu Ala Arg Asp Leu Glu Leu Leu Ile Gln Thr Ala
145                 150                 155                 160

Thr Arg Asp Leu Ala Gln Tyr Asp Ala Ala His Glu Glu Phe Lys
                165                 170                 175

Arg Tyr Glu Met Leu Lys Glu His Glu Arg Arg Tyr Leu Glu Ser
            180                 185                 190

Leu Gly Glu Glu Arg Lys Glu Ala Glu Arg Lys Leu Gln Glu Gln
        195                 200                 205

Gln Arg Arg His Arg Glu His Pro Lys Val Asn Val Pro Gly Ser Gln
    210                 215                 220

Ala Gln Leu Lys Glu Val Trp Glu Glu Leu Asp Gly Leu Asp Pro Asn
```

```
                225                 230                 235                 240
Arg Phe Asn Pro Lys Thr Phe Phe Ile Leu His Asp Ile Asn Ser Asp
                245                 250                 255

Gly Val Leu Asp Glu Gln Glu Leu Glu Ala Leu Phe Thr Lys Glu Leu
                260                 265                 270

Glu Lys Val Tyr Asp Pro Lys Asn Glu Glu Asp Met Arg Glu Met
            275                 280                 285

Glu Glu Glu Arg Leu Arg Met Arg Glu His Val Met Lys Asn Val Asp
            290                 295                 300

Thr Asn Gln Asp Arg Leu Val Thr Leu Glu Glu Phe Leu Ala Ser Thr
305                 310                 315                 320

Gln Arg Lys Glu Phe Gly Glu Thr Ala Glu Gly Trp Lys Thr Val Glu
                325                 330                 335

Met Tyr Pro Ala Tyr Thr Glu Glu Leu Lys Arg Phe Glu Glu Glu
            340                 345                 350

Leu Ala Ala Arg Glu Ala Glu Leu Asn Ala Arg Ala Gln Arg Leu Ser
                355                 360                 365

Gln Glu Thr Glu Ala Leu Gly Arg Ser Gln Asp Arg Leu Glu Ala Gln
            370                 375                 380

Lys Arg Glu Leu Gln Gln Ala Val Leu Gln Met Glu Gln Arg Lys Gln
385                 390                 395                 400

Gln Gln Gln Glu Gln Ser Ala Pro Ser Gln Pro Asp Gly Gln Leu
                405                 410                 415

Gln Phe Arg Ala Asp Thr Gly Asp Ala Pro Val Pro Ala Pro Ala Gly
                420                 425                 430

Asp Gln Lys Asp Val Pro Ala Ser Glu Lys Lys Val Pro Glu Gln Pro
                435                 440                 445

Pro Val Leu Pro Gln Leu Asp Ser Gln His Leu
        450                 455
```

```
<210> SEQ ID NO 89
<211> LENGTH: 1305
<212> TYPE: DNA
<213> ORGANISM: Rattus norvegicus
<220> FEATURE:
<221> NAME/KEY: CDS
<222> LOCATION: (1)..(1305)

<400> SEQUENCE: 89 gtg cct gtg gac cgc gca gca cct cat cag gag gac aac cag gcc act        48
Val Pro Val Asp Arg Ala Ala Pro His Gln Glu Asp Asn Gln Ala Thr
1               5                   10                  15 gag acc ccg gac aca ggc ctg tac tac cat cgg tac ctc cag gag gtc       96
Glu Thr Pro Asp Thr Gly Leu Tyr Tyr His Arg Tyr Leu Gln Glu Val
                20                  25                  30 atc aac gtg cta gag aca gat ggg cac ttc cgg gag aag ctg caa gct      144
Ile Asn Val Leu Glu Thr Asp Gly His Phe Arg Glu Lys Leu Gln Ala
            35                  40                  45 gcc aac gct gag gac att aag agt gga aag ctg agt caa gag ctg gac      192
Ala Asn Ala Glu Asp Ile Lys Ser Gly Lys Leu Ser Gln Glu Leu Asp
        50                  55                  60 ttc gtc agc cac aac gtc cgc acc aag ctg gat gag ctc aag cga cag      240
Phe Val Ser His Asn Val Arg Thr Lys Leu Asp Glu Leu Lys Arg Gln
65                  70                  75                  80 gag gta tca agg ctt cgg atg ctg ctc aag gcc aag atg gat gca aag      288
Glu Val Ser Arg Leu Arg Met Leu Leu Lys Ala Lys Met Asp Ala Lys
                85                  90                  95
```

```
cag gag cct aac ttg cag gtg gac cac atg aac ctt ctg aag cag ttt      336
Gln Glu Pro Asn Leu Gln Val Asp His Met Asn Leu Leu Lys Gln Phe
            100                 105                 110 gaa cac ctg gac cct cag aac cag cac acg ttt gag gct cgg gac cta      384
Glu His Leu Asp Pro Gln Asn Gln His Thr Phe Glu Ala Arg Asp Leu
        115                 120                 125 gag ctg ctg atc cag acg gcc acc cga gac ctc gcc cag tat gac gct      432
Glu Leu Leu Ile Gln Thr Ala Thr Arg Asp Leu Ala Gln Tyr Asp Ala
    130                 135                 140 gca cac cat gaa gag ttc aaa cgc tac gag atg ctc aag gaa cat gag      480
Ala His His Glu Glu Phe Lys Arg Tyr Glu Met Leu Lys Glu His Glu
145                 150                 155                 160 cga aga cgt tac ctg gag tct ctg gga gag gag cag cgg aag gag gct      528
Arg Arg Arg Tyr Leu Glu Ser Leu Gly Glu Glu Gln Arg Lys Glu Ala
                165                 170                 175 gag agg aag cta caa gag cag cag cgc aga cac cgg gaa cac ccc aaa      576
Glu Arg Lys Leu Gln Glu Gln Gln Arg Arg His Arg Glu His Pro Lys
            180                 185                 190 gtc aat gtt cct ggc agc caa gcc cag ttg aag gag gtg tgg gag gag      624
Val Asn Val Pro Gly Ser Gln Ala Gln Leu Lys Glu Val Trp Glu Glu
        195                 200                 205 cta gat gga ttg gac ccc aac agg ttc aac ccc aag acc ttc ttc ata      672
Leu Asp Gly Leu Asp Pro Asn Arg Phe Asn Pro Lys Thr Phe Phe Ile
    210                 215                 220 ctg cat gac atc aac agc gat ggt gtc cta gat gag caa gaa ctg gaa      720
Leu His Asp Ile Asn Ser Asp Gly Val Leu Asp Glu Gln Glu Leu Glu
225                 230                 235                 240 gct ctg ttt acc aag gag ctg gag aag gtg tac gac ccg aag aac gag      768
Ala Leu Phe Thr Lys Glu Leu Glu Lys Val Tyr Asp Pro Lys Asn Glu
                245                 250                 255 gag gac gac atg agg gag atg gag gag gag cgg ctg cgc atg cgg gag      816
Glu Asp Asp Met Arg Glu Met Glu Glu Glu Arg Leu Arg Met Arg Glu
            260                 265                 270 cat gtg atg aag aac gtg gac acc aac cag gac cga ctt gtg acc ctg      864
His Val Met Lys Asn Val Asp Thr Asn Gln Asp Arg Leu Val Thr Leu
        275                 280                 285 gag gaa ttc ctg gca tcc aca cag agg aag gag ttt ggg gaa act gcg      912
Glu Glu Phe Leu Ala Ser Thr Gln Arg Lys Glu Phe Gly Glu Thr Ala
    290                 295                 300 gag gga tgg aag aca gtg gaa atg tat cca gcc tac aca gag gaa gag      960
Glu Gly Trp Lys Thr Val Glu Met Tyr Pro Ala Tyr Thr Glu Glu Glu
305                 310                 315                 320 ctg aag cgt ttt gaa gag gag ctt gct gcc cgg gag gct gag cta aat     1008
Leu Lys Arg Phe Glu Glu Glu Leu Ala Ala Arg Glu Ala Glu Leu Asn
                325                 330                 335 gcc aga gcc cag cgc ctc agc cag gag aca gag gcc ctg ggg cgc tcc     1056
Ala Arg Ala Gln Arg Leu Ser Gln Glu Thr Glu Ala Leu Gly Arg Ser
            340                 345                 350 cag gac cgc cta gag gct cag aag aga gag ctg cag cag gcc gtt ctg     1104
Gln Asp Arg Leu Glu Ala Gln Lys Arg Glu Leu Gln Gln Ala Val Leu
        355                 360                 365 cag atg gag caa agg aag cag caa cag caa gag cag agc gct ccg cct     1152
Gln Met Glu Gln Arg Lys Gln Gln Gln Glu Gln Ser Ala Pro Pro
    370                 375                 380 tcc caa cct gat ggg cag ctg cag ttc cgt gca gac aca ggg gat gct     1200
Ser Gln Pro Asp Gly Gln Leu Gln Phe Arg Ala Asp Thr Gly Asp Ala
385                 390                 395                 400 cct gtc cca gct cca gca ggt gac cag aaa gac gtg cct gct tct gaa     1248
Pro Val Pro Ala Pro Ala Gly Asp Gln Lys Asp Val Pro Ala Ser Glu
                405                 410                 415
```

```
aag aag gtt cca gag cag ccc cct gtg ctg cca cag ctg gat tct cag    1296
Lys Lys Val Pro Glu Gln Pro Pro Val Leu Pro Gln Leu Asp Ser Gln
        420                 425                 430 cat tta taa                                                         1305
His Leu
```

<210> SEQ ID NO 90
<211> LENGTH: 434
<212> TYPE: PRT
<213> ORGANISM: Rattus norvegicus

<400> SEQUENCE: 90

```
Val Pro Val Asp Arg Ala Ala Pro His Gln Glu Asp Asn Gln Ala Thr
 1               5                  10                  15

Glu Thr Pro Asp Thr Gly Leu Tyr Tyr His Arg Tyr Leu Gln Glu Val
            20                  25                  30

Ile Asn Val Leu Glu Thr Asp Gly His Phe Arg Glu Lys Leu Gln Ala
        35                  40                  45

Ala Asn Ala Glu Asp Ile Lys Ser Gly Lys Leu Ser Gln Glu Leu Asp
 50                  55                  60

Phe Val Ser His Asn Val Arg Thr Lys Leu Asp Glu Leu Lys Arg Gln
65                  70                  75                  80

Glu Val Ser Arg Leu Arg Met Leu Leu Lys Ala Lys Met Asp Ala Lys
                85                  90                  95

Gln Glu Pro Asn Leu Gln Val Asp His Met Asn Leu Leu Lys Gln Phe
            100                 105                 110

Glu His Leu Asp Pro Gln Asn Gln His Thr Phe Glu Ala Arg Asp Leu
        115                 120                 125

Glu Leu Leu Ile Gln Thr Ala Thr Arg Asp Leu Ala Gln Tyr Asp Ala
130                 135                 140

Ala His His Glu Glu Phe Lys Arg Tyr Glu Met Leu Lys Glu His Glu
145                 150                 155                 160

Arg Arg Arg Tyr Leu Glu Ser Leu Gly Glu Glu Gln Arg Lys Glu Ala
                165                 170                 175

Glu Arg Lys Leu Gln Glu Gln Gln Arg Arg His Arg Glu His Pro Lys
            180                 185                 190

Val Asn Val Pro Gly Ser Gln Ala Gln Leu Lys Glu Val Trp Glu Glu
        195                 200                 205

Leu Asp Gly Leu Asp Pro Asn Arg Phe Asn Pro Lys Thr Phe Phe Ile
210                 215                 220

Leu His Asp Ile Asn Ser Asp Gly Val Leu Asp Glu Gln Glu Leu Glu
225                 230                 235                 240

Ala Leu Phe Thr Lys Glu Leu Glu Lys Val Tyr Asp Pro Lys Asn Glu
                245                 250                 255

Glu Asp Asp Met Arg Glu Met Glu Glu Glu Arg Leu Arg Met Arg Glu
            260                 265                 270

His Val Met Lys Asn Val Asp Thr Asn Gln Asp Arg Leu Val Thr Leu
        275                 280                 285

Glu Glu Phe Leu Ala Ser Thr Gln Arg Lys Glu Phe Gly Glu Thr Ala
290                 295                 300

Glu Gly Trp Lys Thr Val Glu Met Tyr Pro Ala Tyr Thr Glu Glu Glu
305                 310                 315                 320

Leu Lys Arg Phe Glu Glu Glu Leu Ala Ala Arg Glu Ala Glu Leu Asn
                325                 330                 335
```

```
Ala Arg Ala Gln Arg Leu Ser Gln Glu Thr Glu Ala Leu Gly Arg Ser
                340                 345                 350

Gln Asp Arg Leu Glu Ala Gln Lys Arg Glu Leu Gln Gln Ala Val Leu
            355                 360                 365

Gln Met Glu Gln Arg Lys Gln Gln Gln Glu Gln Ser Ala Pro Pro
        370                 375                 380

Ser Gln Pro Asp Gly Gln Leu Gln Phe Arg Ala Asp Thr Gly Asp Ala
385                 390                 395                 400

Pro Val Pro Ala Pro Ala Gly Asp Gln Lys Asp Val Pro Ala Ser Glu
                405                 410                 415

Lys Lys Val Pro Glu Gln Pro Pro Val Leu Pro Gln Leu Asp Ser Gln
                420                 425                 430

His Leu

<210> SEQ ID NO 91
<211> LENGTH: 1380
<212> TYPE: DNA
<213> ORGANISM: Mus musculus
<220> FEATURE:
<221> NAME/KEY: CDS
<222> LOCATION: (1)..(1380)

<400> SEQUENCE: 91 atg cct acc tcg gtg ccc cgc ggg gcc cct ttt ctt ctc cta cca cct      48
Met Pro Thr Ser Val Pro Arg Gly Ala Pro Phe Leu Leu Leu Pro Pro
1               5                   10                  15 cta ctg atg ctg tct gct gtg ctg gca gtg ccc gtg gac cgc gca gca      96
Leu Leu Met Leu Ser Ala Val Leu Ala Val Pro Val Asp Arg Ala Ala
            20                  25                  30 cct cct cag gag gac agc cag gcc act gag acc ccg gac acg ggc ctg     144
Pro Pro Gln Glu Asp Ser Gln Ala Thr Glu Thr Pro Asp Thr Gly Leu
        35                  40                  45 tac tac cac cgg tac ctc cag gag gtc atc aac gtg cta gag aca gat     192
Tyr Tyr His Arg Tyr Leu Gln Glu Val Ile Asn Val Leu Glu Thr Asp
    50                  55                  60 ggg cac ttc cgg gag aag ctg cag gct gcc aac gct gag gac att aag     240
Gly His Phe Arg Glu Lys Leu Gln Ala Ala Asn Ala Glu Asp Ile Lys
65                  70                  75                  80 agt gga aag ctg agc caa gag ctg gac ttc gtc agc cac aac gtc cga     288
Ser Gly Lys Leu Ser Gln Glu Leu Asp Phe Val Ser His Asn Val Arg
                85                  90                  95 acc aag ctg gat gag ctc aag cga cag gag gtg tcg agg ctg cgg atg     336
Thr Lys Leu Asp Glu Leu Lys Arg Gln Glu Val Ser Arg Leu Arg Met
            100                 105                 110 ctg ctc aag gcc aag atg gat gca aag cag gag ccc aac ttg cag gtg     384
Leu Leu Lys Ala Lys Met Asp Ala Lys Gln Glu Pro Asn Leu Gln Val
        115                 120                 125 gac cac atg aac ctc ctg aag cag ttt gag cac ctg gac cct cag aac     432
Asp His Met Asn Leu Leu Lys Gln Phe Glu His Leu Asp Pro Gln Asn
    130                 135                 140 cag cac acg ttt gag gct cgg gac cta gag ctg ctg atc cag acg gcc     480
Gln His Thr Phe Glu Ala Arg Asp Leu Glu Leu Leu Ile Gln Thr Ala
145                 150                 155                 160 acc cga gac ctc gcc cag tat gac gct gca cac cat gaa gag ttc aaa     528
Thr Arg Asp Leu Ala Gln Tyr Asp Ala Ala His His Glu Glu Phe Lys
                165                 170                 175 cgc tac gag atg ctc aag gaa cat gag agg aga cga tac ctg gag tct     576
Arg Tyr Glu Met Leu Lys Glu His Glu Arg Arg Arg Tyr Leu Glu Ser
            180                 185                 190
```

```
ctg gga gag gag cag cgg aag gag gcc gag agg aag ctc caa gag caa        624
Leu Gly Glu Glu Gln Arg Lys Glu Ala Glu Arg Lys Leu Gln Glu Gln
            195                 200                 205 cag cgc aga cac cgg gaa cac ccc aaa gtc aat gtt cct ggc agc caa        672
Gln Arg Arg His Arg Glu His Pro Lys Val Asn Val Pro Gly Ser Gln
    210                 215                 220 gcc cag ttg aag gag gtg tgg gag gag ttg gat gga ttg gac ccc aac        720
Ala Gln Leu Lys Glu Val Trp Glu Glu Leu Asp Gly Leu Asp Pro Asn
225                 230                 235                 240 agg ttc aac ccc aag acc ttc ttc ata ctg cat gac atc aac agt gat        768
Arg Phe Asn Pro Lys Thr Phe Phe Ile Leu His Asp Ile Asn Ser Asp
                245                 250                 255 ggt gtc cta gat gag caa gaa ctg gaa gct ctc ttt acc aag gag ctg        816
Gly Val Leu Asp Glu Gln Glu Leu Glu Ala Leu Phe Thr Lys Glu Leu
            260                 265                 270 gag aag gtg tat gac ccg aag aat gag gag gat gac atg aga gag atg        864
Glu Lys Val Tyr Asp Pro Lys Asn Glu Glu Asp Asp Met Arg Glu Met
        275                 280                 285 gag gaa gaa cgg ctt cgc atg cgg gag cac gtg atg aag aat gtg gac        912
Glu Glu Glu Arg Leu Arg Met Arg Glu His Val Met Lys Asn Val Asp
290                 295                 300 acc aac cag gac cgg ctt gtg acc ctg gag gag ttc ctg gca tcc acc        960
Thr Asn Gln Asp Arg Leu Val Thr Leu Glu Glu Phe Leu Ala Ser Thr
305                 310                 315                 320 cag agg aag gag ttc ggg gac act ggg gag ggg tgg aag aca gtg gaa       1008
Gln Arg Lys Glu Phe Gly Asp Thr Gly Glu Gly Trp Lys Thr Val Glu
                325                 330                 335 atg tcc cca gcc tac aca gag gag gag ctg aag cgt ttt gaa gag gag       1056
Met Ser Pro Ala Tyr Thr Glu Glu Glu Leu Lys Arg Phe Glu Glu Glu
            340                 345                 350 ctg gct gcc cgg gaa gct gag ctg aat gcc agg gcc cag cgc ctc agc       1104
Leu Ala Ala Arg Glu Ala Glu Leu Asn Ala Arg Ala Gln Arg Leu Ser
        355                 360                 365 cag gag aca gag gcc ctg ggg cgc tcc cag gac cgc ctg gag gca cag       1152
Gln Glu Thr Glu Ala Leu Gly Arg Ser Gln Asp Arg Leu Glu Ala Gln
370                 375                 380 aag aga gag ctg cag cag gct gtt ctg cag atg gag cag agg aag cag       1200
Lys Arg Glu Leu Gln Gln Ala Val Leu Gln Met Glu Gln Arg Lys Gln
385                 390                 395                 400 caa ctg caa gaa cag agc gct ccg cct tcc aaa cct gac ggg cag ctg       1248
Gln Leu Gln Glu Gln Ser Ala Pro Pro Ser Lys Pro Asp Gly Gln Leu
                405                 410                 415 cag ttc cgt gca gac aca gat gac gct cct gtc cca gct cca gca ggt       1296
Gln Phe Arg Ala Asp Thr Asp Asp Ala Pro Val Pro Ala Pro Ala Gly
            420                 425                 430 gac cag aaa gat gtg cct gct tct gag aag aag gtc cca gag cag ccc       1344
Asp Gln Lys Asp Val Pro Ala Ser Glu Lys Lys Val Pro Glu Gln Pro
        435                 440                 445 cct gag ctg cca cag ctg gat tcc cag cat tta taa                        1380
Pro Glu Leu Pro Gln Leu Asp Ser Gln His Leu
            450                 455
```

<210> SEQ ID NO 92
<211> LENGTH: 459
<212> TYPE: PRT
<213> ORGANISM: Mus musculus

<400> SEQUENCE: 92

```
Met Pro Thr Ser Val Pro Arg Gly Ala Pro Phe Leu Leu Pro Pro
1               5                   10                  15
```

-continued

```
Leu Leu Met Leu Ser Ala Val Leu Ala Val Pro Val Asp Arg Ala Ala
         20                  25                  30

Pro Pro Gln Glu Asp Ser Gln Ala Thr Glu Thr Pro Asp Thr Gly Leu
         35                  40                  45

Tyr Tyr His Arg Tyr Leu Gln Glu Val Ile Asn Val Leu Glu Thr Asp
 50                  55                  60

Gly His Phe Arg Glu Lys Leu Gln Ala Ala Asn Ala Glu Asp Ile Lys
 65                  70                  75                  80

Ser Gly Lys Leu Ser Gln Glu Leu Asp Phe Val Ser His Asn Val Arg
                 85                  90                  95

Thr Lys Leu Asp Glu Leu Lys Arg Gln Glu Val Ser Arg Leu Arg Met
            100                 105                 110

Leu Leu Lys Ala Lys Met Asp Ala Lys Gln Glu Pro Asn Leu Gln Val
            115                 120                 125

Asp His Met Asn Leu Leu Lys Gln Phe Glu His Leu Asp Pro Gln Asn
        130                 135                 140

Gln His Thr Phe Glu Ala Arg Asp Leu Glu Leu Leu Ile Gln Thr Ala
145                 150                 155                 160

Thr Arg Asp Leu Ala Gln Tyr Asp Ala Ala His His Glu Glu Phe Lys
                165                 170                 175

Arg Tyr Glu Met Leu Lys Glu His Glu Arg Arg Tyr Leu Glu Ser
            180                 185                 190

Leu Gly Glu Glu Gln Arg Lys Glu Ala Glu Arg Lys Leu Gln Glu Gln
            195                 200                 205

Gln Arg Arg His Arg Glu His Pro Lys Val Asn Val Pro Gly Ser Gln
        210                 215                 220

Ala Gln Leu Lys Glu Val Trp Glu Glu Leu Asp Gly Leu Asp Pro Asn
225                 230                 235                 240

Arg Phe Asn Pro Lys Thr Phe Phe Ile Leu His Asp Ile Asn Ser Asp
                245                 250                 255

Gly Val Leu Asp Glu Gln Glu Leu Glu Ala Leu Phe Thr Lys Glu Leu
            260                 265                 270

Glu Lys Val Tyr Asp Pro Lys Asn Glu Glu Asp Asp Met Arg Glu Met
            275                 280                 285

Glu Glu Glu Arg Leu Arg Met Arg Glu His Val Met Lys Asn Val Asp
        290                 295                 300

Thr Asn Gln Asp Arg Leu Val Thr Leu Glu Glu Phe Leu Ala Ser Thr
305                 310                 315                 320

Gln Arg Lys Glu Phe Gly Asp Thr Gly Glu Gly Trp Lys Thr Val Glu
                325                 330                 335

Met Ser Pro Ala Tyr Thr Glu Glu Leu Lys Arg Phe Glu Glu Glu
            340                 345                 350

Leu Ala Ala Arg Glu Ala Glu Leu Asn Ala Arg Ala Gln Arg Leu Ser
            355                 360                 365

Gln Glu Thr Glu Ala Leu Gly Arg Ser Gln Asp Arg Leu Glu Ala Gln
        370                 375                 380

Lys Arg Glu Leu Gln Gln Ala Val Leu Gln Met Glu Gln Arg Lys Gln
385                 390                 395                 400

Gln Leu Gln Glu Gln Ser Ala Pro Pro Ser Lys Pro Asp Gly Gln Leu
                405                 410                 415

Gln Phe Arg Ala Asp Thr Asp Ala Pro Val Pro Ala Pro Ala Gly
            420                 425                 430

Asp Gln Lys Asp Val Pro Ala Ser Glu Lys Lys Val Pro Glu Gln Pro
```

```
                435                 440                 445
Pro Glu Leu Pro Gln Leu Asp Ser Gln His Leu
    450                 455

<210> SEQ ID NO 93
<211> LENGTH: 1305
<212> TYPE: DNA
<213> ORGANISM: Mus musculus
<220> FEATURE:
<221> NAME/KEY: CDS
<222> LOCATION: (1)..(1305)

<400> SEQUENCE: 93 gtg ccc gtg gac cgc gca gca cct cct cag gag gac agc cag gcc act      48
Val Pro Val Asp Arg Ala Ala Pro Pro Gln Glu Asp Ser Gln Ala Thr
1               5                   10                  15 gag acc ccg gac acg ggc ctg tac tac cac cgg tac ctc cag gag gtc      96
Glu Thr Pro Asp Thr Gly Leu Tyr Tyr His Arg Tyr Leu Gln Glu Val
            20                  25                  30 atc aac gtg cta gag aca gat ggg cac ttc cgg gag aag ctg cag gct     144
Ile Asn Val Leu Glu Thr Asp Gly His Phe Arg Glu Lys Leu Gln Ala
        35                  40                  45 gcc aac gct gag gac att aag agt gga aag ctg agc caa gag ctg gac     192
Ala Asn Ala Glu Asp Ile Lys Ser Gly Lys Leu Ser Gln Glu Leu Asp
    50                  55                  60 ttc gtc agc cac aac gtc cga acc aag ctg gat gag ctc aag cga cag     240
Phe Val Ser His Asn Val Arg Thr Lys Leu Asp Glu Leu Lys Arg Gln
65                  70                  75                  80 gag gtg tcg agg ctg cgg atg ctg ctc aag gcc aag atg gat gca aag     288
Glu Val Ser Arg Leu Arg Met Leu Leu Lys Ala Lys Met Asp Ala Lys
                85                  90                  95 cag gag ccc aac ttg cag gtg gac cac atg aac ctc ctg aag cag ttt     336
Gln Glu Pro Asn Leu Gln Val Asp His Met Asn Leu Leu Lys Gln Phe
            100                 105                 110 gag cac ctg gac cct cag aac cag cac acg ttt gag gct cgg gac cta     384
Glu His Leu Asp Pro Gln Asn Gln His Thr Phe Glu Ala Arg Asp Leu
        115                 120                 125 gag ctg ctg atc cag acg gcc acc cga gac ctc gcc cag tat gac gct     432
Glu Leu Leu Ile Gln Thr Ala Thr Arg Asp Leu Ala Gln Tyr Asp Ala
    130                 135                 140 gca cac cat gaa gag ttc aaa cgc tac gag atg ctc aag gaa cat gag     480
Ala His His Glu Glu Phe Lys Arg Tyr Glu Met Leu Lys Glu His Glu
145                 150                 155                 160 agg aga cga tac ctg gag tct ctg gga gag gag cag cgg aag gag gcc     528
Arg Arg Arg Tyr Leu Glu Ser Leu Gly Glu Glu Gln Arg Lys Glu Ala
                165                 170                 175 gag agg aag ctc caa gag caa cag cgc aga cac cgg gaa cac ccc aaa     576
Glu Arg Lys Leu Gln Glu Gln Gln Arg Arg His Arg Glu His Pro Lys
            180                 185                 190 gtc aat gtt cct ggc agc caa gcc cag ttg aag gag gtg tgg gag gag     624
Val Asn Val Pro Gly Ser Gln Ala Gln Leu Lys Glu Val Trp Glu Glu
        195                 200                 205 ttg gat gga ttg gac ccc aac agg ttc aac ccc aag acc ttc ttc ata     672
Leu Asp Gly Leu Asp Pro Asn Arg Phe Asn Pro Lys Thr Phe Phe Ile
    210                 215                 220 ctg cat gac atc aac agt gat ggt gtc cta gat gag caa gaa ctg gaa     720
Leu His Asp Ile Asn Ser Asp Gly Val Leu Asp Glu Gln Glu Leu Glu
225                 230                 235                 240 gct ctc ttt acc aag gag ctg gag aag gtg tat gac ccg aag aat gag     768
Ala Leu Phe Thr Lys Glu Leu Glu Lys Val Tyr Asp Pro Lys Asn Glu
                245                 250                 255
```

```
gag gat gac atg aga gag atg gag gaa gaa cgg ctt cgc atg cgg gag      816
Glu Asp Asp Met Arg Glu Met Glu Glu Glu Arg Leu Arg Met Arg Glu
            260                 265                 270 cac gtg atg aag aat gtg gac acc aac cag gac cgg ctt gtg acc ctg      864
His Val Met Lys Asn Val Asp Thr Asn Gln Asp Arg Leu Val Thr Leu
        275                 280                 285 gag gag ttc ctg gca tcc acc cag agg aag gag ttc ggg gac act ggg      912
Glu Glu Phe Leu Ala Ser Thr Gln Arg Lys Glu Phe Gly Asp Thr Gly
    290                 295                 300 gag ggg tgg aag aca gtg gaa atg tcc cca gcc tac aca gag gag gag      960
Glu Gly Trp Lys Thr Val Glu Met Ser Pro Ala Tyr Thr Glu Glu Glu
305                 310                 315                 320 ctg aag cgt ttt gaa gag gag ctg gct gcc cgg gaa gct gag ctg aat     1008
Leu Lys Arg Phe Glu Glu Glu Leu Ala Ala Arg Glu Ala Glu Leu Asn
                325                 330                 335 gcc agg gcc cag cgc ctc agc cag gag aca gag gcc ctg ggg cgc tcc     1056
Ala Arg Ala Gln Arg Leu Ser Gln Glu Thr Glu Ala Leu Gly Arg Ser
            340                 345                 350 cag gac cgc ctg gag gca cag aag aga gag ctg cag cag gct gtt ctg     1104
Gln Asp Arg Leu Glu Ala Gln Lys Arg Glu Leu Gln Gln Ala Val Leu
        355                 360                 365 cag atg gag cag agg aag cag caa ctg caa gaa cag agc gct ccg cct     1152
Gln Met Glu Gln Arg Lys Gln Gln Leu Gln Gln Ser Ala Pro Pro
    370                 375                 380 tcc aaa cct gac ggg cag ctg cag ttc cgt gca gac aca gat gac gct     1200
Ser Lys Pro Asp Gly Gln Leu Gln Phe Arg Ala Asp Thr Asp Asp Ala
385                 390                 395                 400 cct gtc cca gct cca gca ggt gac cag aaa gat gtg cct gct tct gag     1248
Pro Val Pro Ala Pro Ala Gly Asp Gln Lys Asp Val Pro Ala Ser Glu
                405                 410                 415 aag aag gtc cca gag cag ccc cct gag ctg cca cag ctg gat tcc cag     1296
Lys Lys Val Pro Glu Gln Pro Pro Glu Leu Pro Gln Leu Asp Ser Gln
            420                 425                 430 cat tta taa                                                         1305
His Leu
```

<210> SEQ ID NO 94
<211> LENGTH: 434
<212> TYPE: PRT
<213> ORGANISM: Mus musculus

<400> SEQUENCE: 94

```
Val Pro Val Asp Arg Ala Pro Pro Gln Glu Asp Ser Gln Ala Thr
1               5                   10                  15

Glu Thr Pro Asp Thr Gly Leu Tyr Tyr His Arg Tyr Leu Gln Glu Val
            20                  25                  30

Ile Asn Val Leu Glu Thr Asp Gly His Phe Arg Glu Lys Leu Gln Ala
        35                  40                  45

Ala Asn Ala Glu Asp Ile Lys Ser Gly Lys Leu Ser Gln Glu Leu Asp
    50                  55                  60

Phe Val Ser His Asn Val Arg Thr Lys Leu Asp Glu Leu Lys Arg Gln
65                  70                  75                  80

Glu Val Ser Arg Leu Arg Met Leu Leu Lys Ala Lys Met Asp Ala Lys
                85                  90                  95

Gln Glu Pro Asn Leu Gln Val Asp His Met Asn Leu Leu Lys Gln Phe
            100                 105                 110

Glu His Leu Asp Pro Gln Asn Gln His Thr Phe Glu Ala Arg Asp Leu
        115                 120                 125
```

```
Glu Leu Leu Ile Gln Thr Ala Thr Arg Asp Leu Ala Gln Tyr Asp Ala
        130                 135                 140

Ala His His Glu Glu Phe Lys Arg Tyr Glu Met Leu Lys Glu His Glu
145                 150                 155                 160

Arg Arg Arg Tyr Leu Glu Ser Leu Gly Glu Glu Gln Arg Lys Glu Ala
                165                 170                 175

Glu Arg Lys Leu Gln Glu Gln Arg His Arg Glu His Pro Lys
            180                 185                 190

Val Asn Val Pro Gly Ser Gln Ala Gln Leu Lys Glu Val Trp Glu Glu
            195                 200                 205

Leu Asp Gly Leu Asp Pro Asn Arg Phe Asn Pro Lys Thr Phe Phe Ile
210                 215                 220

Leu His Asp Ile Asn Ser Asp Gly Val Leu Asp Glu Gln Glu Leu Glu
225                 230                 235                 240

Ala Leu Phe Thr Lys Glu Leu Glu Lys Val Tyr Asp Pro Lys Asn Glu
                245                 250                 255

Glu Asp Asp Met Arg Glu Met Glu Glu Glu Arg Leu Arg Met Arg Glu
            260                 265                 270

His Val Met Lys Asn Val Asp Thr Asn Gln Asp Arg Leu Val Thr Leu
            275                 280                 285

Glu Glu Phe Leu Ala Ser Thr Gln Arg Lys Glu Phe Gly Asp Thr Gly
            290                 295                 300

Glu Gly Trp Lys Thr Val Glu Met Ser Pro Ala Tyr Thr Glu Glu Glu
305                 310                 315                 320

Leu Lys Arg Phe Glu Glu Glu Leu Ala Ala Arg Glu Ala Glu Leu Asn
                325                 330                 335

Ala Arg Ala Gln Arg Leu Ser Gln Glu Thr Glu Ala Leu Gly Arg Ser
            340                 345                 350

Gln Asp Arg Leu Glu Ala Gln Lys Arg Glu Leu Gln Gln Ala Val Leu
            355                 360                 365

Gln Met Glu Gln Arg Lys Gln Gln Leu Gln Glu Gln Ser Ala Pro Pro
            370                 375                 380

Ser Lys Pro Asp Gly Gln Leu Gln Phe Arg Ala Asp Thr Asp Asp Ala
385                 390                 395                 400

Pro Val Pro Ala Pro Ala Gly Asp Gln Lys Asp Val Pro Ala Ser Glu
                405                 410                 415

Lys Lys Val Pro Glu Gln Pro Pro Glu Leu Pro Gln Leu Asp Ser Gln
            420                 425                 430

His Leu

<210> SEQ ID NO 95
<211> LENGTH: 77
<212> TYPE: PRT
<213> ORGANISM: Homo sapiens

<400> SEQUENCE: 95

Val Pro Leu Glu Arg Gly Ala Pro Asn Lys Glu Glu Thr Pro Ala Thr
1               5                   10                  15

Glu Ser Pro Asp Thr Gly Leu Tyr Tyr His Arg Tyr Leu Gln Glu Val
                20                  25                  30

Ile Asp Val Leu Glu Thr Asp Gly His Phe Arg Glu Lys Leu Gln Ala
            35                  40                  45

Ala Asn Ala Glu Asp Ile Lys Ser Gly Lys Leu Ser Arg Glu Leu Asp
        50                  55                  60
```

```
Phe Val Ser His His Val Arg Thr Lys Leu Asp Glu Leu
65                  70                  75

<210> SEQ ID NO 96
<211> LENGTH: 77
<212> TYPE: PRT
<213> ORGANISM: Rattus norvegicus

<400> SEQUENCE: 96

Val Pro Val Asp Arg Ala Ala Pro His Gln Glu Asp Asn Gln Ala Thr
1               5                   10                  15

Glu Thr Pro Asp Thr Gly Leu Tyr Tyr His Arg Tyr Leu Gln Glu Val
            20                  25                  30

Ile Asn Val Leu Glu Thr Asp Gly His Phe Arg Glu Lys Leu Gln Ala
        35                  40                  45

Ala Asn Ala Glu Asp Ile Lys Ser Gly Lys Leu Ser Gln Glu Leu Asp
    50                  55                  60

Phe Val Ser His Asn Val Arg Thr Lys Leu Asp Glu Leu
65                  70                  75

<210> SEQ ID NO 97
<211> LENGTH: 77
<212> TYPE: PRT
<213> ORGANISM: Mus musculus

<400> SEQUENCE: 97

Val Pro Val Asp Arg Ala Ala Pro Pro Gln Glu Asp Ser Gln Ala Thr
1               5                   10                  15

Glu Thr Pro Asp Thr Gly Leu Tyr Tyr His Arg Tyr Leu Gln Glu Val
            20                  25                  30

Ile Asn Val Leu Glu Thr Asp Gly His Phe Arg Glu Lys Leu Gln Ala
        35                  40                  45

Ala Asn Ala Glu Asp Ile Lys Ser Gly Lys Leu Ser Gln Glu Leu Asp
    50                  55                  60

Phe Val Ser His Asn Val Arg Thr Lys Leu Asp Glu Leu
65                  70                  75

<210> SEQ ID NO 98
<211> LENGTH: 231
<212> TYPE: DNA
<213> ORGANISM: Homo sapiens

<400> SEQUENCE: 98
gtccccctgg agcgaggggc gcccaacaag gaggagaccc ctgcgactga gagtcccgac        60
acaggcctgt actaccaccg gtacctccag gaggtcatcg atgtactgga dacggatggg      120
catttccgag agaagctgca ggctgccaat gcggaggaca tcaagagcgg gaagctgagc      180
cgagagctgg actttgtcag ccaccacgtc cgcaccaagc tggatgagct c               231

<210> SEQ ID NO 99
<211> LENGTH: 231
<212> TYPE: DNA
<213> ORGANISM: Rattus norvegicus

<400> SEQUENCE: 99
gtgcctgtgg accgcgcagc acctcatcag gaggacaacc aggccactga daccccggac       60
acaggcctgt actaccatcg gtacctccag gaggtcatca acgtgctaga gacagatggg      120
cacttccggg agaagctgca agctgccaac gctgaggaca ttaagagtgg aaagctgagt      180
```
caagagctgg acttcgtcag ccacaacgtc cgcaccaagc tggatgagct c      231

<210> SEQ ID NO 100
<211> LENGTH: 231
<212> TYPE: DNA
<213> ORGANISM: Mus musculus

<400> SEQUENCE: 100
gtgcccgtgg accgcgcagc acctcctcag gaggacagcc aggccactga gaccccggac      60
acgggcctgt actaccaccg gtacctccag gaggtcatca acgtgctaga gacagatggg      120
cacttccggg agaagctgca ggctgccaac gctgaggaca ttaagagtgg aaagctgagc      180
caagagctgg acttcgtcag ccacaacgtc cgaaccaagc tggatgagct c      231

<210> SEQ ID NO 101
<211> LENGTH: 30
<212> TYPE: PRT
<213> ORGANISM: Homo sapiens

<400> SEQUENCE: 101

Pro Asp Thr Gly Leu Tyr Tyr His Arg Tyr Leu Gln Glu Val Ile Asp
1               5                   10                  15
Val Leu Glu Thr Asp Gly His Phe Arg Glu Lys Leu Gln Ala
            20                  25                  30

<210> SEQ ID NO 102
<211> LENGTH: 30
<212> TYPE: PRT
<213> ORGANISM: Rattus norvegicus

<400> SEQUENCE: 102

Pro Asp Thr Gly Leu Tyr Tyr His Arg Tyr Leu Gln Glu Val Ile Asn
1               5                   10                  15
Val Leu Glu Thr Asp Gly His Phe Arg Glu Lys Leu Gln Ala
            20                  25                  30

<210> SEQ ID NO 103
<211> LENGTH: 30
<212> TYPE: PRT
<213> ORGANISM: Mus musculus

<400> SEQUENCE: 103

Pro Asp Thr Gly Leu Tyr Tyr His Arg Tyr Leu Gln Glu Val Ile Asn
1               5                   10                  15
Val Leu Glu Thr Asp Gly His Phe Arg Glu Lys Leu Gln Ala
            20                  25                  30

<210> SEQ ID NO 104
<211> LENGTH: 90
<212> TYPE: DNA
<213> ORGANISM: Homo sapiens

<400> SEQUENCE: 104
cccgacacag gcctgtacta ccaccggtac ctccaggagg tcatcgatgt actggagacg      60
gatgggcatt tccgagagaa gctgcaggct      90

<210> SEQ ID NO 105
<211> LENGTH: 90
<212> TYPE: DNA
<213> ORGANISM: Rattus norvegicus -continued

<400> SEQUENCE: 105
ccggacacag gcctgtacta ccatcggtac ctccaggagg tcatcaacgt gctagagaca    60
gatgggcact tccgggagaa gctgcaagct    90

<210> SEQ ID NO 106
<211> LENGTH: 90
<212> TYPE: DNA
<213> ORGANISM: Mus musculus

<400> SEQUENCE: 106
ccggacacgg gcctgtacta ccaccggtac ctccaggagg tcatcaacgt gctagagaca    60
gatgggcact tccgggagaa gctgcaggct    90

<210> SEQ ID NO 107
<211> LENGTH: 16
<212> TYPE: PRT
<213> ORGANISM: Homo sapiens

<400> SEQUENCE: 107

Pro Asp Thr Gly Leu Tyr Tyr His Arg Tyr Leu Gln Glu Val Ile Asp
1               5                   10                  15

<210> SEQ ID NO 108
<211> LENGTH: 14
<212> TYPE: PRT
<213> ORGANISM: Homo sapiens

<400> SEQUENCE: 108

Val Leu Glu Thr Asp Gly His Phe Arg Glu Lys Leu Gln Ala
1               5                   10

<210> SEQ ID NO 109
<211> LENGTH: 10
<212> TYPE: PRT
<213> ORGANISM: Homo sapiens

<400> SEQUENCE: 109

Gln Glu Val Ile Asp Val Leu Glu Thr Asp
1               5                   10

<210> SEQ ID NO 110
<211> LENGTH: 16
<212> TYPE: PRT
<213> ORGANISM: Rattus norvegicus

<400> SEQUENCE: 110

Pro Asp Thr Gly Leu Tyr Tyr His Arg Tyr Leu Gln Glu Val Ile Asn
1               5                   10                  15

<210> SEQ ID NO 111
<211> LENGTH: 14
<212> TYPE: PRT
<213> ORGANISM: Rattus norvegicus

<400> SEQUENCE: 111

Val Leu Glu Thr Asp Gly His Phe Arg Glu Lys Leu Gln Ala
1               5                   10

<210> SEQ ID NO 112
<211> LENGTH: 10
<212> TYPE: PRT
<213> ORGANISM: Rattus norvegicus

```
<400> SEQUENCE: 112

Gln Glu Val Ile Asn Val Leu Glu Thr Asp
1               5                   10

<210> SEQ ID NO 113
<211> LENGTH: 16
<212> TYPE: PRT
<213> ORGANISM: Mus musculus

<400> SEQUENCE: 113

Pro Asp Thr Gly Leu Tyr Tyr His Arg Tyr Leu Gln Glu Val Ile Asn
1               5                   10                  15

<210> SEQ ID NO 114
<211> LENGTH: 14
<212> TYPE: PRT
<213> ORGANISM: Mus musculus

<400> SEQUENCE: 114

Val Leu Glu Thr Asp Gly His Phe Arg Glu Lys Leu Gln Ala
1               5                   10

<210> SEQ ID NO 115
<211> LENGTH: 10
<212> TYPE: PRT
<213> ORGANISM: Mus musculus

<400> SEQUENCE: 115

Gln Glu Val Ile Asn Val Leu Glu Thr Asp
1               5                   10

<210> SEQ ID NO 116
<211> LENGTH: 48
<212> TYPE: DNA
<213> ORGANISM: Homo sapiens

<400> SEQUENCE: 116
cccgacacag gcctgtacta ccaccggtac ctccaggagg tcatcgat              48

<210> SEQ ID NO 117
<211> LENGTH: 42
<212> TYPE: DNA
<213> ORGANISM: Homo sapiens

<400> SEQUENCE: 117
gtactggaga cggatgggca tttccgagag aagctgcagg ct                    42

<210> SEQ ID NO 118
<211> LENGTH: 30
<212> TYPE: DNA
<213> ORGANISM: Homo sapiens

<400> SEQUENCE: 118
caggaggtca tcgatgtact ggagacggat                                  30

<210> SEQ ID NO 119
<211> LENGTH: 48
<212> TYPE: DNA
<213> ORGANISM: Rattus norvegicus

<400> SEQUENCE: 119
ccggacacag gcctgtacta ccatcggtac ctccaggagg tcatcaac              48
```

```
<210> SEQ ID NO 120
<211> LENGTH: 42
<212> TYPE: DNA
<213> ORGANISM: Rattus norvegicus

<400> SEQUENCE: 120
gtgctagaga cagatgggca cttccgggag aagctgcaag ct                    42

<210> SEQ ID NO 121
<211> LENGTH: 30
<212> TYPE: DNA
<213> ORGANISM: Rattus norvegicus

<400> SEQUENCE: 121
caggaggtca tcaacgtgct agagacagat                                  30

<210> SEQ ID NO 122
<211> LENGTH: 48
<212> TYPE: DNA
<213> ORGANISM: Mus musculus

<400> SEQUENCE: 122
ccggacacgg gcctgtacta ccaccggtac ctccaggagg tcatcaac              48

<210> SEQ ID NO 123
<211> LENGTH: 42
<212> TYPE: DNA
<213> ORGANISM: Mus musculus

<400> SEQUENCE: 123
gtgctagaga cagatgggca cttccgggag aagctgcagg ct                    42

<210> SEQ ID NO 124
<211> LENGTH: 30
<212> TYPE: DNA
<213> ORGANISM: Mus musculus

<400> SEQUENCE: 124
caggaggtca tcaacgtgct agagacagat                                  30
```